United States Patent
Eitan et al.

(10) Patent No.: US 10,954,313 B2
(45) Date of Patent: Mar. 23, 2021

(54) COMPOSITION COMPRISING SP1 AND CARBON BASED NANOPARTICLES AND USES THEREOF

(71) Applicant: SP NANO LTD, Yavne (IL)

(72) Inventors: Asa Eitan, Tel Aviv (IL); Yana Tesler, Rehovot (IL); Jeanie Tamir, Kibbutz Shiler (IL); Nurit Shalev, Herzliya (IL); Leonid Melekhov, Kibbutz Ein Shemer (IL); Oshrit Poliker, Hadera (IL); Amnon Wolf, Herzeliya (IL); Konstantin Press, Rishon le-Zion (IL)

(73) Assignee: SP Nano Ltd., Kibbutz Reshafim (IL)

( * ) Notice: Subject to any disclaimer, the term of this patent is extended or adjusted under 35 U.S.C. 154(b) by 0 days.

(21) Appl. No.: 16/073,789

(22) PCT Filed: Jan. 29, 2017

(86) PCT No.: PCT/IL2017/050105
§ 371 (c)(1),
(2) Date: Jul. 29, 2018

(87) PCT Pub. No.: WO2017/130202
PCT Pub. Date: Aug. 3, 2017

(65) Prior Publication Data
US 2019/0153121 A1  May 23, 2019

(30) Foreign Application Priority Data
Jan. 28, 2016 (IL) .......................... 243838

(51) Int. Cl.
| | |
|---|---|
| *C07K 17/14* | (2006.01) |
| *C07K 14/415* | (2006.01) |
| *C09C 1/56* | (2006.01) |
| *C09C 1/48* | (2006.01) |
| *C09D 7/62* | (2018.01) |
| *B60C 1/00* | (2006.01) |
| *C09D 107/02* | (2006.01) |
| *C09D 109/04* | (2006.01) |
| *C09D 109/08* | (2006.01) |
| *C09D 111/02* | (2006.01) |
| *C09D 115/00* | (2006.01) |
| *C09D 123/16* | (2006.01) |
| *C09D 161/12* | (2006.01) |
| *C09D 179/02* | (2006.01) |
| *C09D 189/00* | (2006.01) |
| *D06M 11/74* | (2006.01) |
| *D06M 15/15* | (2006.01) |
| *D06M 15/61* | (2006.01) |
| *D06M 15/693* | (2006.01) |
| *D06M 101/32* | (2006.01) |
| *D06M 101/36* | (2006.01) |
| *D06M 101/40* | (2006.01) |

(52) U.S. Cl.
CPC ............ *C07K 17/14* (2013.01); *B60C 1/0016* (2013.01); *C07K 14/415* (2013.01); *C09C 1/48* (2013.01); *C09C 1/56* (2013.01); *C09D 7/62* (2018.01); *C09D 107/02* (2013.01); *C09D 109/04* (2013.01); *C09D 109/08* (2013.01); *C09D 111/02* (2013.01); *C09D 115/00* (2013.01); *C09D 123/16* (2013.01); *C09D 161/12* (2013.01); *C09D 179/02* (2013.01); *C09D 189/00* (2013.01); *D06M 11/74* (2013.01); *D06M 15/15* (2013.01); *D06M 15/61* (2013.01); *D06M 15/693* (2013.01); *B60C 2001/0066* (2013.01); *C01P 2004/03* (2013.01); *D06M 2101/32* (2013.01); *D06M 2101/36* (2013.01); *D06M 2101/40* (2013.01)

(58) Field of Classification Search
CPC .............................. C07K 17/14; C07K 14/415
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |

(Continued)

FOREIGN PATENT DOCUMENTS

| | | |
|---|---|---|
| EP | 0774512 A2 | 5/1997 |
| WO | WO 1999/033940 A1 | 7/1999 |

(Continued)

OTHER PUBLICATIONS

Bachilo et al. "Structure-assigned optical spectra of single-walled carbon nanotubes" science. Dec. 20, 2002;298(5602):2361-6.

(Continued)

*Primary Examiner* — Amber D Steele

(57) ABSTRACT

The present invention, relates to composition of matter comprising sequence variants of Stable Protein 1 (SP1) and carbon nanotubes or carbon black, and optionally comprising latex. This invention also relates to surfaces (e.g. metal wires, cords, and polymeric and non polymeric fibers, yarns, films or fabrics, wood and nano, micro and macro particles) comprising this composition of matter, to methods for producing them, and to uses thereof in the preparation and formation of improved composite materials, including rubber, and rubber compound composites.

25 Claims, 30 Drawing Sheets

Specification includes a Sequence Listing.

(56) References Cited

U.S. PATENT DOCUMENTS

| | | | |
|---|---|---|---|
| 3,879,262 A | 4/1975 | Schuurs et al. | |
| 3,901,654 A | 8/1975 | Gross | |
| 3,935,074 A | 1/1976 | Rubinstein et al. | |
| 3,984,533 A | 10/1976 | Uzgiris | |
| 3,996,345 A | 12/1976 | Ullman et al. | |
| 4,002,531 A | 1/1977 | Royer | |
| 4,179,337 A | 12/1979 | Davis et al. | |
| 4,666,828 A | 5/1987 | Gusella | |
| 4,683,202 A | 7/1987 | Mullis | |
| 4,801,531 A | 1/1989 | Frossard | |
| 5,073,292 A | 12/1991 | Hessel et al. | |
| 5,097,025 A | 3/1992 | Benfey et al. | |
| 5,192,659 A | 3/1993 | Simons | |
| 5,272,057 A | 12/1993 | Smulson et al. | |
| 6,472,505 B1 | 10/2002 | Condon et al. | |
| 7,131,474 B2 | 11/2006 | Sandstrom | |
| 7,253,341 B2 | 8/2007 | Wang et al. | |
| 7,284,583 B2 | 10/2007 | Dheur et al. | |
| 7,304,128 B2 | 12/2007 | Jakota et al. | |
| 7,318,464 B2 | 1/2008 | Hahn et al. | |
| 7,337,815 B2 | 3/2008 | Spadone et al. | |
| 7,354,877 B2 | 4/2008 | Rosenberger et al. | |
| 7,445,764 B1 | 11/2008 | Kratz | |
| 7,528,186 B2 | 5/2009 | Halasa et al. | |
| 7,581,439 B2 | 9/2009 | Rensel et al. | |
| 8,957,189 B2 * | 2/2015 | Wolf | C09K 5/14 530/402 |
| 9,982,181 B2 * | 5/2018 | Wolf | C09K 5/14 |
| 2002/0098999 A1 | 7/2002 | Gallop et al. | |
| 2003/0092624 A1 | 5/2003 | Wang et al. | |
| 2004/0058457 A1 | 3/2004 | Huang et al. | |
| 2004/0173295 A1 | 9/2004 | Zanzig et al. | |
| 2005/0074763 A1 | 4/2005 | Wang et al. | |
| 2005/0277160 A1 | 12/2005 | Shiba et al. | |
| 2006/0074225 A1 | 4/2006 | Chamberlain et al. | |
| 2006/0172298 A1 | 8/2006 | Wang et al. | |
| 2007/0112174 A1 | 5/2007 | Shiba et al. | |
| 2007/0117147 A1 | 5/2007 | Jagota et al. | |
| 2007/0117148 A1 | 5/2007 | Jagota et al. | |
| 2007/0117150 A1 | 5/2007 | Jagota et al. | |
| 2008/0108733 A1 * | 5/2008 | Colvin | B60C 1/00 524/25 |
| 2010/0078103 A1 | 4/2010 | Nakamura | |
| 2012/0202397 A1 * | 8/2012 | Wolf | H01B 1/24 442/111 |
| 2014/0178483 A1 | 6/2014 | Wolf et al. | |
| 2015/0152311 A1 * | 6/2015 | Wolf | B82Y 30/00 252/75 |
| 2015/0202397 A1 * | 7/2015 | Pastoor | A61M 16/0683 128/205.25 |

FOREIGN PATENT DOCUMENTS

| | | |
|---|---|---|
| WO | WO 2000/076550 | 12/2000 |
| WO | WO 2001/009163 A2 | 2/2001 |
| WO | WO 2002/015877 A2 | 2/2002 |
| WO | WO 2002/049676 A2 | 6/2002 |
| WO | WO 2002/070647 A2 | 9/2002 |
| WO | WO 2004/022697 A2 | 3/2004 |
| WO | WO 2007/007325 A2 | 1/2007 |
| WO | WO 2011/027342 A2 | 3/2011 |

OTHER PUBLICATIONS

Chiang et al. "Purification and characterization of single-wall carbon nanotubes (SWNTs) obtained from the gas-phase decomposition of CO (HiPco process)" the Journal of Physical Chemistry B. Sep. 6, 2001;105(35):8297-301.

Dgany et al. "The structural basis of the thermostability of SP1, a novel plant (*Populus tremula*) boiling stable protein" Journal of Biological Chemistry, Dec. 3, 2004;279(49):51516-23.

Dyke et al. Separation of single-walled carbon nanotubes on silica gel. Materials morphology and Raman excitation wavelength affect data interpretation. Journal of he American Chemical Society. Mar. 30, 2005;127(12):4497-509.

Eitan et al. "Non-Toxic Reinforcement Textile for Tires and Mechanical Rubber Goods", Rubber World, vol. 254, No. 6, Sep. 1, 2016 (Sep. 1, 2016), pp. 24-27, XP00951310.

Holten-Andersen et al. "Mussel-designed protective coatings for compliant substrates" Journal of dental research, Aug. 2008;87(8):701-9.

International Search Report for PCT Application No. PCT/IL2017/050105 dated May 3, 2017.

Kase et al. "Affinity selection of peptide phage libraries against single-wall carbon nanohorns identifies a peptide aptamer with conformational variability" Langmuir. Sep. 28, 2004;20(20):8939-41.

Katz et al. "Integrated nanoparticle-biomolecule hybrid systems: synthesis, properties, and applications" Angewandte Chemie International Edition. Nov. 19, 2004;43(45):6042-108.

Medalsy et al. "SP1 protein-based nanostructures and arrays" Nano letters. Feb. 13, 2008;8(2):473-7.

Pender et al. "Peptide-mediated formation of single-wall carbon nanotube composites" Nano letters. Jan. 11, 2006;6(1):40-4.

Sano et al. "A hexapeptide motif that electrostatically binds to the surface of titanium" Journal of the American Chemical Society. Nov. 26, 2003;125(47):14234-5.

Sano et al. "Utilization of the pleiotropy of a peptidic aptamer to fabricate heterogeneous nanodot-containing multilayer nanostructures" Journal of the American Chemical Society. Feb. 8, 2006;128(5):1717-22.

Sano et al. "In aqua structuralization of a three-dimensional configuration using biomolecuies" Nano letters. Oct. 10, 2007;7(10):3200-2.

Sarikaya et al. "Molecular biornimetics: nanotechnology through biology" Nature materials. Sep. 2003;2(9):577-85.

Sarikaya et al. "Materials assembly and formation using engineered polypeptides" Annu. Rev. Mater. Res.. Aug. 4, 2004;34:373-408.

Sun et al. "Thermodynamic stability of human lens recombinant αA-and βB-crystallins" Journal of Biological Chemistry. Nov. 26, 1999;274(48):34067-71.

Supplementary European Search Report for European Application No. 17743854.6 dated Jul. 214, 2019.

Wang et al. "Aspen SP1, an exceptional thermal, protease and detergent-resistant self-assembled nano-particle" Biotechnology and bioengineering. Sep. 5, 2006;95(1):161-8.

Wang et al. "Characterization of SP1, a stress-responsive, boiling-soluble, homo-oligomeric protein from aspen" Plant Physiology, Oct. 1, 2002;130(2):865-75.

Wang et al. "Peptides with selective affinity for carbon rianotubes" Nature materials. Mar. 2003;2(3):196-200.

Weisman et al. "Dependence of optical transition energies on structure for single-walled carbon nanotubes in aqueous suspension: an empirical Kataura plot" Nano letters. Sep. 10, 2003;3(9):1235-8.

Willner I. "Biomaterials for sensors, fuel cells, and circuitry" Science. Dec. 20, 2002;298(5602):2407-8.

Wolf et al. "Improved adhesives containing CNT/SP1 nano fillers" the Journal of Adhesion. Apr. 1, 2012;88(4-6):435-51.

* cited by examiner

|  | CR1 | NBR1 |
|---|---|---|
| RFL | 53 | 69 |
| ut/uw | 29 | 28 |

|      | CR1 | CR2 | CR3 |
|------|-----|-----|-----|
| RFL  | 53  | 66  | 44  |
| ut/uw| 29  | 31  | 18  |

COMPOSITION COMPRISING SP1 AND CARBON BASED NANOPARTICLES AND USES THEREOF

CROSS-REFERENCE TO RELATED APPLICATIONS

This application is a National Phase Application of PCT International Application No. PCT/IL2017/050105, International Filing Date Jan. 29, 2017, claiming priority from IL Patent Application(s) No(s). 243838, filed Jan. 28, 2016, which are hereby incorporated by reference in their entirely.

FIELD AND BACKGROUND OF THE INVENTION

The present invention, in some embodiments thereof, relates to composition of matter comprising sequence variants of Stable Protein 1 (SP1) and carbon nanotubes or carbon black. This invention also relates to surfaces (e.g. metal wires, cords, and polymeric and non polymeric fibers, yarns, films or fabrics, wood and nano, micro and macro particles) comprising this composition of matter, and to uses thereof in the preparation and formation of improved composite materials, including rubber, and rubber compound composites.

Stable protein 1 (SP1) is a homo-oligomeric protein isolated from aspen (*Populus tremula* aspen) plants which forms a ring-shape dodecameric particle with a central cavity. The oligomeric form of SP1 is an exceptionally stable structure that is resistant to proteases, such as trypsin, V8, and proteinase K, high temperatures, organic solvents, and high levels of ionic detergent.

WO 2002/070647, WO 2004/022697, and U.S. Pat. No. 7,253,341, teach novel denaturant-stable, protease resistant, homo-oligomeric stable protein (SP) variants, having chaperone-like activity as well as methods of production and purification of these novel SPs. These documents also provide nucleic acids encoding SPs, methods of isolating nucleic acids encoding SPs, antibodies recognizing SPs, and the use of these SPs for stabilizing, refolding, repairing, preventing aggregation and de-aggregating macromolecules such as proteins, fusion proteins including SPs, nucleic acid constructs encoding the fusion proteins and their uses in a variety of methods and applications.

WO 2007/007325 and U.S. Pat. No. 8,957,189 teach SP1 and modified SP1 variant polypeptides, capable of forming reversible and covalent molecular associations with substances, compositions-of-matter comprising same, and various uses thereof.

It was hypothesized that if substances such as carbon nanotubes or carbon black, and metals (e.g. steel cords) or polymeric and non polymeric materials (e.g., yarns or fibers of aramid, polyester, rayon, nylon, DVA, carbon, glass, basalt, etc.) can bind to SP1 variants in a similar fashion, the protein may serve as an adhesive mediator to promote attachment of these two components to each other, based on the two-sided doughnut shape of SP1 which exhibits binding sites on both sides of the annulus.

Carbon Nanoparticles Reinforced Composite Materials

Carbon nanotubes (CNT) are nano-scale hollow cylinders of graphite carbon atoms. They provide the highest Young's modulus (stiffness), highest thermal conductivity, highest electrical conductivity, and highest current density of any known material, while having a low density. The nanotubes may consist of one (single walled carbon nanotubes) up to tens (multiwalled CNTs) and hundreds of concentric shells of carbons with adjacent shells separation of ~0.34 nm. Single walled carbon nanotubes tend to be stronger, more flexible, more transparent and better electrical conductors and are more transparent, but due to high production costs, and health and safety considerations, multi-walled carbon nanotubes are more widely used in composite materials.

When carbon nanotubes are added to a matrix material, the composite normally takes on some of the carbon nanotubes' properties, due to the rule of mixtures. However, the theoretical property values of carbon nanotubes composites are presently not attained due to the inability to efficiently produce fully integrated composites.

Due to insufficient bonding across the interface of the nanotube and matrix material, before carbon nanotubes can be used in a broad range of applications, methods for manipulating the positioning, orientation, anchoring, grafting and binding of the carbon nanotubes to the matrix are presently required, particularly where such anchoring, grafting and binding is done without metal.

Thus, there is a widely recognized need for, and it would be highly advantageous to have SP1 variants capable of forming molecular complexes with carbon nanotubes, useful for effective production of highly specific composite materials such as polymers, fibers, films and polymeric fabrics with integrated carbon nanotubes.

The regulation, environmental and health considerations favor the use of carbon black (CB) over CNTs. In addition, CB is widely available and less expensive than CNTs. Therefore, it is highly desirable to find an efficient way to attach CB to various surfaces (e.g., metals, polymeric and non polymeric fibers, films, yarns, and fabrics) for their reinforcement and for the effective production of composite elastomers, comprising such materials. However, since CB is not a well-ordered material such as CNT or graphite surfaces, it's bonding to SP1 based polypeptide is challenging and is expected to be very different than for CNTs which have been shown to bind specific CNT targeted peptides.

Carbon Nanoparticles Coated Fabrics and Textiles

Carbon Nanoparticles (CNP) display much bigger surface specific area than fibers, films or fabrics. Therefore, binding of CNPs to fibers, films or fabrics via SP1 protein, increase their surface area, allowing better interaction of matrices with the fiber even at low loading levels. In addition, SP1 protein binding to the fiber by itself may improve the interaction with the polymer through reactive groups on the protein surface.

Specifically designed SP1/CNPs composition utilizing carbon black (CB) or carbon nanotubes (CNT), which forms stable dispersion in aqueous media, can be complexed to broad range of target compounds such as carbon fabrics, aramid, polyester, rayon, glass, or nylon films, fibers and fabrics, forming useful molecular complexes in the production of highly specific composite materials such as SP1-polypeptide-CNP-aramid complex fabrics, films, yarns and polymeric fabrics.

Carbon Nanoparticles (CNP) Coated Aramid Polymers (Kevlar)

Material scientists and engineers are excited by the possibilities for creating super-strong, high-performance polymer composite materials using carbon nanoparticles. Currently, all existing methods of fabricating CNP-polymer composites involve complicated, expensive, time-demanding processing techniques such as solution casting, melting, molding, extrusion, and in situ polymerization, requiring that the CNPs either be incorporated into a polymer solution, molten polymer or mixed with the initial monomer before the formation of the final product (e.g. yarn, ribbon or film).

This is unsuitable for insoluble or temperature sensitive polymers, which decompose without melting, as well as unsuitable for fiber or wire surface coating.

Aramid polymer (e.g. KEVLAR™) is a well-known high-strength polymer with a variety of important applications such as pneumatic tire tread and sidewalls, bullet-proof vests and car armor plating. However, aramid is chemically inert and is not soluble in any common solvent and, having no melting point, decomposes above 400° C. As a result, aramid fibers must be produced by wet spinning from sulphuric acid solutions. Binding of SP1/CNP complex to aramid can enable an effective post-processing incorporation of carbon nanoparticles (e.g., CNT or CB) to the surface of already formed polymer products, such as, for example, aramid yarns, enabling the CNPs to coat the surface of fibers or wires.

CNP Reinforced Rubber Composites

Elastomers (or rubbers) are usually mixed with several different ingredients to form a "rubber compound". The added ingredients are chosen to optimize the physical properties of the compound in order to meet the specification for a particular application. Normally, the rubber is also mixed with a small amount of sulfur or peroxide and cured at elevated temperatures (vulcanization) in order to improve the rubber compound dimensional stability, resilience, modulus, as well as other properties. As a result of the curing process, the rubber compound has a higher modulus and lower extension at break. Normally, rubber compounds also comprise fillers.

A "filler" is defined, in some embodiments, as a finely divided solid that is used to augment weight or size or fill space in the rubber bulk. Although the original purpose is to lower the cost of the products, prime importance is given to selective functional fillers that are capable of modifying the mechanical, electrical and/or optical properties of a material in which they are dispersed. In the elastomer industry, the importance of fillers in providing durability and performance has been recognized. Carbon black is the major reinforcing filler for tires and many other rubber and plastic products. Addition of carbon black (CB) results in the enhancement of the mechanical properties of elastomeric materials, such as increase in both their strength and modulus. Other fillers are also known, including: calcium carbonate, kaolin clay, precipitated silica, talc, barite, amorphous silica, diatomite etc. Application of such fillers on the surface of a rubber compound reinforcing textile may improve the overall performance of the textile reinforced rubber based products due to increasing of fiber surface area, providing scaffold for application of different suitable chemistries and preventing crack propagation along the fiber-matrix interface. However, due to insufficient bonding across the interface between the reinforcing textile and the matrix material (i.e. elastomers), before any type of filler (e.g., carbon nanoparticles, silica, calcium carbonate or clay) can be incorporated through textiles to rubber compounds and be used in a broad range of applications, methods for anchoring, grafting and binding of the fabric to the rubber compound are required.

The properties of SP1 protein, as described above, and its role in binding CNT to polymeric and non-polymeric materials, may be utilized for incorporation of various nanoparticles such as carbon black, clay or silica, to the surface of fabrics, which will further help integrating the fabrics into rubber compounds. Specifically designed SP1/CB composition, can be complexed to broad range of target compounds including: carbon fabrics, polyester, aramid, rayon, glass, basalt, or nylon films, fibers and fabrics, forming useful CB coated fabrics, fibers or films, that can be further incorporated into rubber compounds, (as well as to other matrices) in the production of highly specific textile-reinforced mechanical rubber goods, e.g. tires, belts, hoses, rubber boats, etc. Incorporation of CB to the surface of polymeric and non-polymeric materials through interaction with SP1 protein is therefore highly desirable in the preparation of various elastomeric compounds, or any other composite materials.

Steel Cords to Rubber Adhesion

It is frequently necessary to reinforce rubber compositions, for example, for use in tires, conveyor or timing belts, hoses and like products, by incorporating therein steel wire reinforcing elements. The steel wire forming such elements may be for example in the form of a single strand or a steel wire cord. Unfortunately, bare steel cord adheres poorly to rubber. Steel wire reinforcing elements are in general provided with a coating serving to provide adhesion to the rubber composition which should be reinforced. The state of the art solution is coating with brass and bronze alloys. In order to overcome the drawbacks of brass and bronze and the coating processes that they involve there is a need for finding alternatives for brass and bronze coating of steel cords as the adhesion promoter to rubber.

Textile to Rubber Adhesion

Current methods for depositing carbon nanotubes (CNTs) on fibers (e.g. carbon fiber) include: (a) a modified thermal chemical vapor deposition (CVD) method; (b) Electrophoretic deposition of carbon nanotubes onto carbon-fiber fabric for production of carbon/epoxy composites with improved mechanical properties; and (c) CNT mixing with a sizing reagent (e.g. SIZICYL™ nanocyl).

Though a significant improvement in the interlaminar properties was observed in several cases, the intrinsic mechanical properties of the fiber may be compromised by the CVD process.

Synthetic fibers (e.g., polyester and aramid), have the difficulty of adhering to rubbers because of their smooth polymer surfaces and low reactivity. Therefore, their surface has to first be treated with an adhesion activator to obtain a good bonding to rubber.

The adhesive bond between fabric and rubber is clearly of primary importance. To maintain the integrity of the fabric/rubber composite it has to perform without failure for the life of the composite under a variety of service conditions. Due to environmental factors tire manufacturers are coming under increasing pressure to produce longer lasting tires. This inevitably means that the fabric to rubber bond will become more important.

Adhesion between fabric and rubber compounds is dramatically improved by cord dipping into a rubber-to-substrate adhesives. Resorcinol Formaldehyde Latex adhesives (RFLs) are commonly used to treat textiles in order to enhance their adhesion to rubbers and are used as the gold standard. RFL is a composite material, consisting of several components including resorcinol (R), formaldehyde (F) and latex (L) that enhance the adhesion between fibers and rubber compounds. The major function of the adhesive is to transfer the load stress from the rubber matrix to the reinforcing fiber materials. In the case of an RFL adhesive, the RF resin component of this adhesive preferably bonds to the fiber whereas the rubber-like latex component bonds to the rubber through co-vulcanization. The low viscosity of RFL solution provided good fiber wetting and thereby, increasing the interaction between the fiber and adhesive. The kind of latex used in the RFL adhesive formulation depends on the type of rubber to be bonded. Latex must be compatible with rubber to ensure vulcanization. The superior adhesion of RFL adhesive is due to the interaction between the latex and textile fibers. The major limitations of RFL treatment are its toxicity and the resulting fiber's rigidity (low flexibility). Other limitations include short shelf life and UV light sensitivity of RFL coated textile. Therefore, alternative rubber-to-substrates adhesives, which are not toxic and which retain fibers properties are highly desired.

U.S. Pat. No. 8,957,189 teaches SP1 and modified SP1 variant polypeptides, capable of forming molecular associations with carbon nanotubes, compositions-of-matter comprising same, dispersions thereof and their incorporation to the surface of polymeric and non polymeric surfaces. US '189, however, does not disclose rubber compound composites comprising metal cords, and polymeric fibers or fabrics with integrated SP1/CNT composition of matter within. US '189 is also silent regarding any composition of matter comprising SP1 and CB for metal wires and cords and polymeric and non polymeric materials coating and for use in rubber compound composites. Herein it is demonstrated, that addition of latex to SP1 and CNT (SP1/CNT/latex composition) significantly improves the adhesion between rubber compounds and SP1/CNT/latex-coated fabrics. In addition, utilization of composition of matter which comprises CB and SP1, for metals and textile coating and for the formation of rubber composites, is presented herein for the first time. Accordingly, the SP1/CNP dispersions as described herein provide new compositions of matter, which are useful for the preparation of new coated textiles and metal cords and wires, and new rubber compound composites.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In various embodiments, it is provided herein a composition of matter comprising carbon black (CB) bound to a Stable Protein 1 (SP1) based polypeptide. In other embodiments, the CB is non covalently bound to said SP1 based polypeptide.

In other embodiments, the SP1 base polypeptide has the amino acid sequence as set forth in any one of SEQ ID NOs: 3, 4, 6, 8, 9, 14-18 and 86. In other embodiments, the chimeric SP1 polypeptide has the amino acid sequence as set forth in SEQ ID NO: 8.

In other embodiments, the composition of matter provided herein is in the form of an aqueous dispersion in a concentration of between 0.001% and 30% w/w. In other embodiments, the composition is in the form of an aqueous dispersion in a concentration of between 1% and 20% w/w. In other embodiments, the composition is in the form of an aqueous dispersion in a concentration of 0.05%, 0.1%, or between 0.05% and 0.15%. In other embodiments, the composition is in the form of an aqueous dispersion in a concentration of 15% w/w.

In other embodiments, the composition of matter provided herein further comprises latex. In other embodiments, the latex is natural latex or synthetic latex. In other embodiments, the latex is selected from: Carboxylated Styrene Butadiene polymers (Genflo®), Styrene-butadiene-2-vinylpyridine, vinyl pyridine latex (VP), vinyl pyridine/butadiene/styrene blend (GENTAC®), ammonia prevulcanized natural rubber (Revultex), colloidal dispersion of a polymer of 2-chlorobutadiene (1,3) (Lipren), Anionic stabilized aqueous latex of a carboxylated butadiene based product (Litex), an aqueous dispersion of a terpolymer of butadiene, styrene and 2-vinylpyridine (Pyratex, Encord-106 VP, Styrene-butadiene-2-vinylpyridine), a random ter-polymer of Vinyl Pyridine, Styrene and Butadiene monomer dispersed in an aqueous medium or any combination thereof.

In other embodiments, the composition of matter provided herein, has a CB:latex ratio of between 1:10 to 50:1. In other embodiments, the CB:latex ratio is between 1:5 to 10:1. In other embodiments, the CB:latex ratio is between 20:1 to 40:1. In other embodiments, the composition of matter is in the form of an aqueous dispersion in a concentration of between 0.001% and 30% w/w. In other embodiments, in a concentration of 0.05%, 0.1%, or between 0.05% and 0.15%. In other embodiments, in a concentration of between 1% and 20%. In other embodiments, in a concentration of 2%, 4%, 6%, 8%, 10%, or 15%.

In other embodiments, the composition of matter provided herein, has a CB:SP1 ratio of between 0.1:1 to 30:1 dry w/w. In other embodiments, the CB:SP1 ratio is between 5:1 to 7:1 dry w/w.

In various embodiments, it is provided herein a surface coated with the composition of matter of this invention. In other embodiments, the surface is a metal wire, or cord, or a polymeric or non polymeric fiber, yarn, film, or fabric. In other embodiments, the fiber, yarn, film, or fabric comprises at least one of: carbon, basalt, cotton, wool, silk, nylon, polyester, polypropylene, glass fiber, elastane, rayon, DVA and aramid. In other embodiments, the metal wire or cord is a steel wire or cord. In other embodiments, the surface further comprises at least one layer of latex. In other embodiments, the latex is Styrene-butadiene-2-vinylpyridine. In other embodiments, the surface further comprises at least one layer of polyethyleneimine (PEI). In other embodiments, the surface further comprises a rubber to substrate adhesive. In other embodiments, the surface comprises a plurality of layers of the composition of matter according to this invention bound to said cord, fiber, yarn, film or fabric. In other embodiments, the surface comprises two layers of the composition of matter bound to said surface. In other embodiments, the applied load of said composition on said surface is between 0.1 gr/kg and 50 gr/kg. In other embodiments, the applied load of said composition on said surface is between 1 gr/kg and 14 gr/kg.

In various embodiments, it is provided herein a surface according to this invention, attached to a rubber compound.

In various embodiments, it is provided herein, a rubber compound composite comprising the surface according to this invention.

In various embodiments, provided herein are mechanical rubber goods comprising the SP1/CB composition of matter of this invention or the surface of this invention. In other embodiments, the mechanical rubber goods are selected from: a tire, a belt, a hydraulic hose, a transmission belt, a timing belt and a rubber boat.

In various embodiments, it is provided herein a pneumatic or semi-pneumatic tire comprising the composition of matter according to this invention or the surface according to this invention.

In various embodiments, provided herein is a method of producing the surface according to this invention, said method comprises contacting a dispersion comprising the composition of this invention with a surface. In other embodiments, the method further comprises a step of washing the unbound composition from said surface. In other embodiments, the method further comprises a step of desizing of said surface prior to contacting it with said composition. In other embodiments, the method further comprises a step of contacting the surface with latex prior to and/or after contacting the surface with said composition, and after said desizing. In other embodiments, the method further comprises a step of contacting the surface, with a solution comprising polyethyleneimine (PEI) prior to contacting the surface with said composition, and after said desizing. In other embodiments, the solution comprising PEI further comprises latex. In other embodiments, the PEI:latex ratio in said solution is between 1:20 to 20:1. In other embodiments, the PEI:latex ratio in said solution is between 1:5 to 5:1. In other embodiments, the method is repeated at least once. In other embodiments, the method further comprises a step of contacting said surface with PEI as the last step. In other embodiments, the method further comprises a step of contacting said surface with latex as the last step. In other embodiments, the method further comprises a step of contacting said surface with a silane coupling agent as the last step. In other embodiments, the method further comprises a step of contacting said surface with a rubber-to-substrate adhesive.

In various embodiments, provided herein is a method of producing the surface according to this invention, comprising:
 a. Optionally desizing a surface;
 b. Optionally contacting said surface, with a solution comprising polyethyleneimine (PEI);
 c. Optionally contacting said surface, with latex;
 d. Contacting a dispersion comprising the composition of this invention with said surface;
 e. Optionally repeating steps (b) and/or (c) and/or (d) at least once; and
 f. Optionally contacting said surface, with at least one of: PEI, latex, a silane coupling agent, or a rubber-to-substrate adhesive.

In other embodiments, the method is for producing a coated steel wire or cord, and it comprises:
 a. optionally scouring a steel wire or cord with an acid;
 b. contacting said wire or cord with a solution comprising polyethyleneimine (PEI);
 c. optionally contacting said wire or cord with latex;
 d. contacting a dispersion comprising the composition according to this invention with said wire or cord;
 e. optionally repeating steps (b) and/or (c) and/or (d) at least once;
 f. contacting said wire or cord with a solution comprising PEI; and
 g. contacting said wire or cord with latex.

In other embodiments, the acid is $NHO_3$. In other embodiments, the applied loading of PEI solution to the wire or cord, is between 0.005% to 30% (weight PEI/weight cord), between 0.05% to 5%, 0.05% or between 1% to 5%. In other embodiments, the applied loading of latex to the wire or cord is 0.4%, between 0.001 to 20%, or between 2% to 5%. In other embodiments, the applied loading of SP1/CB to the wire or cord is 0.1%, 0.25% or between 0.05% to 1%.

In other embodiments, the method is for producing a coated polymeric or non polymeric fiber, yarn, film or fabric, and it comprises:

a. desizing a polymeric or non polymeric fiber, yarn, film or fabric;
 b. contacting said polymeric or non polymeric fiber, yarn, film or fabric with solution comprising polyethyleneimine (PEI);
 c. optionally contacting said polymeric or non polymeric fiber, yarn, film or fabric with latex;
 d. contacting a dispersion comprising the SP1/CB composition according to this invention with said polymeric or non polymeric fiber, yarn, film or fabric;
 e. contacting said polymeric or non polymeric fiber, yarn, film or fabric with solution comprising PEI; and
 f. contacting said polymeric or non polymeric fiber, yarn, film or fabric with a solution comprising latex or a silane coupling agent.

In other embodiments, the silane coupling agent is Tetrasulfidosilane, the latex is Styrene-butadiene-2-vinylpyridine latex, or combination thereof. In other embodiments, the method further comprises a step of washing said surface with a buffer or water after each step of the method.

BRIEF DESCRIPTION OF THE DRAWINGS

The principles and operation of the present invention may be better understood with reference to the drawings and accompanying descriptions. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

FIG. 1A depicts an HR SEM image of SP1/CB (N326) dispersion and FIG. 1B depicts a polyester yarn coated with the SP1/CB (N326) complex.

FIG. 2A depicts the effect of time of sonication on SP1/CB dispersion at different SP1/CB dry w/w ratio. FIG. 2B depicts the effect of time of sonication and SP1/N326 CB concentration on stability upon centrifugation. N326 CB; SP1/CB dry w/w ratio=5.5 or 7; SP1/CB concentration=4%. Sonication conditions and measurement of stability upon centrifugation were determined as described in Table 4. FIG. 2B depicts the effect of time of sonication and SP1/N326 CB dry w/w ratio on stability upon centrifugation. CB concentration=4%; SP1/CB=5.5; SP1/CB concentration=4, 6 or 8%. Sonication conditions and measurement of stability upon centrifugation were determined as described in Table 4. Measurements conditions: Using a Hielscher Ultrasonics processor UIP1000 (1000 W), frequency: 20 kHz (autoscan), amplitude: 25 mm (85%). Fraction of CB remaining using an absorption at 600 nm, in the supernatant upon high-speed centrifugation under standard conditions (0.1% in phosphate buffer; 30 min at 3000 g, at room temperature) Note that in the absence of any protein the dispersion precipitate even after long sonication time.

FIG. 3 depicts co-precipitation of SP1/CB/latex. Precipitation conditions: addition of HCL, 0.3%, followed by centrifugation (10 min, 4700 g; 25 deg). While latex beads (1) are stable at low pH, both the SP1/CNP complex (5) and the SP1/CNP/latex (3) precipitate.

FIG. 4 depicts a flow chart describing an example of the coating process of SP1/CB/genflo of polyester threads or Kevlar cord. (Step 2). 1100/1/2 dtex low-twist yarn Desizing is conducted using Soda ash triton or KTS treatment, using Ugolini dyeing machine; Yarn weight 100 g; Yarn/liquire ratio=7. Pump work parameters: in-out time 2 min, out-in time 1 min, pump output 80%, pressure during the process ~1 bar, Δ pressure ~0.1 bar. (Step 4). High molecular weight (60 KDa) branched PEI is dissolved in carbonate buffer (20 mM pH=8.8) and is applied on the fabric at 45° C.; when PEI/Fabric ratio=0.035%-1.4% (PEI concentration in solution 0.005-0.2%). Extensive wash is needed because PEI at low concentration leads to CNP aggregation and precipitation. (Step 6). SP1/CB/Latex is applied on the fabric when CNP/Fabric ratio=0.35%-0.9% at 45° C. (CNP concentration in solution 0.05-0.13%); Typically this process takes about 1 hr until full depletion of the SP1/CB/Latex from the applied dispersion is reached.

FIG. 5A depicts that polyester yarn coating with the SP1/CB/genflo complex improves adhesion in four rubber compounds H-test results. FIG. 5B depicts hose test results (texture coded as in FIG. 5A).

FIGS. 6A-6C depict images of Polyester Yarns after H-test failure. FIG. 6A depicts untreated yarns. Poor adhesion to rubber. Adhesive failure. FIG. 6B depicts RFL-coated yarn. Good adhesion to rubber. Yarns are glued to each other, Low surface area and cohesive failure; and FIG. 6C depicts SP1/CB/coated yarn. Yarns are spread. High surface area. Cohesive failure.

FIGS. 7A-7C depict a demonstration of uniform SP1/CNT/Genflo coating of nylon film. FIG. 7A depicts untreated film (reference) (200 nm resolution (left) and 2 μm resolution (right)). FIG. 7B SP1/CNT/Genflo coated film (200 nm resolution (left) and 1 μm resolution (right). FIG. 7C depicts SP1/CNT/Genflo coated film (200 nm resolution (left) and 1 μm resolution (right)) after peel test.

FIG. 8 depicts the results from a Peel Test—Rubber Nitrile 6031 from Nylon fabric coated with various loads of SP1/CNT/latex in various CNT/latex ratios. Fabrics with higher peel strength (SP1/CNT/Genflo/ratio 1:20 2-layers 0.05%) showed partial cohesive failure. The negative control (wash only) showed adhesive failure and poor peel strength. Higher Latex/CNT concentrations and low CNT/genflo ratio show lower adhesion. No obvious correlation between the latex/CNT ratio and the peel strength was observed, indicating that low amounts of latex allow good adhesion.

FIG. 9 depicts adhesion results {H-test, ASTM 4776} with different rubber compounds of polyester yarn coated under different conditions. Rubber compounds: 1-3 are Neoprene based rubber compounds; and 4-6 are Nitrile based rubber compounds.

FIG. 10A depicts that combination of increased CB load (7 g/Kg→10.5 g/Kg) in two layers and PEI top coating in the third layer improves adhesion in 5 rubber compounds (three neoprene and two Nitrile compounds). FIG. 10B depicts the control values for two rubbers. Negative control—untreated unwashed yarn (UT/UW) and positive control—RFL treated yarn (RFL).

FIGS. 11A-11D depict the effect of SP1/CB ratio on adhesion at constant latex (Genflo) to CB ratio (1:30) in three Neoprene rubbers: (FIG. 11A) CR1; (FIG. 11B) CR2; (FIG. 11C) CR3; and (FIG. 11D) depicts the control values for the rubbers. Negative control—untreated unwashed yarn (UT/UW) and positive control—RFL treated yarn (RFL).

FIG. 12 depicts the effect of latex loading on adhesion to Neoprene rubber. Positive control: top line, RFL-treated yarn; Negative controls: bottom line, Untreated yarn (washed or unwashed). CNT/Latex W/W ratio=20 (suboptimal condition). Optimal loading: 0.1%*2 or 0.05%*2. With the same loading, two layers are better than one layer. Lower loading yielded uneven coating as evident from electrical resistance measurements.

Figure 26:
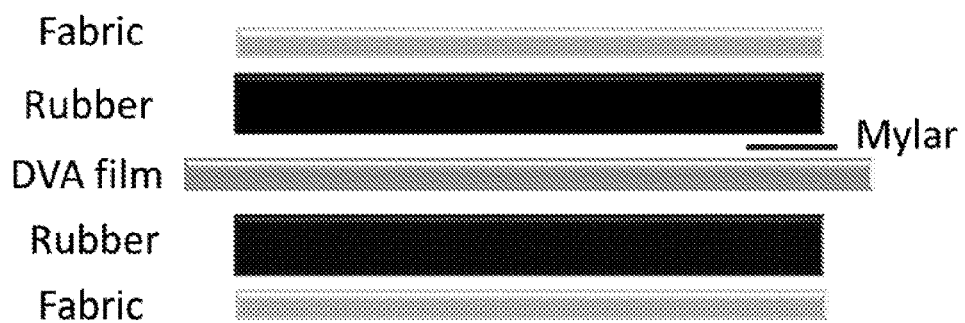

FIG. 26 depicts a typical sample construction for the DVA film reinforced rubber. A DVA film was placed between two NR sheets reinforced with Charmeuse fabric. The total thickness of the sample was 2 mm, and its dimensions were 5×6 inch.

Figure 27:
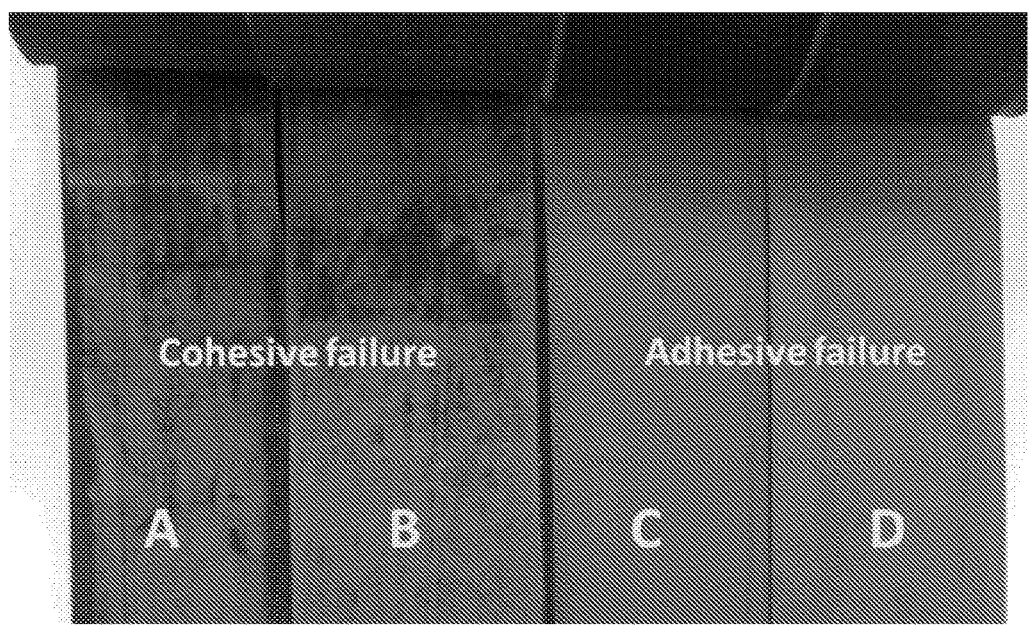

FIG. 27 depicts peel samples of treated film (A and B) versus untreated film (C and D) and NR/CR reinforced rubber produced at 155° C.

Figure 28:
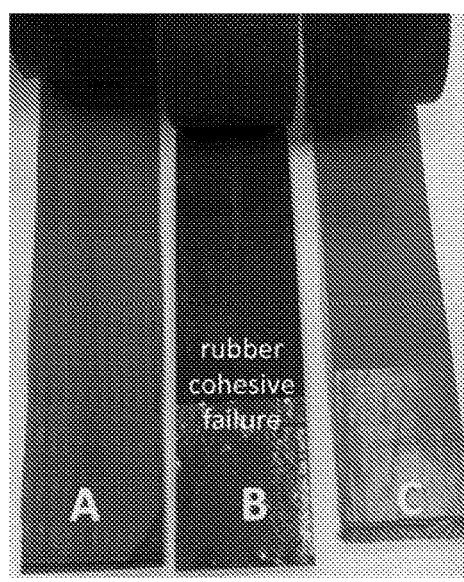

FIG. 28 depicts peel samples of latex treated film having low adhesion (without SP1/CB complex) (A), SP1/CB/latex treated film with great adhesion to NR (B) and untreated film (C). All films were vulcanized with NR at the same conditions.

Figure 29:
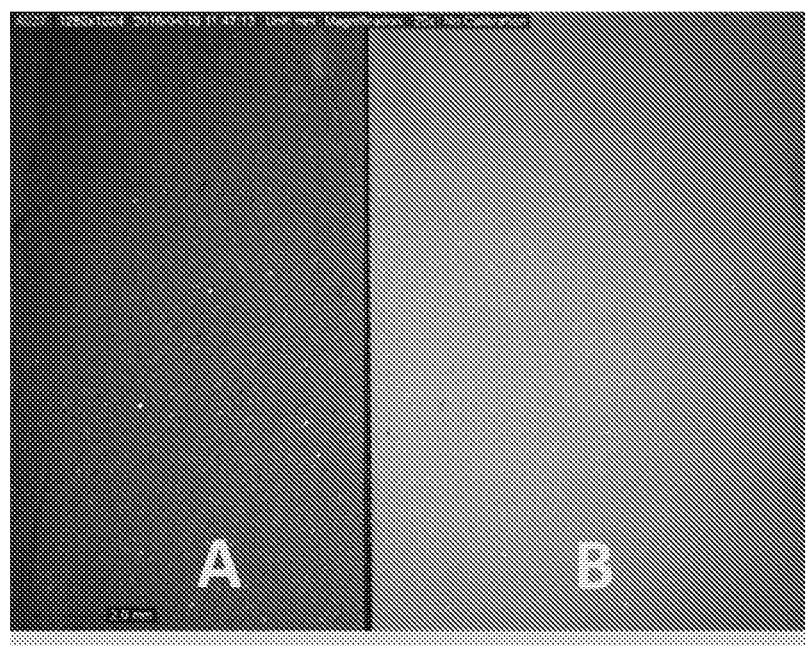

FIG. 29 depicts optical microscopy image of post peel test samples of SP1/CB/latex treated film (A) and untreated film (B) with NR.

DESCRIPTION OF EMBODIMENTS OF THE INVENTION

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention, in some embodiments thereof, relates to sequence variants of Stable Protein 1 (SP1), to composition thereof, to composition thereof comprising latex (SP1/latex), to composition thereof comprising carbon black (SP1/CB), to composition thereof comprising carbon black and latex (SP1/CB/latex), and to composition thereof comprising carbon nanotubes and latex (SP1/CNT/latex), production of composite metal cords, polymers and polymeric and non polymeric materials, such as fibers, yarns, fabrics, films, and polymeric fabrics, based on SP1-polypeptide-carbon nanotube/carbon black-complexes, and uses thereof, for example, for enhancing the mechanical, electrical and thermal properties of metal-reinforced and textile-reinforced mechanical rubber goods (e.g. tires, hoses, belts, boats).

The present invention, in some embodiments thereof, relates to coated polymer elements (e.g. fibers, yarns, films and fabrics) or coated metal elements (e.g. steel cords), incorporating integrated carbon black (CB) or carbon nanotubes (CNT) via SP1 variants (with or without latex), having enhanced thermal, electrical and mechanical properties, which can be used, for example, for incorporation into mechanical rubber goods such as tires, for improved rolling resistance in tires, static discharge, heat dissipation, tire condition monitoring and control of physical parameters of the tire. Additional aspects and applications of the invention are further discussed below.

The present invention, in some embodiments thereof, also relates to polymer elements (e.g., fibers, yarns, fabrics or films) or metal elements (e.g. steel cords), coated with SP1 variants (with or without latex), without CB or CNT, having enhanced mechanical properties, and improved adhesion to rubber compounds that can be used for applications where colorless coating is desired.

SP1 polypeptide is an exceptionally stable polypeptide, forming hetero- and homo-oligomers which are resistant to denaturation by heat and most chemical denaturants, resistant to protease digestion, and capable of stabilizing molecular interactions and forming three dimensional structures (Dgany et al, JBC, 2004; 279:51516-23, and U.S. Pat. No. 7,253,341 to Wang et al)

The present inventors have previously uncovered SP1 proteins fused to other protein or non-protein molecules, for enhancement of binding properties of binding molecules, for stabilization of the fused molecules (such as enzymes) and for enhancement or alteration of immunological properties of the fused molecules (U.S. Pat. No. 7,253,341 to Wang et al.). SP1 fusion proteins, as disclosed in U.S. Pat. No. 7,253,341, comprise recombinant SP1 molecules having additional polypeptide sequences added by genetic engineering techniques, and SP1 molecules having additional non-protein moieties added by chemical means, such as cross linking. The present inventors have further disclosed the therapeutic use of SP1 proteins for strengthening skin, hair, nails, etc.

PCT IL 2006/000795 discloses SP1 and SP1 variants forming molecular complexes with small molecules, peptides, nucleic acid fragments, inorganic nanostructures and other ligands, for molecular complexing of drugs and delivery as well as control release of complexed ligands.

U.S. Pat. No. 8,957,189 discloses that a chimeric polypeptide comprising an SP1 polypeptide and a heterologous inorganic substance binding peptide can form highly specific and controllable complexes with a variety of inorganic substances, molecules and surfaces. Such chimeric SP1 polypeptides, where found useful in for example, enhancing dispersion of poorly soluble materials, for example carbon nanotubes, in solvents and polymers, and modification of inorganic materials, polymers and surfaces by binding of complexed chimeric SP1-inorganic substances. The chimeric SP1 polypeptides can be used to produce composite materials having enhanced physical characteristics such as improved storage modulus, increased tensile strength, ballistic resistance, electrical conductivity, optical activity, heat conductivity, surface interactivity, magnetic properties, electromagnetic radiation absorption spectrum and the like.

SP1 Based Polypeptides

The bi- and multi-functional binding properties of chimeric SP1 polypeptides enable their use for securing uniform coatings to surfaces, such as pigments, flame retardants and the like. Chimeric SP1 polypeptides of the present invention can also bind to various surfaces, including metals, fibers, films and fabrics and can be used to modify the physical properties of metal cords such as steel; fibers, films and fabrics such as aramid (Kevlar™ and Twaron™), silk, polyester, basalt, glassfiber, polyamide, cotton, nylon, rayon, DVA, and carbon fibers.

SP1 based polypeptides can be used as a protein scaffold for the presentation of surface active moieties. A versatile protein scaffold should generally constitute a conformationally stable folding entity that is able to display a multitude of loop structures or amino-acid sequences in a localized surface region. SP1 can be engineered to display various moieties contributing to their binding capability in a cooperative manner. Moreover, peptide exposure can be manipulated under solvent conditions that reduce non-specific binding.

Thus, according to one aspect of the present invention the SP1 based polypeptide comprised in the composition of matter according to this invention is characterized by: i) at least 65% amino acid homology to native SP1 (SEQ ID NO: 4); and ii) stable dimer-forming capability.

According to another aspect of the present invention the composition of matter according to this invention comprises isolated chimeric polypeptides comprising an SP1 polypeptide and a target binding peptide, wherein the SP1 polypeptide is characterized by: i) at least 65% amino acid homology to native SP1 (SEQ ID NO: 4); ii) stable dimer-forming capability; and iii) at least one conserved amino acid sequence in at least one region corresponding to amino acids 9-11, 44-46 and/or 65-73, of SEQ ID NO:4.

As used herein the phrase "SP1 based polypeptide" refers to a protein having at least the following characteristic properties: at least 65% sequence homology to SEQ ID NO:4; and being capable of forming stable dimers. In other embodiments, the phrase refers to a protein having at least the following characteristic properties: at least 65% sequence homology to SEQ ID NO:4; being capable of forming stable dimers, and having at least one conserved amino acid sequence in at least one region corresponding to amino acids 9-11, 44-46 and/or 65-73, of SEQ ID NO:1, as determined using a Best Fit algorithm of GCG, Wisconsin Package Version 9.1, using a plurality of 10.00, a threshold of 4, average weight of 1.00, average match of 2.91 and average mismatch of minus 2.00. In some embodiments, the SP1 polypeptide has conserved consensus sequences: "HAFESTFES" (65-73, SEQ ID NO:1), "VKH" (9-11, SEQ ID NO:1) and "KSF" (44-46, SEQ ID NO:1). According to one embodiment of the invention, "wild-type" or "native" SP1 is the stress related SP1 protein from aspen (SEQ ID NO:4), as disclosed by Wang et al (U.S. patent application Ser. No. 10/233,409, filed Sep. 4, 2002, now U.S. Pat. No. 7,253,341, issued Aug. 7, 2007, which is a Continuation in Part of PCT IL 02/00174, filed Mar. 5, 2002, both of which are incorporated by reference as if fully set forth herein.). The term "SP1 based polypeptide" refers in the context of this invention also to chimeric SP1 based polypeptide, i.e., polypeptides comprising an SP1 based polypeptide and a non-SP1 oligo- or polypeptide. In various embodiments, the SP1 based polypeptide is the crude SP1, i.e., is the heat stable fraction of the crude extract obtained from the bacteria that expressed it. In other embodiments, the SP1 based polypeptide is the pure SP1, obtained by further purification of the heat stable fraction of the crude extract expressed by the bacteria.

In various embodiments, the SP1 based polypeptide comprised in the composition of matter according to this invention is 70%, 75%, 80%, 85%, 90%, 95%, or up to 100% homologous to SEQ ID NO: 4. It will be appreciated that SP1 homologues have been identified in plant species other than aspen, and that these SP1 homologues can be suitable for use with the present invention, when fulfilling the abovementioned criteria.

The SP1 based polypeptide comprised in the composition of matter according to this invention, can be native SP1 (for example, SEQ ID NO: 4), or can be a chimera, i.e., an SP1 polypeptide having a modified amino acid sequence. In some embodiments modified SP1 polypeptides retain the above-mentioned activities of native SP1 polypeptide such as ability of forming oligomer and complexes that are pH-stable, heat-stable and denaturant- and protease-resistant.

As mentioned hereinabove, SP1 variant polypeptides can be modified to impart specific properties to the SP1 variant, thereby rendering the molecular complexing with, and release of other substances more efficient and controllable, and adaptable to specific conditions. Dgany et al (JBC 2004 279:51516-523) have identified a number of structurally significant regions in the SP1 polypeptide.

In some embodiments, the chimeric SP1 polypeptides contemplated in the composition of matter of this invention include, but are not limited to, modifications to side chains, incorporation of unnatural amino acids and/or their derivatives during peptide synthesis and the use of crosslinkers and other methods which impose conformational constraints on the peptides or their analogues.

According to one embodiment of the present invention any type of SP1 based polypeptide, may bind carbon fibers or surfaces. Thus, SP1 wild type or chimeric polypeptides can be used to bind carbon nanoparticles (e.g., carbon nanotubes, carbon black) and/or graphitic surfaces. Thus, according to further aspects of the present invention there is provided a composition comprising wild type SP1 protein and a carbon nanotube, carbon black, or graphitic surfaces. According to further aspects of the present invention there is provided a chimeric polypeptide comprising an SP1 based polypeptide and a carbon nanotube, carbon black, or graphitic surfaces binding peptide, and a carbon nanotube, carbon black, or graphitic surface.

According to one embodiment of the present invention the target binding peptide binds carbon nanoparticles or carbon surfaces. Thus, the chimeric polypeptides can be used to bind carbon nanoparticles (e.g., carbon nanotubes, carbon black) and/or graphitic surfaces. Thus, according to further aspects of the present invention there is provided a chimeric polypeptide comprising an SP1 based polypeptide and a carbon nanotube, carbon black, or graphitic surfaces binding peptide. Carbon nanotube binding peptides suitable for use with the chimeric polypeptide of the invention are well known in the art, for example, the peptides disclosed in U.S. Pat. No. 7,304,128 to Jagoda et al. According to some embodiments, the carbon nanotube, carbon black or graphitic surfaces binding peptide is HWSAWWIRSNQS (SEQ ID NO: 10), HSSYWYAFNNKT (SEQ ID NO: 11), DYFSSPYYEQLF (SEQ ID NO:12) or SNQS (SEQ ID NO:13) and the chimeric SP1 based polypeptide has an amino acid sequence as set forth in SEQ ID NOs:6, 8, 9 and 14-18. In certain embodiments, the carbon nanotube, carbon black or graphitic surfaces binding peptide is located at the N-terminus of the SP1 polypeptide.

In some embodiments, peptides that non-specifically bind to materials can be used in the chimeric SP1 based polypeptides comprised in the composition of matter according to this the invention. These include, but are not limited to repeated tyrosine rich motifs from specific mussel proteins (mfp1), where the tyrosine residues may be converted to L-DOPA (L-3,4-dihydroxyphenylalanine) (Holten-Andersen & Waite J Dent Res 87(8):701-709, 2008), such as AKPSYPPTYK, (SEQ ID NO: 20), AKPTYK (SEQ ID NO: 21), PKISYPPTYK (SEQ ID NO: 22), APPPAXTAXK (SEQ ID NO: 23), ATPKPXTAXK (SEQ ID NO: 24), PYVK (SEQ ID NO: 25), AKPSPYVPTGYK (SEQ ID NO: 26), GQQKQTAYDPGYK (SEQ ID NO: 27).

As used herein, a "chimeric polypeptide" refers to an amino acid sequence having two or more parts which generally are not found together in a single amino acid sequence in nature. Chimeric SP1 based polypeptides are defined herein as polypeptides comprising an SP1 based polypeptide and a non-SP1 oligo- or polypeptide having binding affinity for target molecules such as carbon nanoparticles (e.g., carbon black, carbon nanotubes, etc.) metals and other ions, the SP1 polypeptide and the non-SP1 component connected through a peptide bond.

Surprisingly, it was uncovered that SP1-CBD fusion protein binds fibers, fabrics and fabric substrates, as well as to carbon nanotubes with high affinity. Thus, according to one aspect of the present invention there is provided a composition of matter comprising an SP1-CBD chimeric polypeptide complexed with carbon nanotubes. According to another aspect there is provided a composition of matter comprising an SP1-CBD chimeric polypeptide complexed with carbon black.

The SP1-CBD chimeric polypeptide complexed with carbon nanotubes or carbon black can be used to incorporate carbon nanotubes or carbon black into textiles, yarns, fabrics and the like. Thus, in various embodiments, there is further provided an SP1-CBD chimeric polypeptide-CNT-complexed polymer, fiber, film, fabric or polymeric fabric. In other embodiments, there is further provided an SP1-CBD chimeric polypeptide-CB-complexed polymer, fiber, film, fabric or polymeric fabric.

The chimeric SP1 polypeptides of the present invention can also be used to bind carbon nanotube, carbon black and/or graphite surfaces.

Preferred SP1 based polypeptides to be used in composition of matter according to this invention include SP1 protein extracts represented by: SEQ ID NO: 4 (WT), SEQ ID NO: 6 (L1-SP1), SEQ ID NO: 14 (L2-SP1), SEQ ID NO: 8 (L3-SP1), SEQ ID NO: 15 (L6-SP1), SEQ ID NO: 3 (mtbSP-SP1), SEQ ID NO: 9 (L4-SP1), SEQ ID NO: 86 (SP1-CBD) or any combination thereof. In various embodiments, the protein extracts are pure, i.e., undergo a further step of purification after obtaining the heat stable fraction of the crude extract expressed by the bacteria. In other embodiments, the protein extracts are crude extracts, i.e., the heat stable fraction of the crude extract, used as obtained from the bacteria that expressed them.

In some embodiments, the SP1 based polypeptide interact with the target substance, or with the chemical environment via a reversible interaction such as Van Der Waals (VDW), hydrogen bonds, or electrostatic interactions, or via non-reversible covalent bonds, all are referred to herein as molecular associations. As used herein the phrase "molecular association" refers to a chemical association or a physical association or both, which takes place on a molecular level. For example, a bond or association can be a covalent bond, a VDW interaction, hydrogen bonds, electrostatic interactions, hydrophobic interactions, etc.

Types of reversible molecular associations or bonds suitable for use in the present invention are associations selected from the group consisting of electrostatic bonding, hydrogen bonding, van der Waals forces, ionic interaction or donor/acceptor bonding. The reversible association can be mediated by one or more associations between the substance (i.e., CNP, e.g., CB or CNT) and the SP1 based polypeptide. For example, the reversible association can include a combination of hydrogen bonding and ionic bonding between the complexing substance and the SP1 polypeptide. Additionally, or alternatively, the reversible association can be in combination with, for example, covalent or other noncovalent interactions between components, such as between a substance and an SP1 based polypeptide or chimeric polypeptide. In various embodiments, the SP1 based polypeptide or the chimeric SP1 based polypeptide interact with the CNP via hydrophobic interactions. In other embodiments, via hydrogen bonds. In other embodiments, via VDW interactions; or In other embodiments, via electrostatic interactions. In other embodiments, the SP1 based polypeptide or the chimeric SP1 based polypeptide interact with the CNP via combination of hydrophobic interactions, hydrogen bonds, VDW interactions, and electrostatic interactions. Such interactions between the SP1 based polypeptide or the chimeric SP1 polypeptide and the CNP are also regarded herein as "complexation", whereas the bound SP1-CNP material is regarded herein as an SP1/CNP "complex".

The SP1 based polypeptides, chimeric SP1 polypeptides and compositions of matter comprising the same have been shown to enhance dispersal of bound substances in a solvent. For example, highly insoluble carbon nanotubes were found to disperse with up to 1000-fold greater concentration in both aqueous and organic environments when complexed with a chimeric, carbon nanotube-binding L1 SP1 (see U.S. Pat. No. 8,957,189 herein incorporated by reference in its entirely).

As used herein, the term "dispersion" refers to the ability of a solute or a colloid to be evenly distributed and/or dissolved in a solvent, in order to form a solution or suspension comprising the solvent and solute. It will be appreciated that all solutes are, in theory, soluble in all solvents. However, poorly or negligibly soluble (immiscible) solutes or colloids do not form solutions or suspensions of any significant concentration with given solvents.

Thus, as used herein, "enhancing the dispersion" refers to increasing the concentration of said substance, as a solute or colloid, in a solution or suspension with a solvent. In a preferred embodiment, the substance is a hydrophobic substance, typically insoluble or poorly soluble in water, and the solvent is an aqueous solvent.

Stability under centrifugation under standard conditions is used as a measure for dispersion ability. The stability of SP1 based polypeptides and chimeric SP1 based polypeptides bound to CNT (SP1/CNT complexes) to boiling, protease digestion and pH extremes is shown in U.S. Pat. No. 8,957,189. Addition of latex to SP1-CNT complex dispersion in aqueous solutions, does not affect the dispersion, and enhances the adhesion of the composition of SP1-CNT and latex, to polymeric materials (i.e., fibers, films, and fabrics), as well as improve their mechanical properties and the mechanical properties of the composite materials comprising them, as described in details below.

Following is a sequence listing associated with SP1.

| | |
|---|---|
| SEQ ID NO. 1 | CTGCTCGATCTCATTCCAAGCTGTA AGAGTTTCAATTGGGGCACG |
| SEQ ID NO. 2 | GCAAGTCTGGTTTGCAAGA GTACTGCGATTCTGCTGCTCTTGCTG |
| SEQ ID NO. 3 | MRKLPDAATRTPKLVKHTLLTRFKDEITREQIDNYINDYTNLLDLIPSMKSFNWG<br>TDLGMESAELNRGYTHAFESTFESKSGLQEYLDSAALAAFAEGFLPTLSQRLVIDYFLY |
| SEQ ID NO. 4 | MATRTPKLVKHTLLTRFKDEITREQIDNYINDYTNLLDIPSMKSFNWGTDLGMESAE<br>LNRGYTHAFESTFESKSGLQEYLDSAALAAFAEGFLPTLSQRLVIDYFLY |
| SEQ ID NO. 5 | RKLPDAA |
| SEQ ID NO. 6 | MHWSAWWIRSNQSATRTPKLVKHTLLTRFKDEITREQIDNYINDYTNLLDLIPSMKSF<br>NWGTDLGMESAELNRGYTHAFESTFESKSGLQEYLDSAALAAFAEGFLPTLSQRLVIDYFLY |
| SEQ ID NO. 7 | CCACAGAGAG AAAGGGAAGA CATGAAGCTT GTGAAGCACA CATTGTTGAC<br>TCGGTTCAAG GATGAGATCA CACGAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID NO. 8 | MDYFSSPYYEQLFATRTPKLVKHTLLTRFKDEITREQIDNYINDYTNLLDLIPSMKSFNWG<br>TDLGMESAELNRGYTHAFESTFESKSGLQEYLDSAALAAFAEGFLPTLSQRLVIDYFL |
| SEQ ID NO. 9 | MHWSAWWIRSNQSATRTPKLVKHTLLTRFKDEITKEQIDNYINDYTNLLDLIPSMKSFNW<br>GTDLGMESAELNRGYTHAFESTFESKSGLQEYLDSAALAAFAEGFLPTLSQRLVIDYFLY |

-continued

| | |
|---|---|
| SEQ ID NO. 10 | HWSAWWIRSNQS |
| SEQ ID NO. 11 | HSSYWYAFNNKT |
| SEQ ID NO. 12 | DYFSSPYYEQLF |
| SEQ ID NO. 13 | SNQS |
| SEQ ID NO. 14 | MHSSYWYAFNNKTATRTPKLVKHTLLTRFKDEITREQIDNYINDYTNLLDLIPSMKSFNW GTDLGMESAELNRGYTHAFESTFESKSGLQEYLDSAALAAFAEGFLPTLSQRLVIDYFLY |
| SEQ ID NO. 15 | MSNQSATRTPKLVKHTLLTRFKDEITREQIDNYINDYTNLLDLIPSMKSFNWGTDLG MESAELNRGYTHAFESTFESKSGLQEYLDSAALAAFAEGFLPTLSQRLVIDYFLY |
| SEQ ID NO. 16 | MHWSAWWIRSNQSATRTPKLVKHTLLTRFKDEITREQIDNYINDYTNLLDLIPSMKSF NWGTDLGMESAELNRGYTHAFESTFESKSGLQEYLDSAALAAFAEGFLPTLSQRLVIDYFLY |
| SEQ ID NO. 17 | MHWSAWWIRSNQSATRTPKLVKHTLLTRFKDEICREQIDNYINDYTNLLDLIPSMKSFN WGTDLGMESAELNRGYTHAFESTFESKSGLQEYLDSAALAAFAEGFLPTLSQRLVIDYFLY |
| SEQ ID NO. 18 | MHWSAWWIRSNQSATRTPKLVKHTLLTRFKDEITKEQIDNYINDYTNLLDLIPSM KSFNWGTDLGMESAELNRGYTHAFESTFESKSGLQEYLDSAALAAFAEGF LPTLSQRLVIDYFLY |
| SEQ ID NO. 19 | RALPDA |
| SEQ ID NO. 20 | AKPSYPPTYK |
| SEQ ID NO. 21 | AKPTYK |
| SEQ ID NO. 22 | PKISYPPTYK |
| SEQ ID NO. 23 | APPPAXTAXK |
| SEQ ID NO. 24 | ATPKPXTAXK |
| SEQ ID NO. 25 | PYVK |
| SEQ ID NO. 26 | AKPSPYVPTGYK |
| SEQ ID NO. 27 | GQQKQTAYDPGYK |
| SEQ ID NO. 28 | ATCCACAGAG AGAAAGGGAA GACATGGCAA CCAGAACTCC AAAGCTTGTG AAGCACACAT TGTTGACTCG GTTCAAGGAT GAGATCACAC GAGAACAGAT CGACAACTAC ATTAATGACT ATACCAATCT GCTCGATCTC ATTCCAAGCA TGAAGAGTTT CAATTGGGGC ACGGATCTGG GCATGGAGTC TGCGGAGCTA AACCGAGGAT ACACTCATGC CTTTGAATCT ACATTTGAGA GCAAGTCTGG TTTGCAAGAG TACCTCGATT CTGCTGCTCT TGCTGCATTT GCAGAAGGGT TTTTGCCTAC TTTGTCACAG CGTCTTGTGA TAGACTACTT TCTCTACTAA ACGCTCAGGA GTAACGACTT CGGCCGGGCT ATTTCATGGT AATAAAGTAA TGTAATGTTC AATAAATGCT GGTTTTGAAC CACTGAATGT TCGTGTCTTG ATTTCTTGTC TGTGCTAAGT GAAGGGAGTG CTGCTATTCC TTTAAAAATA AAGCCCTTGG GGTTGAGTTG TAGTTTTTCA ATCTTTTTCC CCGATTTATT TCGGTCTTGG TGTTGTT |
| SEQ ID NO. 29* | VVKHLVIVQFKEDVTPERLDGLIRGYAGLVDKVPSMKAFHWGTDVSIE Xaa Xaa NMH QGFTHVFESTFESTEGVKEYVYHEFATDFLGSTEKVLIIDF |
| SEQ ID NO. 30* | VVKHLVIVQFKEDVTPERLDGLIRGYAGLVDKVPSMKAFH WGTDVSIEN Xaa Xaa MHQGFTHVFESTFESTEGVKEYVYHPAHVEFATDFLGSTEKVLIIDF |
| SEQ ID NO. 31* | VVKHLVIVQFKEDVTPERLEGLIRGYAGLVDKVPSMKAFHWGTDVSIEN Xaa Xaa MHQGFTHVFESTFESTEGVKEYVYHPAHVEFATDFLGSTEKVLIIDF |
| SEQ ID NO. 32* | VVKHILLASFKEEVTQERLDELIRGYAALVGVVPSMKAFHWGTDVSIEN Xaa Xaa MHQGFTHVFESTFESTEGIKEYIEHPAHVEFAK |

SEQ ID
NO. 33*      VVKHILLARFKEDVAPERLDQLIRGYAGLVDLVPSMKAFHWGTDVSIEN Xaa Xaa
             MHQGFTHVFESTFESTEGVKEYIEHPAHVEFANEFLPVLEKTLIIDY

SEQ ID       VVKHLVLARFKEEATPEALD Xaa LIRRYAGLVDAVPSMKAFHWGTDVTV Xaa Xaa
NO. 34*      LDTHEGFTHVFESTFESAEGVKEYIAHPSHVEFVDEFLALAEKMLIVDY

SEQ ID       MEEAKGPVKHVLLASFKDGVSPEKIEELIKGYANLVNLIEPMKAFHWGKDVSIEN
NO. 35       LHQGYTHIFESTFESKEAVAEYIAHPAHVEFATIFLGSLDKVLVIDYKPTSVSL

SEQ ID       LHQGYTHILESTFESKEAVAEYIAHPAHVEFATIFLGSLDKVLVIDY
NO. 36

SEQ ID       VVKHVLLAKFKDDVTPERIEELIKDYANLVNLIPPMKSFHWGKDVSAEN Xaa Xaa
NO. 37*      LHQGFTHVFESTFESPEGVAEYVAHPAHVEYANLFLSCLEKVIVIDY

SEQ ID       VVKHILLAKFKDGIPPEQIDQLIKQYANLVNLVEPMKAFQWGKDVSIEN Xaa Xaa
NO. 38*      LHQGFTHVFESTFDSLEGVAEYIAHPVHVEYANTLLPQLEKFLIVDY

SEQ ID       HVLLPKLKDYFTPERIELMVDYANLVNLMPRMKSFHSGRDVSAEYLHL Xaa Xaa
NO. 39*      GCTHVYESTFDSPGVAEYVAHAAHVEYANQDLSCLEKVIAIDY

SEQ ID       MATRTPKLVKHTLATRFKDEITREQIDNYINDYTNLLDLIPSMKSFNWGTDLGMESA
NO. 40       ELNRGYTHAFESTFESKSGLQEYLDSAALAAFAEGFLPTLSQRLVIDYFLY

SEQ ID       KHLCLVRFKEGVVVEDI Xaa Xaa Xaa IEELTKLAAE Xaa LDTVKFFGWGKDVLN
NO. 41*      QEALTQGFTHVFSMSFASAED LAAYMGHEKHSAFAATFMAVLDKVVVLDF

SEQ ID       KHLCLVRFKEGVVVEDI Xaa Xaa Xaa IEELTKLAAELD TVKFFGWGKDVLNQEA Xaa
NO. 42*      LTQGFTHVFSMSFASAEDLAACMGHEKHSAFAATFMAVLDKVVVLDF

SEQ ID       KHLCMAKFKEGVVVEDI Xaa Xaa Xaa IQELTKLAAELDTVKYFGWGKDVLNQEA Xaa
NO. 43*      LTQGFTHVFVMTFASAEDLAACMGHEKHTAFAATFMAALDKVVVMDF

SEQ ID       VKHLCLVKFKEEVL Xaa Xaa Xaa VDDILQGMTKLVS EMDMVKSFEWGKDV Xaa
NO. 44*      LNQEMLTQGFTHVFSLTFAS SEDLTTYMSHERHQEFAGTFMAAIDKVVVVDF

SEQ ID       RRPTMGEVKHLCLVKFKEGVVVEDVLKGMTDLVAGMDMV Xaa Xaa Xaa KSFEWGQDV
NO. 45*      Xaa LNQEMLTQGFTHVFSLTFAFADDLATYMGHDRHAAFAATFMAALDKVVVIDF

SEQ ID       ESTFESTEGIKEYIEHPAHVEFAK Xaa LNQEMLTQGFTHVFSLTFATAADLAAYMAHDSH
NO. 46*      TAFAATFMAAIDKVLVVDF

SEQ ID       KHLVLVKFKEDVVVEDILKELEKLVQEMDIV Xaa Xaa Xaa KSFVWGKDV Xaa Xaa
NO. 47*      ESHEMLRQGFTHAI IMTFNSKEDYQTFANHPNHVGFSATFATVIDKAVLLDF

SEQ ID       LLVKFKQDVVEEDVLKQIEQLVNEIDLI Xaa Xaa Xaa KSFVWGKDT Xaa Xaa
NO. 48*      ESNEMVTQGYTHAMIMTFNSKEDYEACVVKEV Xaa EFSAIFVTVVEKILVLNF

SEQ ID       HYVIVKFKDGVA Xaa Xaa Xaa VDDLIQGLEKMVFGIDHVKSFEWGKDI Xaa Xaa E
NO. 49*      SHDMLRQGFTHAFLMTFNGKEEFNAFQTHPNHLEFSGVFSPAIEKIVVLDF

SEQ ID       HYVIVKFKDGVA Xaa Xaa Xaa VDELIQGL EKMVSGIDHVKSFEWGKDI Xaa Xaa
NO. 50*      ESHDMLRQGFTHVFLMAFNGKEEFNAFQTHPNHLEFTGVFSPAIEKIVVLDF

SEQ ID       KHFVIVKFKEGVA Xaa Xaa Xaa VDELTKGMEKLVTEIGAVKSFEWGQDI Xaa Xaa
NO. 51*      ESLDVLRQGFTHAFLMTFNKKEDFV AFQSHPNHVEFSTKFSAAIENIVLLDF

SEQ ID       LVSEIHAVKSFEWGQDI Xaa Xaa ESLDVLRQGFTHAFLMTFNKKRRL
NO. 52*

SEQ ID       MATSGFKHLVVVKFKEDTKVDEILKGLENLVSQIDTVKSFEWGEDKESHDMLRQGFT
NO. 53       HAFSMTFENKDGYVAFTSHPLHVEFSAAFTAVIDKIVLLDFPVAAVKSSVVATP

SEQ ID       KTVEHIVLFKVKEETEPSKVSDMVNGLGSLVSLDPVLH Xaa LSVGPLLRNRSSALT Xaa
NO. 54*      Xaa FTHMLHSRYKSKEDLEAYSAHPSHVSVVKGYVLPIIDDIMSVDW

SEQ ID       AAAACATATG CGCAAACTTC CGGATGCGGC AACCAGAACT CCAAAGCTTG
NO. 55       TGAAGCACAC ATTGTTGACT CGGTTCAAGG ATGAGATCAC ACGAGAACAG
             ATCGACAACT ACATTAATGA CTATACCAAT CTGCTCGATC TCATTCCAAG
             CATGAAGAGT TTCAATTGGG GCACGGATCT GGGCATGGAG TCTGCGGAGC
             TAAACCGAGG ATACACTCAT GCCTTTGAAT CTACATTTGA GAGCAAGTCT
             GGTTTTGCAAG AGTACCTCGA TTCTGCTGCT CTTGCTGCAT TTGCAGAAGG
             GTTTTTGCCT ACTTTGTCAC AGCGTCTTGT GATAGACTAC TTTCTCTACT AA

SEQ ID       AAGGAGATAT ACAAAAACAT ATGCACTGGT CAGCATGGTG GATACGATCA
NO. 56       AATCAATCAG CAACCAGAAC TCCAAAGCTT GTGAAGCACA CATTGTTGAC
             TCGGTTCAAG GATGAGATCA CACGAGAACA GATCGACAAC TACATTAATG
             ACTATACCAA TCTGCTCGAT CTCATTCCAA GCATGAAGAG TTTCAATTGG

| | |
|---|---|
| | GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID<br>NO. 57 | GAAGGAGATA TACAAAACA TATGCACTCA TCATACTGGT ACGCATTCAA<br>CAACAAAACA GCAACCAGAA CTCCAAAGCT TGTGAAGCAC ACATTGTTGA<br>CTCGGTTCAA GGATGAGATC ACACGAGAAC AGATCGACAA CTACATTAAT<br>GACTATACCA ATCTGCTCGA TCTCATTCCA AGCATGAAGA GTTTCAATTG<br>GGGCACGGAT CTGGGCATGG AGTCTGCGGA GCTAAACCGA GGATACACTC<br>ATGCCTTTGA ATCTACATTT GAGAGCAAGT CTGGTTTGCA AGAGTACCTC<br>GATTCTGCTG CTCTTGCTGC ATTTGCAGAA GGGTTTTTGC CTACTTTGTC<br>ACAGCGTCTT GTGATAGACT ACTTTCTCTA CTAA |
| SEQ ID<br>NO. 58 | ATACAAAAAC ATATGGATTA TTTTTCATCA CCATATTATG AACAATTATT<br>TGCAACCAGA ACTCCAAAGC TTGTGAAGCA CACATTGTTG ACTCGGTTCA<br>AGGATGAGAT CACACGAGAA CAGATCGACA ACTACATTAA TGACTATACC<br>AATCTGCTCG ATCTCATTCC AAGCATGAAGAGTTTCAATT GGGGCACGGA<br>TCTGGGCATG GAGTCTGCGG AGCTAAACCG AGGATACACTCATGCCTTTG<br>AATCTACATT TGAGAGCAAG TCTGGTTTGC AAGAGTACCT CGATTCTGCT<br>TACTTTCTCT ACTAA |
| SEQ ID<br>NO. 59 | AGAAGGAGAT ATACAAAAC ATATGTCAAA TCAATCAGCA ACCAGAACTC<br>CAAAGCTTGT GAAGCACACA TTGTTGACTC GGTTCAAGGA TGAGATCACA<br>CGAGAACAGA TCGACAACTA CATTAATGAC TATACCAATC TGCTCGATCT<br>CATTCCAAGC ATGAAGAGTT TCAATTGGGG CACGGATCTG GGCATGGAGT<br>CTGCGGAGCT AAACCGAGGA TACACTCATG CCTTTGAATC<br>TACATTTGAG AGCAAGTCTG GTTTGCAAGA GTACCTCGAT TCTGCTGCTC<br>TTGCTGCATT TGCAGAAGGG TTTTTGCCTA CTTTGTCACA GCGTCTTGTG<br>ATAGACTACT TTCTCTACTA A |
| SEQ ID<br>NO. 60 | AAGGAGATAT ACAAAAACAT ATGCACTGGT CAGCATGGTG GATACGATCA<br>AATCAATCAG CAACCAGAAC TCCAAAGCTT GTGAAGCACA CATTGTTGAC<br>TCGGTTCAAG GATGAGATCA CAAAGAACA GATCGACAAC TACATTAATG<br>ACTATACCAA TCTGCTCGAT CTCATTCCAA GCATGAAGAG TTTCAATTGG<br>GGCAVGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID<br>NO. 61 | AAGGAGATAT ACAAAAACAT ATGCACTGGT CAGCATGGTG GATACGATCA<br>AATCAATCAG CAACCAGAAC TCCAAAGCTT GTGAAGCACA CATTGTTGAC<br>TCGGTTCAAG GATGAGATCT GCCGAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID<br>NO. 62 | AAGGAGATAT ACAAAAACAT ATGCACTGGT CAGCATGGTG GATTCGTTCA<br>AATCAATCAG CAACCAGAAC TCCAAAGCTT GTGAAGCACA CATTGTTGAC<br>TCGGTTCAAG GATGAGATCA CACGAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID<br>NO. 63 | AAGGAGATAT ACAAAAACAT ATGCACTGGT CAGCATGGTG GATTCGTTCA<br>AATCAATCAG CAACCAGAAC TCCAAAGCTT GTGAAGCACA CATTGTTGAC<br>TCGGTTCAAG GATGAGATCA CAAAGAACA GATCGACAAC TACATTAATG<br>ACTATACCAA TCTGCTCGAT CTCATTCCAA GCATGAAGAG TTTCAATTGG<br>GGCACGGATC TGGGCATGGA GTCTGCGGAG CTAAACCGAG GATACACTCA<br>TGCCTTTGAA TCTACATTTG AGAGCAAGTC TGGTTTGCAA GAGTACCTCG<br>ATTCTGCTGC TCTTGCTGCA TTTGCAGAAG GGTTTTTGCC TACTTTGTCA<br>CAGCGTCTTG TGATAGACTA CTTTCTCTAC TAA |
| SEQ ID<br>NO. 64 | MKLVKHTLLTRFKDEITREQIDNYINDYTNLLDLIPSMKSFNWGTDLGMESAELNR<br>GYTHAFESTFESKSGLQEYLDSAALAAFAEGFLPTLSQRLVIDYFLY |
| SEQ ID<br>NO. 65 | CTGCTCGATCTCATTCCAAGCTGTG AGAGTTTCAATTGGGGCACG |
| SEQ ID<br>NO. 66 | GCAAGTCTGGTTTGCAAGA GTACTGCGATTCTGCTGCTCTTGCTG |
| SEQ ID<br>NO. 67 | AAAACATATGCGCAAACTTCCGGATGCGGCAACCAGAACTCCAAAGCTTG |

| | |
|---|---|
| SEQ ID NO. 68 | AAAAGAGCTCTTAGTAAAGAAAGTAATCAATAAC |
| SEQ ID NO. 69 | ATGAAGCTTG TGAAGCACAC ATTGTTGACT CGGTTCAAGG ATGAGATCAC ACGAGAACAG ATCGACAACT ACATTAATGA CTATACCAAT CTGCTCGATC TCATTCCAAG CTGTAAGAGT TTCAATTGGG GCACGGATCT GGGCATGGAG TCTGCGGAGC TAAACCGAGG ATACACTCAT GCCTTTGAAT CTACATTTGA GAGCAAGTCT GGTTTGCAAG AGTACCTCGA TTCTGCTGCT CTTGCTGCAT TTGCAGAAGG GTTTTTGCCT ACTTTGTCAC AGCGTCTTGT GATAGACTAC TTTCTCTACT AA |
| SEQ ID NO. 70 | AAGGAGATATACAAAAACATATGCACTGGTCAGCATGGTGGATACGATCA AATCAATCAGCAACCAGAACTCCAAAG |
| SEQ ID NO. 71 | CTTTGGAGTTCTGGTTGCTGATTGATTTGATCGTATCCACCATGCTGA CCAGTGCATATGTTTTTGTATATCTCCTT |
| SEQ ID NO. 72 | AGAAGGAGATATACAAAAACATATGCACTCATCATACTGGTACGCATTCA ACAACAAAACAGCAACCAGAACTCCAAAGC |
| SEQ ID NO. 73 | GCTTTGGAGTTCTGGTTGCTGTTTTGTTGTTGAATGCGTACCAGTAGATGA GTGCATATGTTTTTGTATATCTCCTTCT |
| SEQ ID NO. 74 | ATACAAAAACATATGGATTATTTTTCATCACCATATTATGAACAATTATTTG CAACCAGAACTCC |
| SEQ ID NO. 75 | GGAGTTCTGGTTGCAAATAATTGTTCATAATATGGTGATGAAAAATAATCC ATATGTTTTTGTAT |
| SEQ ID NO. 76 | AGAAGGAGATATACAAAAACATATGTCAAATCAATCAGCAACCAGAACTC CAAAGC |
| SEQ ID NO. 77 | GCTTTGGAGTTCTGGTTGCTGATTGATTTGACATATGTTTTTGTATATCTCCTT CT |
| SEQ ID NO. 78 | ACTGGTCAGCATGGTGGATTCGATCAAATCAATCAG |
| SEQ ID NO. 79 | CTGATTGATTTGATCGAATCCACCATGCTGACCAGT |
| SEQ ID NO. 80 | GTCAGCATGGTGGATTCGTTCAAATCAATCAGCAACC |
| SEQ ID NO. 81 | GGTTGCTGATTGATTTGAACGAATCCACCATGCTGAC |
| SEQ ID NO. 82 | TGACTCGGTTCAAGGATGAGATCACAAAAGAACAGATCGACA |
| SEQ ID NO. 83 | TGTCGATCTGTTCTTTTGTGATCTCATCCTTGAACCGAGTCA |
| SEQ ID NO. 84 | ACTCGGTTCAAGGATGAGATCTGCCGAGAACAGATCGACAACTAC |
| SEQ ID NO. 85 | GTAGTTGTCGATCTGTTCTCGGCAGATCTCATCCTTGAACCGAGT |
| SEQ ID NO. 86 | MAATSSMSVEFYNSNKSAQTNSITPIIKITNTSDSDLNLNDVKVRYYYTSDGTQ GQTFWCDHAGALLGNSYVDNTSKVTANFVKETASPTSTYDTYV EFGFASGRATLKKGQF ITIQGRITKSDWSNYTQTNDYSFDASSSTPV VNPKVTGYIGGAKVLGTAPAVPSGSVTSTS KTTTTASKTSTSTSSTSEFMATSTPKLVKHTLLTRFKDEITREQ IDNYINDYTNLLDLI PSMKSFNWGTDLGMESAELNRGYTHAFESTFESKSGLQEYLDSAALA AFAEGFLPTLSQRLVIDYFLY |
| SEQ ID NO. 87 | MAATSSMSVEFYNSNKSAQTNSITPIIKITNTSDSDLNLNDVKVRYYYTSDGTQGQTFWC DHAGALLGNSYVDNTSKVTANFVKETASPTSTYDTYVEFGFASGRATLKKGQFITIQGRI TKSDWSNYTQTNDYSFDASSSTPVVNPKVTGYIGGAKVLGTAP |
| SEQ ID NO. 88 | MATSTPKLVKHTLLTRFKDEITREQIDNYINDYTNLLDLIPSMKSFNWGTDLGMESAELN RGYTHAFESTFESKSGLQEYLDSAALAAFAEGFLPTLSQRLVIDYFLY |
| SEQ ID NO. 89 | AVPSGSVTSTSKTTTTASKTSTSTSSTSEF |

*-Xaa can be any naturally occurring amino acid.

In some embodiments, the SP1 polynucleotide sequence is 70%, 75%, 80%, 85%, 90%, 95%, or up to 100% homologous to SEQ ID NO: 28. It will be appreciated that polynucleotides encoding SP1 homologues SEQ ID NOs: 29-54 can be suitable for producing the SP1 polypeptide of the present invention, when fulfilling the abovementioned criteria.

In some embodiments, this invention is directed to compositions comprising SP1 based polypeptide (referred herein as "SP1 composition"). In some embodiments, this invention describes compositions consisting essentially of SP1 based polypeptide. Such compositions were found to dramatically improve the adhesion of various surfaces, including metal wires, cords, and polymeric and non polymeric fibers, yarns, films or fabrics coated therewith to rubber compounds, compared to metal wires, cords, and polymeric and non polymeric fibers, yarns, films or fabrics comprising carbon nanoparticles without SP1. Metal wires, cords, and polymeric and non polymeric fibers, yarns, films or fabrics, coated with SP1 composition according to this invention have improved adhesion to rubber compounds, forming composite rubber compounds which have improved mechanical, electrical and thermal properties.

As used herein, the term "surface" refers to, in some embodiments, to the outside part or uppermost layer of any solid object. Examples for surfaces include but are not limited to: metal wires, metal cords; polymeric and non polymeric fibers, yarns, films or fabrics; wood; nano, micro and macro particles of any form or matter. In one embodiment, the surface is a metal wire or cord. In another embodiment, the surface is polymeric fiber, yarn, film or fabric. In another embodiment, the surface is non-polymeric fiber, yarn, film or fabric. In another embodiment, the surface is wood. In another embodiment, the surface is a nanoparticle.

As used herein, strands or "fibers" grouped together through entanglement or twisting form "yarn". Yarn wound together forms thread (e.g. cord) and thread or yarn woven together form a woven "fabric". According to other embodiments, the fibers coated with the SP1/CNP composition according to this invention (i.e., SP1/CB, SP1/CB/latex and SP1/CNT/latex), afforded due to mediation by SP1 variants, can be used to produce non-woven fabrics and sheets. In various embodiments, the term "fiber" refers to "chopped fiber". Examples of "chopped fibers" include carbon chopped fibers, which are fibers cut into short lengths of graphitic carbon with numerous applications as the stiffest and strongest known fibers and because of their unique electrical properties.

As used herein, "films" refer to thin continuous polymeric material. Thicker plastic material is often called a "sheet". These thin plastic membranes are used to separate areas or volumes, to hold items, to act as barriers, or as printable surfaces. Plastic films are used in a wide variety of applications. These include: packaging, plastic bags, labels, building construction, landscaping, electrical fabrication, photographic film, film stock for movies, video tape, etc. Examples for plastic films include but are not limited to: Polyethylene film (Low-density polyethylene, Medium-density polyethylene, High-density polyethylene, and Linear low-density polyethylene), Polypropylene film (a cast film, biaxially oriented film (BOPP), or a uniaxially oriented film), Polyester film (BoPET is a biaxially oriented polyester film), Nylon film, DVA film, Polyvinyl chloride film (with or without a plasticizer), and a variety of bioplastics and biodegradable plastic films.

In some embodiments, "metal cord" refers to a fine metal wire strand or rope, which is made of metal. In some embodiment, metal refers to steel metal.

In some embodiments, "steel cord" refers to a fine steel wire strand or rope for special purposes, which are made of superior high-carbon steel. Normally, its surface is plated with brass. It is mainly applied in car tires, light truck tires, cargo truck tires, heavy equipment tires and plane tires and other rubber framework materials.

In some embodiments, "DVA film" refers to Dynamically Vulcanized Alloy (DVA) resin. DVA is comprised of an innovative blend of thermoplastic elastomers for use in tire and other industrial rubber applications, as well as in other manufactured products. In various embodiments, the thermoplastic elastomer composition comprises a low-permeability thermoplastic resin, such as polyamide or a blend of polyamides, in which there is dispersed a low-permeability rubber, such as butyl rubber, halobutyl rubbers, or brominated isobutylene para-methylstyrene copolymers. The rubber is cured under conditions of dynamic vulcanization (curing the rubber during melt mixing as opposed to static curing that typically occurs in a rubber mold) and is intimately and uniformly dispersed as a particulate phase within a continuous phase of the thermoplastic resin. Because the rubber is cured under shear mixing conditions, these compositions are commonly known as dynamically vulcanized alloys ("DVAs"). Shear mixing of the resin and rubber allows the composition to possess near thermoelastic properties. This thermoelastic nature is desired for the flexibility, strength, and elongation desired for tire innerliners. In various embodiments, DVA are useful as tire innerliners, where the novel material characteristics are targeted to achieve excellent permeability, durability, and light-weighting. Optimal combination of these performance attributes are expected to deliver sustainable benefits such as fuel economy and lower tire maintenance costs. In one embodiment, DVA is a type of nylon.

Optionally, the SP1 composition according to this invention further comprise latex, which in various embodiments, improves the surface properties; In other embodiments, improves the adhesion of the SP1 coated surfaces to rubber compounds; and in other embodiments, improves the mechanical and electrical properties of the rubber compound, which comprises them.

According to some embodiments of the present invention, the SP1 based polypeptides can form composition, which can further bind to various surfaces, including metal cords such as steel cords; and polymer fibers such as carbon fibers, polyester, aramid (e.g. Kevlar™), nylon, rayon, DVA, cotton, wool and the like, and can be used to modify the properties of such surfaces. For example, the SP1 composition can bind to metal cords and to polymer fibers to facilitate their adhesion to rubber compounds and to provide added strength.

In various embodiments, this invention is directed to metal cords or metal wires, coated with, or complexed to a composition of matter comprising SP1 based polypeptide and optionally comprising latex. In other embodiments, the cord or wire is made of steel. In other embodiments, the cord/wire is further coated with at least one of: PEI, latex, silane and rubber-to-substrate adhesive. In other embodiments, the SP1 composition coating layer is on top of a PEI coating layer (PEI primer). In other embodiments, the metal comprises aluminum, copper, iron, palladium, platinum; each possibility represents a separate embodiment according to this invention. In other embodiments, the metal comprises aluminum alloy, copper alloy, iron alloy, palladium alloy, platinum alloy; each possibility represents a separate embodiment according to this invention. In other embodiments, the metal comprises any combination of aluminum, copper, iron, palladium and platinum.

In various embodiments, this invention is directed to polymeric or non-polymeric fibers, yarns, fabrics, films coated with, or complexed to a composition of matter comprising SP1 based polypeptide and optionally comprising latex. In other embodiments, the polymeric or non-polymeric fibers, yarns, fabrics, films are further coated with at least one of: PEI, latex, silane and rubber-to-substrate adhesive. In other embodiments, the SP1 composition coating layer is on top of a PEI coating layer (PEI primer). In other embodiments, the fiber, yarn, film, or fabric comprises at least one of: cotton, wool, silk, nylon, polyester, polypropylene, glass fiber, elastane, rayon, DVA and aramid. In other embodiments, the fiber, yarn, film, or fabric is polyester. In other embodiments, the fiber, yarn, film, or fabric is Aramid. In other embodiments, the fiber, yarn, film, or fabric is rayon. In other embodiments, the fiber, yarn, film, or fabric is nylon. In other embodiments, the nylon is a nylon fabric. In other embodiments the nylon is a nylon film. In other embodiments the nylon film is a DVA film. In other embodiments the film is a DVA film.

In some embodiments, this invention is directed to a metal wire or cord or polymeric or non-polymeric fiber, yarn, film, or fabric complexed with a composition of matter comprising SP1 based polypeptide according to this invention and optionally comprising latex (i.e., SP1 or SP1/latex composition), attached to a rubber compound.

In various embodiments, this invention is directed to a rubber compound composite comprising a wire, cord, fiber, yarn, film, or fabric coated with at least one layer of composition of matter comprising SP1 based polypeptide according to this invention and optionally comprising latex. In other embodiments, the wire, cord, fiber, yarn, film, or fabric is further coated with at least one of: PEI, latex, silane and rubber-to-substrate adhesive. In other embodiments, the SP1 composition coating layer is on top of a PEI coating layer (PEI primer).

This invention also relates to methods of producing surfaces such as metal cords, polymer fibers, yarns, films, fabrics or polymeric fabrics coated with SP1 or SP1/latex. In various embodiments, the method for producing such surfaces comprise contacting a dispersion or a solution comprising composition of matter comprising SP1 based polypeptide according to this invention, with a surface. In various embodiments, the dispersion or solution further comprises latex (SP1/latex). Preferably, the method comprises a prestep of desizing of said surface prior to contacting it with the composition.

In various embodiments, the method further comprises a step of washing the unbound composition from said surface with buffer or water. In other embodiments, the method further comprises a step of contacting the surface, with a solution comprising polyethyleneimine (PEI) prior to contacting the surface with said composition, and after the desizing prestep. Preferably, the steps of contacting the surface with a solution comprising PEI, contacting the dispersion with the surface, and washing the unbound composition, are repeated at least once; In other embodiments, they are repeated twice; three or four times. In various embodiments, the solution comprising PEI further comprises latex. In various embodiments, the method further comprises a post-treatment step of contacting the surface with PEI as the last step (i.e., PEI capping). In other embodiments, the method further comprises a step of contacting the surface with latex. In various embodiments, the method further comprises a post-treatment step of contacting the surface with latex as the last step (i.e., latex capping). In various embodiments, the method further comprises a step of contacting said surface with a rubber-to-substrate adhesive. In various embodiments, the method further comprises a step of contacting said surface with a silane coupling agent. In other embodiments, the silane coupling agent is a tetrasulfido silane. In other embodiments, the silane is Bis-Triethoxysilylpropyltetrasulfidosilane.

In various embodiments, this invention is directed to a method of producing a surface such as a metal wire or cord, or a polymeric or non polymeric fiber, yarn, cord, film, or fabric coated with SP1 based polypeptide, said method comprises:
a. Optionally desizing a surface;
b. Optionally contacting said surface with a solution comprising polyethyleneimine (PEI);
c. Optionally contacting said surface with latex;
d. Contacting a dispersion comprising a composition of SP1 Based polypeptide according to this invention with the surface;
e. Optionally repeating steps (b), (c) and/or (d) at least once;
f. Optionally contacting said surface with a solution comprising at least one of: polyethyleneimine (PEI), latex, a silane coupling agent or rubber-to-substrate adhesive.

In other embodiments, the dispersion further comprises latex. In other embodiments, the method further comprises a step of washing the surface with a buffer or water after each step. In other embodiments, the latex is vinyl pyridine latex. In other embodiments, the latex is Styrene-butadiene-2-vinylpyridine latex. In other embodiments, the silane coupling agent is Bis-Triethoxysilylpropyltetrasulfidosilane. In other embodiments, the solution comprising PEI further comprises latex. In other embodiments, the SP1 composition further comprises latex. In other embodiments, step b is mandatory.

SP1/Carbon Nanoparticle

This invention describes compositions comprising SP1 Based polypeptide, and carbon nanoparticles (CNPs) such as: carbon black (CB) and carbon nanotubes (CNT) (referred herein as "SP1/CNP" composition). Such compositions were found to dramatically improve the adhesion of surfaces such as metal wires and cords, and polymeric and non-polymeric fibers, yarns, films or fabrics coated therewith to rubber compounds, compared to such surfaces comprising carbon nanoparticles without SP1. Such surfaces, coated with SP1/CNP composition of matter according to this invention have improved adhesion to rubber compounds, forming composite rubber compounds which have improved mechanical, electrical and thermal properties.

This invention, in some embodiments thereof, relates to a dispersion of SP1/CNP composition which can be used for coating of various surfaces (directly or via a PEI primer), thereby, enlarging the surface area and providing a scaffold for the further addition of functional groups to the surfaces.

According to this invention, the term "carbon nanoparticle" refers both to carbon nanotubes and to carbon black.

Optionally, the SP1/CNP compositions (e.g., dispersion) according to this invention further comprise latex, which in various embodiments, improve the surface properties; In other embodiments, improve the adhesion of the SP1/CNP/latex coated surfaces to rubber compounds; and in other embodiments, improve the mechanical, thermal and electrical properties of the rubber compound which comprises them.

Accordingly, another aspect of this invention is directed to a composition comprising SP1 based polypeptide according to this invention, carbon nanoparticle (CNP) and latex (referred herein as "SP1/CNP/latex" composition).

As referred herein, "latex" is a stable dispersion (emulsion) of polymer microparticles in an aqueous medium. Although latex itself is natural, here it refers both to natural and synthetic latex. Natural latex is a milky fluid found in 10% of all flowering plants (angiosperms). It is a complex emulsion consisting of proteins, alkaloids, starches, sugars, oils, tannins, resins, and gums that coagulate on exposure to air. Synthetic latexes can be made by polymerizing a monomer such as styrene that has been emulsified with surfactants. Examples for synthetic latex include but not limited to stable dispersion of: Carboxylated Styrene Butadiene polymers (Genflo®), Styrene-butadiene-2-vinylpyridine, Aqueous dispersion of a styrene butadiene vinylpyridine terpolymer, vinyl pyridine/butadiene/styrene blend (GENTAC®), ammonia prevulcanized natural rubber (Revultex), colloidal dispersion of a polymer of 2-chlorobutadiene (1,3) (Lipren®), Anionic stabilized aqueous latex of a carboxylated butadiene based product (Litex®), an aqueous dispersion of a terpolymer of butadiene, styrene and 2-vinylpyridine (Pyratex®, Styrene-butadiene-2-vinylpyridine, Encord 106 VP), vinyl pyridine latex (VP), or any combination thereof.

Both naturally occurring latex and synthetic latex can be used for the preparation of SP1/CNP/latex-coated surfaces according to this invention. Such SP1/CNP/latex-coated surfaces have increased adhesion to rubber compounds, compared to the adhesion of SP1/CNP-coated surfaces to rubber compounds (without the latex). In other embodiments, the latex in the composition according to this invention is natural latex. In other embodiments, the latex is synthetic latex. In various embodiments, the latex is a carboxylated styrene butadiene polymer (e.g., Genflo® latex). In various embodiments, the latex is Styrene-butadiene-2-vinylpyridine. In various embodiments, the latex is vinyl pyridine latex (VP).

The SP1/CNP and SP1/CNP/latex compositions of matter according to this invention are preferably obtained as dispersion in a solvent. The solvent used for the dispersion can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloraomethane, chloroform, dichloroethane, di methysulfoxide, dimethylformamide, dimethylacetamide, dioxane, methanol, ethanol, ethyl acetate, acetonitrile, acetone and carbon tetrachloride. Preferably, the solvent is an aqueous solution. More preferably the solvent is water.

According to some embodiments of the present invention the SP1 based polypeptides, and chimeric SP1-carbon surfaces (i.e. CNT or graphitic surfaces) polypeptides can bind to carbon nanoparticles, forming composition which can further bind to various surfaces, such as metal cords (e.g., steel cords); and polymer and non polymer fibers (e.g., carbon fibers, polyester, aramid (e.g. Kevlar™), nylon, rayon, DVA, glass, basalt, cotton, wool and the like), and can be used to modify the properties of such surfaces. For example, the SP1/CB, SP1/CNT/latex or SP1/CB/latex compositions can bind to metal cords and to polymer fibers to facilitate their adhesion to rubber compounds, to provide added strength, or can be used to promote binding of carbon nanoparticles to metal cords, synthetic or natural fabrics, fabric precursors and films, such as polyester, aramid (Kevlar™), nylon, rayon, DVA, carbon, glass, basalt, wool or cotton, in a uniform manner, to provide surfaces that have unique chemical, electrical, and thermal properties. Such surfaces may comprise layers comprising carbon nanoparticle surfaces associated with certain polymeric substances and resins.

According to some embodiments of the present invention, there are provided compositions of matter comprising an SP1 based polypeptide of the present invention and carbon nanoparticle (e.g., CNT, CB), having a target binding peptide component, and the target substance. Such a composition of matter can include, in some embodiments, for example, L1SP1 chimera (SEQ ID NO: 6) bound to carbon nanotube, L1SP1 (SEQ ID NO: 6) bound to carbon fibers, L3SP1 (SEQ ID NO: 8) bound to carbon black, L3SP1 (SEQ ID NO: 8) bound to carbon nanotube, and the like. In other embodiments, the composition of matter according to this invention may comprise a non-chimeric SP1 based polypeptide, i.e., without a target binding peptide component, e.g., SP1 wild-type, while still comprising a target substance such as carbon nanoparticle (e.g., CNT, CB).

Where a rubber compound is required to adhere to a metal cord or to a polymeric substrate (e.g., yarns, fibers, fabric or films), special compounding techniques are used. In some cases, one or more bonding layers such as latex resin mixtures are interposed between the substrate and the rubber compound, which bond well to both surfaces, while in other cases special compounding ingredients (e.g., organic cobalt salts) are added to promote adhesion.

As used herein, the phrase "SP1 based polypeptide-CNP complex" or "SP1/CNP" refers to a composition of matter comprising an SP1 or chimeric SP1 based polypeptide, bound to at least one carbon nanoparticle. The term "SP1/CNP/latex" refers to a composition of matter comprising an SP1 based- or chimeric SP1 based polypeptide, bound to carbon nanoparticle and latex. In various embodiments, the carbon nanoparticle is carbon black. In other embodiments the carbon nanoparticle is carbon nanotube. In other embodiments, the composition is in the form of dispersion. In a preferred embodiment, the dispersion is an aqueous dispersion.

In various embodiments, this invention is directed to metal cords or metal wires, coated with, or complexed to a composition of matter comprising SP1 based polypeptide, CNP and optionally comprising latex as described herein above. In other embodiments, the cord or wire is made of steel. In other embodiments, the metal comprises aluminum, copper, iron, palladium, or platinum; each possibility represents a separate embodiment according to this invention. In other embodiments, the metal comprises aluminum alloy, copper alloy, iron alloy, palladium alloy, or platinum alloy; each possibility represents a separate embodiment according to this invention. In other embodiments, the metal comprises any combination of aluminum, copper, iron, palladium, and platinum.

In various embodiments, this invention is directed to polymeric or non-polymeric fibers, yarns, fabrics, films coated with, or complexed to a composition of matter comprising SP1 based polypeptide, CNP and optionally comprising latex as described herein above. In other embodiments, the fiber, yarn, film, or fabric comprises at least one of: cotton, wool, silk, nylon, polyester, polypropylene, glass fiber, elastane, rayon, DVA, carbon, basalt and aramid. In other embodiments, the fiber, yarn, film, or fabric is polyester. In other embodiments, the fiber, yarn, film, or fabric is Aramid. In other embodiments, the fiber, yarn, film, or fabric is rayon. In other embodiments, the fiber, yarn, film, or fabric is nylon. In other embodiments, the nylon is a nylon fabric. In other embodiments the nylon is a nylon film. In other embodiments the nylon film is a DVA film. In other embodiments the film is DVA film.

As used herein, the phrase "SP1 polypeptide-CNP-polymer complex", also regarded as "SP1/CNP coated fiber" refers to polymeric fiber, yarn, cord, film or fabric coated with, or complexed to a composition comprising an SP1 based- or chimeric SP1 based polypeptide and CNP bound thereto. In various embodiments, the CNP is carbon black (CB). In other embodiments the CNP is carbon nanotube (CNT).

In various embodiments, the coated surface according to this invention further comprises latex. In various embodiments, the surface according to this invention further comprises a latex layer. In other embodiments, the surface according to this invention further comprises a latex capping. In other embodiments, the surface according to this invention is coated with at least one layer of latex. In other embodiments, with one layer; two layers; three layers; or four layers of latex; each possibility represents a separate embodiment of the invention. In other embodiments, the latex is vinyl pyridine latex (VP). In other embodiments, the latex is Styrene-butadiene-2-vinylpyridine.

In other embodiments, the loading of the latex applied to the surface is between about 0.05% and about 20% (weight latex/weight fabric). In other embodiments, between about 0.5% and about 10%. In other embodiments, between about 5% and about 8%. In other embodiments, between about 6% and about 9%. In other embodiments, between about 6% and about 8%. In other embodiments, between about 2% and about 5%. In other embodiments, between about 0.1% and about 6%. In other embodiments, between about 1% and about 10%. In other embodiments, 0.2%; 0.4%; 0.6%; 0.8%; 1%; 3%; 5%; 7%; 9%; each possibility represents a separate embodiment according to this invention.

In other embodiments, the surface according to this invention further comprises a polyethyleneimine (PEI). In other embodiments, the surface comprises a PEI primer (i.e., a first coating layer of PEI). In other embodiments, the surface according to this invention is coated with at least one layer of polyethyleneimine (PEI). In other embodiments, with one layer; two layers; three layers; or four layers of PEI; each possibility represents a separate embodiment of the invention.

"Polyethylenimine" (PEI) (also called "polyaziridine") is a polymer with repeating unit composed of the amine group and two carbon aliphatic $CH_2CH_2$ spacer. Linear polyethyleneimines contain all secondary amines, in contrast to branched PEIs which contain primary, secondary and tertiary amino groups. PEI is available at various molecular weights. In various embodiments, the PEI that finds utility in the context of this invention has a molecular weight of between 800 Da and 750,000 Da. In other embodiments, the PEI is high molecular weight PEI. In other embodiments the PEI is low molecular weight PEI. In other embodiments, the molecular weight of the PEI is between 1 KDa and 10,000 KDa; In other embodiments, between 10 KDA and 100 KDa; In other embodiments, between 25 KDa and 80 KDa; In other embodiments, between 50 KDa and 70 KDa. In other embodiments, the molecular weight of the PEI is about 60 KDa.

In various embodiments, the PEI layer is mixed with latex. In other embodiments, the PEI:latex ratio is between about 1:20 to 20:1; 10:1 to 1:10; 1:5 to 5:1; 10:1 to 2:1; 8:1 to 4:1; 8:1 to 6:1; or 6:1 to 4:1; each possibility represents a separate embodiment according to this invention. In various embodiments, the PEI:latex ratio is 10:1; 9:1, 8:1; 7:1; 6:1; 5.5:1; 5:1; 4:1; 3:1; 2:1 or 1:1; each possibility represents a separate embodiment according to this invention. In other embodiments, the latex is vinyl pyridine latex (VP). In other embodiments, the latex is Styrene-butadiene-2-vinylpyridine.

In various embodiments, the loading of the PEI applied to the surface is between about 0.05% and about 5% (weight PEI/weight fabric). In other embodiments, between about 0.5% and about 2.5%. In other embodiments, between about 0.5% and about 1.5%. In other embodiments, between about 1.8% and about 2.0%. In other embodiments, between about 0.1% and about 1.0%. In other embodiments, between about 0.05% and about 0.3%. In other embodiments, between about 0.2% and about 0.4%. In other embodiments, between about 0.1% and about 0.5%. In other embodiments, between about 0.05% and about 0.1%. In other embodiments, between about 0.05% and about 0.3%. In other embodiments, between about 1% and about 5%. In other embodiments, the applied loading of the PEI on the surface is 0.05%; 0.07%; 0.09%; 0.1%; 0.12%, 0.14%, 0.16%, 0.18%, 0.2%, 0.21%, 0.25%, 0.28%, 0.3% or 0.56%; each possibility represents a separate embodiment according to this invention. In other embodiment, the applied PEI is mixed with latex.

In various embodiments, the surface according to this invention further comprises a silane. In various embodiments, the surface according to this invention further comprises a silane capping. In other embodiments, the surface according to this invention is capped with a silane layer. In other embodiments, the surface according to this invention is coated with at least one layer of silane. In other embodiments, with one layer; two layers; three layers; or four layers of silane; each possibility represents a separate embodiment of the invention. In other embodiments, the silane is tetrasulfido silane. In other embodiments, the silane is Bis-Triethoxysilylpropyltetrasulfidosilane.

In other embodiments, the surface according to this invention further comprises a rubber to substrate adhesive. In other embodiments, the surface according to this invention is coated with at least one layer of rubber to substrate adhesive. In other embodiments, with one layer; two layers; three layers; or four layers of rubber to substrate adhesive; each possibility represents a separate embodiment of the invention.

As referred herein, "rubber to substrate adhesive" is defined as compositions used for bonding a variety of rubber compounds to various substrates including metal, fabrics and plastic substrates, such as steel, stainless steel, aluminum, zinc, copper, polyamides, polyacetals, polyesters, aramid and PTFE. Rubber to substrate adhesives normally bond the substrate to the elastomer during the vulcanization process. The bonding agents are normally low-viscosity, organic, solvent-based solutions and/or dispersions of polymers and other reactive chemicals. They can be either used as one-coat bonding agents or as two-coat primer and cover-cement systems. These bonding agents are composed of polymers, reactive components and other ingredients dissolved or dispersed in a volatile organic solvent system. Non limiting examples of rubber to substrate adhesives brands include: various types of latex as defined herein above, RFL as defined above, MEGUM™, ROBOND™ and THIXON™, Chemlok®, and Chmosil®. In various embodiments, the rubber to substrate adhesive is Chemosil® 211 primer, which is a heat-activated bonding agent designed for use as a substrate primer under other Chemosil covercoat bonding agents, or as a one-coat bonding agent for bonding unvulcanized nitrile elastomer compounds. It is composed of a mixture of polymers, organic compounds and mineral fillers dissolved or dispersed in an organic solvent system. In other embodiments, the rubber to substrate adhesive is Chemlok® 220 which is a covercoat adhesive which can bond a wide variety of elastomers such as natural rubber (NR), styrene-butadiene (SBR), polychloroprene (CR), nitrile (NBR) and polyisoprene (IR) to various substrates during vulcanization of the elastomer. It is composed of a mixture of polymers, organic compounds and mineral fillers dissolved or dispersed in an organic solvent system.

In various embodiments, the surface coated with the composition of matter according to this invention comprises a woven or non-woven fiber, yarn, cord, film, or fabric. In other embodiments said woven and non-woven fiber, yarn, cord, film, or fabric is selected from natural fiber, yarn, cord, film, or fabric, synthetic fiber, yarn, cord, film, or fabric, a mixture of natural and synthetic fiber, yarn, cord, film, or fabric, and inorganic material based fiber, yarn, cord, film, or fabric. Exemplary natural fabrics include, but are not limited to cotton, wool, and silk. Exemplary synthetic fabric fiber or film include, but are not limited to nylon, polyester, aramid, rayon, polypropylene, polyethylene naphthanate (PEN), polyolefin ketone (POK), DVA, and elastane (Lycra™-Spandex™). Examples of garments, rope, sewn, molded and woven items fashioned from fabric and yarns coated with the SP1/CNT/latex according to the present invention include, but are not limited to: parachutes, clothing, sleeping bags, bicycle parts and equipment, skis, etc (for further detailed examples, see U.S. Pat. Nos. 7,354,877, and 8,957, 189, which are incorporated herein by reference).

In various embodiments, the surface of this invention comprises a plurality of layers of the composition of matter of this invention bound to the surface. In other embodiments, it comprises one layer of said composition of matter bound to the surface. In other embodiments, it comprises two layers of said composition of matter bound to the surface. In other embodiments, it comprises three layers of said composition of matter bound to the surface. In other embodiment, the surface is metal wire or cord or polymeric or non polymeric fiber, yarn, film, or fabric.

In various embodiments, this invention is directed to a surface coated with at least one layer of a composition of matter comprising SP1 based polypeptide according to this invention, Carbon nanoparticle and optionally comprising latex (i.e., SP1/CB, SP1/CB/latex or CP1/CNT/latex), attached to a rubber compound. In various embodiments the surface is coated with at least one layer of SP1/CB. In other embodiments, the surface is coated with at least one layer of SP1/CB/latex. In other embodiments, the surface is coated with at least one layer of SP1/CNT/latex.

In various embodiments, this invention is directed to a surface complexed with a composition of matter comprising SP1 based polypeptide according to this invention, Carbon nanoparticle and optionally comprising latex (i.e., SP1/CB, SP1/CB/latex or CP1/CNT/latex), attached to a rubber compound. In various embodiments the surface is complexed with SP1/CB. In other embodiments, the surface is complexed with SP1/CB/latex. In other embodiments, the surface is complexed with SP1/CNT/latex. In other embodiments, the surface is metal wire or cord or polymeric or non polymeric fiber, yarn, film, or fabric.

In various embodiments, this invention is directed to a rubber compound composite comprising a surface coated with at least one layer of composition of matter comprising SP1 based polypeptide according to this invention, CNP and optionally comprising latex. In various embodiments, the rubber compound composite comprises a surface coated with SP1/CB. In other embodiments, the rubber compound composite comprises a surface coated with SP1/CB/latex. In other embodiments, the rubber compound composite comprises a surface coated with SP1/CNT/latex. In various embodiments, the rubber compound composite is prepared by contacting rubber compound with surface coated with at least one layer of composition of matter according to this invention. In other embodiments, the surface is metal wire or cord or polymeric or non polymeric fiber, yarn, film, or fabric.

In the context of this invention, the term "rubber" or "elastomer" encompasses both natural rubber and synthetic ones. Natural rubber (NR), coming from latex of *Hevea brasiliensis*, is mainly poly-cis-isoprene containing traces of impurities like protein, dirt etc. Synthetic rubber, invariably a polymer, is any type of artificial elastomer mainly synthesized from petroleum byproducts. It is made by the polymerization of a variety of petroleum-based precursors called monomers. The most prevalent synthetic rubbers are styrene-butadiene rubbers (SBR) derived from the copolymerization of styrene and 1,3-butadiene. Other synthetic rubbers are prepared from isoprene (2-methyl-1,3-butadiene), chloroprene (2-chloro-1,3-butadiene), and isobutylene (methylpropene) with a small percentage of isoprene for cross-linking. These and other monomers can be mixed in various proportions to be copolymerized to produce products with a range of physical, mechanical, and chemical properties. The monomers can be produced pure and the addition of impurities or additives can be controlled by design to give optimal properties. An elastomer is a material with the mechanical (or material) property that it can undergo much more elastic deformation under stress than most materials and still return to its previous size without permanent deformation. A wide variety rubbers (elastomers) are available, each exhibit unique physical and chemical properties, including temperature resistance. Examples of synthetic rubbers which can be utilized according to this invention include but not limited to: Polychloroprene (CR)—Neoprene®, Nitrile (NBR), Ethylene Propylene, Ethylene-propylene-diene (EPDM), Buna-N (Nitrile-butadiene), natural rubber, Aflas (AG Fluoropolymers), Butyl (isobutene-isoprene, IIR), Chlorsulfonated Polyethylene (CSM)—Hypalon®, Epichlorohydrin (ECO), Fluoroelastomer (Hexaflouropropylene-vinylidene fluoride)(FKM)—Viton®, Flurosilicone (FQ), Hydrogenated Nitrile (HNBR), Perfluoroelastomer (FFKM), Polyacrylic (ACM), Plyurethan (PU, Urethane (Polyethylene-apdate, Poly (oxy-1, 4, butylene) ether)), Silicone (polysiloxane, Q), Styrene Butadiene (SBR), Hydrogenated Nitrile (Hydrogenated Acrylonitrile-butadiene rubber), and Carboxylated Nitrile. Mechanical rubber goods include materials which are made of rubber that further contain other materials, such as textile-enforced mechanical rubber goods.

Elastomers (or rubbers), as described above, are usually mixed with several different ingredients to form a "rubber compound". The added ingredients are chosen to optimize the physical properties of the compound in order to meet the specification for a particular application. Cheap mineral powders (e.g., CB, silica or calcium carbonate) are normally added to the rubber compound to reduce the cost, and to increase the elastic modulus of the cured compound.

According to one aspect of the invention as claimed, there is provided a pneumatic or semi-pneumatic tire having a component which comprises at least one SP1 based polypeptide-CNP complexed surface attached to a rubber compound. In various embodiments, the tire component is a rubber compound composite formed with said SP1 based polypeptide-CNP-complexed surface. In other embodiments, the tire component comprises layers of rubber compounds and at least one layer of the SP1 based polypeptide-CNP-complexed surface, for example, as in a reinforcement belt below the tread. In yet another embodiment, the tire component is selected from a sidewall, a tread base of a tread of cap/base construction and a tire apex. In various embodiments, the carbon nanoparticle (CNP) is carbon black. In other embodiments the carbon nanoparticle (CNP) is carbon nanotube. In other embodiments, the surface is metal wire or cord or polymeric or non polymeric fiber, yarn, film, or fabric.

SP1 based polypeptide-CNP-complexed polymers (or SP1/CNP coated fibers) can be incorporated into the basic matrix (e.g. rubber) of any portion of a tire, such as tread, sidewall, internal belts, bead, apex, etc. Exemplary methods for producing aramid-rubber and aramid-rubber-carbon black composites suitable for use in tires are well known in the art, as detailed, for example, in US Patent Application 20040173295 to Zanzig et al.

Tires, and particularly automotive and aviation tires, having improved mechanical properties, heat and electrical conductivity resulting from incorporation of SP1 based polypeptide-CNP-polymer complexes of the invention into the tire matrix, can be more efficiently heated and cooled than conventional tires, for example, by applying an appropriate electrical current to the conductive elements of the tire.

Further embodiments of the invention include, but are not limited to, tires having at least one SP1 based polypeptide-CNT-complexed surface element forming a conductive path for discharging static electric charge buildup (for details of construction of such tires, see, for example, US Patent Application 2010078103, to Nakamura, U.S. Pat. No. 7,528,186 to Halas a, U.S. Pat. No. 7,284,583 to Dheur et al and U.S. Pat. No. 7,131,474 to Sandstrom), tires having at least one SP1 based polypeptide-CNT-complexed surface element having improve thermal conductivity and heat transfer to the road during use (for details of construction and use of such tires, see, for example, U.S. Pat. No. 7,337,815 to Spadone), tires having at least one SP1 based polypeptide-CNT-complexed surface element capable of communicating information on tire status and performance, such as tire pressure, deformation, tread and sidewall wear and failure, rolling resistance, etc. at rest and in motion, during use (for details of construction and use of such tires, see, for example, U.S. Pat. No. 7,318,464 to Hahn et al and U.S. Pat. No. 7,581,439 to Rensel, et al.) and electrical energy generating tires with a conductive strip of a SP1 based polypeptide-CNT-complexed surface, and an energy generating component (such as a piezo-ceramic or thermal-harvesting material) incorporated into the tread and/or sidewall of the tire ((for details of construction and use of such tires, see, for example, U.S. patent application Ser. No. 00/700,28958 to Retti and U.S. patent application Ser. No. 00/903,14404 to Rodgers et al).

SP1 based polypeptides complexed with target substances can be added to various surfaces in a variety of methods. In some embodiments, the complex of SP1 based polypeptide and target substance (for example, L3-SP1-CB complex) is prepared similarly to the method described in U.S. Pat. No. 8,957,189 for SP1-CNT complexes. Alternatively, the complex of SP1 based polypeptide and target substance (e.g. carbon nanotube, carbon black) is prepared by as described herein below.

This invention also relate to methods of producing surfaces such as metal wires and cords, and polymeric and non polymeric fibers, yarns, films or fabrics coated with carbon nanoparticles (CNP). In various embodiments, the method for producing such surfaces comprise contacting a dispersion comprising composition of matter comprising SP1 based polypeptide according to this invention and CNP (SP1/CNP), with a surface. In various embodiments, the dispersion further comprises latex (SP1/CNP/latex). Preferably, the method comprises a prestep of desizing of said surface prior to contacting it with the composition.

The term "Desizing" refers in some embodiments, to a process which is done in order to remove the size from the warp yarns of the woven fabrics. Warp yarns are coated with sizing agents prior to weaving in order to reduce their frictional properties, decrease yarn breakages on the loom and improve weaving productivity by increasing weft insertion speeds. The sizing material present on the warp yarns can act as a resist towards dyes and chemicals in textile wet processing. It is therefore should be removed before any subsequent wet processing of the fabric. In various embodiments, the desizing process is done by hydrolytic method. In various embodiments, the desizing process is done by oxidative method. In various embodiments, desizing refers to scouring. In various embodiments, desizing refers to scouring with an acid In various embodiments, the method further comprises a step of washing the unbound composition from said surface with buffer or water. In other embodiments, the method further comprises a step of contacting the surface, with a solution comprising polyethyleneimine (PEI) prior to contacting the surface with said composition, and after the desizing prestep (i.e., PEI primer). Preferably, the steps of contacting the surface with the solution comprising PEI, contacting the dispersion with the surface, and washing the unbound composition, are repeated at least once; In other embodiments, they are repeated twice; three or four times. In various embodiments, the PEI solution further comprises latex. In various embodiments, the method further comprises a post-treatment step of contacting the surface with PEI as the last step (i.e., PEI capping). In other embodiments, the method further comprises a step of contacting the surface, with latex. In various embodiments, the method further comprises a post-treatment step of contacting the surface with latex as the last step (i.e., latex capping). In various embodiments, the method further comprises a step of contacting said surface with a a silane coupling agent. In various embodiments, the method further comprises a post-treatment step of contacting the surface with a silane coupling agent as the last step (i.e., silane capping). In other embodiments, the silane coupling agent is a tetrasulfido silane. In other embodiments, the silane coupling agent is Bis-Triethoxysilylpropyltetrasulfidosilane. In various embodiments, the method further comprises a step of contacting said surface with a rubber-to-substrate adhesive. In various embodiments, the rubber-to-substrate adhesive is Chemlok® or Chemosil®. In other embodiments, the method comprises a step of contacting the surface, with a solution comprising at least one of: PEI, latex, a silane coupling agent or rubber to substrate adhesive as the last step (i.e., capping). In various embodiments, the CNP is CB. In other embodiments, the CNP is CNT. In other embodiments, said step of contacting the dispersion comprising the composition of this invention with the surface, is performed using a textile dying machine. Non limiting examples of textile dying machines are: Jigger coating machine for woven fabrics or vertical or horizontal yarn or fabric package dyeing system. In other embodiments, the surface is metal wire or cord or polymeric or non polymeric fiber, yarn, film, or fabric.

In various embodiments, this invention is directed to a method of producing a surface coated with carbon nanoparticles, said method comprises:
 a. Optionally desizing a surface;
 b. Optionally contacting said surface with a solution comprising polyethyleneimine (PEI);
 c. Optionally contacting said surface with latex;
 d. Contacting a dispersion comprising a composition of SP1 Based polypeptide and CNP according to this invention with the surface;
 e. Optionally repeating steps (b), and/or (c) and/or (d) at least once;
 f. Optionally contacting said surface, with a solution comprising at least one of: polyethyleneimine (PEI), latex, a silane coupling agent, or a rubber-to-substrate adhesive.

In other embodiments, the surface is metal wire or cord or polymeric or non polymeric fiber, yarn, film, or fabric. In other embodiments, the dispersion further comprises latex. In other embodiments, the method further comprises a step of washing the surface with a buffer or water after each step. In other embodiments, the latex is vinyl pyridine latex. In other embodiments, the latex is Styrene-butadiene-2-vinylpyridine latex. In other embodiments, the rubber-to-substrate adhesive is Chemlok® or Chemosil®. In other embodiments, the silane coupling agent is a tetrasulfido silane. In other embodiments, the silane coupling agent is Bis-Triethoxysilylpropyltetrasulfidosilane. In other embodiments, the solution comprising PEI, further comprises latex. In other embodiments, the PEI:latex ratio in the solution is 5:1. In other embodiments, the dispersion comprising a composition of SP1 Based polypeptide and CNP further comprises latex. In other embodiments, the CNP:latex ratio in the solution is 5:1; 7:1; 10:1; 20:1; or 30:1; each possibility represents a separate embodiment according to this invention.

In other embodiments, said step of contacting the dispersion comprising the composition of this invention with the surface is performed using a textile dying machine.

In various embodiments, this invention is directed to a method of producing a surface coated with carbon nanoparticles, said method comprises:
 a. Optionally desizing a surface;
 b. Optionally contacting said surface with a solution comprising polyethyleneimine (PEI);
 c. Optionally contacting said surface with latex;
 d. Contacting a dispersion comprising a composition of SP1 Based polypeptide and CNP according to this invention with the surface;
 e. Optionally repeating steps (b), (c) and/or (d) at least once;
 f. Optionally contacting said surface with a solution comprising at least one of: polyethyleneimine (PEI), latex, a silane coupling agent, or rubber-to-substrate adhesive.

SP1/Carbon Black (CB)

The present invention provides, in some embodiments thereof, the ability to weave carbon black into various surfaces including: metal wires and cords; polymeric and non polymeric fibers, yarns, films and fabrics that may be applied to a wide range of uses.

Unexpectedly, it was found by the inventors of the subject Application, that SP1 based polypeptides are capable to enhance the dispersion of not only CNT but also CB in aqueous solutions. Such SP1/CB dispersions can be utilized for the coating of various surfaces, and for preparation of rubber compound composites with these coated surfaces.

CB binding to fibers via the SP1 protein increases their surface area, allowing better interaction with the fiber and induces cross linking between the fibers. In addition, protein binding to the fiber by itself may improve the interaction with the polymer through reactive groups on the protein surface. It is demonstrated that SP1 variants according to this invention, are capable of binding CB to structural fibers.

Successful incorporation of CB to the surface of textiles allows the textiles to adopt some of the mechanical, thermal, electrical, physical and chemical properties associated with carbon black. The SP1/CB compositions of matter according to this invention can be utilized to incorporate the CB to the surface of textiles.

"Carbon black" (CB) is a form of paracrystalline carbon that has a high surface-area-to-volume ratio, albeit lower than that of activated carbon. It is dissimilar to soot in its much higher surface-area-to-volume ratio and significantly lower (negligible and non-bioavailable) PAH (polycyclic aromatic hydrocarbon) content. It is produced by the incomplete combustion of heavy petroleum products such as FCC tar, coal tar, ethylene cracking tar, and a small amount from vegetable oil. The highest volume use of carbon black is as a reinforcing filler in rubber products, especially tires. Carbon black also helps conduct heat away from the tread and belt area of the tire, reducing thermal damage and increasing tire life. It is used often in the Aerospace industry in elastomers for aircraft vibration control components such as engine mounts. Practically all rubber products where tensile and abrasion wear properties are crucial use carbon black, so they are black in color. Carbon blacks for rubber use have a variety of grades depending upon their properties and are generally classified on the basis of analytical properties including: surface area, structure (DBP absorption) and the like. The properties of the grade of carbon black become an important factor in determining various performances of the rubber composition wherein the carbon blacks are incorporated. It is generally desirable in the production of tires to utilize carbon blacks which impart high levels of abrasion resistance and low levels of rolling resistance to the tires. The reinforcing properties of a carbon black are generally related to the level of abrasion resistance imparted to the rubber compositions. Generally, carbon blacks with increased reinforcing properties result in tires with increased abrasion resistance. In the context of this invention, any type of CB can be used. The various CB types and brands are differing in their surface area, aggregate size distribution and morphological structure. Non-limiting examples of CB types include: conductive CB, CB-N326, CRX™ 1346, CRX™ 1490, PROPEL™ D11, PROPEL™ E3, PROPEL™ E6, PROPEL™ E7, REGAL® 300, VULCAN® 10, VULCAN® 10H, VULCAN® 10HD, VULCAN® 1345, VULCAN® 1380, VULCAN® 1391, VULCAN® 1436, VULCAN® 3, VULCAN® 3H, VULCAN® 6, VULCAN® 6-LP, VULCAN® 7H, VULCAN® 8, VULCAN® 9, VULCAN® 9H, VULCAN® J, VULCAN® M.

The properties of SP1 protein, as described above, and its role in binding CNP to polymers, can be utilized for the integration of carbon black into the surface of metals and textiles, and further for the incorporation of the SP1/CB-coated surfaces into rubber compounds.

Accordingly provided herein a composition of matter comprising carbon black (CB) bound to an SP1 based polypeptide according to this invention (referred herein as "SP1/CB" composition). In other embodiments, the carbon black is non-covalently bound to the SP1 based polypeptide. In other embodiments, the SP1 based polypeptide is a wild type SP1 protein. In other embodiments, the SP1 based polypeptide is a chimeric SP1 based polypeptide as described herein above. In other embodiments, the SP1 based polypeptide comprises a carbon nanotube or graphitic surfaces binding peptide. In other embodiments, the chimeric SP1 polypeptide has the amino acid sequence as set forth in SEQ ID NO: 8.

Where rubber compounds are required to adhere to polymeric substrates (e.g., yarns, fibers, fabric or films), special compounding techniques are used. In some cases, one or more bonding layers such as latex resin mixtures are interposed between the substrate and the rubber compound, which bond well to both surfaces, while in other cases special compounding ingredients (e.g., organic cobalt salts) are added to promote adhesion.

Accordingly, in other embodiments, provided herein is a composition of matter comprising: carbon black (CB), SP1 based polypeptide according to this invention, and latex (referred herein as "SP1/CB/latex" composition). In various embodiments, the CB is non-covalently bound to the SP1 based polypeptide.

The SP1/CB and SP1/CB/latex compositions of matter according to this invention are preferably obtained as dispersions in solvent. The solvent used for the dispersion can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloraomethane, chloroform, dichloroethane, di methysulfoxide, dimethylformamide, dimethylacetamide, dioxane, methanol, ethanol, ethyl acetate, acetonitrile, acetone and carbon tetrachloride. Preferably, the solvent is an aqueous solution. More preferably the solvent is water.

In various embodiments, the SP1/CB and/or the SP1/CB/Latex compositions are in the form of aqueous dispersions in a concentration of between 0.001% and 50% w/w. In other embodiments, the composition is in the form of an aqueous dispersion in a concentration of between 0.5% and 30%. In other embodiments, the composition is in the form of an aqueous dispersion in a concentration of between 1% and 20%. In other embodiments, the composition is in the form of an aqueous dispersion in a concentration of between 4% and 17%. In other embodiments, the composition is in the form of an aqueous dispersion in a concentration of 1% w/w, 2% w/w, 3% w/w, 4% w/w, 6% w/w, 8% w/w, 10% w/w, 12% w/w, 14% w/w, 15% w/w, 16% w/w, 17% w/w, 18% w/w, 20% w/w, 22% w/w, 24% w/w, 25% w/w, 28% w/w, 30% w/w; each value represents a separate embodiment of the invention. Preferably, the dispersion concentration is up to 17% w/w; more preferably, the dispersion concentration is 15% w/w.

For use in surface coating methods, the SP1/CB or SP1/CB/latex dispersion is normally diluted to a concentration of between 0.001% and 0.5% w/w. In another embodiment, the concentration is between 0.05% and 0.15% w/w. In another embodiment, the concentration is 0.05%, 0.1% or between 0.05% and 0.1% w/w; each value represents a separate embodiment of the invention.

The SP1/CB and SP1/CB/latex dispersions can be formed in various CB:SP1 ratios as stable dispersion. In various embodiments, the CB:SP1 ratio in the dispersion ratio is between 0.1:1 to 30:1 dry weight/weight. In another embodiment, the CB:SP1 ratio is between 0.3:1 to 10:1 dry w/w. In another embodiment, the CB:SP1 ratio is between 3:1 to 8:1 dry w/w. In various embodiments, the CB:SP1 ratio is 5.5 dry w/w. In other embodiments, the CB:SP1 ratio is 3.0 dry w/w, 3.5 dry w/w, 4.0 dry w/w, 4.5 dry w/w, 5.0 dry w/w, 5.5 dry w/w, 6.0 dry w/w, 6.5 dry w/w, 7.0 dry w/w, 7.5 dry w/w, 8.0 dry w/w, 9.0 dry w/w, 10.0 dry w/w, 15 dry w/w, 20 dry w/w, 25 dry w/w, or 30 dry w/w; each value represents a separate embodiment of the invention. In various embodiments, the SP1 is an isolated SP1. In other embodiments, the SP1 is the crude SP1, i.e. the heat stable fraction of an extract of bacteria expressing the SP1 protein.

The SP1/CB/latex dispersion can be formed in various CB:latex ratios as stable dispersion. In other embodiments, the CB:latex ratio in the dispersion is between 1:10 to 50:1. In other embodiments, the CB:latex ratio in the dispersion is between 5:1 to 50:1. In other embodiments, the CB:latex ratio is between 1:1 to 10:1. In various embodiments, the CB:latex ratio is between 10:1 to 40:1. In other embodiments, the CB:latex ratio is between 20:1 to 40:1. In other embodiments, the CB:latex ratio is between 1:5 to 10:1. In other embodiments, the CB:latex ratio is between 10:1 to 30:1. In other embodiments, the CB:latex ratio is 30:1. Preferably, CB:latex ratio is 10:1 or larger.

In various embodiments, this invention is directed to a fiber, yarn, film, or fabric coated with at least one layer of a composition of matter comprising SP1 based polypeptide, CB (SP1/CB) and optionally comprising latex (SP1/CB/latex) as described herein above. In other embodiments, the fiber, yarn, film, or fabric comprises at least one of: cotton, wool, silk, carbon, basalt, nylon, polyester, polypropylene, glassfiber, elastane, rayon, DVA and aramid. In other embodiments, the fiber, yarn, film, or fabric is polyester. In other embodiments, the fiber, yarn, film, or fabric is Aramid. In other embodiments, the fiber, yarn, film, or fabric is rayon. In other embodiments, the fiber, yarn, film, or fabric is nylon. In other embodiments, the nylon is a nylon fabric. In other embodiments the nylon is a nylon film. In other embodiments the nylon film is a DVA film. In other embodiments the nylon film is DVA film.

In various embodiments, this invention is directed to metal cords or metal wires, coated with at least one layer of a composition of matter comprising SP1 based polypeptide, CB (SP1/CB) and optionally comprising latex (SP1/CB/latex) as described herein above. In other embodiments, the cord or wire is made of steel. In other embodiments, the metal comprises steel, aluminum, copper, iron, palladium, platinum, zinc, aluminum alloy, iron alloy, copper alloy, zinc alloy, each possibility is a separate embodiment according to this invention. In other embodiments, the metal comprises any combination of aluminum, copper, iron, palladium, platinum and zinc.

In various embodiments, the surface according to this invention further comprises latex. In various embodiments, the surface according to this invention further comprises a latex layer. In other embodiments, the surface according to this invention further comprises a latex capping. In other embodiments, the surface according to this invention is capped with a latex layer. In other embodiments, the surface according to this invention is coated with at least one layer of latex. In other embodiments, with one layer; two layers; three layers; or four layers of latex; each possibility represents a separate embodiment of the invention. In other embodiments, the latex is vinyl pyridine latex (VP). In other embodiments, the latex is Styrene-butadiene-2-vinylpyridine.

In other embodiments, the loading of the latex applied to the surface is between about 0.05% and about 20% (weight latex/weight fabric). In other embodiments, between about 0.5% and about 10%. In other embodiments, between about 5% and about 8%. In other embodiments, between about 6% and about 9%. In other embodiments, between about 6% and about 8%. In other embodiments, between about 2% and about 5%. In other embodiments, between about 0.1% and about 6%. In other embodiments, between about 1% and about 10%. In other embodiments, 0.2%; 0.4%; 0.6%; 0.8%; 1%; 3%; 5%; 9%; 7%; each possibility represents a separate embodiment according to this invention.

In other embodiments, the surface according to this invention further comprises at least one layer of polyethyleneimine (PEI). In other embodiments, the surface according to this invention is coated with at least one layer of polyethyleneimine (PEI). In other embodiments, the surface according to this invention is coated with a PEI primer. In other embodiments, the PEI is high molecular weight PEI. In other embodiments the PEI is low molecular weight PEI. In various embodiments, the PEI that finds utility in the context of this invention has a molecular weight of between 800 Da and 750,000 Da. In other embodiments, the PEI is high molecular weight PEI. In other embodiments the PEI is low molecular weight PEI. In other embodiments, the molecular weight of the PEI is between 1 KDa and 10,000 KDa; In other embodiments, between 10 KDA and 100 KDa; In other embodiments, between 25 KDa and 80 KDa; In other embodiments, between 50 KDa and 70 KDa. In other embodiments, the molecular weight of the PEI is about 60 KDa.

In various embodiments, the PEI layer is mixed with latex. In other embodiments, the PEI:latex ratio is between about 1:20 to 20:1; 10:1 to 1:10; 1:5 to 5:1; 10:1 to 2:1; 8:1 to 4:1; 8:1 to 6:1; or 6:1 to 4:1; each possibility represents a separate embodiment according to this invention. In various embodiments, the PEI:latex ratio is 10:1; 9:1, 8:1; 7:1; 6:1; 5.5:1; 5:1; 4:1; 3:1; 2:1 or 1:1; each possibility represents a separate embodiment according to this invention. In other embodiments, the latex is vinyl pyridine latex (VP). In other embodiments, the latex is Styrene-butadiene-2-vinylpyridine.

In various embodiments, the applied loading of the PEI on the surface is between about 0.05% and about 5%. In other embodiments, between about 0.5% and about 2.5%. In other embodiments, between about 0.5% and about 1.5%. In other embodiments, between about 1.8% and about 2.0%. In other embodiments, between about 0.1% and about 1.0%. In other embodiments, between about 0.05% and about 0.3%. In other embodiments, between about 0.2% and about 0.4%. In other embodiments, between about 0.1% and about 0.5%. In other embodiments, between about 0.05% and about 0.1%. In other embodiments, between about 0.05% and about 0.3%. In other embodiments, between about 1% and about 5%. In other embodiments, the applied loading of the PEI on the fiber, film or fabric is 0.05%, 0.07%, 0.09%, 0.1%, 0.12%, 0.14%, 0.16%, 0.18%, 0.2%, 0.21%, 0.25%, 0.28%, 0.3% or 0.56%; each possibility represents a separate embodiment of the invention. In other embodiments, the applied PEI is mixed with latex.

In various embodiments, the surface according to this invention further comprises a silane. In various embodiments, the surface according to this invention further comprises a silane capping. In other embodiments, the surface according to this invention is capped with a silane layer. In other embodiments, the surface according to this invention is coated with at least one layer of silane. In other embodiments, with one layer; two layers; three layers; or four layers of silane; each possibility represents a separate embodiment of the invention. In other embodiments, the silane is tetrasulfido silane. In other embodiments, the silane is Bis-Triethoxysilylpropyltetrasulfidosilane.

In other embodiments, the surface according to this invention further comprises a rubber to substrate adhesive. In other embodiments, the surface according to this invention is coated with a rubber to substrate adhesive. In other embodiments, the rubber to substrate adhesive is Chemosil®. In other embodiments, the rubber to substrate adhesive is Chemlok®.

In various embodiments, this invention is directed to a surface coated with at least one layer of a composition of matter comprising SP1 based polypeptide, CB and optionally comprising latex according to this invention (i.e., SP1/CB or SP1/CB/latex), wherein the applied loading of said composition on said surface is between 0.1 gr/kg and 100 gr/kg (gr CB/Kg yarn). In other embodiments, the applied loading of said composition on said surface is between 5 gr/kg and 15 gr/kg. In other embodiments, the applied loading is between 7 gr/kg and 14 gr/kg. In other embodiments, the applied loading is about 7 gr/kg. In other embodiments, the applied loading is about 10 gr/kg. In other embodiments, the applied loading is about 10.5 gr/kg. In other embodiments, the applied loading is about 14 gr/kg. In other embodiments, the applied loading is about 3.5 gr/kg. In other embodiments, the applied loading is about 1 gr/Kg, 2 gr/Kg, 3 gr/Kg, 3.5 gr/Kg, 4 gr/Kg, 5 gr/Kg, 5.5 gr/Kg, 6 gr/Kg, 7 gr/Kg, 8 gr/Kg, 9 gr/Kg, 10 gr/Kg, 11 gr/Kg, 12 gr/Kg, 14 gr/Kg, 16 gr/Kg, 18 gr/Kg, 20 gr/Kg, 30 gr/Kg, 40 gr/Kg, 50 gr/Kg, 60 gr/Kg, 70 gr/Kg, 80 gr/Kg, 90 gr/Kg, 100 gr/Kg; each value represents a separate embodiment of the invention. Preferably, the applied loading is 7 gr/Kg. The applied loading can be achieved by one layer coating or by multi-layer coating; In various embodiments, the applied loading is achieved by one layer coating; In other embodiments, the applied loading is achieved by two layer coating; In other embodiments, the applied loading is achieved by three layer coating; preferably the coating is achieved by two layer coating; e.g. two loadings of 3.5 g/Kg.

In various embodiments, this invention is directed to a surface coated with at least one layer of a composition of matter comprising SP1 based polypeptide, CB and optionally comprising latex according to this invention (i.e., SP1/CB or SP1/CB/latex), wherein the applied loading of said composition on said surface is between 0.01% and 10% (w/w). In other embodiments, the applied loading of said composition on said surface is between 0.5% (w/w) and 1.5% (w/w). In other embodiments, the applied loading is between 0.7% (w/w) and 1.4% (w/w). In other embodiments, the applied loading is about 0.7% (w/w). In other embodiments, the applied loading is about 1% (w/w). In other embodiments, the applied loading is about 1.05% (w/w). In other embodiments, the applied loading is about 1.4% (w/w). In other embodiments, the applied loading is about 0.35% (w/w). In other embodiments, the applied loading is about 0.1% (w/w), 0.2% (w/w), 0.3% (w/w), 0.35% (w/w), 0.4% (w/w), 0.5% (w/w), 0.55% (w/w), 0.6% (w/w), 0.7% (w/w), 0.8% (w/w), 0.9% (w/w), 1.0% (w/w), 1.1% (w/w), 1.2% (w/w), 1.4% (w/w), 1.6% (w/w), 1.8% (w/w), 2.0% (w/w), 3.0% (w/w), 4.0% (w/w), 5.0% (w/w), 6.0% (w/w), 7.0% (w/w), 8.0% (w/w), 9.0% (w/w), 10.0% (w/w); each value represents a separate embodiment of the invention. Preferably, the applied loading is 0.7% (w/w). Preferably the coating is achieved by two layer coating; e.g. two loadings of 0.35% (w/w).

In various embodiments, this invention is directed to a surface coated with a composition of matter comprising SP1 based polypeptide and CB according to this invention (i.e., SP1/CB composition), attached to a rubber compound. In other embodiments, the composition of matter further comprises latex (i.e., SP1/CB/latex composition).

In various embodiments, this invention is directed to a rubber compound composite comprising a metal cord or a surface coated with a composition of matter comprising SP1 based polypeptide and CB according to this invention (i.e., SP1/CB composition). In other embodiments, the composition of matter further comprises latex (i.e., SP1/CB/latex composition).

In one specific embodiment, SP1 based polypeptides and chimeric SP1 polypeptides, are used to bind carbon black, and the resulting SP1 polypeptide-CB-complex (i.e., SP1/CB composition) is then used to bind the CB to a metal cord or polymer fiber, film or fabric, such as aramid (e.g. Kevlar™), for incorporation into rubber tires, in order to enhance the mechanical and/or physical properties (e.g. electrical, mechanical and/or thermal) and function of the tires.

As used herein, the phrase "SP1 based polypeptide-CB complex" or "SP1/CB composition" refers to a composition comprising an SP1 or chimeric SP1 polypeptide, bound to carbon black. The term "SP1/CB/latex" refers to a composition comprising an SP1 or chimeric SP1 polypeptide, bound to carbon black and latex.

As used herein, the phrase "SP1 polypeptide-CB-polymer complex" or SP1/CB-coated fiber" refers to a surface coated with an SP1/CB composition according to this invention. The phrase "SP1 polypeptide-CB-latex-polymer complex" or "SP1/CB/latex-coated fiber" refers to a surface coated with an SP1/CB/latex composition according to this invention. In various embodiments, the surface is a metal wire or cord; a polymeric fiber, yarn, film or fabric; or a non-polymeric fiber, yarn, film or fabric.

In various embodiments, this invention is directed to a pneumatic or semi-pneumatic tire comprising the SP1/CB or SP1/CB/latex composition of matter according to this invention. In other embodiments, the tire comprises an SP1 polypeptide-CB-polymer complex according to this invention. In other embodiments, the tire comprises an SP1 polypeptide-CB-latex-polymer complex according to this invention. In other embodiments, the tire comprises a surface coated with a SP1/CB or SP1/CB/latex composition of matter according to this invention. In various embodiments, the surface is a metal wire or cord; a polymeric fiber, yarn, film or fabric; or a non-polymeric fiber, yarn, film or fabric.

This invention also relate to methods of producing various surfaces, including metal wires and cords, and polymeric and non-polymeric fibers, yarns, cords, films or fabrics coated with carbon black. In various embodiments, the method for producing such surfaces comprise contacting a dispersion comprising composition of matter comprising SP1 based polypeptide according to this invention, CB (SP1/CB) and optionally latex (SP1/CB/latex) with a surface. Preferably, the method comprises a prestep of desizing of said surface prior to contacting it with the composition. In various embodiments, the method further comprises a step of washing the unbound composition from said surface. In other embodiments, the method further comprises a step of contacting the surface with a solution comprising polyethyleneimine (PEI) prior to contacting the surface with said composition, and after the desizing prestep (PEI primer). Preferably, the steps of contacting the dispersion with the surface, washing the unbound composition and contacting with a solution comprising PEI are repeated at least once; In other embodiments, they are repeated twice; three or four times. In various embodiments, the PEI solution further comprises latex. In various embodiments, the method further comprises a post-treatment step of contacting the surface with PEI as the last step (i.e., PEI capping). In other embodiments, the method further comprises a step of contacting the surface, with latex. In various embodiments, the method further comprises a post-treatment step of contacting the surface with latex as the last step (i.e., latex capping). In various embodiments, the method further comprises a step of contacting said surface with a silane coupling agent. In other embodiments, the silane coupling agent is a tetrasulfido silane. In other embodiments, the silane coupling agent is Bis-Triethoxysilylpropyltetrasulfidosilane. In various embodiments, the method further comprises a step of contacting said surface with a rubber-to-substrate adhesive. In various embodiments, the rubber-to-substrate adhesive is Chemlok® or Chemosil®. In other embodiments, the method comprises a step of contacting the surface, with either one of: PEI solution, latex, a silane coupling agent or a rubber to substrate adhesive as the last step (i.e., capping). In other embodiments, said step of contacting the dispersion comprising the composition of this invention with the surface, is performed using a textile dying machine. Non limiting examples of textile dying machines are: Jigger coating machine for woven fabrics or vertical or horizontal yarn or fabric package dyeing system. In various embodiments, the surface is a metal wire or cord; a polymeric fiber, yarn, film or fabric; or a non-polymeric fiber, yarn, film or fabric.

In various embodiments, this invention is directed to a method of producing a surface coated with carbon black (CB), said method comprises:
 a. Optionally desizing a surface;
 b. Optionally contacting said surface with a solution comprising polyethyleneimine (PEI);
 c. Optionally contacting said surface with latex;
 d. Contacting a dispersion comprising a composition of SP1 Based polypeptide, CB and optionally comprising latex according to this invention with the surface;
 e. Optionally repeating steps (b), and/or (c) and/or (d) at least once;
 f. Optionally contacting said surface, with a solution comprising polyethyleneimine (PEI);
 g. Optionally contacting said surface with latex;
 h. Optionally contacting said surface with a silane coupling agent; and
 i. Optionally contacting said surface with a rubber-to-substrate adhesive.

In various embodiments, the surface is a metal wire or cord; a polymeric fiber, yarn, film or fabric; or a non-polymeric fiber, yarn, film or fabric.

In various embodiments, this invention is directed to a method of producing a surface coated with carbon black (CB), said method comprises:
 a. Optionally desizing a surface;
 b. Optionally contacting said surface with a solution comprising polyethyleneimine (PEI);
 c. Optionally contacting said surface with latex;
 d. Contacting a dispersion comprising a composition of SP1 Based polypeptide, CB and optionally comprising latex according to this invention with the surface;

e. Optionally repeating steps (b), and/or (c) and/or (d) at least once;
f. Optionally contacting said surface with a solution comprising at least one of: polyethyleneimine (PEI), latex, a silane coupling agent, or a rubber-to-substrate adhesive.

In various embodiments, the surface is a metal wire or cord; a polymeric fiber, yarn, film or fabric; or a non-polymeric fiber, yarn, film or fabric. In other embodiments, the dispersion further comprises latex. In other embodiments, the latex is vinyl pyridine latex. In other embodiments, the latex is Styrene-butadiene-2-vinylpyridine latex. In other embodiments, the method further comprises a step of washing the surface with a buffer or water after each step. In other embodiments, the rubber-to-substrate adhesive is Chemlok® or Chemosil®. In other embodiments, the silane coupling agent is a tetrasulfido silane. In other embodiments, the silane coupling agent is Bis-Triethoxysilylpropyltetrasulfidosilane. In other embodiments, the solution comprising PEI, further comprises latex. In other embodiments, the PEI:latex ratio in the solution is 5:1. In other embodiments, the dispersion comprising a composition of SP1 Based polypeptide and CB further comprises latex. In other embodiments, the CB:latex ratio in the solution is between 1:10 to 50:1; between 20:1 to 40:1; between 1:5 to 10:1; or 5:1; 7:1; 10:1; 20:1; or 30:1; each possibility represents a separate embodiment according to this invention.

In other embodiments, said step of contacting the dispersion comprising the composition of this invention with the surface, is performed using a textile dying machine.

Methods of preparing composite materials using SP1/CB complexes include, but are not limited to contacting an SP1/CB dispersion in a solvent with various surfaces, including metal wires and cords, polymers, fibers, films, or fabrics under conditions sufficient to form an SP1/CB-metal or polymer composite, wherein the SP1/CB complex is deposited on the surface. In various embodiments, the surface is dipped into the SP1/CB dispersion to form a SP1/CB coated composite material. The solvent used for the SP1/CB dispersion can be water, common organic solvents or a mixture thereof. Preferably, the solvent is an aqueous solution. In other embodiments, the SP1 variant-CB complex is mechanically blended with latex to form the SP1/CB/latex dispersion. In yet another embodiment, the SP1 variant-CB complex is mixed with latex under a melt-processing condition.

SP1/Carbon Nanotubes/Latex

This invention further describes compositions comprising SP1 Based polypeptide, carbon nanotubes and latex. Such compositions were found to dramatically improve the adhesion of various surfaces, including: metal wires and cords, polymeric and non-polymeric fibers, yarns, films or fabrics, coated therewith to rubber compounds, compared to CNT/SP1 compositions without latex. Such surfaces coated with SP1/CNT/latex composition according to this invention, have improved adhesion to rubber compounds, forming composite rubber compounds which have improved mechanical, electrical and thermal properties.

The present invention provides, in some embodiments thereof, the ability to weave carbon nanotubes into metals and textiles that may be applied to a wide range of uses. Carbon nanotubes with differing characteristics can be woven together to create unique fabrics. For example, carbon nanotubes that serve to electrically insulate can be combined or layered with highly electrically conductive carbon nanotubes to create garments that shield and protect the wearer from electric shock, while electrically conductive carbon nanotubes can be combined in fabric to protect against static buildup. Similarly, thermally conductive carbon nanotubes can be woven into materials that when tethered to a heat sink or source, serve to protect a user from intense thermal environments.

In general, the structural arrangement of the fabric exhibits the mechanical, thermal, electrical, physical and chemical properties associated with carbon nanotubes and the SP1-modified CNT can be incorporated to their surfaces using compositions comprising SP1 CNT and latex.

Carbon nanotubes (CNTs), according to the present invention, include, but are not limited to, multi-wall carbon nanotubes (MWNTs), single-wall carbon nanotubes (SWNTs), double-wall carbon nanotubes (MWNTs), small-diameter carbon nanotubes (having diameters less than ca. 3.5 nm), buckytubes, fullerene tubes, carbon fibrils, and combinations thereof. Such carbon nanotubes can be synthesized via a variety of routes and can be of a variety of lengths, diameters, chiralities (helicities), and purity. Such carbon nanotubes can be endohedrally-doped. Furthermore, the population of a CNT sample can be substantially homogeneous or inhomogeneous in terms of length, diameter, chirality, and/or electronic type. In some embodiments, efforts are taken to purify the nanotubes, and/or separate the nanotubes by type. See, e.g., Chiang et al., J Phys. Chem. B, 2001, 105:8297-8301; and Dyke et al., J. Am. Chem. Soc. 2005, 127:4497-4509; respectively. For a discussion of SWNT types, see Bachilo et al., Science, 2002, 298:2361-2366; and Weisman et al., Nano Lett., 2003, 3:1235-1238.

According to some embodiments, this invention is directed to a composition of matter comprising carbon nanotube (CNT) bound to an SP1 based polypeptide according to this invention and latex (referred herein as "SP1/CNT/latex"). In other embodiments, the carbon nanotube is non-covalently bound to the SP1 based polypeptide. In other embodiments, the SP1 based polypeptide is a wild type SP1 protein. In other embodiments, the SP1 based polypeptide is a chimeric SP1 polypeptide as described herein above. In other embodiments, the SP1 based polypeptide comprises a carbon nanotube or graphitic surfaces binding peptide. In other embodiments, the chimeric SP1 polypeptide has the amino acid sequence as set forth in SEQ ID NO: 8.

In other embodiments, this invention in directed to a composition comprising SP1 based polypeptide according to this invention, CNT and latex (SP1/CNT/latex).

The SP1/CNT/latex composition of matter according to this invention is preferably obtained as a dispersion in solvent. Preferably the solvent is an aqueous solvent. More preferably the solvent is water.

In various embodiments, the SP1/CNT/latex composition is in the form of an aqueous dispersion in a concentration of between 0.001% and 50% w/w. In other embodiments, the composition is in the form of an aqueous dispersion in a concentration of between 0.5% and 30%. In other embodiments, the composition is in the form of an aqueous dispersion in a concentration of between 1% and 20%. In other embodiments, the composition is in the form of an aqueous dispersion in a concentration of between 2% and 8%. In other embodiments, the composition is in the form of an aqueous dispersion in a concentration of 1% w/w, 2% w/w, 3% w/w, 4% w/w, 6% w/w, 8% w/w, 10% w/w, 12% w/w, 14% w/w, 15% w/w, 16% w/w, 17% w/w, 18% w/w, 20% w/w, 22% w/w, 24% w/w, 25% w/w, 28% w/w, 30% w/w; each value represents a separate embodiment of the invention. Preferably, the dispersion concentration is up to 4% w/w; more preferably, the dispersion concentration is 4% w/w.

For use in surface coating methods, the SP1/CNT/latex dispersion is normally diluted to a concentration of between 0.001% and 0.5% w/w. In one embodiment, the concentration is between 0.05% and 0.15% w/w. In other embodiments, the concentration is 0.05%, 0.1% or between 0.05% and 0.1% w/w; each value represents a separate embodiment of the invention.

The SP1/CNT/latex dispersion can be formed in various CNT:SP1 ratios as stable dispersion. In various embodiments, the CNT:SP1 ratio in the dispersion ratio is between 0.1:1 to 10:1 dry weight/weight. Preferably the CNT:SP1 ratio is between 0.3:1 to 6:1 dry w/w. More preferably, the CNT:SP1 ratio is between 2.5:1 to 3:1 dry w/w. In various embodiments, the CNT:SP1 ratio is 2.8 dry w/w. In other embodiments, the CNT:SP1 ratio is 0.2 dry w/w, 0.3 dry w/w, 0.4 dry w/w, 0.5 dry w/w, 0.6 dry w/w, 0.7 dry w/w, 0.8 dry w/w, 0.9 dry w/w, 1.0 dry w/w, 2.0 dry w/w, 2.5 dry w/w, 2.6 dry w/w, 2.7 dry w/w, 2.8 dry w/w, 2.9 dry w/w, 3.0 dry w/w, 3.5 dry w/w, 4.0 dry w/w, 4.5 dry w/w, 5.0 dry w/w, 6.0 dry w/w, or 7.0 dry w/w; each value represents a separate embodiment of the invention. In various embodiments, the SP1 is an isolated SP1. In other embodiments, the SP1 is the crude SP1, i.e. the heat stable fraction of an extract of bacteria expressing the SP1 protein.

The SP1/CNT/latex dispersion can be formed in various CNT:latex ratios as stable dispersion. In various embodiments, the CNT:latex ratio in the dispersion is between 5:1 to 50:1. In other embodiments, the CNT:latex ratio is between 1:1 to 50:1. In other embodiments, the CNT:latex ratio is between 1:1 to 10:1. In various embodiments, the CNT:latex ratio is between 10:1 to 40:1. In other embodiments, the CNT:latex ratio is between 20:1 to 40:1. In other embodiments, the CNT:latex ratio is between 10:1 to 30:1. Preferably, CNT:latex ratio is 10:1 or larger.

In various embodiments, this invention is directed to a polymeric or non polymeric, synthetic or natural fiber, yarn, film, or fabric coated with at least one layer of composition of matter comprising SP1 based polypeptide, CNT and latex according to this invention (SP1/CNT/latex). In other embodiments, the fiber, yarn, film, or fabric is polyester. In other embodiments, the fiber, yarn, film, or fabric is Aramid. In other embodiments, the fiber, yarn, film, or fabric is rayon. In other embodiments, the fiber, yarn, film, or fabric is nylon. In other embodiments, the nylon is a nylon fabric. In other embodiments the nylon is a nylon film. In other embodiments the nylon film is a DVA film. In other embodiments the nylon film is DVA. In other embodiments, the fiber, yarn, film, or fabric according to this invention further comprises a rubber to substrate adhesive.

In various embodiments, this invention is directed to metal cords or metal wires, coated with at least one layer of a composition of matter comprising SP1 based polypeptide, CNT and latex (SP1/CNT/latex) as described herein above. In other embodiments, the cord or wire is made of steel. In other embodiments, the metal comprises steel, aluminum, copper, iron, palladium, platinum, zinc, aluminum alloy, iron alloy, copper alloy, zinc alloy, palladium alloy, platinum alloy, each possibility is a separate embodiment according to this invention. In other embodiments, the metal comprises any combination of aluminum, copper, iron, palladium, platinum and zinc.

In various embodiments, the surface according to this invention further comprises a latex layer. In other embodiments, the surface according to this invention further comprises a latex capping. In other embodiments, the surface according to this invention is capped with a latex layer. In other embodiments, the surface according to this invention is coated with at least one layer of latex. In other embodiments, with one layer; two layers; three layers; or four layers of latex; each possibility represents a separate embodiment of the invention. In other embodiments, the latex is vinyl pyridine latex (VP). In other embodiments, the latex is Styrene-butadiene-2-vinylpyridine In other embodiments, the loading of the latex applied to the surface is between about 0.05% and about 20% (weight latex/weight fabric). In other embodiments, between about 0.5% and about 10%. In other embodiments, between about 5% and about 8%. In other embodiments, between about 6% and about 9%. In other embodiments, between about 6% and about 8%. In other embodiments, between about 2% and about 5%. In other embodiments, between about 0.1% and about 6%. In other embodiments, between about 1% and about 10%. In other embodiments, 0.2%; 0.4%; 0.6%; 0.8%; 1%; 3%; 5%; 7%; 9%; each possibility represents a separate embodiment according to this invention.

In other embodiments, the surface further comprises a polyethyleneimine (PEI). In other embodiments, the PEI is mixed with latex. In other embodiments, the PEI:latex ratio is between about 1:20 to 20:1; 10:1 to 1:10; 1:5 to 5:1; 10:1 to 2:1; 8:1 to 4:1; 8:1 to 6:1; or 6:1 to 4:1. Each possibility represents a separate embodiment according to this invention. In various embodiments, the PEI:latex ratio is 10:1; 9:1, 8:1; 7:1; 6:1; 5.5:1; 5:1; 4:1; 3:1; 2:1 or 1:1. Each possibility represents a separate embodiment according to this invention. In other embodiments, the latex is vinyl pyridine latex (VP). In other embodiments, the latex is Styrene-butadiene-2-vinylpyridine.

In various embodiments, the surface according to this invention further comprises a silane. In various embodiments, the surface according to this invention further comprises a silane capping. In other embodiments, the surface according to this invention is capped with a silane layer. In other embodiments, the surface according to this invention is coated with at least one layer of silane. In other embodiments, with one layer; two layers; three layers; or four layers of silane; each possibility represents a separate embodiment of the invention. In other embodiments, the silane is tetrasulfido silane. In other embodiments, the silane is Bis-Triethoxysilylpropyltetrasulfidosilane.

In various embodiments, this invention is directed to a surface coated with at least one layer of composition of matter comprising SP1 based polypeptide, CNT and latex according to this invention (SP1/CNT/latex), wherein the applied loading of said composition on said surface is between 0.1 gr/kg and 20 gr/kg. In other embodiments, the applied loading of said composition on said surface is between 5 gr/kg and 15 gr/kg. In other embodiments, the applied loading is between 7 gr/kg and 14 gr/kg. In other embodiments, the applied loading is 7 gr/kg. In other embodiments, the applied loading is about 10 gr/kg. In other embodiments, the applied loading is about 10.5 gr/kg. In other embodiments, the applied loading is about 14 gr/kg. In other embodiments, the applied loading is about 3.5 gr/kg. In other embodiments, the applied loading is about 1 gr/Kg, 2 gr/Kg, 3 gr/Kg, 3.5 gr/Kg, 4 gr/Kg, 5 gr/Kg, 5.5 gr/Kg, 6 gr/Kg, 7 gr/Kg, 8 gr/Kg, 9 gr/Kg, 10 gr/Kg, 11 gr/Kg, 12 gr/Kg, 14 gr/Kg, 16 gr/Kg, 18 gr/Kg, 20 gr/Kg, 30 gr/Kg, 40 gr/Kg, 50 gr/Kg, 60 gr/Kg, 70 gr/Kg, 80 gr/Kg, 90 gr/Kg, 100 gr/Kg; each value represents a separate embodiment of the invention. Preferably, the applied loading is 7 gr/Kg. The loading can be achieved by one layer coating or by multi-layer coating; In various embodiments, the loading is achieved by one layer coating; In other embodiments, the loading is achieved by two layer coating; In other embodiments, the loading is achieved by three layer coating; preferably the coating is achieved by two layer coating; e.g. two loadings of 3.5 g/Kg.

In various embodiments, this invention is directed to a surface coated with at least one layer of composition of matter comprising SP1 based polypeptide, CNT and latex according to this invention (SP1/CNT/latex), wherein the applied loading of said composition on said surface is between 0.01% (w/w) and 2.0% (w/w). In other embodiments, the applied loading of said composition on said surface is between 0.5% (w/w) and 1.5% (w/w). In other embodiments, the applied loading is between 0.7% (w/w) and 1.4% (w/w). In other embodiments, the applied loading is 0.7% (w/w). In other embodiments, the applied loading is about 1.0% (w/w). In other embodiments, the applied loading is about 1.05% (w/w). In other embodiments, the applied loading is about 1.4% (w/w). In other embodiments, the applied loading is about 0.35% (w/w). In other embodiments, the applied loading is about 0.1% (w/w), 0.2% (w/w), 0.3% (w/w), 0.35% (w/w), 0.4% (w/w), 0.5% (w/w), 0.55% (w/w), 0.6% (w/w), 0.7% (w/w), 0.8% (w/w), 0.9% (w/w), 1.0% (w/w), 1.1% (w/w), 1.2% (w/w), 1.4% (w/w), 1.6% (w/w), 1.8% (w/w), 2.0% (w/w), 3.0% (w/w), 4.0% (w/w), 5.0% (w/w), 6.0% (w/w), 7.0% (w/w), 8.0% (w/w), 9.0% (w/w), 10.0% (w/w); each value represents a separate embodiment of the invention. Preferably, the applied loading is 0.7% (w/w). The loading can be achieved by one layer coating or by multi-layer coating; In various embodiments, the loading is achieved by one layer coating; In other embodiments, the loading is achieved by two layer coating; In other embodiments, the loading is achieved by three layer coating; preferably the coating is achieved by two layer coating; e.g. two loadings of 0.35% (w/w).

In various embodiments, this invention is directed to a surface coated with a composition of matter comprising SP1 based polypeptide, CNT and latex according to this invention (i.e. SP1/CNT/latex composition), attached to a rubber compound.

In various embodiments, this invention is directed to a rubber compound composite comprising a surface coated with a composition of matter comprising SP1 based polypeptide, CNT and latex according to this invention (i.e., SP1/CNT/latex composition).

In one specific embodiment, SP1 based polypeptides and chimeric SP1 polypeptides, are used to bind carbon nanotubes, and the resulting SP1 polypeptide-CNT-complex is then used to bind the CNT to a polymer fiber, film or fabric, such as aramid (e.g. Kevlar™), for incorporation into rubber tires, in order to enhance the mechanical and/or physical properties (e.g. electrical, mechanical and/or thermal) and function of the tires.

As used herein, the phrase "SP1 based polypeptide-CNT complex" or "SP1/CNT" refers to a composition comprising an SP1 or chimeric SP1 polypeptide, bound to at least one carbon nanotube, for example, as described in detail in Examples 1-3. The phrase "SP1 based polypeptide-CNT-latex complex" or "SP1/CNT/latex" refers to a composition comprising latex and an SP1 or chimeric SP1 polypeptide, bound to at least one carbon nanotube.

As used herein, the phrase "SP1 polypeptide-CNT-latex-polymer complex" or "SP1/CNT/latex-polymer" or "SP1/CNT/latex-coated fiber" refers to a surface such as a metal wire or cord, polymeric and non-polymeric fiber, yarn, cord, film or fabric coated with an SP1/CNT/latex composition according to this invention. In various embodiments, the SP1 polypeptide-CNT-latex complex comprises multiwalled carbon nanotubes (MWCNT). In other embodiments, the SP1 polypeptide-CNT-latex complex comprises single walled carbon nanotubes (SWCNT).

In various embodiments, this invention is directed to a pneumatic or semi-pneumatic tire comprising the SP1/CNT/latex composition of matter according to this invention. In other embodiments, the tire comprises an SP1 polypeptide-CNT-latex-polymer complex according to this invention. In other embodiments, the tire comprises a surface coated with an SP1/CNT/latex composition of matter according to this invention.

This invention also relate to methods of producing surfaces such as metal wires and cords, polymeric and non polymeric fibers, yarns, cords, films or fabrics coated with carbon nanotubes. In various embodiments, the method for producing such surfaces comprise contacting a dispersion comprising composition of matter comprising SP1 based polypeptide according to this invention, CNT and latex (SP!/CNT/latex) with a surface. Preferably, the method comprises a prestep of desizing of said surfaces prior to contacting it with the composition. In various embodiments, the method further comprises a step of washing the unbound composition from said surface with buffer or water. In other embodiments, the method further comprises a step of contacting the surface, with a solution comprising polyethyleneimine (PEI) prior to contacting the surface with said composition, and after the desizing prestep (i.e., PEI primer). Preferably, the steps of contacting the dispersion with the surface, washing the unbound composition and contacting with a solution comprising PEI are repeated at least once; In other embodiments, they are repeated twice; three or four times. In various embodiments, the PEI is mixed with latex. In various embodiments, the method further comprises a post-treatment step of contacting the surface with PEI as the last step (i.e., PEI capping). In other embodiments, the method further comprises a step of contacting the surface, with latex. In various embodiments, the method further comprises a post-treatment step of contacting the surface with latex as the last step (i.e., latex capping). In various embodiments, the method further comprises a step of contacting said surface with a silane coupling agent. In other embodiments, the silane coupling agent is a tetrasulfido silane. In other embodiments, the silane coupling agent is Bis-Triethoxysilylpropyltetrasulfidosilane. In various embodiments, the method further comprises a step of contacting said surface with a rubber-to-substrate adhesive. In various embodiments, the rubber-to-substrate adhesive is Chemlok® or Chemosil®. In other embodiments, the method comprises a step of contacting the surface with at least one of: PEI solution, latex, a silane coupling agent or rubber to substrate adhesive as the last step (i.e., capping). In other embodiments, said step of contacting the dispersion comprising the composition of this invention with the surface, is performed using a textile dying machine. Non limiting examples of textile dying machines are: Jigger coating machine for woven fabrics or vertical or horizontal yarn or fabric package dyeing system.

In various embodiments, this invention is directed to a method of producing a surface such as metal wire or cord, or a polymeric or non polymeric fiber, yarn, cord, film, or fabric coated with carbon nanotubes, said method comprises:

a. Optionally desizing a surface;
b. Optionally contacting said surface with a solution comprising polyethyleneimine (PEI);
c. Optionally contacting said surface with latex;

d. Contacting a dispersion comprising a composition of SP1 Based polypeptide, CNT and latex according to this invention with the surface;
e. Optionally repeating steps (b) and/or (c) and/or (d) at least once;
f. Optionally contacting said surface, with a solution comprising polyethyleneimine (PEI);
g. Optionally contacting said surface, with latex;
h. Optionally contacting said surface, with a silane coupling agent; and
i. Optionally contacting said surface with a rubber-to-substrate adhesive.

In various embodiments, the surface is a metal wire or cord, a polymeric fiber, yarn, film or fabric, or a non-polymeric fiber, yarn, film or fabric.

In various embodiments, this invention is directed to a method of producing a surface coated with carbon nanotubes (CNT), said method comprises:
a. Optionally desizing a surface;
b. Optionally contacting said surface with a solution comprising polyethyleneimine (PEI);
c. Optionally contacting said surface with latex;
d. Contacting a dispersion comprising a composition of SP1 Based polypeptide and CNT and latex according to this invention with the surface;
e. Optionally repeating steps (b), and/or (c) and/or (d) at least once;
f. Optionally contacting said surface with a solution comprising at least one of: polyethyleneimine (PEI), latex, a silane coupling agent, or a rubber-to-substrate adhesive.

In other embodiments, the latex is vinyl pyridine latex. In other embodiments, the latex is Styrene-butadiene-2-vinylpyridine latex. In other embodiments, the method further comprises a step of washing the surface with a buffer or water after each step. In other embodiments, the latex is vinyl pyridine latex. In other embodiments, the latex is Styrene-butadiene-2-vinylpyridine latex. In other embodiments, the rubber-to-substrate adhesive is Chemlok® or Chemosil®. In other embodiments, the silane coupling agent is a tetrasulfido silane. In other embodiments, the silane coupling agent is Bis-Triethoxysilylpropyltetrasulfidosilane. In other embodiments, the PEI has high molecular weight. In other embodiments, the solution comprising PEI, further comprises latex. In other embodiments, the PEI:latex ratio in the solution is 5:1.

In other embodiments, said step of contacting the dispersion comprising the composition of this invention with the surface, is performed using a textile dying machine.

Methods of preparing composite materials using SP1/CNT/latex complexes include, but are not limited to contacting an SP1/CNT/latex dispersion in a solvent with a surface under conditions sufficient to form an SP1/CNT/latex-polymer composite, wherein the SP1/CNT/latex complex is deposited on the surface. In various embodiments, the surface is dipped into the SP1/CNT/latex dispersion to form a SP1/CNT/latex coated composite material. The solvent used for the SP1/CNT/latex dispersion can be water, common organic solvents or a mixture thereof. Non-limiting exemplary organic solvents include less polar hydrocarbon solvent, such as pentanes, hexanes, petroleum ether, benzene and toluene; and polar solvents, such as ether, tetrahydrofuran, dichloraomethane, chloroform, dichloroethane, dimethysulfoxide, dimethylformamide, dimethylacetamide, dioxane, methanol, ethanol, ethyl acetate, acetonitrile, acetone and carbon tetrachloride. Preferably, the solvent is an aqueous solution. In other embodiments, the SP1 variant-CNT complex is mechanically blended with the latex to form the SP1/CNT/latex dispersion. In yet another embodiment, the SP1 variant-CNT complex is mixed with the latex under a melt-processing condition.

Various techniques are suitable for the formation of nanocomposite materials. These include injection molding, extrusion, blow molding, thermoforming, rotational molding, cast and encapsulation and calendaring.

Definitions

As used herein the term "H-Test" Adhesion Method, also known as the "H-block", or "H-pull", refers to a method used for measuring the adhesion of a cord to a rubber. It is used to determine the static adhesion (or force) required to pull a cord (fabric or steel) in the direction of its axis, from a strip of rubber (shaped like an "H") in which the ends of the cords are embedded in the rubber. Failure at the rubber to adhesive interface is considered when there is low rubber coverage of cords after the test. Cord breakage can be considered as a failure of cord.

As used herein the term "Peel Adhesion" Test Method, also regarded herein as "peel test" refers to a test for measuring the overall cord to rubber adhesion. It is used to determine the force required to separate two laminated layers of cords (fabric or steel) bonded together by an intermediate layer of rubber. Good rubber to cord adhesion is considered when a high separation force is needed and high rubber coverage results.

As used herein the term "wire pull-out test" or "ASTM D2229" refers in some embodiments to a Standard Test Method for Adhesion Between Steel Tire Cords and Rubber. Accordingly, the steel cords are vulcanized into a block of rubber and the force necessary to pull the cords linearly out of the rubber is measured.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate some embodiments of the invention in a non-limiting fashion.
General Experimental Concept The studies presented below demonstrate two strategies for altering the binding properties of SP1 variants, namely the affinity and avidity of SP1 variants to various substrates and controlling the immobilization of SP1 on various surfaces. Affinity and avidity are two terms used in protein biochemistry to describe strength of non covalent interactions, the phenomenon whereby certain atoms or molecules have the tendency to aggregate or bond.

The term "affinity" is used to describe the strength of a single bond, while the term "avidity" is use to describe the combined strength of multiple bond interactions affinity. Dissociation constant (Kd), or equilibrium constant, is the inverse of the affinity constant, measures the propensity of a larger object to separate (dissociate) reversibly into smaller components, as when a complex falls apart into its component molecules, or when a salt dissociates into its component ions. The dissociation constant is usually denoted Kd and is the inverse of the affinity constant. In the special case of salts, the dissociation constant can also be called the ionization constant.

The first strategy involves positioning of the anchoring side-chains, such as found in cysteine residues, on the dodecameric protein's ring rim, and comparing the binding properties of the resulting construct with those of a protein construct having anchoring side-chains positioned at the inner side of the annulus (the pore or "hole" of the ring). This strategy uncovers the capacity of the SP1 basic architecture to protect certain regions on its surface, and ligands attached thereat, from surface exposure.

In the second strategy, several binding moieties are attached to the SP1 dodecameric protein at the protein's annulus inner pore by genetic engineering. By fusing these specific affinity peptides at a putative protected part of the protein, the binding moieties are expected to be less available for binding with large entities which are excluded from the protein's pore. This experimental strategy is designed to study the effect of changing the conditions of the media of the protein, and to show that entering a factor to the media, which can affect the structure of the SP1 monomers and thus the structure of the entire dodecamer, can control the degree of exposure of the binding moieties to the media. The event of adding the structure altering factor, such as a denaturating agent, can thus increase the ability of the binding moieties to interact and bind large entities in the media. The capacity to switch from a non-binding entity to a binding entity by adding and removing a chemical factor constitutes a chemical switch.

The concept of a chemical switch was demonstrated by fusing several specific affinity peptides, such as silicon binding peptides, to each of the SP1 basic skeleton, at inner pore position, to thereby obtain a silicon binding protein switch, which is sensitive to the media levels of denaturating agents, such as guanidinium hydrochloride (GuHCl). The affinity peptide was isolated by Sano and coworkers [Sano, K. I. et al. JACS. 125, pp 14234-14235, 2003; Sano, K. I et al., JACS, 128, pp 1717-1722, 2006; and Sano, K. I. et al., Nano Lett., 7, pp 3200-3202, 2007] using a peptide-phage display system. This six amino acids peptide, referred to herein and in the art as mTBP, was reported by Sano and coworkers to bind to Ti, Ag and Si surfaces, but not to Au, Cr, Pt, Sn, Zn, Cu, or Fe.

Thus, a SP1 scaffold was modified to present 12 copies of the mTBP hexapeptide in a switchable manner. A positive cooperative effect is demonstrated when the peptide is presented on the SP1 dodecamer, as compared to the free peptide, accompanied with significant reduction in non-specific binding of the fused peptides compared to that of the free peptide.

Example 1

Construction of SP1 Variants with High Affinity to Various Materials

WO 2007/007325 provides a non-limiting list of peptides forming complexes with inorganic ionic substances, adapted from Sarikaya et al. [Ann. Rev. Mater. Res., 2004, 34, 373-408]. These relatively short peptides are suitable for fusion to the SP1 protein as part of the modification of the SP1 polypeptide. Many more examples of peptides with high affinity to different materials are disclosed in the literature.

Table 1 presents the SP1 variants used in this context, their binding ability, primers used for their construction, mutation or insertion at the N-terminus, SP1 template, reference, and growth conditions/induction. All mutant proteins demonstrated characteristics similar to the wild type SP1 in terms of heat stability, protease resistance and complex formation. Standard nomenclature of mutations is used i.e., amino acids position using wild type sequence including first methionine residue.

TABLE 1

| SP1 variant/ Relevant activity | PCR Primers | Mutation and/or Insertion at the N-terminus | SP1 Template and reference | Growth conditions/ induction |
|---|---|---|---|---|
| Wild type SP1 (SEQ ID NO: 4) | | | U.S. patent application No. 2006/0172298 | Terrrfic broth or Luria broth/ 37° C./ IPTG 1 mM |
| Δ2-6 (SEQ ID NO: 64) | | Δ2-6 | Wang et al. (2006); WO 2007/007325 | Luria broth/ 37° C./ IPTG 1 mM |
| M43C Δ2-6 (SEQ ID NO: 1) | 5'CTGCTCGATC TCATTCCAAGCT GTAAGAGTTTCA ATTGGGGCACG 3' (SEQ ID NO: 65) | M43C Δ2-6 | Δ2-6 | Luria broth/ 37° C./ IPTG 1 mM |
| L81C Δ2-6 Flat gold binding (SEQ ID NO: 2) | 5'GCAAGTCTGG TTTGCAAGAGTA CTGCGATTCTGC TGCTCTTGCTG 3'. (SEQ ID NO: 66) | L81C Δ2-6 | Δ2-6 | Luria broth/ 37° C./ IPTG 1 mM |
| mtbSP Switchable silicon oxide binding CNT dispersion (SEQ ID NO: 3) | 5'-AAAACATAT GCGCAAACTTCC GGATGCGGCAAC CAGAACTCCAAA GCTTG-3' and SP1rev (SEQ ID NO: 67) 5'-AAAAGAGCT CTTAGTAAGAAA GTAATCAATAA C-3') (SEQ ID NO: 68) | RKLPDAA (SEQ ID NO: 5) | M43C Δ2-6 Medalsy et al. (2008); WO 2007/007325 | Terrific broth or Luria broth/ 37° C./ IPTG 1 mM |
| L1-SP1 CNT dispersion (SEQ ID NO: 6) | 5'AAGGAGATAT ACAAAAACATAT GCACTGGTCAGC ATGGTGGATACG ATCAAATCAATC AGCAACCAGAAC TCCAAAG 3' (SEQ ID NO: 70) 5'-CTTTGGAGT TCTGGTTGCTGA TTGATTTGATCG TATCCACCATGC TGACCAGTGCAT ATGTTTTTGTAT ATCTCCTT 3' (SEQ ID NO: 71) | HWSAWW IRSNQS (SEQ ID NO: 10) | Wild type | Terrific broth/ 28° C./ IPTG 1 mM |
| L2-SP1 CNT dispersion (SEQ ID NO: 14) | 5'AGAAGGAGAT ATACAAAAACAT ATGCACTCATCA TACTGGTACGCA TTCAACAACAAA ACAGCAACCAGA ACTCCAAAGC 3' (SEQ ID NO: 72) 5'GCTTTGGAGT TCTGGTTGCTGT TTTGTTGTTGAA TGCGTACCAGTA TGATGAGTGCAT ATGTTTTTGTAT ATCTCCTTCT 3' (SEQ ID NO: 73) | HSSYWY AFNNKT (SEQ ID NO: 11) | Wild type | Terrific broth/ 37° C./, IPTG 0.1 mM |
| L3-SP1 CNT dispersion Kevlar binding (SEQ ID NO: 8) | 5'ATACAAAAAC ATATGGATTATT TTTCATCACCAT ATTATGAACAAT TATTTGCAACCA GAACTCC 3' (SEQ ID NO: 74) 5'GGAGTTCTGG TTGCAAATAATT GTTCATAATATG GTGATGAAAAAT AATCCATATGTT TTTGTAT 3' (SEQ ID NO: 75) | DYFSSP YYEQLF (SEQ ID NO: 12) | Wild type | Terrific broth/ 37° C./ IPTG 0.5 mM |
| L6-SP1 CNT dispersion (SEQ ID NO: 16) | 5'AGAAGGAGAT ATACAAAAACAT ATGTCAAATCAA TCAGCAACCAGA ACTCCAAAGC 3' (SEQ ID NO: 76) 5'GCTTTGGAGT TCTGGTTGCTGA TTGATTTGACAT ATGTTTTTGTAT ATCTCCTTCT 3 (SEQ ID NO: 77) | SNQS (SEQ ID NO: 13) | Wild type | IPTG 1 mM/ 37° C./ Terrific broth |

Example 2

Carbon Nanotubes (CNT) Dispersion by SP1 Variants

The Examples presented below provide SP1 variants, fused to CNT-binding peptides, which are capable of binding to CNT and thereby enable the aqueous dispersion of these protein-coated CNT. Several examples of short peptides that were isolated from phage display libraries as CNT-binding peptides are disclosed in the literature. See, for example, Nature materials, 2003, 2, 196; Nano lett., 2006, 6, 40-44; and Langmuir, 2004, 20, 8939-8941).

Table 2 below presents the terminus sequence of these variants, as well as their purification method and grade, N-terminal sensitivity to digestion by alcalase, and the SP1 variant concentration which is required for CNT dispersion. All mutant proteins demonstrated characteristics similar to the wild type SP1 in terms of heat stability, protease resistance and complex formation. Shift in molecular weight relatively to samples that were not treated with alcalase was observed both in samples that were not boiled or boiled in SDS gel application buffer (complex and monomer, respectively). In all cases the apparent molecular weight of the alcalase treated SP1 variants was higher than those of wild type, indicating that some but not all the added amino-acids were removed, and they are different from published sequences.

TABLE 2

| | | | SDS PAGE analysis | | | |
|---|---|---|---|---|---|---|
| SP1 variant | Peptide fused to the N-terminus | Grade | Complex Formed | N-terminal sensitivity to digestion by alcalase | SP1 concentration required for CNT dispersion (mg/ml) | References |
| Wild type | None | 80° C. plus alcalase treatment | Yes | No | 1 | |
| | | Ion exchange purified protein | Yes | | <1 | |
| mtbSP | RKLPDAA (SEQ ID NO: 5) | 80° C. treatment | Yes | No | 0.2 | U.S. Application No. 20070112174 |
| | | Ion exchange purified protein | Yes | | 0.1 | U.S. Application No. 20070117148 *Nano Lett.*, 2007, 6, 1579-1579. |
| L1-SP1 | HWSAWWIRSNQS (SEQ ID NO: 10) | 80° C. plus alcalase treatment | Yes | Yes | 0.004 | U.S. Pat. No. 7,304,128 U.S. Application No. 20070117147 |
| | | Ion exchange purified | Yes | | 0.004 | |
| | | Ion exchange purified plus alcalase treatment | Yes | | 0.004 | U.S. Application No. 20070117150 U.S. Application No. 20070117148 U.S. Application No. 20040058457 *Nature Materials*, 2003, 2, 196 |
| L2-SP1 | HSSYWYAFNNKT (SEQ ID NO: 11) | 80° C. plus alcalase treatment | Yes | Yes | 0.04 | U.S. Application No. 20060172282 |
| | | Dissolved inclusion bodies | No | Complete digestion | 0.100 | *Nano Lett.*, 2006, 6, 40-44 |
| | | Refolding of IBs | Yes | Yes | 0.1 | |
| L3-SP1 | DYFSSPYYEQLF (SEQ ID NO: 12) | Refolding of IBs 80° C. plus alcalase treatment | Yes | Small shift | 0.1 | U.S. Application No. 20050277160 |
| | | 80° C. plus alcalase treatment | Yes | Small shift | 0.01 | *Langmuir*, 2004, 20, 8939-8941 |
| L6-SP1 | SNQS (SEQ ID NO: 13) | 80° C. plus alcalase treatment | Yes | No | 0.05 | |

Surprisingly, treatment with alcalase and partial digestion of the N-terminus doesn't reduce its ability to disperse CNT. This is probably because in each complex not all N-termini are digested and the L1 variant (SEQ ID NO: 6) complex appears as a double band. For example, N-terminus sequencing and MALDY-TOF analysis of alcalase treated L1-SP1 revealed that 8 amino acids were digested by the protease and the N-terminus was SNQS but the digestion doesn't reduce its ability to disperse CNT. In agreement with this conclusion insertion of the SNQS peptide to SP1 N-terminus yields a variant, L6 (SEQ ID NO: 15), with lower CNT dispersion activity, lower than L1 (SEQ ID NO: 6) (50-100 μg/ml versus 4 μg ml, respectively).

Example 3

Tri-Complexes of SP1 Variants, CNT and Aramid (KEVLAR™) or Epoxy Resin

The capacity of the SP1 variants of the present embodiments to bind to advanced materials, such as KEVLAR™, was studied and demonstrated, as presented in detail in U.S. Pat. No. 8,957,189 herein incorporated by reference in its entirely.

SP1 variants were studied for their capacity as multi-functional reagents which can bind CNT through the N-terminus to form a SP1/CNT complex, which in turn can bind to epoxy resin through exposed primary amines. Such reagents can be highly useful in many practical applications involving water interfaces with CNT, including dispersion in epoxy resin. While water and other mediating solvents can be removed by combination of ultra filtration and freeze drying, these processes are energy consuming and hard to control. The process presented herein takes advantage of the fact that SP1 precipitates in the presence of 70-80% ethanol after 2 hours incubation at −20° C., and so does the CNT protein complex. The precipitated SP1/CNT complex can be easily dispersed in water. The freeze-dried precipitated SP1/CNT complex can be dispersed in epoxy resin as demonstrated in U.S. Pat. No. 8,957,189 herein incorporated by reference in its entirely.

In addition, it was hypothesized that if CNT and aramid (e.g. KEVLAR™—a brand name of a strong and heat-resistant aramid fiber developed by DuPont and used in bullet-proof vests, tires, fiber-optic cables and more) bind to SP1 variants in a similar fashion, the protein may serve as an adhesive mediator to promote attachment of these two components to each other, based on the two-sided doughnut shape of SP1 which exhibits binding sites on both sides of the annulus.

Materials and Methods

Bacterial Strain and Culture Conditions:

*Escherichia coli* strain DH5a was used for cloning and *E. coli* strain BL21 (DE3) was used for expression. Cells were grown in either Luria Bertani medium (ΔNSP1, M43CΔNSP1 and L81CΔNSP1), Terrific broth (L1-SP1, L2-SP1, L3-SP1, L6-SP1), or either Luria or Terrific broth interchangeably (native SP1, mtbSP), at 37° C. (except for L1-SP1, which was grown at 28° C.). After induction with isopropyl P-D-thiogalactopyranoside (IPTG)(1 mM for native SP1, mtbSP1, ΔNSP1, M43CΔNSP1, L81CΔNSP1, L1-SP1 and L-6 SP1, 0.5 mM for L3-SP1 and 0.1 mM for L2-SP1) bacteria were grown for additional 4 hours, followed by harvesting by centrifugation at 14,000×g for 15 minutes.

Vector Construction:

Both M43C ΔNSP1 mutant and L81C ΔNSP1 mutant were constructed using site directed mutagenesis on the ΔNSP1 coding sequence (SEQ ID NO: 7) template (previously described by Medalsy et al. [Nano lett., 8, 473-477, 2008]), performed in accordance to the Stratagene Quickchange (Stratagene, La Jolla, Calif.) protocol with the Pfu-Turbo or Deep-vent DNA polymerase.

Primers used for site directed mutagenesis were: C43 (5' CTGCTCGATCTCATTCCAAGCTGTA AGAGTTT-CAATTGGGGCACG 3')(SEQ ID NO: 65) for M43C, and C81 (5' GCAAGTCTGGTTTGCAAGA GTACTGCGAT-TCTGCTGCTCTTGCTG 3') (SEQ ID NO: 66) for L81C.

The mtbSP1 mutant (SEQ ID NO: 3) was constructed using 2 primers: mTB forward primer (5'AAAA-CATATGCGCAAACTTCCG-GATGCGGCAACCAGAACTCCAAAGCTTG-3') (SEQ ID NO: 67) and SP1 reverse primer (5'-AAAAGAGCTCT-TAGTAAAGAAAGTAATCAATAAC-3') (SEQ ID NO: 68) with M43C ΔNSP1 coding sequence (SEQ ID NO: 69) as a template.

The L1-SP1CNT mutant (SEQ ID NO: 6) was constructed using the primers: forward primer (5'AAGGAGATATA-CAAAAACATATGCACTGGTCAGCATGGTGGATAC-GATCA AATCAATCAGCAACCAGAACTCCAAAG 3') (SEQ ID NO: 70) and reverse primer (5'CTTTG-GAGTTCTGGTTGCTGATTGATTTGATCGTATCCAC-CATGCTGACCAGTGCATATGTTTTTGTATATCTCCTT 3') (SEQ ID NO: 71) with native SP1 coding sequence (SEQ ID NO: 28) as a template.

The L2-SP1CNT mutant (SEQ ID NO: 14) was constructed using the primers: forward primer (5'AGAAGGAGATATACAAAAACATATGCACTCAT-CATACTGGTACGCATT-CAACAACAAAACAGCAACCAGAACTCCAAAGC 3') (SEQ ID NO: 72) and reverse primer (5'GCTTTG-GAGTTCTGGTTGCTGTTTTGTTGTT-GAATGCGTACCAGTATGATGAGTG-CATATGTTTTTGTATATCTCCTTCT 3') (SEQ ID NO: 73) with native SP1 coding sequence (SEQ ID NO: 28) as a template.

The L3-SP1CNT mutant (SEQ ID NO: 12) was constructed using the primers: forward primer (5'ATA-CAAAAACATATGGATTATTTTTCATCACCATATTAT-GAACAATTATTTGCAACCAGAACTCC 3') (SEQ ID NO: 74) and reverse primer (5'GGAGTTCTGGTTGCAAATAATTGTTCAT-AATATGGTGATGAAAAATAATC-CATATGTTTTTGTAT) 3 (SEQ ID NO: 75) with native SP1 coding sequence (SEQ ID NO: 28) as a template.

The L6-SP1CNT mutant (SEQ ID NO:15) was constructed using the primers: forward primer (5'AGAAGGAGATATACAAAAACATATGTCAAAT-CAATCAGCAACCAGAACTCCAAAGC 3') (SEQ ID NO: 76) and reverse primer (5' GCTTTG-GAGTTCTGGTTGCTGATTGATTTGA-CATATGTTTTTGTATATCTCCTTCT 3) (SEQ ID NO: 77) with native SP1 coding sequence (SEQ ID NO: 28) as a template.

The L7-SP1CNT mutant (SEQ ID NO: 16) is identical to L1-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAG-CATGGTGGATTCGATCAAATCAATCAG-3') (SEQ ID NO: 78) and reverse primer (5'-CTGATTGATTT-GATCGAATCCACCATGCTGACCAGT-3') (SEQ ID NO: 79). For A27T mutant, forward primer (5'-GTCAG-CATGGTGGATTCGTTCAAATCAATCAGCAACC-3') (SEQ ID NO: 80) and reverse primer (5'-GGTTGCTGAT-TGATTTGAACGAATCCACCATGCTGAC-3') (SEQ ID NO: 81), using "QuikChange Site-Directed Mutagenesis Kit" of "Stratagene" (La Jolla, Calif.).

The L4-SP1 CNT mutant (SEQ ID NO: 9) is identical to L1-SP1CNT sequence, except for mutation of R23K of the inserted peptide. The mutant polypeptide was constructed using the primers: for R23K mutant, forward primer (5'-TGACTCGGTTCAAGGATGAGATCACAAAAGAACA-GATCGACA-3') (SEQ ID NO: 82), and reverse primer (5'-TGTCGATCTGTTCTTTTGTGATCTCATCCTT-GAACCGAGTCA-3') (SEQ ID NO: 83) using "QuikChange Site-Directed Mutagenesis Kit" of "Stratagene" (La Jolla, Calif.).

The L5-SP1CNT mutant (SEQ ID NO: 17) is identical to L1-SP1CNT sequence, except for mutation of T22C of the inserted peptide. The mutant polypeptide was constructed using the primers: for T22C mutant, forward primer (5'-ACTCGGTTCAAGGATGAGATCTGCCGAGAACA-GATCGACAACTAC-3') (SEQ ID NO: 84), and reverse primer (5'-GTAGTTGTCGATCTGTTCTCGGCAGATCT-CATCCTTGAACCGAGT-3') (SEQ ID NO: 85) using "QuikChange Site-Directed Mutagenesis Kit" of "Stratagene" (La Jolla, Calif.).

The L8-SP1CNT mutant (SEQ ID NO: 18) is identical to L4-SP1CNT sequence, except for mutation of the nucleotide sequence encoding the inserted peptide at 5Ile from ata to att, and at 6Arg from cga to cgt, to improve codon usage. The mutant polypeptide was constructed using the primers: for A24T mutant, forward primer (5'-ACTGGTCAG-CATGGTGGATTCGATCAAATCAATCAG-3') (SEQ ID NO: 78) and reverse primer (5'-CTGATTGATTT-GATCGAATCCACCATGCTGACCAGT-3') (SEQ ID NO: 79). For A27T mutant, forward primer (5'-GTCAG-CATGGTGGATTCGTTCAAATCAATCAGCAACC-3') (SEQ ID NO:80) and reverse primer (5'-GGTTGCTGATT-GATTTGAACGAATCCACCATGCTGAC-3')(SEQ ID NO:81), using "QuikChange Site-Directed Mutagenesis Kit" of "Stratagene" (La Jolla, Calif.).

Wild type SP1 was used as a template for PCR reaction (5'-ACTGGTCAGCATGGTGGATTCGATCAAAT-CAATCAG-3') (SEQ ID NO: 78) and reverse primer (5'-

CTGATTGATTTGATCGAATCCACCATGCTGACCAGT-3') (SEQ ID NO: 79) with native SP1 coding sequence (SEQ ID NO: 28) as a template.

All constructs were inserted into pET 29a expression plasmid (Novagen Inc. Madison Wis., USA).

Protein Purification and Refolding:

After centrifugation, cell pellets were resuspended in lysis buffer (50 mM Tris HCL 1 mM EDTA, 10 mM MgCl2, pH 8) and sonicated on ice for several minutes with pulsed bursts. Variants were expressed as soluble proteins [mtbSP (SEQ ID NO: 3), L1-SP1 (SEQ ID NO: 6), L6-SP1 (SEQ ID NO: 15)], or aggregated into inclusion bodies [L2 SP1 (SEQ ID NO: 14) and L3-SP1 (SEQ ID NO: 8)].

The insoluble pellets were separated by centrifugation at 14000×g for 15 minutes. Soluble mutated proteins (M43C ΔNSP1 and mtbSP1; L1-SP1; L2-SP1; L3-SP1; L6-SP1) were then heat treated at 85° C. for 30 minutes and treated by protease (alcalase, Novozyme 10<6>-fold dilution: 30 min 40° C.)

Inclusion bodies of L81C ΔNSP1 (SEQ ID NO: 2) mutant were washed first for 15 minutes with the IB washing buffer (20 mM Tris HCL, 2 M urea, pH 8) and thereafter centrifuged at 14000×g for 15 minutes. The pellets were resuspended in denaturation buffer (20 mM Tris HCl, 6 M urea, 10 mM dithiothreitol, pH 8) and diluted to protein concentration of 5 mg/ml. Denaturated proteins were then refolded by dialysis against a folding buffer (20 mM Tris HCl, 1 mM DTT, pH 7) for 4 days.

Ion Exchange FPLC:

Hitrap Q Sepharose XL column (1 ml) (Amersham Biosciences, Piscataway, N.J. USA), was used to purify the proteins. Samples were loaded on the column using 20 mM piperazine pH 6.3 buffer at a flow rate of 3 ml/min Elution was conducted with a gradient of 1 M NaCl in the same buffer and determined at 27-33% salt.

mTBP Appendage Peptide:

mTBP peptide (SEQ ID NO: 5) was synthetically manufactured by BioSight ltd. (Karmiel, Israel).

Stability Characterization of Mutated Proteins:

Three different stability analyses were performed on the wild-type SP1 (SEQ ID NO: 4) and each of the mutated proteins.

1. Heat treatment (H.T) at 80° C. for 30 minutes;

2. Boiling treatment (B.T.) at 100° C. for 30 minutes; and

3. Resistance to proteolysis by proteinase K (PK) at a concentration of 50 ug/ml of the enzyme for one hour at 37° C. PK was eliminated by B.T. for 5 minutes.

Alternatively, alcalase was used to determine stability: Alcalase (Novozyme, 1:1000 dilution) was added at 40° C. for 30 mM Reaction was stopped by inhibition of alcalase at 80° C. for 30 min All treatment were followed by centrifugation at 14,000×g for 15 minutes, and analyzed by SDS-PAGE.

Silica Binding:

mtbSP1 (SEQ ID NO: 3) was mixed with 10 mg silica gel (product no: 28,860-8, Sigma-Aldrich, USA) in 10 mM MES pH 6.5, 150 mM NaCl, with or without 3M GuHCl. The solution was then incubated for one hour on a rotary shaker at room temperature. Thereafter the silica was washed three times with the same buffer without GuHCl. Bound protein was analyzed either by SDS-PAGE or by measuring protein concentration using the Micro BCA assay kit (Pierce, Rockford, USA).

Surface Preparation and Binding:

SP1/CNT Binding:

SP1/CNT Binding to Aramid was Evaluated Using Three Methods:

1. Determination of the difference between CNT content in solution (suspension) before and after its binding to the fabric. CNT content of a suspension is determined by precipitating the SP1/CNT from a sample of the suspension using guanidinium hydrochloride (100 mM) or HCl (0.3%), before and after its incubation with the fabric (combined with the washing solution), drying the pelleted CNT, and weighing;

2. Spectroscopy: CNT content can be evaluated using spectroscopic method, namely, light transmittance by visualization of a fabric or surface coated by CNT at high resolution under a scanning electron microscope (HR-SEM); and 3. Surface resistivity-CNT content of a coated fabric or surface can be assessed by measuring surface resistivity to current flow (this method is relevant only in cases in which the untreated fabric is a insulator or very poor conductor).

Example 4

Carbon Nanotubes (CNT) Dispersion by SP1 Variants

Materials and Methods:

Multi wall carbon nanotubes (MWCNT) were obtained either from Arkema Inc., France (GRAPHISTRENGTH™ C100) or from Bayer MaterialScience AG, Germany (Baytubes C150 P). Single wall carbon nanotubes (SWCNT) were obtained from Teijin, Ltd (Yamaguchi, Japan).

For small scale production, between 1.0 and 1.3 mg of MWNTs were weighed in 1 ml screw-cap glass tube (Fisherbrand, cat. no. 03-338 AA, size 12×35 mm, ½ DR). A 1 ml protein solution in NaPi buffer (10 mM; pH 8.0) was added to the screw-cap glass tubes containing pre-weighted MWNTs. The resulting mixture was sonicated for 2 hours at 80° C. using an Elma Transsonic Sonifier. The sonicated samples were first centrifuged in an Eppendorf centrifuge tube for 20 minutes at 20000×g. Ninety percent of the upper supernatant was separated using a pipette, avoiding taking the sediment at the bottom, and transferred to another Eppendorf centrifuge tube. The separated supernatant samples were diluted ten-fold. The CNT dispersion by L2-SP1 (SEQ ID NO: 14) was also tested in Tris buffer (10 mM; pH 8.0) with or without urea.

For larger scale production, 400-mg of MWCNT were weighed into a glass flask, a protein solution (400 ml in NaPi buffer; 10 mM; pH 8.0) was added, and the mixture sonicated at a power setting of 260 W for 4 hours, maintaining a maximal temperature of less than 50° C., using a Misonix 4000 Sonicator with a booster home, a 1 inch flat tip and a temperature control unit or a Hielcher sonicator (UIP1000 hd). In order to obtain full dispersion of the sample, the sonicated samples were centrifuged in an Eppendorf centrifuge tube for 20 minutes at 20000×g until only a minor pellet was formed. After pelleting of the undispersed material, the supernatant was very dark with the CNT, even after 100 fold dilution in the same buffer. The last step was centrifugation of the suspension for 60 minutes at 7000 rpm using a Sorval SLA 3000 centrifuge.

Results:

Table 2 hereinabove, presents the results of the CNT dispersion experiments. The SP1 variants described in Table 2, are heat stable and generally protease resistant, however, incubation with alcalase (1000-fold dilution) causes a shift in the molecular weight relative to samples not treated with alcalase. In all cases the apparent molecular weight of the alcalase-treated SP1 variants was still higher than those of native SP1, indicating that some but not all the amino-acids derived from the CNT binding peptides were removed.

As can be seen in Table 2, fusion of copies of these CNT binding peptides to SP1 N-terminus improves the SP1's ability to disperse multi wall carbon nanotubes (MWCNT) in a solvent, while native SP1 protein affords MWCNT dispersion only at high SP protein concentrations (approx. 1 mg/ml). As can further be seen in Table 2, the fusion proteins have a much higher CNT-binding activity. The greatest CNT dispersing capability was observed with L1 (SEQ ID NO: 6), an SP1 polypeptide with the HWSAWWIRSNQS peptide (SEQ ID NO: 10) fused to the N-terminus, which allowed MWCNT dispersion at the relatively low concentration 0.004 mg/ml. Fusion of SP1 with the other CNT-specific peptides L2 (SEQ ID NO: 14) and L3 (SEQ ID NO: 8) [HSSYWYAFNNKT (SEQ ID NO: 11) and DYFSSPYYEQLF (SEQ ID NO: 12) peptides respectively] also resulted in greater CNT dispersing activity than native SP1. Using the L3-SP1 the Hielcher sonicator, maximal CNT concentration was 40 mg CNT/gr fabric, or 4%. If SP1 solubility is as high as 150 mg/ml theoretically, maximal CNT concentration, can be as high as 30%.

Variants L2-SP1 (SEQ ID NO: 14) and L3-SP1 (SEQ ID NO: 8) differ from other SP1 variants in that they form both soluble and insoluble protein found in inclusion bodies (IB). The protein found in IB can be dissolved in the presence of urea and refolds upon urea dilution. While properly folded L2-SP1 forms complexes and was protease resistant, the dissolved L2-SP1 from IB did not form complexes and was protease sensitive. The L2-SP1 and L3-SP1 from inclusion bodies can disperse CNT but with much less efficiency than the soluble protein (Table 2).

As can be seen in Table 2 hereinabove, the minimal SP1 concentration required for CNT dispersion depends on the sequence of the peptide fused to the N-terminus.

In the case of L1-SP1 (SEQ ID NO: 6), an ion exchange purified protein was treated with alcalase, and the protein underwent N-terminus sequencing and molecular weight determination using MOLDY-TOF. The results indicated that 8 amino acids were digested by the alcalase from its N-terminus, leaving the SNQS peptide fused to the protein N-terminus. It is noted herein that the SP1 variant with an insertion of the SNQS peptide at the N-terminus (L6-SP1, SEQ ID NO: 15) exhibited similar characteristics, namely mobility in SDS PAGE and CNT dispersion ability, as compared to the alcalase-treated L1-SP1.

In addition to the CNT specific peptides, fusion of the silicon/titanium oxide binding peptide (RKLPDAA) (SEQ ID NO: 5), which yields the SP1 variant mtbSP1 (SEQ ID NO: 3), was found to facilitate CNT dispersion at lower concentration than native SP1.

For industrial applications it is preferred to keep the protein production costs as low as possible, and to make sure that other peptides that may exist in the crude extract of transformed cells expressing a recombinant protein do not interfere with the variant SP1's CNT dispersion capability. To test this facet, crude extract obtained from bacteria transformed to express L1-SP1 was exposed to combinations of heat and protease treatments, and was then assessed for the retention or loss of CNT dispersion activity, as presented in Table 3.

TABLE 3

| Crude extract treatment | | | CNTs dispersion | |
|---|---|---|---|---|
| | Heat treatment | Alcalase treatment | Maximal dilution | Minimal protein concentration μg/ml |
| Standard treatment. | 80° C., 30 minutes X 2 | + | 1:26 | 10 |
| Heat treatment. | 80° C., 120 minutes | − | 1:26 | 9.3 |
| Alcalase treatment with final inactivation of alcalase | 80° C., 30 minutes after alcalase treatment | + | 1:26 | 6 |
| Alcalase treatment without final Inactivation of alcalase. | — | + | 1:26 | 11 |

As can be seen in Table 3, the heat treatment of crude extract of L1-SP1, up to 120 minutes at 80° C. and proteolysis used during the preparation of the mutant, did not abolish the capacity to disperse CNT.

A direct demonstration that L1-SP1 binds to CNT and forms a complex was obtained by comparing a suspension of a sample of L1-SP1 (SEQ ID NO: 6) with CNT (L1-SP1/CNT), a sample of the protein without CNT (L1-SP1) and a filtrate (0.22 micron filter) of these two samples before and after boiling. Both the boiled and not boiled samples were analyzed by SDS PAGE.

The boiled L1-SP1 was detected as a band of the monomeric form and a band of the trimeric form, while the unboiled L1-SP1 appears as a high molecular weight complex only.

A large fraction of the CNT was excluded by filtration, therefore longer than 0.22 micron. The proportion of the SP1 trimer bands in the absence of CNT was lower than that detected in the presence of CNT, both in the filtrates and in the unfiltered samples. Apparently not all the protein dissociated upon mixing with the SDS Tricine sample buffer and SDS PAGE application.

Another indication that the L1-SP1 protein (SEQ ID NO: 6) binds to the CNT comes from the protein determination assay (Bradford protein assay) of both mtbSP-SP1/CNT suspension and the microfiltration (0.2 micron) flow-through, demonstrating that about 50% of the protein after CNT complexing is larger than the 0.2 micron pore size and is retained by the filter (data not shown).

Yet further evidence for the formation of a SP1-CNT complex is seen in the results of ethanol precipitation (Table 3): While uncomplexed protein does not precipitate with 50% ethanol, SP1-CNT does precipitate with 50% ethanol. CNT precipitate also with GuHCl (100 mM) and in acidic pH (by adding HCl or acetic acid), however, while GuHCl does not induce uncomplexed protein precipitation but acidic pHs does. This phenomenon is used to determine CNT concentration to fabrics.

Heat stability, protease and alkali resistance of L1-SP1-CNT complex: To assess the stability of the complex, L1-SP1/CNT was subjected to heat treatment (100° C.; 10 minutes or 80° C.; 30 minutes) both at pH 8.0 and pH 11, or proteolysis at pH 8.0. Incubation of L1SP1/CNT samples, at different pHs, were followed by high speed centrifugation (20 minutes; 20000×g) and 10-fold dilution of the supernatant. The results of the heat and proteinase assays demonstrate that the SP1/CNT complex is heat stable and protease resistant, allowing economically desirable heat drying and powdering of the complex prior to its dispersion in important polymeric compounds, such as epoxy.

The high durability of the SP1/CNT complex allowed the development of simple method to obtain a dry pellet of SP1/CNT complex that can easily re-dispersed in water. The process includes first dispersion of 4% CNT, followed by three steps of wash and precipitation by 1:5 dilution in ethanol (final 99% ethanol), and dehydration using a vacuum pump.

Example 5

SP1 Variants Binding to Aramid (e.g. KEVLAR™)

Material scientists and engineers are excited by the possibilities for creating super-strong, high-performance polymer composite materials using carbon nanotubes. Currently, all existing methods of fabricating CNT-polymer composites involve complicated, expensive, time-demanding processing techniques such as solution casting, melting, molding, extrusion, and in situ polymerization, requiring that the nanotubes either be incorporated into a polymer solution, molten polymer or mixed with the initial monomer before the formation of the final product (e.g. yarn, ribbon or film). This is unsuitable for insoluble or temperature sensitive polymers, which decompose without melting.

Aramid polymers (e.g. KEVLAR™) is a well known high-strength polymer with a variety of important applications such as pneumatic tire tread and sidewalls, bullet-proof vests and car armor plating. However, aramid (e.g. KEVLAR™) is not soluble in any common solvent and, having no melting point, decomposes above 400° C. As a result, aramid (e.g. KEVLAR™) fibers must be produced by wet spinning from sulphuric acid solutions. Binding of SP1/CNT complex to aramid (KEVLAR™) was assessed for effective post-processing incorporation of carbon nanotubes to the surface of already formed polymer products, such as, for example, aramid (KEVLAR™) yarns.

CNT binding to the fabric via the protein increases its surface area, allowing better interaction with the fiber and induces cross linking between the fibers. In addition, protein biding to the fiber by itself may improve the interaction with the polymer through reactive groups on the protein surface. It is demonstrated that some SP1 variants that bind CNT also bind to structural fibers.

Materials and Methods

L3SP1/CNT solution (SEQ ID NO: 8), in different concentrations (22 µg/ml, 44 µg/ml, and 88 µg/ml samples in 10 mM NaPi, pH-8) was incubated with 100 mg of aramid (KEVLAR™) fabric in a rotary shaker at 25° C. for 16 hours, followed by extensive wash with the same buffer to remove traces of the unbound protein and CNT, until the solution was colorless, indicating absence of CNT, and until no protein was detected in the wash. CNT binding to the aramid (KEVLAR™) was assessed by darkening of the aramid (KEVLAR™) fibers. SP1 binding to the washed aramid (KEVLAR™) was determined by reacting the aramid (KEVLAR™) with 2 ml of BCA protein assay reagent (Pierce, cat No. 23227) for 30 minutes at 37° C., and measurement of optical density at 562 nm. The amount of protein bound was calculated and plotted, and the results are presented in U.S. Pat. No. 8,957,189 herein incorporated by reference in its entirely.

SP1/CNT binding to aramid was evaluated by precipitation, light transmittance (spectroscopy, visual inspection) and surface resistivity, as detailed above.

Results

Comparison of the bound and unbound fibers after incubation with the L3 SP1/CNT complex, indicated extensive binding of the CNT, even after exhaustive washing (not shown). BCA protein assay also showed that SP1/fabric (w/w) ratio is approximately 2 mg protein/g fiber (2/1000). In parallel experiments it was demonstrated that L-1-SP1 (SEQ ID NO: 6) and L-4 SP1 (SEQ ID NO: 9) also bind to aramid (KEVLAR™). Following incubation with L3-SP1/CNT aramid (KEVLAR™) fibers turned dark in color, indicating binding of the CNT thereto even after extensive wash. Incubation of 30 mg aramid with 180/1000 w/w L4-SP1-CNT dispersion, followed by bath sonication (90 min temperature ranging between 30-70° C.), fiber removal, extensive washing (using the buffer) and boiling (10 min in 60 ul) to extract bound protein and CNT produced darkened fibers bearing bound protein as well as bound CNT.

CNT dispersion (0.1% CNT (Arkema, code C100), using L3SP1 (SEQ No 8)) was incubated with aramid fabric (KEVLAR style 120 plain weave 195 Denier, 58 g/m square; 22 ml suspension per g fabric) by agitation (1 h; 25° C.; 150 rpm) followed by extensive wash in the same buffer, and drying in the open air, overnight. CNT content on fabric was about 9 mg/g fabric. Note that the bound CNT dramatically increases surface area, and that the CNT are in close contact with one-another, affording improved electrical conductive properties.

Example 6

SP1 Variants Binding to Carbon Fabric

Carbon fabric is a well-known high-strength material with a variety of important applications in aerospace and automotive fields, as well as in sailboats and sport equipment, where its high strength-to-weight ratio is of importance. Continuous carbon fiber/epoxy composites have been widely used for structural applications due to their excellent mechanical properties. The polymer is most often epoxy, but other polymers, such as polyester, vinyl ester or nylon, are also used. However, their matrix-dominant properties, such as in-plane and interlaminar shear properties, are much weaker than their fiber-dominated properties, thus limiting the benefits of these conventional composites. In addition, it is known that composites exhibit lower longitudinal compressive strength, a matrix-dominated property, than tensile strength.

CNT binding to the fabric via the protein increases its surface area, allowing better interaction with the fiber, and induces cross linking between the fibers. In addition, protein binding to the fiber by itself may improve the interaction with the polymer through reactive groups on the protein surface. It is demonstrated that some SP1 variants that bind CNT also bind to structural fibers.

Materials and Methods

Production of SP1-CBD Dissolved Inclusion Bodies:

SP1-CBD is expressed in bacterial hosts as insoluble inclusion bodies (IBs), as described in U.S. Pat. No. 7,253,341 to Wang et al. Briefly, SP1 cDNA encoding a 108 SP1 amino acid sequence (SEQ ID NO: 88) was cloned into an expression vector bearing a nucleotide sequence encoding a 163 amino acid CBD domain of *Clostridium cellulovorans* cellulose binding protein A (SEQ ID NO: 87). The resulting nucleic acid construct encoded a SP1-CBD fusion protein which includes a peptide linker (SEQ ID NO: 89). Following cloning, the resulting plasmid was used to transform *E. coli* strain BL21 (DE3). Recombinant CBD-SP1 fusion protein synthesis was induced in BL21 (DE3) by the addition of IPTG (isopropyl-D-thiogalactoside) to a final concentration of 1 mM to mid-log phase of the bacterial culture, followed by five additional hours induction at 37° C. Recombinant SP1-CBD fusion protein (SEQ ID NO: 86) was detected in inclusion bodies (IB), and the inclusion bodies isolated and purified. Briefly, IBs containing SP1-CBD were dissolved in Trisma base (20 mM), NaOH (8 mM) (30, min on ice, 1:200 ratio (w/v)), followed by high speed centrifugation, 13,000 rpm for 30 min. The supernatant was diluted 1:10 in water and the pH was adjusted to pH=8.2 (using NaPi buffer, 100 mM pH=6.8).

SP1 Polypeptide-CNT-Complex Binding to Carbon Fiber

Carbon (also glass and aramid) fabrics were washed with phosphate buffer (10 mM; pH 8) in a rotary shaking bath (160 r/min, 10 min, at room temperature) and then incubated in a rotary shaking bath (1 h each side, 160 r/min, room temperature) containing aqueous SP1/CNT (SEQ ID NO: 8) suspension (suspension/fabric w/w ratio was 5:15; CNT concentration was 0.05-0.4%, termed the "applied fraction"). The remaining suspension of CNTs was termed the "unbound fraction". SP1/CNT PAN fabrics were then extensively washed with deionized water, termed the "wash fraction", until the washing solution became colorless. The treated fabrics were then air-dried for 1 week. To confirm and quantify CNT binding to the fabric, the amount of CNT in the "unbound ḃ washed" fractions was subtracted from its amount in the "applied" fraction. For analytical purposes, the concentrations of SP1/CNT complex in dispersions were determined by two methods with similar results. The maximal CNT binding as measured by this "subtraction" method was about 4 mg CNT/gr fabric 0.4%:

1. Gravimetric method when the dispersion is coagulated & flocculated by using HCl (0.3%), followed by centrifugation (10 min, 2500 g) and pellet dehydration in the oven (80C, overnight), followed by dry weight measurements.
2. Measuring absorption of diluted L3-SP1/CNT suspension before and after its incubation with the fabric, including the fabric washing solutions, using standard spectrophotometer or 96-well plate reader at 405 nm
3. Bound SP1/CNT can be extracted from wet fabric using 0.5% SDS, but not by using water. However, this extraction method is not practical for evaluation of amount of bound SP1/CNT because of the following reasons: even after very intensive extraction a significant proportion of the CNT is still bound to the fibers (evaluated by HR-SEM analysis); small broken pieces of fibers are released by the extraction mixture.

Taken together, the results brought herein show that broad variation of specifically designed SP1 variants can form molecular complexes with CNT, enhancing physico-chemical characteristics of these molecules such as dispersion in solvents, which molecular complexes can be useful, for example, in the production of highly specific composite materials such as SP1-polypeptide-CNT-aramid complex fabrics, yarns and polymeric fabrics, and CNT-nanostructures.

Example 7

Preparation and Characterization of Carbon Nanoparticle (CNP)/Latex Dispersions A heat stable crude extract of recombinant L3SP1 protein was used to disperse carbon nanoparticles including carbon nanotubes (CNT) and carbon black (CB) in different grades: dispersions of Graphistrength® C-100 Arkema and carbon black particles CB-N326 were thoroughly characterized (Table 4). Dispersion was conducted using Sonication (Hielscher Ultrasonics processor UIP1000 (1000 W), frequency: 20 kHz (autoscan), amplitude: 25 mm (85%), 40 min sonication). Stability upon centrifugation was used as a measure for dispersion quality, by calculating the fraction of CNP remaining in the supernatant under standard centrifugation conditions. Both gravimetric and spectral methods were used to determine the ratio of CNP concentration before and after centrifugation (Table 4). Note that in the absence of any protein the dispersion precipitate even after long sonication time (not shown).

Table 4 and FIG. 1A show the characterization of the water based MWCNT and Carbon black (CB) nanometric dispersion.

TABLE 4

Characterization of dispersion made by conjugation of the SP1 protein together with carbon nanoparticles (CNP; multiwall carbon nanotube and carbon black)

| | MWCNT Graphi | Carbon Black | | | | |
|---|---|---|---|---|---|---|
| Carbon nanoparticle | strength ® C-100 Arkema | N326 | Conductive CB | CB 220 | CB 550 | CB 660 |
| SP1 Variant | Heat stable crude extract of recombinant L3SP1 protein | | | | | |
| Maximal SP1/CNP dry weight/weight ratio | 2.9 ± 0.5 | 7 | 5.5 | 4.5 | 5.5 | 5.5 |
| Dispersion Method | Sonication[1] | | | | | |
| SP1/CNP concentration | 4% | 17% | 4% | 4% | 4% | 4% |
| Fraction of CNP remain in supernatant upon centrifugation[2] | <25% | <30% | 45% | 25% | 20% | 75% |

TABLE 4-continued

Characterization of dispersion made by conjugation of the SP1 protein together with carbon nanoparticles (CNP; multiwall carbon nanotube and carbon black)

Figure 3:
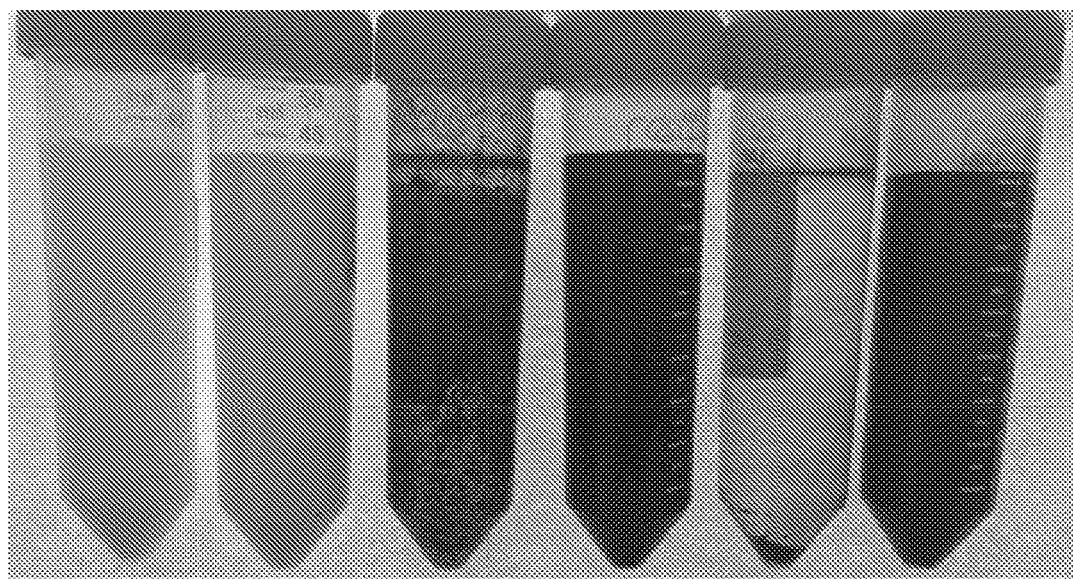

| Carbon nanoparticle | MWCNT Graphi strength ® C-100 Arkema | Carbon Black N326 | Conductive CB | CB 220 | CB 550 | CB 660 |
|---|---|---|---|---|---|---|
| Long term stability at room temp[3] | <12 months | <4 month | ND | ND | ND | ND |
| pH stability | 5.5-11 | 5.5-11 | ND | ND | ND | ND |
| stability in the presence of divalent cation ($Ca^{+2}$ $Mg^{+2}$) | >0.3 mM | >3 mM | | | | |
| Relative adhesion of Polyester yarn coated with the SP1/CNP/genflo with neoprene rubber[4] | 100% | 100% | 56% | 70% | 70% | 70% |

[1]Sonication was conducted using a Hielscher Ultrasonics processor UIP1000 (1000 W), requency: 20 kHz (autoscan), amplitude: 25 mm (85%), 40 min sonication.

[2]Stability upon centrifugation, a quantify measure for dispersion quality, was assessed by calculating the fraction of CNP remaining in the supernatant under centrifugation (dispersion was diluted to 0.1% in sodium phosphate buffer (10 mM; pH 8.0); Supernatant was collected after centrifugation (30 min; 3000 g, in 50 ml Falcon tube; 25° C.)). Both gravimetric and spectral methods were used to determine the ratio of CNP concentration before and after centrifugation. Gravimetric method: CNPs were flocculated with 0.3% HCl, spun down (10 min, 4700 g), followed by pellet dehydrated (80 C., overnight), and dry weight measurement (detonated supernatant (S)). The same procedure was conducted also on the dispersion before centrifugation (detonated total (T)). Stability upon centrifugation was calculated according to the following equation: 1 − (T − S)/(T). Spectral method: optical density of diluted dispersion was determined at 405 nm using 96 plate reader. Note that there is a linear correlation between CB concentration and optical density. Ratio of the optical density of the dispersion before and after centrifugation was determined.

[3]Long term stability was determined upon long term storage of concentrated dispersion at room temperature as described in 2.

[4]H-test results (Load at Maximum Load (N), ASTM 4776) of yarns coated with SP1/CNP/latex, (1.05 g/Kg in two layers), was determined with a neoprene rubber compound. Results are expressed relative to untreated yarn (UT, 31N) and resorcinol-formaldehyde/latex coated yarn (RFL, 66N), according to the following equation: (X − UT)/(RFL − UT).

FIG. 1A shows the HR SEM image of SP1/CB (N326) dispersion.

The effect of time of sonication on SP1/CB dispersion at different SP1/CB concentration and dry SP1/CB w/w ratio is shown in FIG. 2A. Minimal time of sonication is 30 min at low dry SP1/CB w/w ratio (5.5) regardless SP1/CB concentration, but longer time of sonication (60 min) is required at higher dry SP1/CB w/w ratio (7). Maximal SP1/CNT and SP1/CB concentration are 4% and 17%, respectively. Long term stability tests at room temperature of 4% dispersion SP1/CNT and SP1/CB-N326 are <12 m and <4 m, respectively (Table 4). The SP1/CNT and SP1/CB dispersions are stable at wide range of pHs (pH=5.5-11) but precipitate in the presence of divalent cations (Mg+2 and Ca+2) in concentrations of >0.3 mM and >3 mM, respectively.

SP1/CNP precipitation at low pH and in the presence of divalent cations have several practical implications: for example, low pH and the presence of divalent cations are useful conditions for CNP recycling and for toxic waste reduction. All steps with the water based dispersion of SP1/CNT and SP1/CB were carried out with de-ionized water (Concentration of divalent cations<10 μM).

High resolution SEM images of SP1/CB (N326) dispersion (FIG. 1A) demonstrate that the dispersion is nanometric (particle/aggregate size is <500 nm). SP1/CNT dispersions were already shown to be nanometric by high resolution SEM and TEM images (U.S. Pat. No. 8,957,189).

Dispersion of Other Types of Carbon Black: Conductive CB, CB220, CB550 and CB660.

The same methodology used for Graphistrength® C-100 and CB-N326, was used to disperse other types of carbon black: conductive CB, CB220, CB550 and CB660. All CNPs were dispersed to some degree (Table 4). The difference in stability upon centrifugation may be attributed to differences in specific gravity.

CNP/protein (Heat stable crude extract of recombinant L3SP1 protein) ratio is 2.8 and 7 for multiwall carbon nanotube (MWCNT) and carbon black (CB), respectively. Maximal dispersion concentration is 4-5% and 17% for multiwall carbon nanotube (MWCNT) and carbon black (CB), respectively. Note that for single wall CNTs which display much higher surface specific area, CNT/protein ratio is 8-fold lower. Therefore, much lower protein concentrations are needed in order to disperse CNP with pure protein (MWCNT/protein ratio=20), but since protein purification is costly, crude extract is used without further purification. In the absence of protein, the CNPs are not dispersed but rather readily precipitate on the bench. Dispersions stability for few months, also at elevated temperature is essential for industrial application. The complexation of CNP with SP1 protein enables the dispersion of CNPs and enhances its stability. Dispersion of latex with CNPs was made by mixing the SP1/CNP dispersion with various brands of latex dispersions (Genflo, GENTAC® 2002, Encord-106 VP, Pyratex) using sonication (See Table 5 for the brands that were used). Evidence for the formation of a SP1/CNP/latex complex was given by the acid precipitation of SP1/CNT/latex mixture and nanoparticle tracking analysis. While latex beads (e.g., genflo2002® latex) don't precipitate at low pH (0.3%), both the SP1/CNP complex and the SP1/CNP/latex composite precipitate (FIG. 3). However, interestingly, while precipitation of the SP1/CNP complex leads to formation of a stable pellet in the bottom of the tube, in the case of the SP1/CNP/latex complex, the pellet is stuck to the walls of the tube indicating that the pellet density is different (FIG. 3).

Table 5 shows a list of various latex beads that when combined with SP1/CNT or SP1/CB improve adhesion of polyester yarns to rubber. Improved adhesion was obtained when Latex/CNP dry weight to weight ratio was around 10-30.

TABLE 5

Effect of latex beads in combination with both SP1/CNT and SP1/CB on rubber adhesion with polyester yarns. Latex beads in combination with SP1/CNT improve neoprene rubber adhesion with polyester and Kevlar yarns.

| | | H-test Results[2] Polyester yarn coated with | |
|---|---|---|---|
| name | Description | SP1/CNT/ latex[1] | SP1/CB/ latex[1] |
| No latex | | About 5%[3] | 100% |
| Genflo | Carboxylated Styrene Butadiene polymers | 125% | 100% |
| GENTAC ® 2002 | vinylpyridine/butadiene/ styrene | 81% | ND |
| Encord-106 VP | Styrene:Butadiene:Vinyl Pyridine: (15:70:15) dispersed in an aqueous medium | ND | 100% |
| Pyratex | an aqueous dispersion of a copolymer of butadiene, styrene and 2-vinylpyridine. | ND | %96 |

Figure 1A:
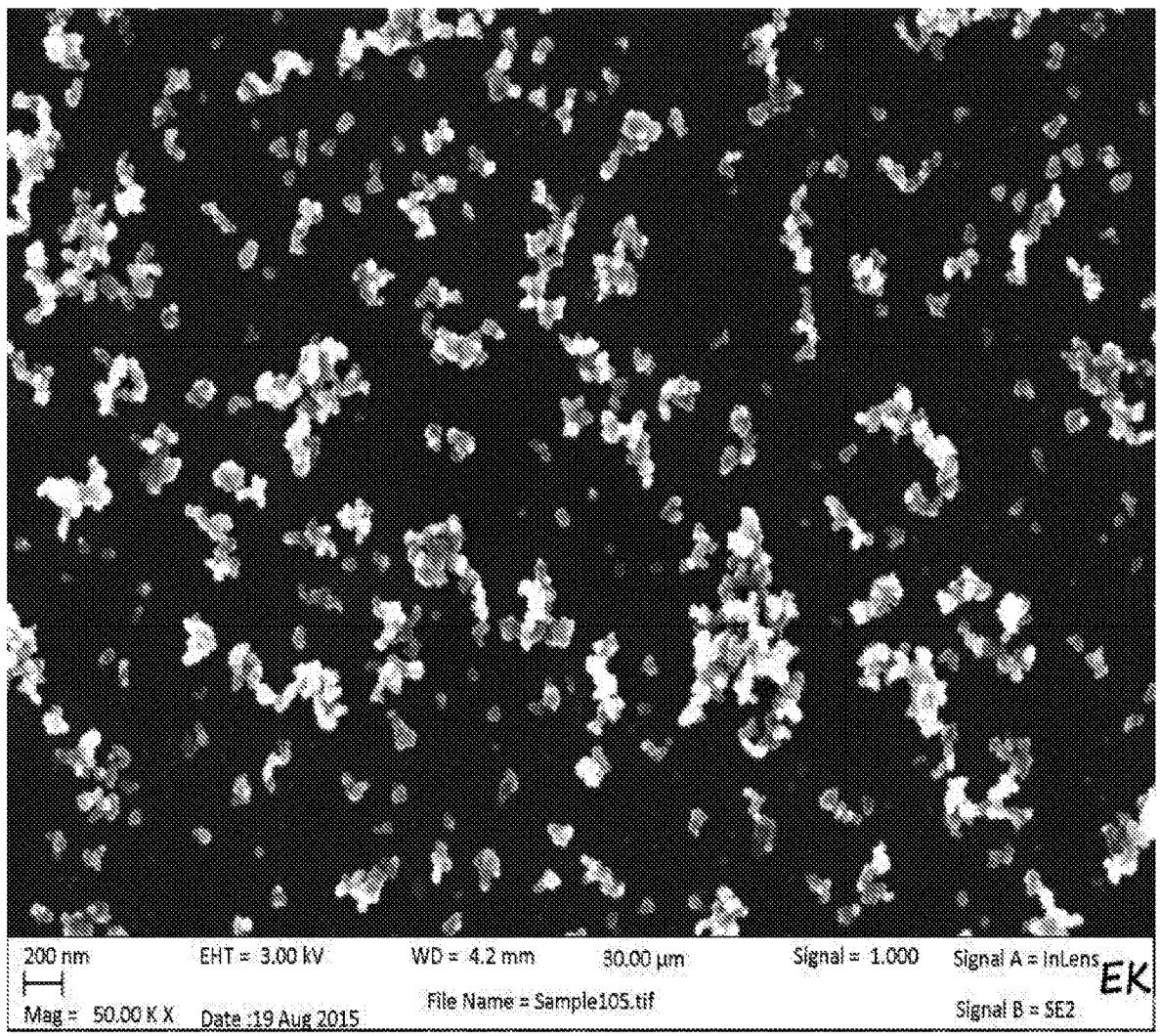
Figure 1B:
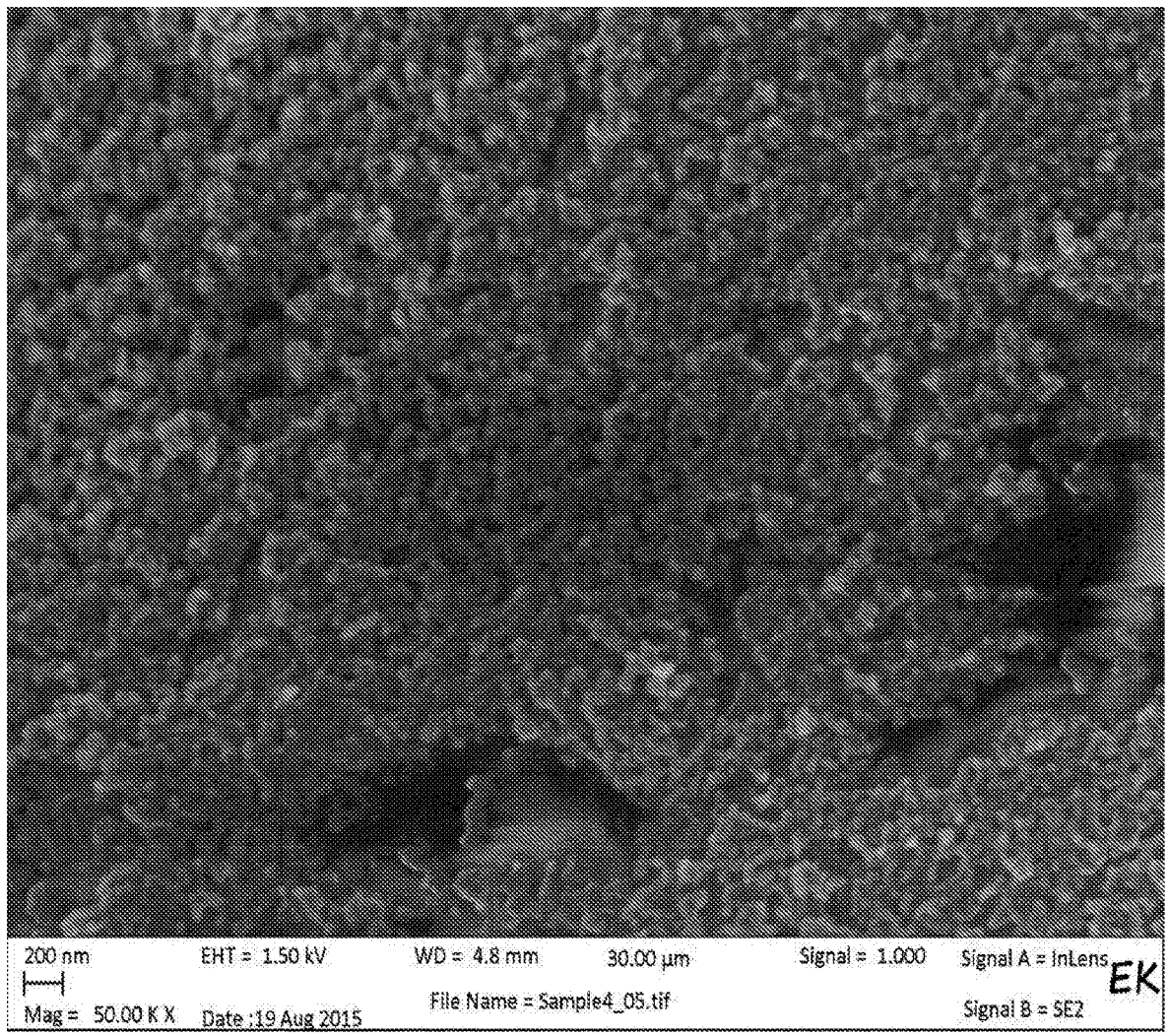
Figure 2A:
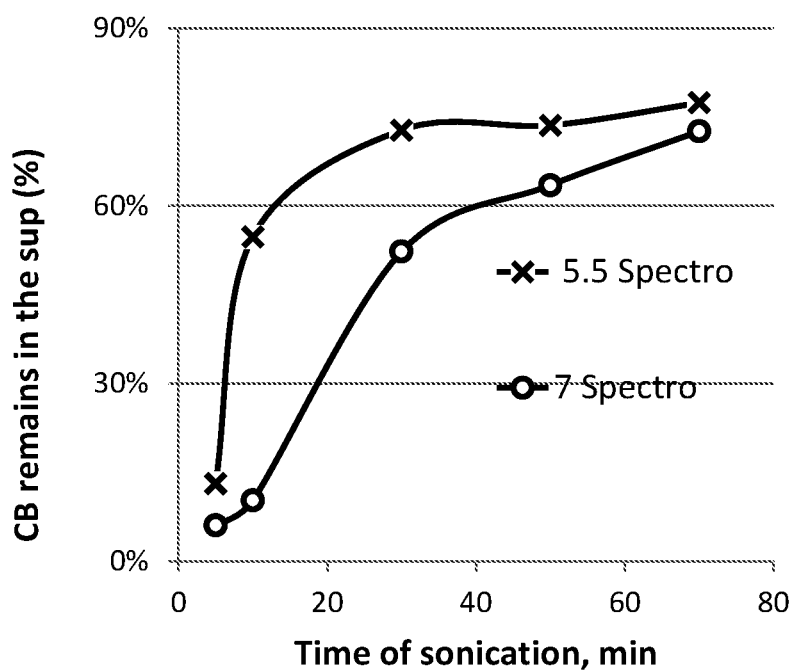
Figure 2B:
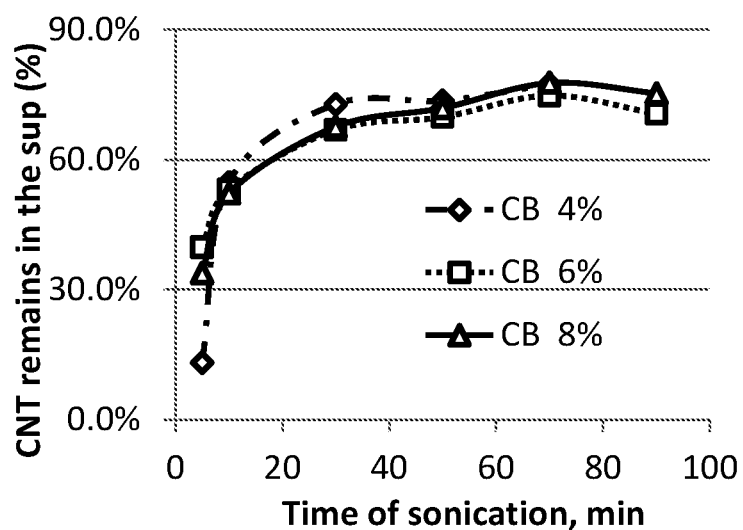

[1]SP1/CNP dispersions (4%) were mixed with latex beads by sonication, polyester yarns were coated with the SP1/CNP/latex dispersion as described in FIG. 2A-2B.
[2]H-test Results of yarns coated with SP1/CNP/latex, (0.7 g/Kg in two layers, without PEI cap), with neoprene rubber: Results are expressed relative to untreated yarn (UT, 31) and resorcinol-formaldehyde/latex coated yarn (RFL 66), according to the following equation: (X-UT)/(RFL-UT). Using Arkema CNT and N326 CB.
[3]Tested with one layer of 3.5 gr/Kg SP1/CNP Dispersions with Latex Beads SP1/CNP dispersions (4-17%%) were mixed with different types of latex beads by sonication, polyester yarns were coated with the SP1/CNP/latex dispersion as described in FIG. 4. Table 5 shows that addition of latex beads to the SP1/CNT complex dramatically improves the H-test results. Optimal CNT/genflo ratio is 20-40, when SP1/CNP/latex load is 7-14 g/Kg yarn (data not shown). However, Table 5 shows that addition of genflo latex to the SP1/CB complex does not improve the H-test results. The reason for the differences between the two experiments is not clear, and may be attributed to differences in the coating conditions rather than the different carbon nanoparticles. The outcome of coated latex level on the surface of the reinforcing yarns may also result from the vulcanization system; latex beads may affect peroxide- and sulfur-based vulcanization system, differently.

Figure 4:
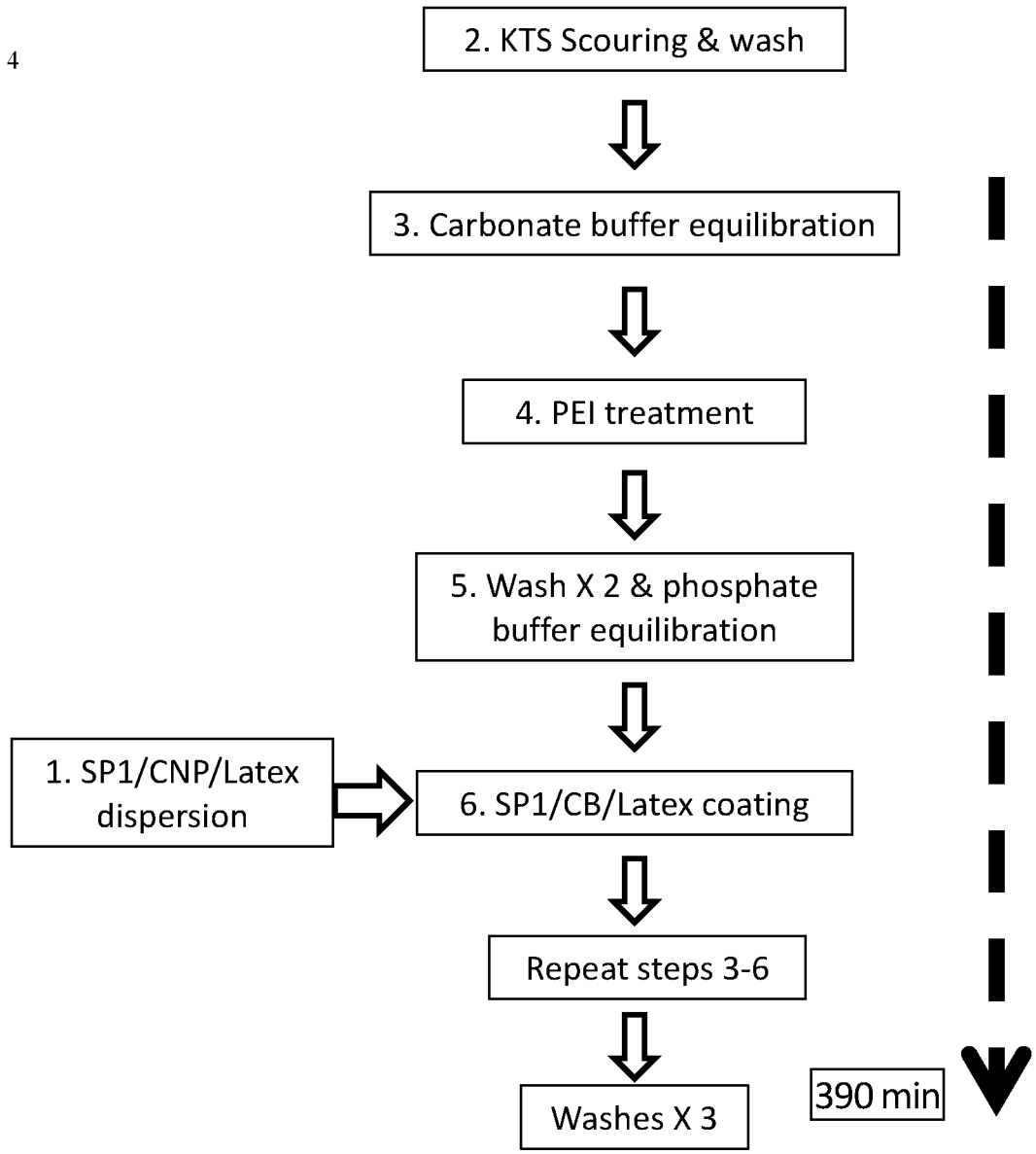

Polyester yarns were coated with carbon nanoparticles in combination with genflo latex (see details in FIG. 4). H-test results (Load at Maximum Load (N), ASTM 4776) of yarns coated with SP1/CNP/latex, (1.05 g/Kg in two layers), were determined with a neoprene rubber compound. Results are expressed relative to untreated yarn (UT, 31 N) and resorcinol-formaldehyde/latex coated yarn (RFL, 66N), according to the following equation: (X-UT)/(RFL-UT). The results demonstrate that all CNP improve adhesion to various extents.

Example 8

Polyester and Kevlar Yarn Coating with SP1/CNT/Latex and SP1/CB/Latex Dispersions and their Adhesion to Rubber The SP1/CNP dispersion spontaneously binds to structural textile material (carbon, glass, polyester, aramid fabrics and yarns) by a simple exhaustion mechanism. However, prior to SP1/CNP dispersion application, the sizing applied on the textile surface should optimally be removed. Yarn sizing is essential to reduce breakage of the yarn and thus production stops on the weaving machine. On the weaving machine, the yarns are subjected to several types of actions i.e. cyclic strain, flexing, abrasion at various loom parts and inter yarn friction. With sizing, the strength—abrasion resistance—of the yarn improves and the hairiness of yarn decreases. The degree of improvement of strength depends on adhesion force between the fiber and size, size penetration, as well as encapsulation of yarn.

Different types of water soluble polymers called textile sizing agents/chemicals such as modified starch, polyvinyl alcohol (PVA), carboxymethyl cellulose (CMC), acrylates are used to protect the yarn. Also wax is added to reduce the abrasiveness of the warp yarns. The type of yarn material (e.g. cotton, polyester, linen), the thickness of the yarn, and type of weaving machinery determine the sizing recipe.

Coating Procedure

FIG. 4 shows an example of the coating process with SP1/CB/genflo of 1100/1/2 dtex low-twist polyester yarn or Kevlar cord, conducted using Ugolini batch dyeing machine; Yarn weight 100 g; Yarn/liquor ratio=7. Note that the process was also conducted with Obem batch dyeing machine when Yarn weight 2*1 Kg; Yarn/liquor ratio=14 when the other parameters were comparable. After each step the yarn is washed with buffer or water.

| 1 | S1/CB/latex dispersion: SP1/CB/latex dispersion was conducted as described in Table 4. The process is conducted using textile dying machine such as Ugolini or Obem yarn batchwise machine. |
|---|---|
| 2 | De-sizing: De-sizing is important to improve batch to batch variations in the textile surface treatment by the manufacturer. Yarn De-sizing was conducted using soda ash triton or KTS treatment at 55° C., followed by extensive wash with water and equilibration with carbonate buffer (20 mM pH = 8.8). |
| 3, 4 | Polyethylenimine (PEI) application and wash: Application of Polyethylenimine (PEI) to the yarns (dissolved in carbonate buffer (20 mM pH = 8.8 at 45° C.; PEI concentration = 0.005%; PEI/Fabric ratio = 0.035%; or 0.35 gr/Kg - applied loading) improves the affinity of the SP1/CNP/Latex to the fabric. It should be noted that PEI was successfully applied by others to functionalize CNTs by polymer wrapping). Note that mixture of PEI with the dispersion is not useful because it leads to coagulation and precipitation of the CNP dispersion (at CNP/PEI |

-continued

| | |
|---|---|
| | dry weight/weight ratio <0.01), it also leads to SP1 protein precipitation. PEI access is extensively washed to prevent agglomeration of the SP1/CNP complex in the next step. High molecular weight (60 KDa) PEI is more useful than low molecular weight PEI. |
| 5, 6 | SP1/CNP/Latex dispersion application and wash: Application of SP1/CNP/Latex dispersion to the yarns (diluted in sodium phosphate buffer (10 mM; pH = 8.0 at 45° C.; SP1/CNP/Latex concentration in dispersion = 0.05%; SP1/CNP/Latex/Fabric ratio = 3.5 gr/Kg applied loading). The coating process is designed such that all SP1/CNP/Latex is depleted from the applied dispersion within 1 hr. Amount (fraction of) of unbound SP1/CNP/Latex was determined as described in Table 4. Unbound SP1/CNP/Latex is washed to prevent agglomeration of the SP1/CNP complex in the next step. |
| | Repeat steps 3-6 Finally steps 3-6 are repeated to increase the load of SP1/CNP/Latex and PEI load. When applied PEI loads in the second and third layers are increased by two-fold in each layer. |

Characterization of SP1/CNP/Latex-Coated Yarns and Cords Involves:

1. Calculation of the amount of CNP depleted from the applied solution (including washes) was measured by both spectroscopic and gravimetric method, with similar results (Table 4). Note that the limitation of this method is that when depletion of the SP1/CNP complex is low the measure is less reliable.
2. Lightness value was determined using a reflectance spectrophotometer. Untreated yarns were light and displayed high ΔL values and CNP coated yarns were dark and displayed low ΔL values.
3. Electrical resistance was measured from dried coated yarn with a standard electrode device (10 cm distance). Untreated yarn were electrical insulators and CNT coated fabrics were conductive.
4. Extraction of bound SP1/CNP complex using ionic detergent such as SDS (0.5% in water). Note that the limitation of this method is that it is hard to prove that all bound material was extracted.
5. High Resolution scanning electron microscopy (SEM) image of SP1/CB (N326-coated yarn (FIG. 1A-1B).
6. A functional assay: H-test results (Load at Maximum Load (N), ASTM 4776) of yarns coated with SP1/CNP/latex, in comparison with untreated unwashed yarns and the industry standard RFL-coated yarns (see more details below)

Layer by Layer Coating

An important feature of the current invention is the "layer by layer coating" procedure, as described above, since it allows controlling CNP load on the yarn in a cost effective way with no waist of expensive nanoparticles. When low SP1/CNP concentration is applied (0.05% in dispersion; when liquor/fabric ratio=7 this value is equivalent to 3.5 g/Kg yarn) it is totally depleted from the applied fraction and when PEI is used in the next step it allows binding of higher load of SP1/CNP (equivalent to 7 g/Kg yarn with total load of 10.5 g/Kg), and so on. It is important to note that though increasing SP1/CNP concentration in the applied fraction may increase bound SP1/CNP, it does not improve the H-test results: Two layers of SP1/CNT/genflo promote adhesion better than one layer of SP1/CNT/genflo (same final load=7 g/Kg) and three layers of SP1/CNT/genflo (final SP1/CNT/genflo load=10.5 g/Kg).

Example 9

Polyester Yarn Coated with the SP1/CNT/Latex and SP1/CB/Latex Complexes with Neoprene and Nitrile Rubber Compounds

Improved Adhesion of SP1/CNT/Genflo Treated Yarns to Six Neoprene and Nitrile Rubber Compounds As mentioned above, incorporation of carbon black into the rubber, results in a large increase in both strength and modulus. The reinforcing effect increases with the amount added (up to about 30% by volume), and also with reduction in particle size. CNT may replace carbon black and improve mechanical properties at lower loads. The basic hypothesis is that placement of carbon nanoparticles (with some additives) in the yarn/rubber interphase would improve the adhesion. The formation of SP1/CNP complex allows yarn coating with both CNT and CB.

Test Method ASTM D4776 for the determination of the H-test adhesion of reinforcing cords to rubber compounds is used for the acceptance testing of commercial shipments of reinforcing cords. Since the method display several limitations concerning variation, and absolute adhesion values depends on multiple factors which are not well understood. In this study it is used as a comparative test with untreated yarn/cord and RFL-treated yarn/cord.

Experimental Conditions

1100/1/2 dtex low-twist polyester yarns were coated with the SP1/CNT/genflo complex as described in FIG. 4. CNT/genflo=30; final SP1/CNT/genflo concentration in the kier (tank) is 0.05% in two layers; final SP1/CNT/genflo load on yarn is 7 g/Kg. These yarns together with the positive and negative controls: RFL-coated yarn and untreated yarn, respectively (all 1100/1/2 dtex low-twist polyester yarns) were vulcanized in an H-test mold (ASTM 4776) with six Neoprene and Nitrile rubber compounds. Table 6 shows the H-test results an average of 10 tests for each yarn are expressed both in absolute value (N) and relative value (%) to RFL-treated and untreated (UT) yarns {(X-UT)/(RFL-UT)}. Protein alone does not promote adhesion.

TABLE 6

| | | Rubber and compound | | | | | |
|---|---|---|---|---|---|---|---|
| | | Neoprene | | | Nitrile | | |
| Yarn treatment | | 1 | 2 | 3 | 1 | 2 | 3 |
| Absolute value (N) | RFL | 47.57 | 45.44 | 32.28 | 56.35 | 69.25 | 38.16 |
| | Untreated unwashed | 31.43 | 23.5 | 17.84 | 20.46 | 29.52 | 21.97 |
| | SP1/CNT/genflo | 52.26 | 49.07 | 36.63 | 36.72 | 43.84 | 39.63 |
| Relative adhesion (%) | | 129% | 117% | 130% | 45% | 36% | 109% |

The conclusion is that in comparison with untreated yarn, SP1/CNT/genflo coating improves adhesion with Neoprene and Nitrile rubber compounds. In all three Neoprene compounds and one nitrile compound the adhesion is similar or even higher than in RFL-treated yarn, but in two nitrile compound the adhesion is poorer than of RFL-treated yarn. Other experiments demonstrated that optimal CNT/genflo ratio is 20-40, when SP1/CNP/latex load is 7 g/Kg yarn (data not shown). It is important to note that by applying higher SP1/CNP/latex concentrations in solution (0.1% versus 0.05%) or three layers of 0.05% does not improve adhesion. Moreover, higher Latex loads (CNT/genflo wt. ratio <20), decrease adhesion.

Example 10

Improved Adhesion to Rubber with CB—Polyester Yarns Coated with SP1/CB/Latex

Carbon Black Display Several Advantages Over CNT:
a. cost reduction: the cost of carbon black is much lower than of Multiwall carbon nanotubes (2 versus 80 $/Kg);
b. Less protein is needed to disperse CB than CNT: 7 or even 10, versus 2.9 dry w/w ratio, Table 4;
c. Stable SP1/CB dispersion can be made at much higher concentration than SP1/CNT dispersion and in much shorter sonication time per gr CNP (17% versus 4%, respectively); and
d. Regulation, environmental and health considerations favors the use of carbon black over CNT.

The first three points dramatically reduce the cost of production of reinforcement textile.

Figure 5A:
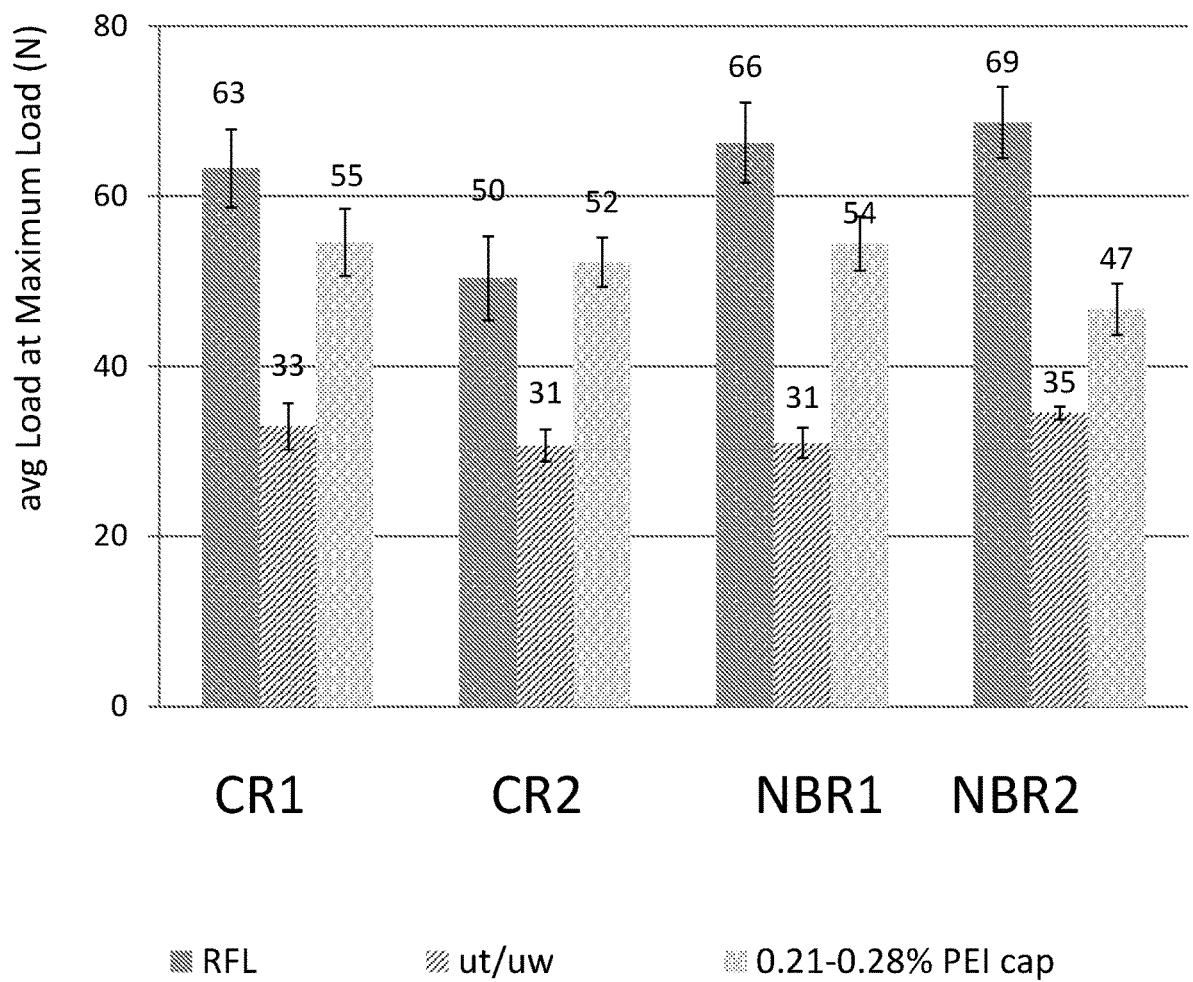
Figure 5B:
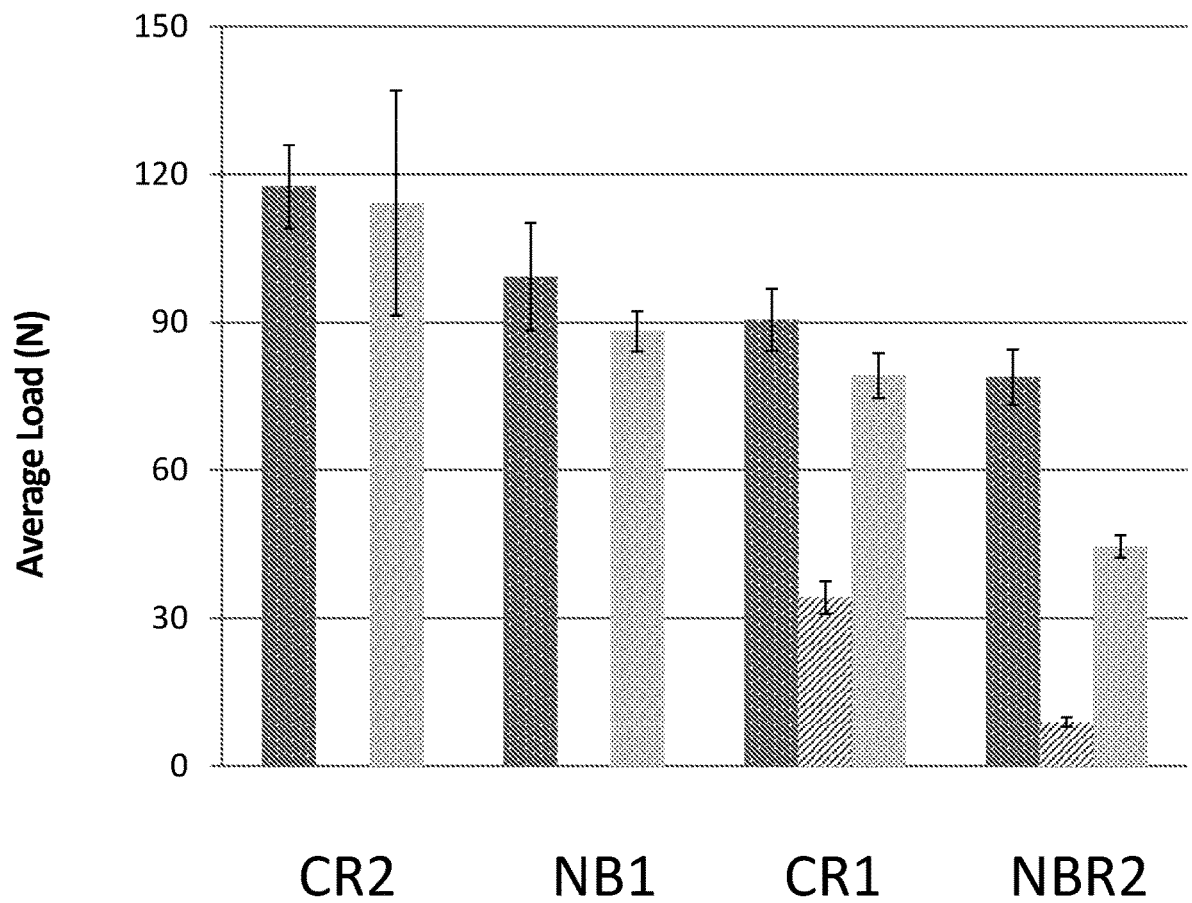

Experimental Conditions:

1100/1/2 dtex low-twist polyester yarns were coated with the SP1/CB/genflo complex using ugolini or obem dying machines in several different independent experiments. SP1/CB/genflo loads were 3.5 gr/Kg and 5.5-6 g/Kg in the $1^{st}$ and $2^{nd}$ layer, respectively (final CB load was 9-9.5). Applied PEI loads (% wt) was 0.07%, 0.14% and 0.28% in the $1^{st}$, $2^{nd}$ and $3^{rd}$ layers respectively ((final applied PEI load was 0.49%)). Genflo latex loads varied between 0-0.021%. These yarns together with the positive and negative controls: RFL-coated yarn and untreated yarn, respectively (all) were vulcanized in an H-test mold (ASTM 4776) with four Neoprene and Nitrile rubber compounds. The results (FIG. 5A-5B) show that SP1/CB/genflo coating improves adhesion with Neoprene and Nitrile rubber compounds, two cases the adhesion results are similar to the adhesion results obtained with RFL.

Figure 6A:
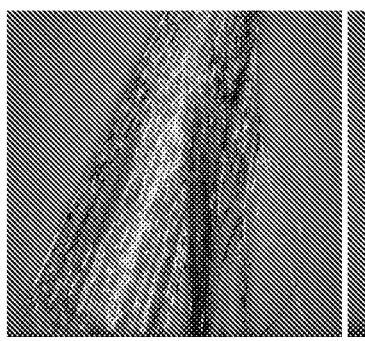
Figure 6B:
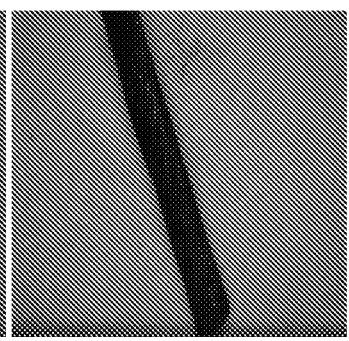
Figure 6C:

FIG. 6A-6C demonstrates that the failure mechanisms of RFL- and of SP1/CB-treated yarn are very different. In RFL-treated yarns the filaments are glued to each other and in SP1/CB/coated- and untreated Yarns they are spread after failure. In both RFL-SP1/CB/coated yarns rubber pieces are observed on the surface of the yarns after failure, indicating a cohesive failure. The same observation can be seen even in a more details in HR-SEM image of a SP1/CB-coated Kevlar filament after H-test (FIG. 15). The HR-SEM image further demonstrates the presence of coated SP1/CB/Latex after failure, indicating the coating is stable even after vulcanization and the H-test. Additional H-test experiments demonstrated that increased CB load and PEI top coating did not improves H-test results (not shown).

One of the major limitations of the H-test is that the yarns surface that comes in contact with the rubber is very small, only few mm with potential yarn edge effect. To overcome this problem the hose test was employed (FIG. 5B) with the same yarn and rubber compounds. In the hose test the yarns surface that comes in contact with the rubber is much bigger, with minor potential edge effect. In the hose test the tested yarns are wind on a cured rubber foundation, three yarns per mandrel; 15 cm segments, followed by winding the tested rubber (1 mm each time) twice this rubber on the wound yarn. Curing (90 minutes, 300° F.). Cooling to room temp and wait at least 12 hours before removal of the curing tape. Testing involves cutting 2.5 cm rubber strip and pull rubber off yarn to test adhesion. The results from the hose test (FIG. 5A) show that SP1/CB/genflo coating improves adhesion with Neoprene and Nitrile rubber compounds, in three cases the adhesion results are similar to the adhesion results obtained with RFL and only in one case the adhesion is lower.

Example 11

Kevlar Yarn Coated with the SP1/CNT/Latex and SP1/CB/Latex Complexes with EPDM Rubber Compounds Kevlar cords (Para aramid DTex 1200/4)) were coated with the SP1/CB/genflo complex using ugolini or obem dying machines under several different experimental conditions. SP1/CB/genflo loads (% wt) were 7 g/Kg in both the $1^{st}$ and $2^{nd}$ layer, respectively (final 14 g/Kg). Applied PEI loads (% wt) were 0.21% in both the $1^{st}$ and $2^{nd}$ layers respectively (final applied PEI loads=0.42%). Genflo latex loads were varied between 0-0.021%. These yarns together with the positive and negative controls: RFL-coated cord and untreated cord, respectively (all) were vulcanized in a H-test mold (ASTM 4776) with a EPDM compounds.

The results (Table 7) show that Kevlar cord (Para aramid DTex 1200/4) coated with SP1/CB composition improves aramid cord adhesion to EPDM rubber (H-test), to a level close to 80% of RFL. Top coating with water based substrate to rubber adhesive—Chemosil®, further improves adhesion to a level close 88% of RFL. Moreover, SP1/CNT/latex coating also improves aramid cord adhesion to EPDM rubber. Additional H-test experiments demonstrated that increased CB load improve H-test results.

TABLE 7

Kevlar cord (Para aramid DTex 1200/4) coated with SP1/CB composition improves aramid cord adhesion to EPDM rubber (H-test), to a level close to 80% of RFL. Top coating of water based Chemosil ® further improve adhesion to a level close 88% of RFL

|  |  | Coating | | |
| --- | --- | --- | --- | --- |
|  |  | Untreated | SP1/CB Chemosil | SP1/CB only | RFL |
| Load at Maximum Load (N) | Average | 58.3 | 100.8 | 92 | 115.5 |
|  | STDev | 2.9 | 3.9 | 7.9 | 9.3 |

An important limitation of the RFL treatment is that it increase cord rigidity, and while strength at maximal load and elongation at Break (%) are not reduced, strength at 1% elongation is dramatically increases (Table 8). However, SP1/CB/Latex coating (with or without top coating with chemosil) doesn't significantly change strength at maximal load and strength at 1% elongation but may increase elongation at Break) (Table 8).

TABLE 8

Unlike RFL treatment, which increases Kevlar cord rigidity, SP1/CB coated cord is flexible, similar to untreated aramid.

|  |  | Coating | | |
| --- | --- | --- | --- | --- |
|  |  | Untreated | SP1/CB Chemosil | SP1/CB only | RFL |
| Strength at Max load (N) | Average | 556 | 571 | 561 | 575 |
|  | STDev | 70 | 55 | 31 | 27 |
| Strength at 1% elongation (N) | Average | 52.8 | 46.9 | 41 | 97.6 |
|  | STDev | 7.0 | 5.5 | 4.4 | 14.2 |
| Elongation at Break (%) | Average | 4.7 | 4.8 | 5.6 | 4.3 |
|  | STDev | 0.7 | 0.3 | 0.64 | 0.3 |

Example 12

Nylon Film Coating

Figure 7A:
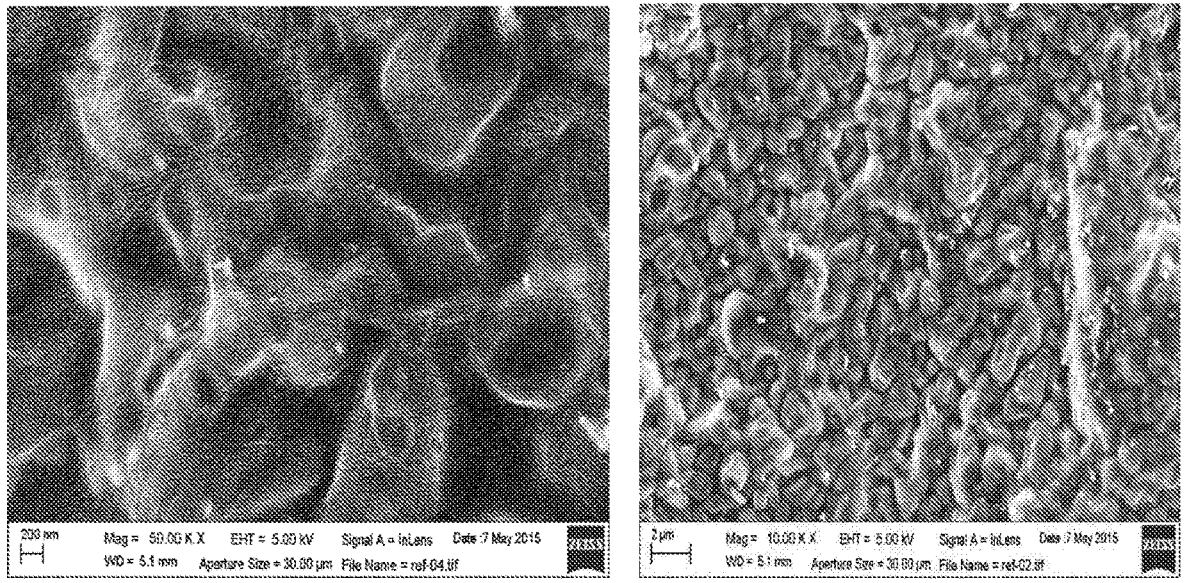
Figure 7B:
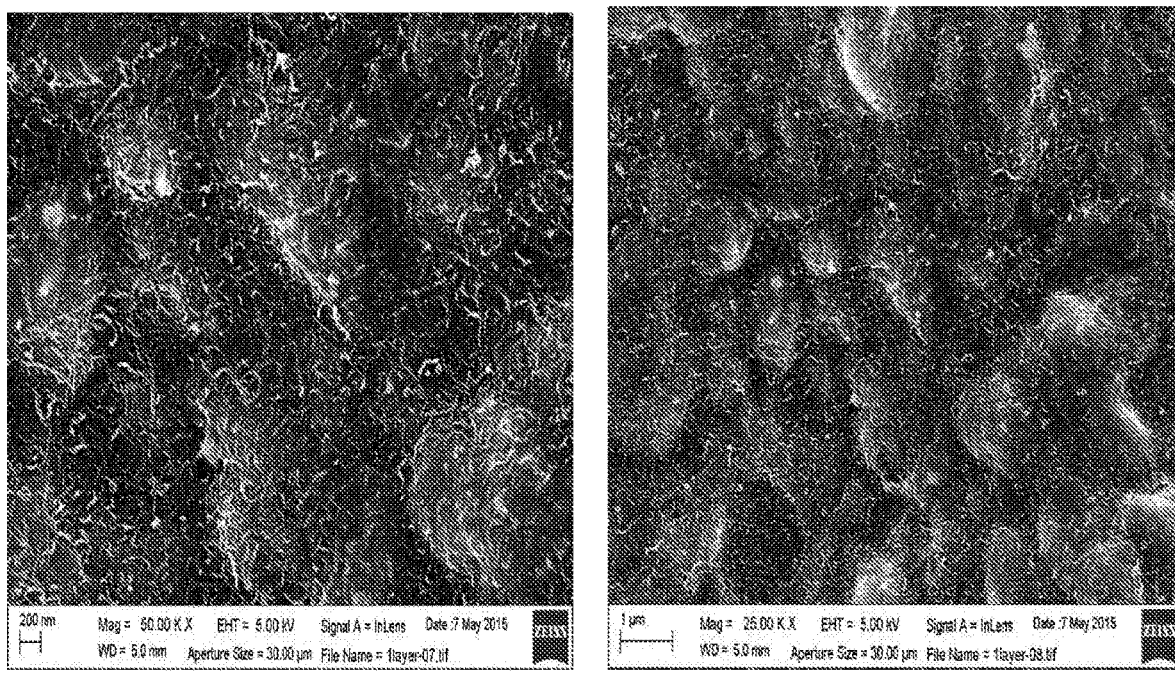
Figure 7C:
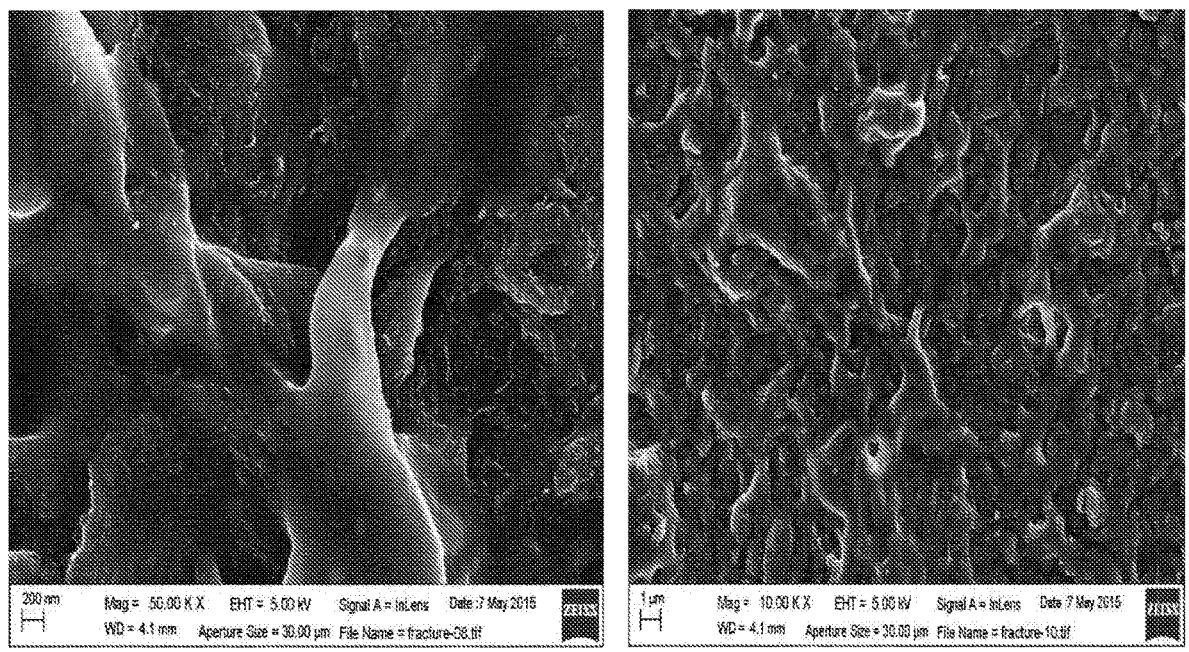

Evidence is provided that the SP1/CNT/genflo complex binds to nylon surface. A rotary shaking bath was used for Nylon fabric coating with the complex; FIG. 7A-7C demonstrates uniform SP1/CNT/Genflo coating of nylon film.

Example 13

Figure 8:

Nylon Fabric Coating with SP1/CNT and SP1/CNT/Latex Complex and its Adhesion to Rubber FIG. 8 demonstrates SP1/CNT/Genflo SP1/CNT/gentac coating of nylon fabric improved peel strength with Nitril rubber.

A rotary shaking bath was used for Nylon fabric coating with the complex; 180° peel test was used to assess adhesion. Coating with the SP1/CNT/latex-complex (genflo or gentac) improves adhesion to neoprene rubber (FIG. 8) and also to nitrile rubber (not shown). Two layers yield much higher adhesion than one layer coating. Optimal CNT/latex ratio was 20 or 10 for genflo and gentac respectively. Too much latex interferes with the adhesion, CNT/latex ratio of 1 or 3 for genflo and gentac respectively. In the absence of SP1/CNT, latex don't improve adhesion.

Example 14

Comparison Between RFL and SP1/CNP/Latex Performance on Rubber

Resorcinol Formaldehyde Latex adhesives (RFLs) are commonly used to treat textiles in order to enhance their adhesion to rubbers and are used as the gold standard. The major limitations of RFL treatment are its toxicity and the resulting fiber's rigidity (low flexibility).

Figure 9:
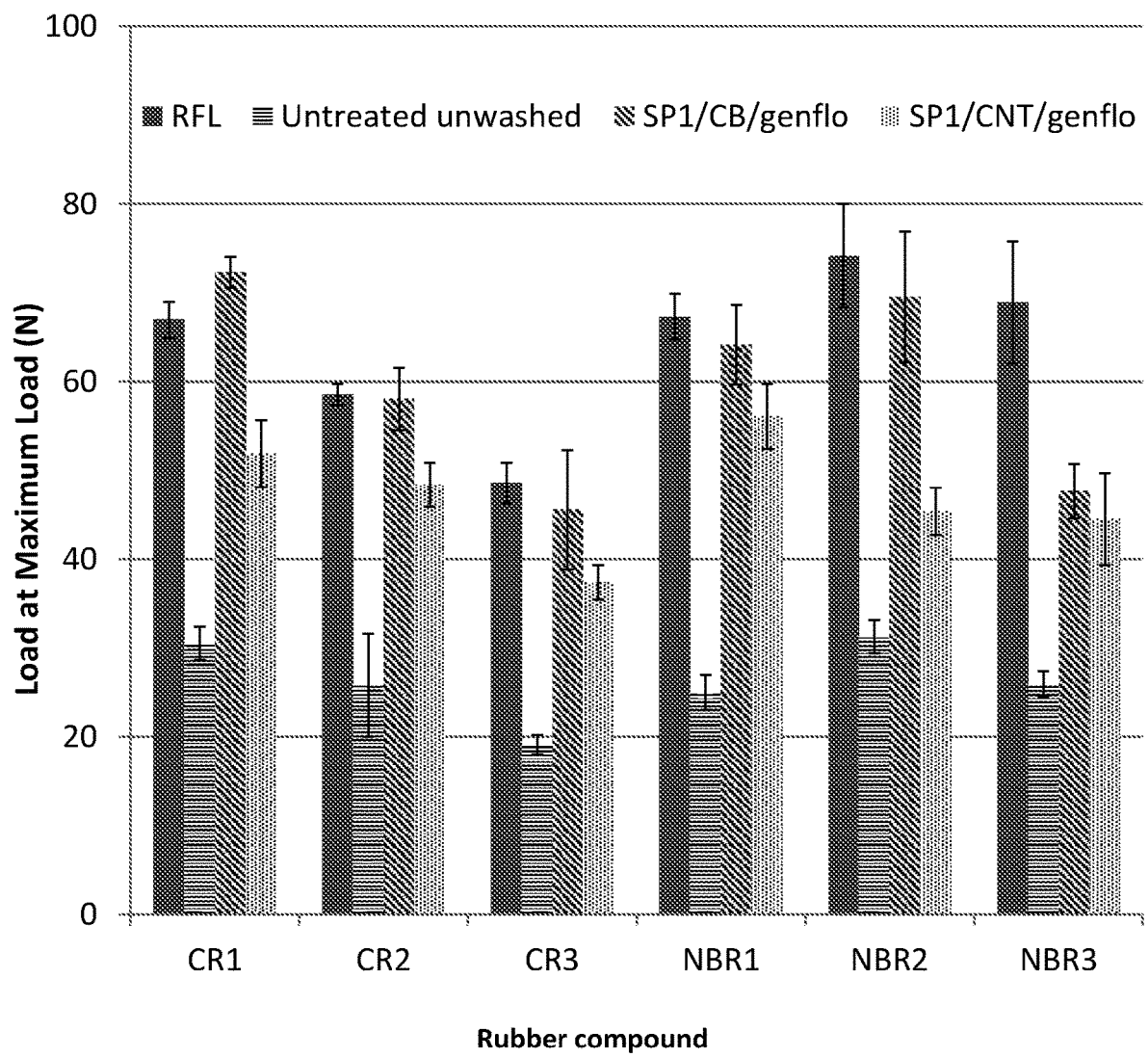

In the following experiment the adhesion of RFL and untreated yarn were tested as positive and negative controls, respectively. FIG. 9 shows the results expressed as load at maximum load (N)) when polyester yarn adhesion to six rubber compound, (Neoprene based rubber compounds (NR1-3); and Nitrile based rubber compounds (CR1-3)) were tested using the H-Test (ASTM 4776). Polyester yarn coated with both SP1/CB/genflo and SP1/CNT/genflo were tested when CNP load was 7 g/Kg, coated in two layers (3.5 g/Kg each) using the Ugolini coating machine 100 g bobbins; CNT/genflo dry weight to weight ratio was 30.

The results show that both SP1/CB/genflo and SP1/CNT/genflo treatment improves adhesion relative to untreated unwashed yarns. In five out of the six cases adhesion to SP1/CB/genflo-coated yarns are close to or even better than the adhesion to RFL-treated yarn. The adhesion to SP1/CNT/genflo-coated yarns, however, is lower than the adhesion to RFL-coated yarns.

Example 15

Figures 10A, 10B:
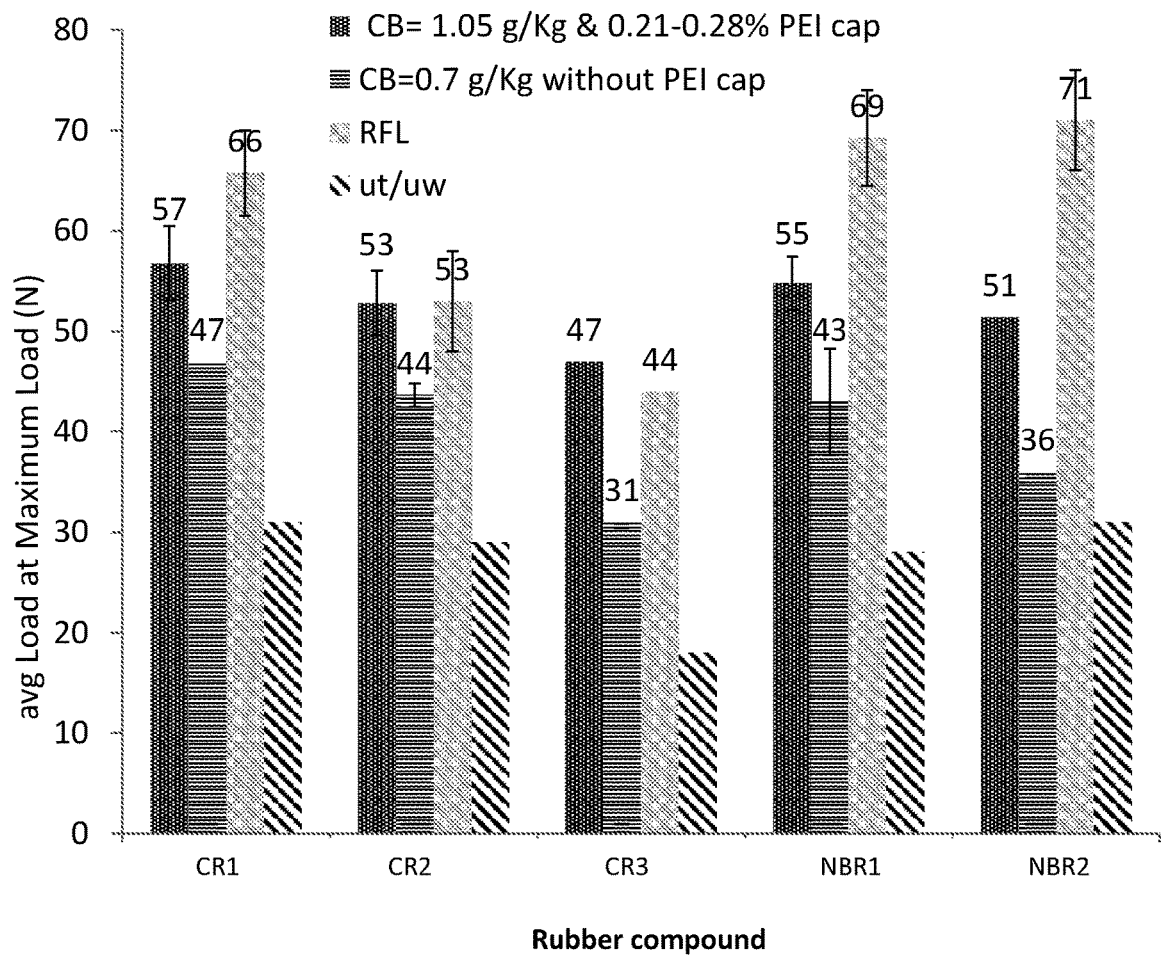
Figure 11A:
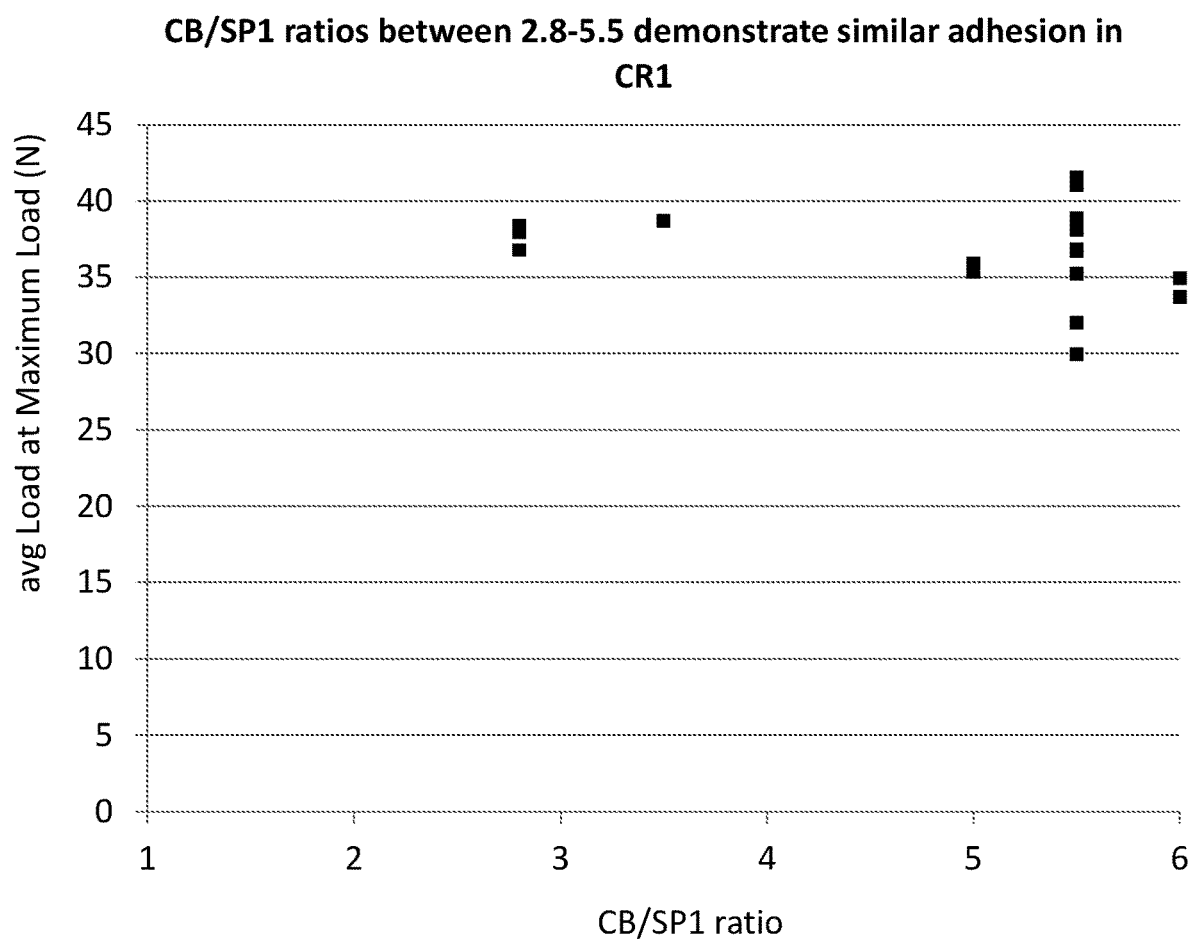
Figure 11B:
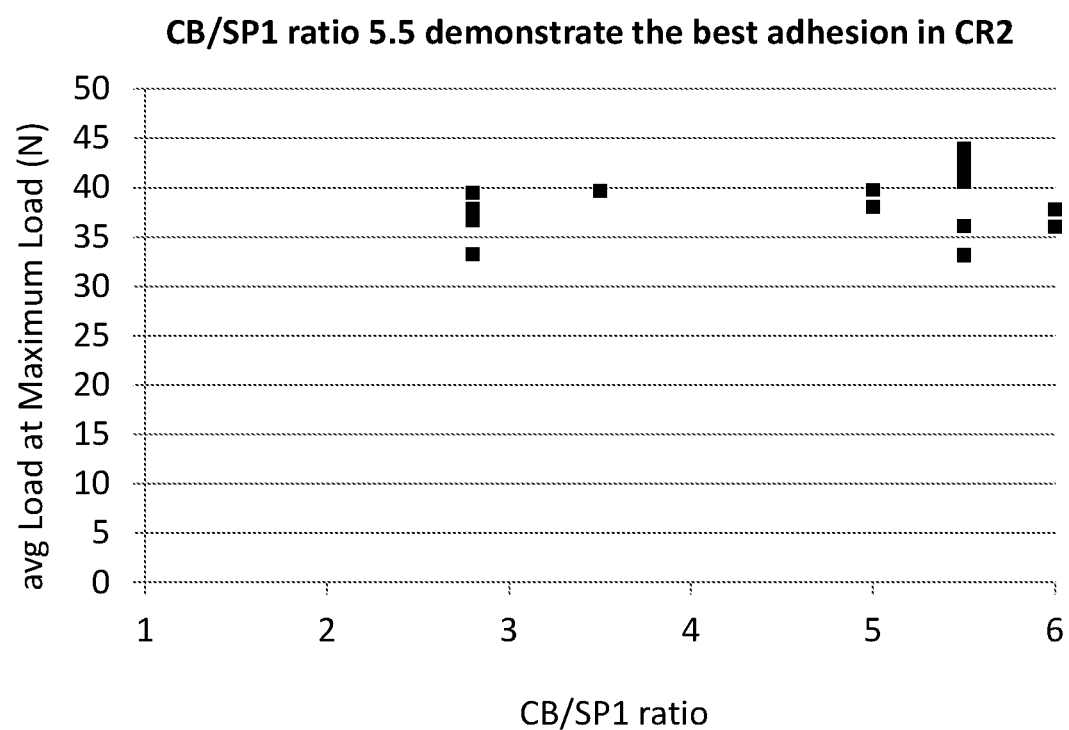
Figures 11C, 11D:
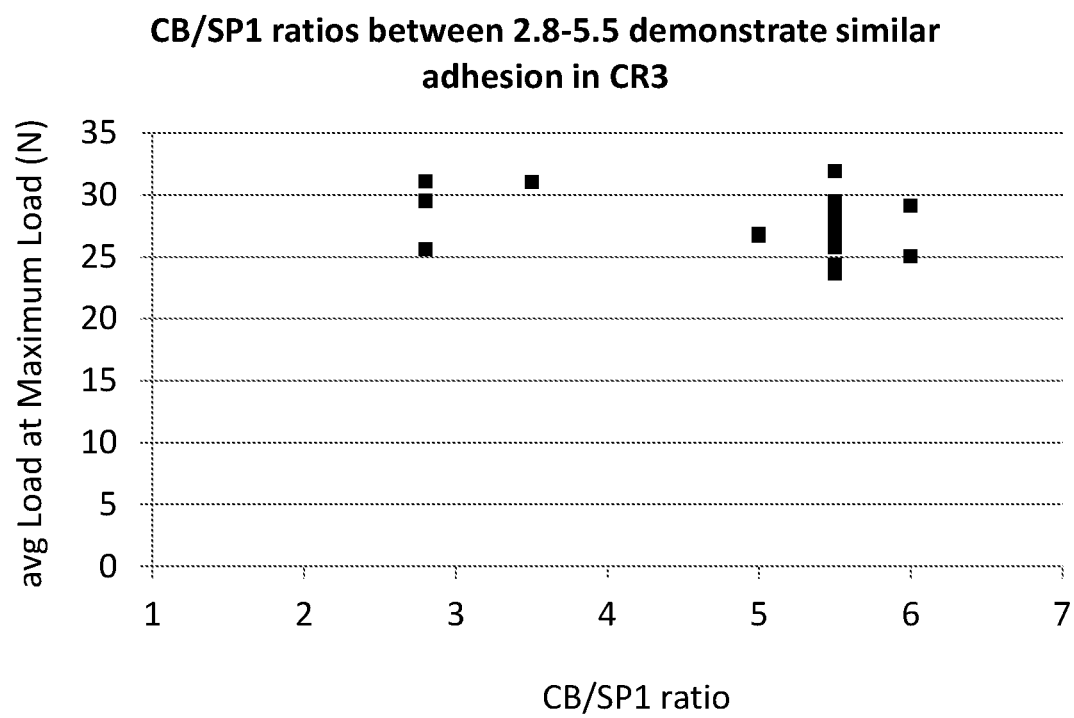

The Effect of CNP Load, Latex Brand, CNP/SP1 Ratio, CNP/Latex Ratio and PEI Post Treatment on Adhesion to Rubber The optimal CB load for neoprene compounds is above 9-10.5 g/Kg (applied in two layers 03.5 and 5.5-7 g/Kg in the first and the second layer, respectively. FIG. 10A-10B shows that combination of increased CB load (7→10.5 g/Kg) in two layers and PEI top coating in the third layer improves adhesion in 6 rubber compounds.

FIG. 11A-11D shows the Effect of CB/SP1 dry weight ratio (dry weight of the heat stable crude extract of recombinant L3SP1 protein) on adhesion at constant latex (Genflo) to CB ratio (1:30) in three Neoprene rubbers. CB/SP1 ration of 5.5 demonstrates the best adhesion in CR2 (FIG. 11B), while any CB/SP1 ration between 2.8 and 5.5, demonstrates similar adhesion in CR1 and CR3. The adhesion in all cases, however, is better than adhesion of untreated yarns (FIG. 10B). Good adhesion was observed also when CB/SP1 ratio was 7, which is important to reduce the cost of production Several Modifications to the Above Protocols were Tested:
1. Optimal CNT/genflo, dry weight to weight ratio is 20-40. Higher or lower ratio exhibit lower adhesion.
2. Optimal CNP load was 7-10.5 g/Kg, lower loads exhibited lower adhesion.
3. PEI post treatment of both SP1/CB/genflo and SP1/CNT/genflo-treated yarn improves the adhesion.
4. Adhesion to SP1/CNT-coated yarns (no latex) is lowered than the adhesion to SP1/CNT/genflo-coated yarns. Replacement of genflo with other latex brands also show improved adhesion (relative to untreated yarns)

Example 16

Effect of Latex Loading on Adhesion to Neoprene Rubber Compound

Figure 12:
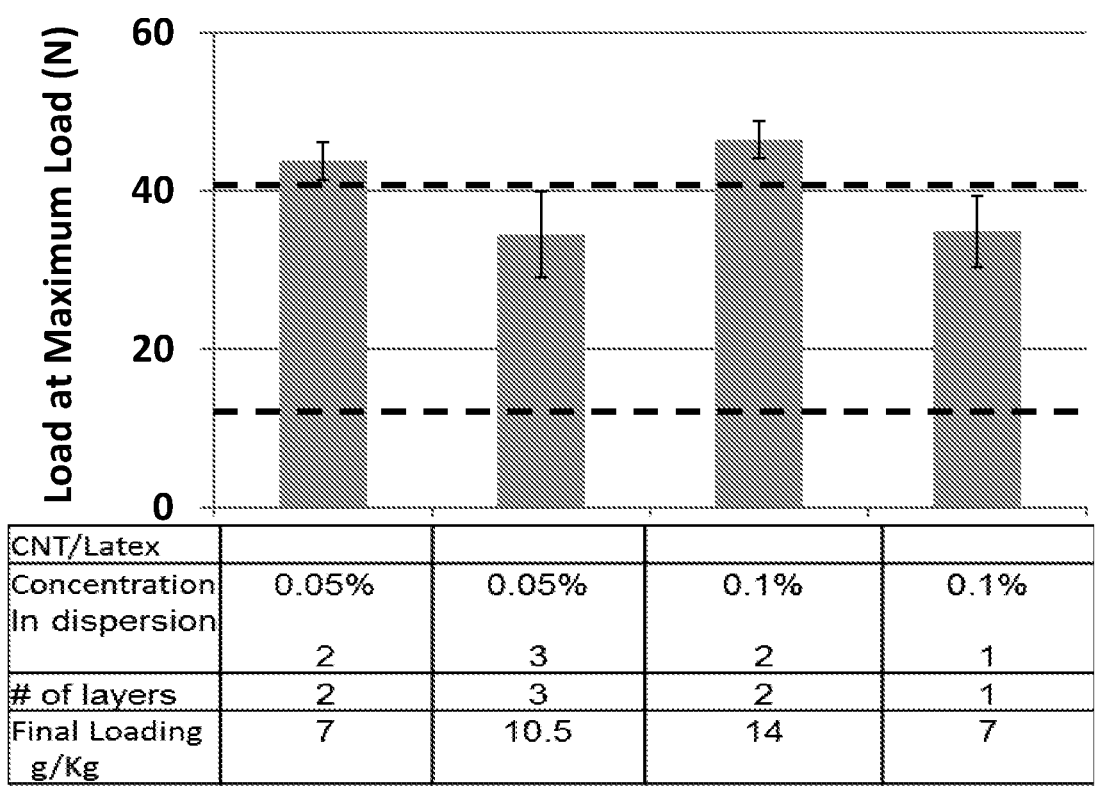
Figure 13:
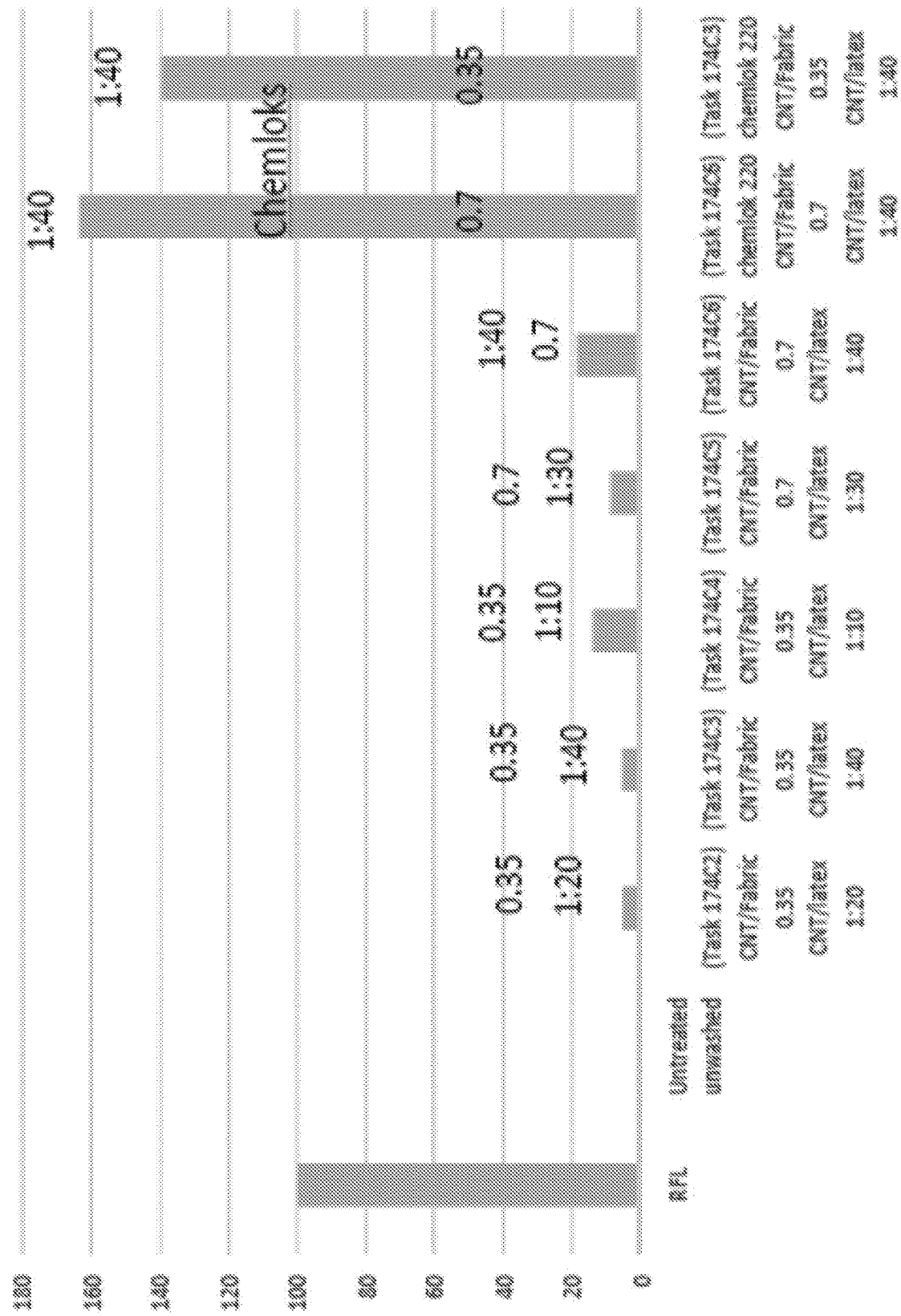
FIG. 13 depicts Kevlar cord Peel Test—natural rubber compound.
Figure 14:
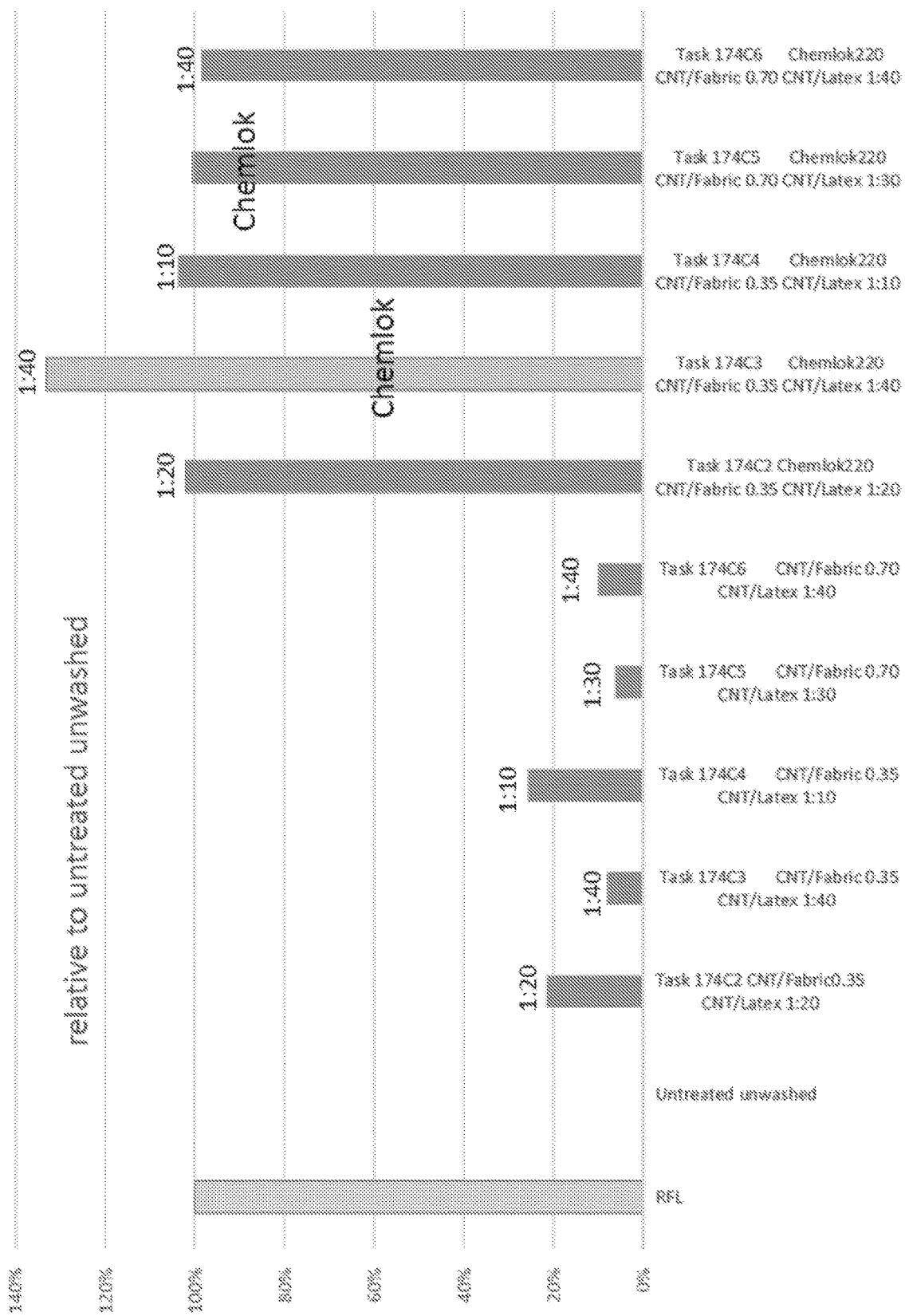
FIG. 14 depicts Kevlar cord H-Test—natural rubber compound.

FIG. 12: The effect of SP1/CNT/genflo loading level as well as its coating protocol was studied using CR1. Positive control: top line, RFL-treated yarn; Negative controls: bottom line, Untreated yarn (washed or unwashed). CNT/Latex W/W ratio=20 (suboptimal condition). The conclusion is that SP1/CNT/genflo optimal loadings is 7 g/Kg in two layers. With the same loading two layers are better than one layer. Higher SP1/CNT/genflo loading 10.5 g/Kg in 3 layers) results in lower adhesion, presumably as a result of CNT aggregate formation on the surface of the yarn. Lower loading yielded uneven coating as evident from electrical resistance measurements.

Example 17

Improved Adhesion of SP1/CNT/Genflo Treated Kevlar Yarns with EPDM Rubber Compounds Kevlar cord coating with both SP1/CB/genflo and SP1/CNT/genflo improves adhesion with EPDM rubber compounds. Chemosil® top coating of SP1/CNP/genflo coated yarn improves adhesion. Increased PEI top coating may improve adhesion (the difference is probably insignificant).

The contribution of genflo to adhesion is not clear yet, In sulphur cured NR, chemical bonds are generated with the latex particles in the RFL structure, so that rubber and latex covulcanize. Aging results in saturation of the outer surface of the latex which in addition contains the highest concentration of curatives. As a result the adhesion forces decrease significantly. For peroxide cured EPDM, chemical bonds are also generated between latex and rubber, but peroxide is able to connect the rubber to the resin as well to some extent. Considering this and also the fact that peroxide is able to generate cross-linking even in polymers with saturated chains, the adhesion between such systems and rubbers should not be affected by aging. This latter has been proved by the adhesion experiments.

TABLE 10

The adhesion of SP1/CNT/genflo and SP1/CB/genflo treated Kevlar yarns to EPDM rubber in comparison to RFL treated and untreated yarns.

| | CNP, load | SP1/CB = 2.8, CB = 11 g/Kg | | SP1/CB = 5.5, CB = 11 g/Kg | | | SP1/CNT = 2.8, CNT = 7 g/Kg | |
|---|---|---|---|---|---|---|---|---|
| | 30% Rubber to substrate adhesive (e.g. chemosill XW7500) | none | Yes | none | none | yes | none | yes |
| | PEI top coating | none | none | none | yes | yes | none | none |
| Absolute value (N) | RFL | 109.8 | | 102.8 | | | 95.4 | |
| | Untreated unwashed | | | 47.1 | | | | |
| | SP1/CNP/genflo | 94.8 | 99.5 | 69 | 76.67 | 88.65 | 79.1 | 88.2 |

Example 18

Figure 15A:
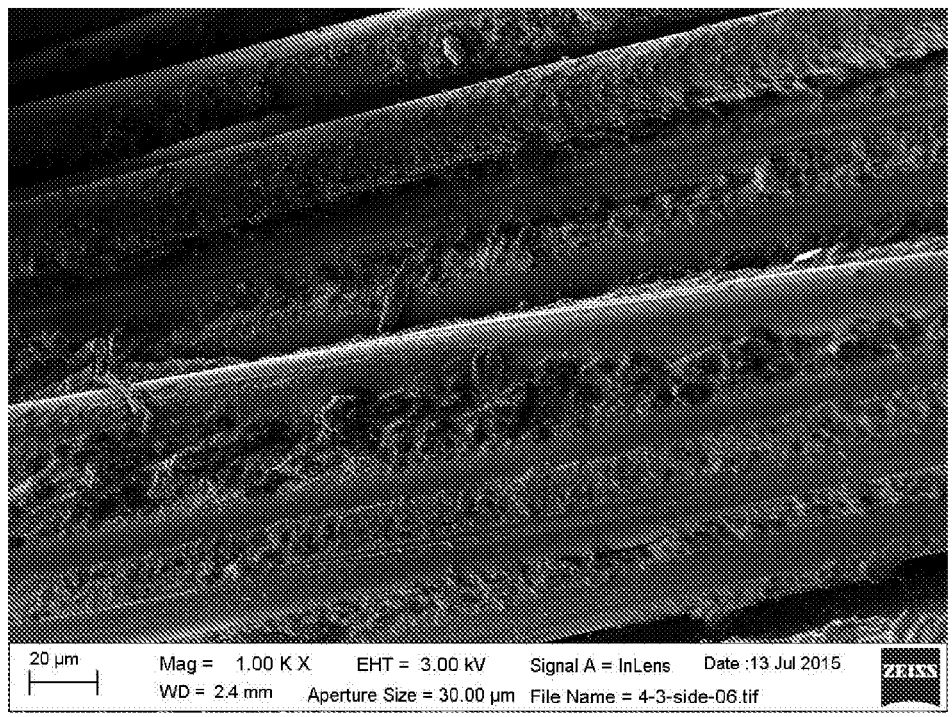
FIGS. 15A-15B depict HR-SEM images of a Kevlar filament after H-test failure. A Kevlar CORD was coated with 7 gr/Kg SP1/CB/genflo+chemosil 211 post treatment vulcanized with EPDM rubber and underwent H-TEST: evidence that the rubber is still glued to the yarn after failure.
Figure 15B:
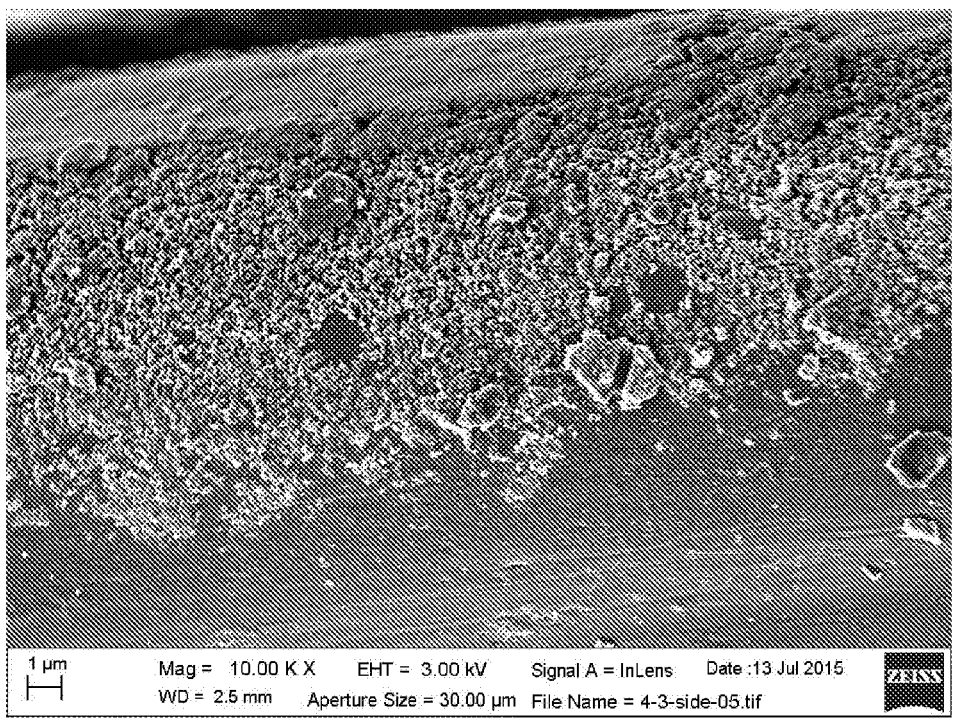

The Effect of Fiber Top Coating with "Substrate-to-Rubber" Adhesives on Adhesion of Kevlar to Natural Rubber FIG. 15A-15B depicts HR-SEM images of a Kevlar filament after H-test failure. A Kevlar CORD was coated with 7 gr/Kg SP1/CB/genflo+chemosil 211 post treatment vulcanized with EPDM rubber and underwent H-TEST: evidence that the rubber is still glued to the yarn after failure.

Example 19

Tensile Strength Results of SP1/CNT/Latex, SP1/CB/Latex as Well as RFL-Treated Kevlar Yarns The following example demonstrate that the tensile strength of Kevlar cord treated with SP1/CNP/latex with or without rubber to substrate adhesive top coating, didn't decrease its strength, in comparison with untreated Kevlar cord, as measured according to ASTM D-7269. Similar conclusions were drawn from tensile strength measurements of Polyester yarn treated with SP1/CNP/latex with or without rubber to substrate adhesive top coating, which did not decrease its strength (not shown). In addition, it is demonstrated that the stretching ability (Strength at 1% elongation (N)), of Kevlar cord treated with SP1/CNP/latex with or without rubber to substrate adhesive top coating do not change, in contrast to Kevlar cord treated with RFL, which lead to a dramatic increase in Strength at 1% elongation.

TABLE 11

Effect of Kevlar cord treatment with SP1/CNP/latex with or without rubber to substrate adhesive (like Chemosill) top coating or with RFL, on Strength at Max load, Strength at 1% elongation & Elongation at Break

|     |                                    | Strength at Max load (N) | | Strength at 1% elongation (N) | | Elongation at Break (%) | |
| --- | --- | --- | --- | --- | --- | --- | --- |
|     |                                    | Average | STDev | Average | STDev | Average | STDev |
|     | Untreated Aramid                   | 555.54 | 69.72 | 52.82 | 7.0 | 4.74 | 0.66 |
|     | Scoured Aramid                     | 512.04 | 80.96 | 40.6 | 5.30 | 4.89 | 0.7 |
| CNT | Rubber to substrate adhesive top coating | 600.9 | 45.6 | 53 | 8.1 | 5.1 | 0.43 |
|     | w/o top coating                    | 608.3 | 32.4 | 42.4 | 6.33 | 5.0 | 0.62 |
| CB  | Rubber to substrate top coating    | 570.9 | 54.7 | 46.9 | 5.54 | 4.8 | 0.32 |
|     | RFL treated                        | 575.17 | 27.44 | 97.63 | 14.24 | 4.31 | 0.33 |

Results:

Kevlar treatment with both RFL and SP1/CNP don't change strength at max load and elongation at break. SP1/CNP treatment don't change Strength at 1% elongation (N)) (reduces flexibility), in contrast with the RFL treatment that dramatically increase Strength at 1% elongation, which is important when the reinforcement cord should be stretched.

Example 20

Improved Adhesion of SP1/CB Treated Rayon with NR and SBR Rubber Compounds

Figure 16:
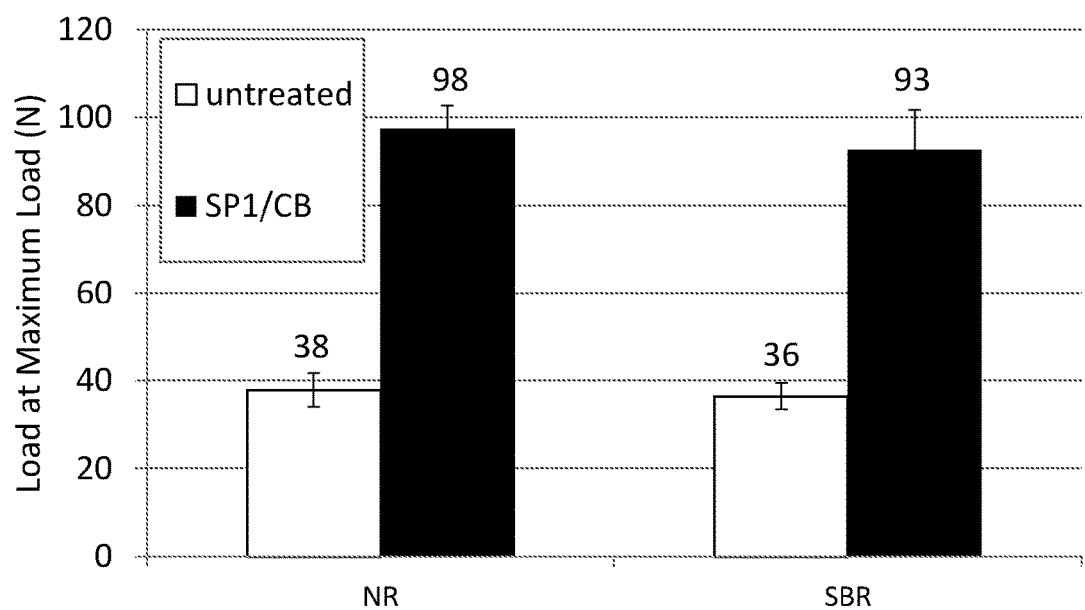
FIG. 16 depicts H-test (ASTM D4776) results with rayon: SP1/CB treatment improves adhesion of untreated Rayon by 160% to both NR and SBR compounds.

H-test (ASTM D4776) results with rayon demonstrate that SP1/CB coating of Rayon improves adhesion of untreated Rayon by 160% to both NR and SBR compounds (FIG. 16).

According to this specific example, in each step of the coating procedure, both when coating with SP1/CB and when coating with PEI, latex was added to the coating mixture (Styrene-butadiene-2-vinylpyridine latex in a ratio of 1:5 latex to PEI or CB), and in the last step a latex capping was added.

Experimental details: Soda ash/triton X-100 scouring (i.e. yarn desizing), PEI (0.2-0.4% i.e., applied load to yarn of 2-4 gr/Kg PEI mixed with latex in a ratio of 1:5 latex:PEI), SP1/CB (0.3% i.e., applied load of 3 gr/Kg SP1/CB mixed with latex in a ratio of 1:5 latex:CB), PEI (0.3-0.5%), SP1/CB (0.6%), PEI (0.4-0.6%), Styrene-butadiene-2-vinylpyridine latex (1:5 in PEI & CB)+7% (i.e. 70 g/Kg applied load of latex capping) Styrene-butadiene-2-vinylpyridine latex cap. (SP1/CB ratio 1:7).

Example 21

Figure 17:
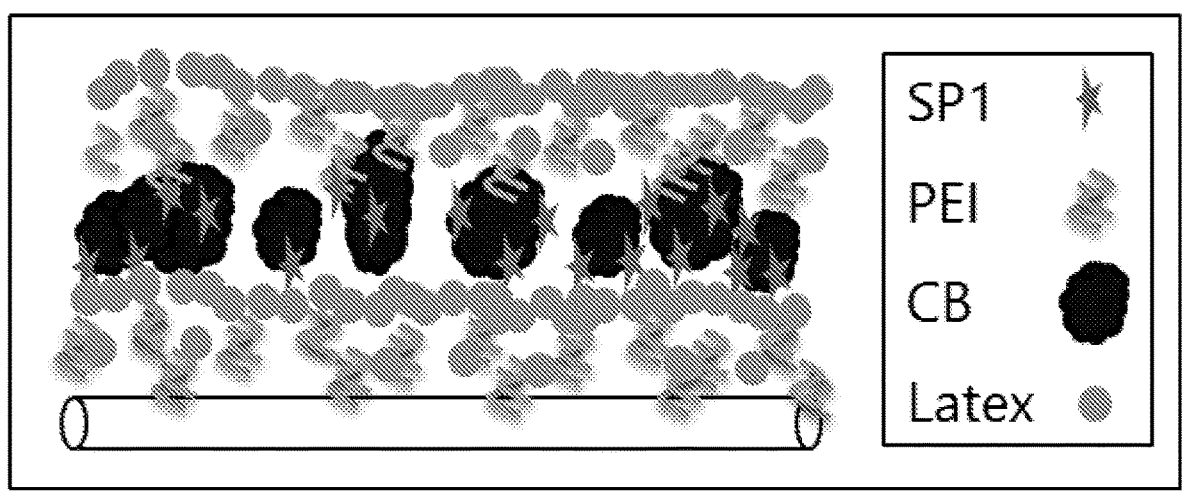
FIG. 17 illustrates the construction of an exemplary yarn's coating treatment according to the invention, which results in five coating layers, of which the middle one is constituted of SP1/CB.
Figure 18:
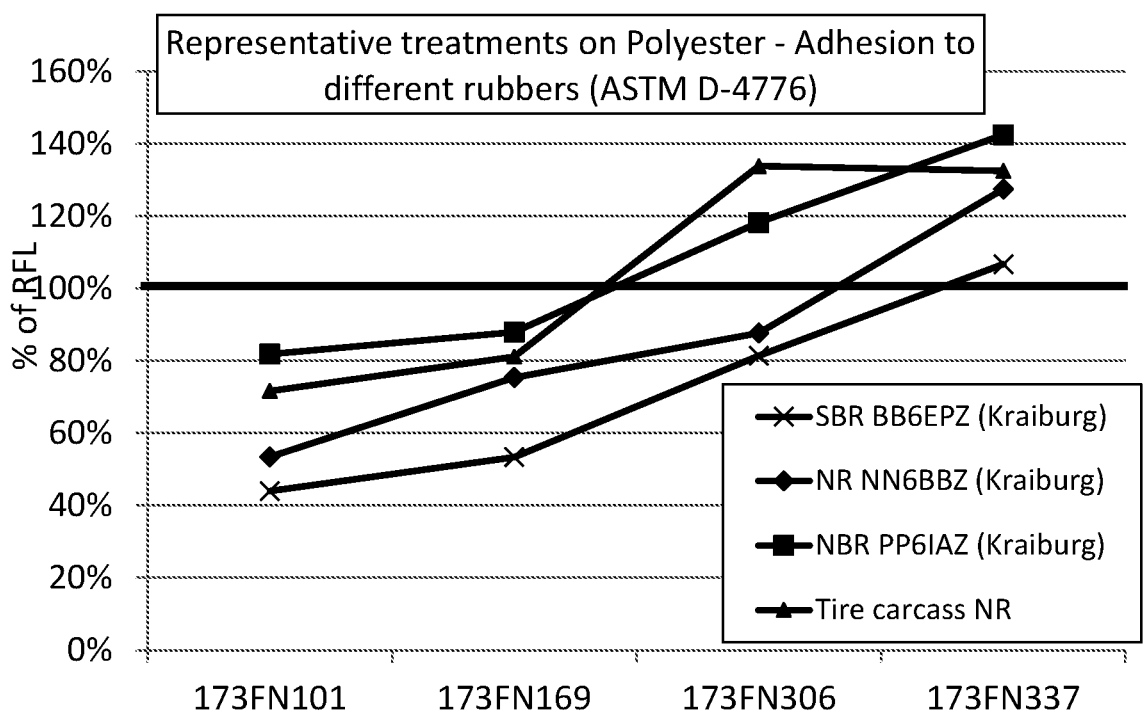
FIG. 18 depicts the improvement in the adhesion of SP1/CB treated polyester yarns to rubbers with respect to RFL, by optimization of the coating conditions with SP1/CB (up to 142% of RFL).
Figure 19:
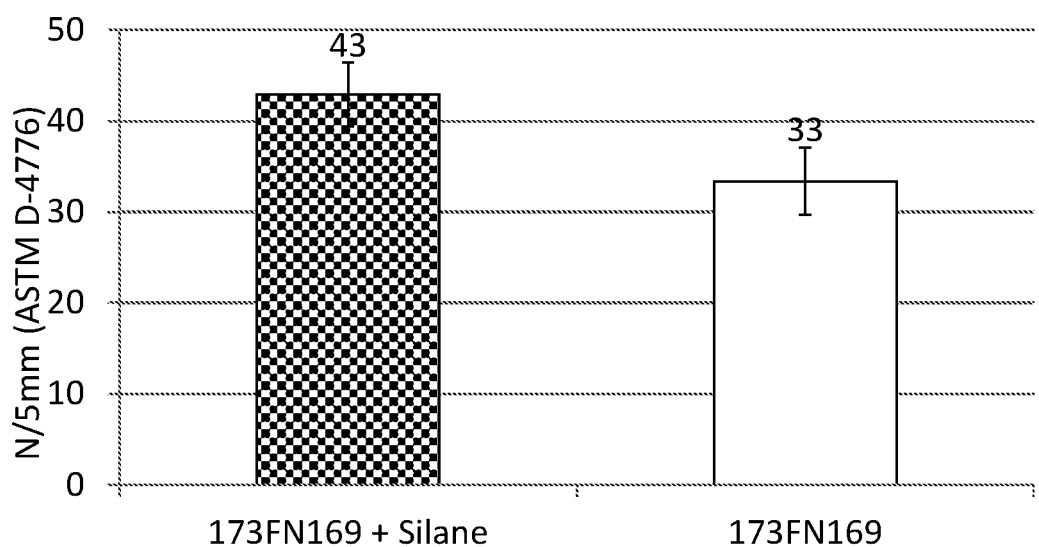
FIG. 19 depicts the effect of tetrasulfidosilane capping on the adhesion of treated polyester yarns to EPDM rubber (adhesion is improved by 30%).

Improved Adhesion of SP1/CB Treated Yarns to Rubbers by Optimization of the Coating Procedure The adhesion of polyester yarns to rubber compounds was further improved by optimization of coating layers configuration, layers content (see FIG. 17) and by the introduction of Styrene-butadiene-2-vinylpyridine latex (FIG. 18) and or silane (e.g. Bis-Triethoxysilylpropyltetrasulfidosilane) (FIG. 19).

Exemplary Coating Conditions According to this Invention by Optimization of Coating Layers Configuration and Layers Content:

Experiment No. 173FN337: KTS scouring, PEI (0.14%, i.e. applied loading of 1.4 g/Kg PEI mixed with latex at a ratio of latex:PEI 1:5), 3% Styrene-butadiene-2-vinylpyridine latex (coating with 3 g/Kg applied load of latex), SP1/CB (0.4%, applied loading of 4 g/Kg of SP1/CB), PEI (0.28%, i.e. applied loading of 2.8 g/Kg PEI mixed with latex at a ratio of latex:PEI 1:5), Styrene-butadiene-2-vinylpyridine latex (1:5 in PEI)+3% Styrene-butadiene-2-vinylpyridine latex cap. (SP1/CB ratio 1:7).

According to this specific example, the coating procedure took place as follows: first a PEI mixture with latex (Styrene-butadiene-2-vinylpyridine latex) was applied, than latex alone, then SP1/CB was applied, followed by a second load of PEI mixture with latex, and finally a latex capping was provided.

Exemplary Improved Coating Conditions by Introduction of Styrene-Butadiene-2-Vinylpyridine Latex:

FIG. 18 demonstrate how optimization of the coating conditions with SP1/CB can result in stronger adhesion than RFL (up to 142%) to rubbers.

Description of the Various Coating Conditions:

Experiment No. 173FN101: KTS scouring, PEI (0.07%), SP1/CB (0.35%), PEI (0.14%), SP1/CB (0.7%), PEI (0.28%), Styrene-butadiene-2-vinylpyridine latex (1:30 in CB). (SP1/CB ratio 1:5.5). i.e., three layers of PEI, two layers of SP1/CB. latex was mixed only with SP1/CB (not with PEI). No latex capping.

Experiment No. 173FN169: KTS scouring, PEI (0.07%), SP1/CB (0.3%), PEI (0.14%), SP1/CB (0.6%), PEI (0.28%), Styrene-butadiene-2-vinylpyridine latex (1:5 in PEI & CB). (SP1/CB ratio 1:7). i.e., three layers of PEI, two layers of SP1/CB. latex was mixed both with SP1/CB and with PEI. No latex capping.

Experiment No. 173FN306: KTS scouring, PEI (0.07%), SP1/CB (0.26%), PEI (0.14%), SP1/CB (0.51%), PEI (0.28%), Styrene-butadiene-2-vinylpyridine latex (1:5 in PEI & CB)+3% Styrene-butadiene-2-vinylpyridine latex cap. (SP1/CB ratio 1:7). i.e., three layers of PEI, two layers of SP1/CB. latex was mixed both with SP1/CB and with PEI. Latex capping is provided.

Experiment No. 173FN337: KTS scouring, PEI (0.14%), 3% Styrene-butadiene-2-vinylpyridine latex, SP1/CB (0.4%), PEI (0.28%), Styrene-butadiene-2-vinylpyridine latex (1:5 in PEI)+3% Styrene-butadiene-2-vinylpyridine latex cap. (SP1/CB ratio 1:7). i.e., two layers of PEI, one layer of SP1/CB. One layer of latex between PEI and SP1/CB. latex was mixed only with PEI, not with SP1/CB. Latex capping is provided.

Exemplary Improved Coating Conditions by Introduction of Bis-Triethoxysilylpropyltetrasulfidosilane:

FIG. 19 demonstrates the effect of the addition of Tetrasulfidosilane (Bis-Triethoxysilylpropyltetrasulfidosilane) to the coating procedure, on the adhesion to EPDM rubber. Addition of silane improves the adhesion to EPDM rubber by 30%.

Experiment No. 173FN169: KTS scouring, PEI (0.07%), SP1/CB (0.3%), PEI (0.14%), SP1/CB (0.6%), PEI (0.28%), Styrene-butadiene-2-vinylpyridine latex (1:5 in PEI & CB). (SP1/CB ratio 1:7).). i.e., three layers of PEI, two layers of SP1/CB. Latex was mixed both with SP1/CB and with PEI. No latex capping. Silane capping is provided in Experiment 173FN169+Silane.

Good adhesion was achieved with other rubber compounds for which different formulas of the SP1 based coating were developed (Table 12)

TABLE 12

H-test (ASTM D4776) results with different rubbers

| Yarn | Construction (dtex) | Rubber | Adhesion [N/5 mm] ASTM D-4776 |
|---|---|---|---|
| Polyester (PET) | 1100X2 | CR1 | 57 |
| | | CR2 | 46 |
| | | EPDM SAA1467/05 | 59 |
| | | NBR (PP6IAZ) | 46 |
| | | NR (NN6BBZ) | 78 |
| | | SBR (BB6EPZ) | 73 |
| | | EPDM (peroxide) | 67 |
| | | NR tire carcass | 79 |
| | | EPDM | 53 |
| | | IIR | 58 |

Example 22

Colorless SP1 Based Coating Procedure, with Improved Adhesion to Rubbers

Figure 20:
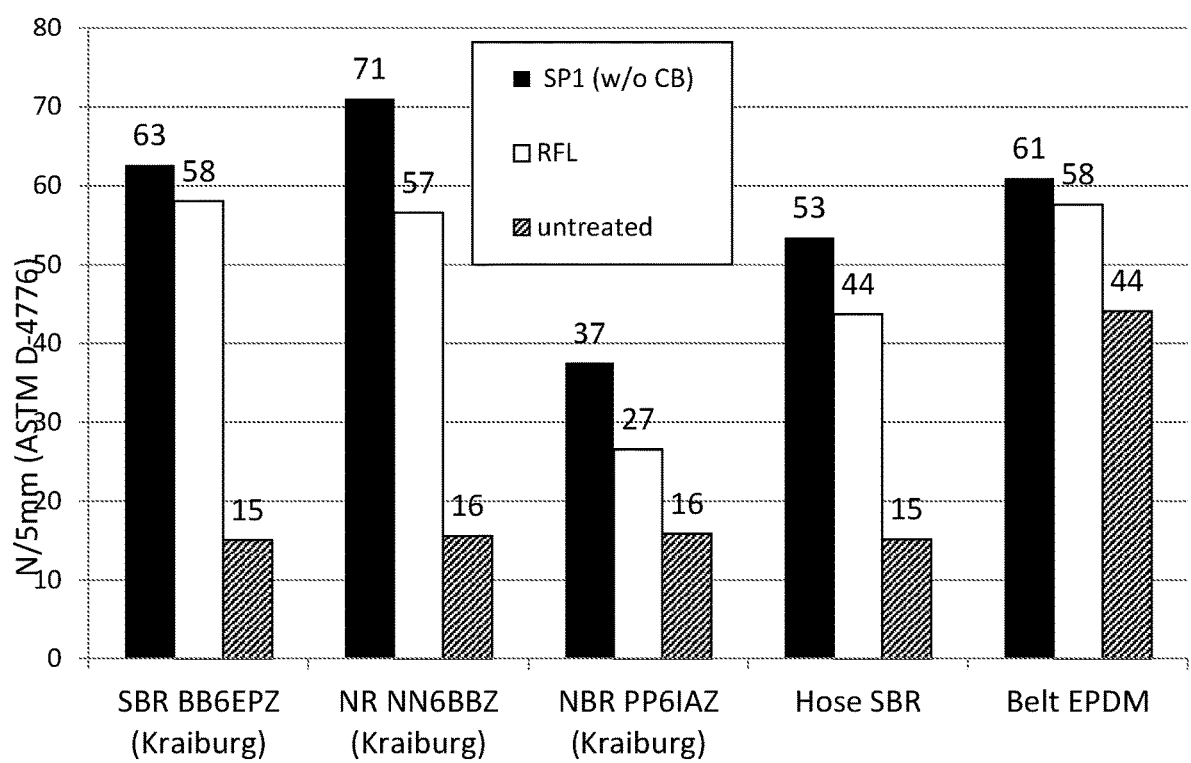
FIG. 20 depicts the effect of adhesion of SP1 treated polyester (PET) (without CB, i.e., colorless coating) (1100×2 dtex) on different rubber compounds, with respect to RFL.

For applications in which the reinforcing yarns should not have a dark color or contain carbon black, colorless SP1 based complexes which devoid of CB were developed (FIG. 20).

Experimental Conditions for SP1 Coating of Polyester Yarns without CB:

KTS scouring, PEI (0.07%), SP1 (0.043%), PEI (0.14%), SP1 (0.086%), PEI (0.28%), Styrene-butadiene-2-vinylpyridine latex (1:5 in PEI)+3% Styrene-butadiene-2-vinylpyridine latex cap. i.e., three layers of PEI mixed with latex, two layers of SP1 (no CB), and latex capping is provided.

Example 23

SP1 Based Coating Compatibility with Rubbers that Undergo Peroxide Based Vulcanization Cross-compatibility was demonstrated with rubber compounds based on different vulcanization systems (i.e., sulphur based, peroxide based). The different coatings that were developed against rubbers with Sulphur based vulcanization were tested against a peroxide based vulcanization EPDM rubber. It was found that also in a different vulcanization system an SP1 based coating [KTS scouring, PEI (0.07%), SP1/CB (0.3%), PEI (0.14%), SP1/CB (0.6%), PEI (0.28%), Styrene-butadiene-2-vinylpyridine latex (5:1 in PEI & CB)+3% Styrene-butadiene-2-vinylpyridine latex cap. (SP1/CB ratio 1:7)] demonstrated strong adhesion: 67N/5 mm were achieved in H-test of 1100×2 dtex PET in a peroxide based vulcanization EPDM rubber. Styrene-butadiene-2-vinylpyridine latex contributed to the adhesion in this system, but Bis-Triethoxysilylpropyltetrasulfidosilane had no contribution as expected.

Example 24

Tensile Strength of SP1 Based Coated Yarns with Respect to RFL Coated Yarns

Tensile strength of polyester (PET) 1100/2 dtex yarns demonstrated that while RFL decreases tensile strength of the yarn by 9% and increase the standard deviation, SP1 based coating treatment does not decrease tensile strength and keeps the standard deviation low, same as untreated (Table 13).

TABLE 13

Tensile strength measurments of polyester Yarn (1100/2 dtex). Exp. No. 173FN169 conditions.

| | Load at Break (N) | | |
|---|---|---|---|
| | SP1/CB | Untreated | RFL |
| | 149 | 142 | 122 |
| | 148 | 145 | 140 |
| | 144 | 145 | 137 |
| | 148 | 144 | 125 |
| | 140 | 144 | 112 |
| | 142 | 145 | 141 |
| | 145 | 141 | 130 |
| | 146 | 142 | 135 |
| | 149 | 145 | 132 |
| | 147 | 140 | 137 |
| avg | 146 | 144 | 131 |
| stdev | 3 | 2 | 9 |
| % of untreated | 102% | 100% | 91% |

Example 25

Improving the Adhesion of Steel Cords to Rubber Using SP1/CB

Aim: replacing the brass coat on steel cord as the adhesion promoter to rubber.

It is frequently necessary to reinforce rubber compositions, for example, for use in tires, conveyor or timing belts, hoses and like products, by incorporating therein steel wire reinforcing elements. The steel wire forming such elements may be for example in the form of a single strand or a steel wire cord. The problem is that bare steel cord adheres poorly to rubber (23% of the adhesion level of brass coated wire; Table 14) as measured by wire pull-out test [ASTM D2229]. Such steel wire reinforcing elements are in general provided with a coating serving to provide adhesion to the rubber composition which it is to reinforce. The state of the art solution is coating with brass alloy (Table 14).

Since untreated steel cord oxidizes readily, a brass coated cord was scoured with $NHO_3$ in order to remove brass completely before coating with our SP1 based coating. A coat of SP1/CB/PEI/Latex was found to yield adhesion to relevant rubbers as high as standard brass treatment (Table 14).

TABLE 14

Pull out of steel wire from rubber after co-vulcanization (ASTM D2229)

| Rubber | Brass (ref.) | HNO₃ scoured | SPnano coat on scoured |
|---|---|---|---|
| Bead wire SBR based compound | 311N | 71N (23% of brass) | 257N (83% of brass) |
| Tire cord adhesion NR based compound | 406N | 95N (23% of brass) | 342N (84% of brass) |

Preliminary Screen:

First, different coating conditions and coat configurations were screened (Table 15).

TABLE 15

Screening of coating configurations and coating conditions.

| step | time (min) | repetitions | Container A | Container B | Container C |
|---|---|---|---|---|---|
| 0 | 30 sec | 3 | ~70% HNO₃ pretreatment (RT, wash thoroughly with DI—H₂O) | | |
| 1 | 1 | 1 | 20 mM carbonate pH 8.8 | 20 mM carbonate pH 8.8 | 20 mM carbonate pH 8.8 |
| 2 | 20 | 1 | 0.05% PEI in 20 mM carbonate pH 8.8 | 0.05% PEI with 5:1 Encord 106 VP (i.e., styrene-butadiene-2-vinylpyridine latex) in 20 mM carbonate pH 8.8 | 0.05% PEI with 5:1 Encord 106 VP in 20 mM carbonate pH 8.8 |
| 3 | 10 sec | 5 | 20 mM carbonate pH 8.8 | 20 mM carbonate pH 8.8 | 20 mM carbonate pH 8.8 |
| 4 | 50 | 1 | 0.1% SP1/CB (1:7) in 20 mM carbonate pH 8.8 | 0.1% SP1/CB (1:7) in 20 mM carbonate pH 8.8 | 0.1% SP1/CB (1:7) with 5:1 Encord 106 VP in 20 mM carbonate pH 8.8 |
| 5 | 10 sec | 5 | 20 mM carbonate pH 8.8 | 20 mM carbonate pH 8.8 | 20 mM carbonate pH 8.8 |
| 6 | | | Repeat 2-5 | Repeat steps 2-4 | Repeat steps 2-4 |
| 7 | 20 | 1 | 0.05% PEI in 20 mM carbonate pH 8.8 | 0.05% PEI with 5:1 Encord 106 VP in 20 mM carbonate pH 8.8 | 0.05% PEI with 5:1 Encord 106 VP in 20 mM carbonate pH 8.8 |
| 8 | 10 sec | 5 | DI—H₂O | DI—H₂O | DI—H₂O |
| 9 | | | Dry at 50° C. for 1 hour | | |

The screen was designed to yield 28 differently coated steel wires, which then tested according to ASTM D2229. The coating procedure of the ~0.8 mm steel wire was conducted in a shaking bath (45° C., 120 rpm, 200 ml). Steel wire: 1 m×10 pieces in each plastic container. Two wire pieces were taken out of each container following the washes that follows each coating step (steps 2, 4, 7 and their repeats: PEI or CB coating). One of the two pieces was rinsed with DI-H₂O and dried, while the other was further coated (30', 45° C., 120 rpm) with Encord 106 VP latex (Styrene-butadiene-2-vinylpyridine latex) 0.4% (w/v) in 20 mM carbonate pH 8.8 and then washed×3 in DI-H₂O and dried.

Figure 21A:
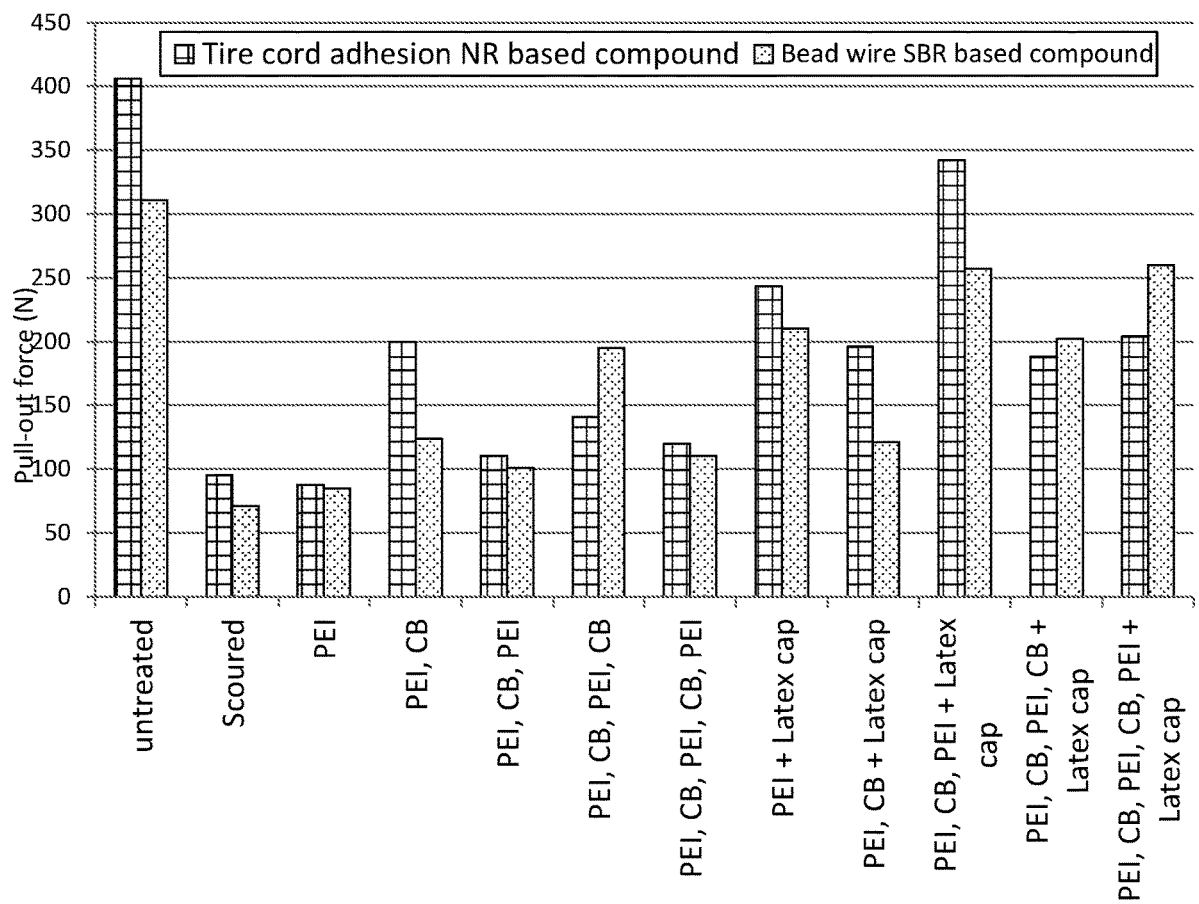
FIGS. 21A-21C depict pull-out force of steel wire, treated with various SP1/CB based coating procedures from two rubber compounds.
Figure 21B:
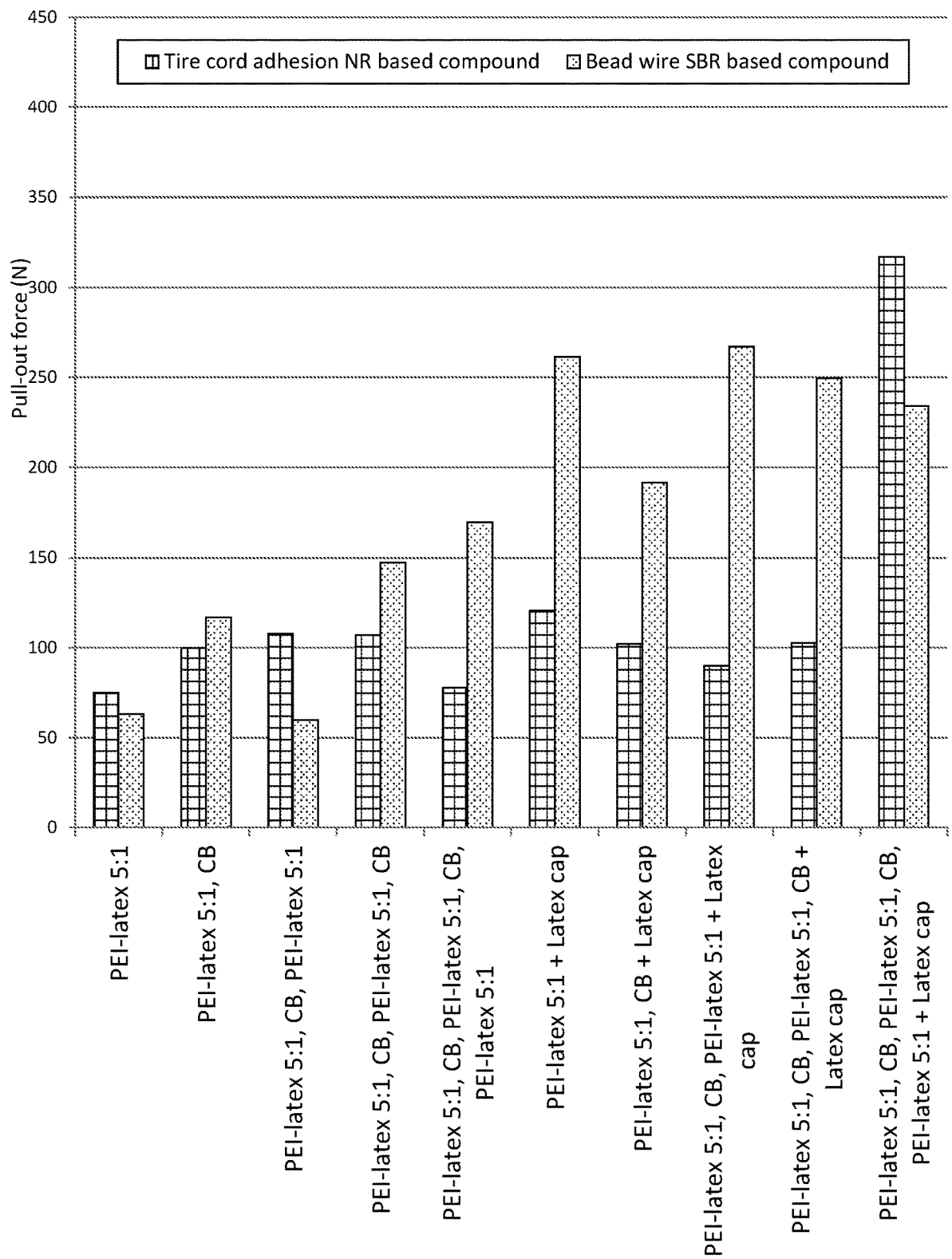
Figure 21C:
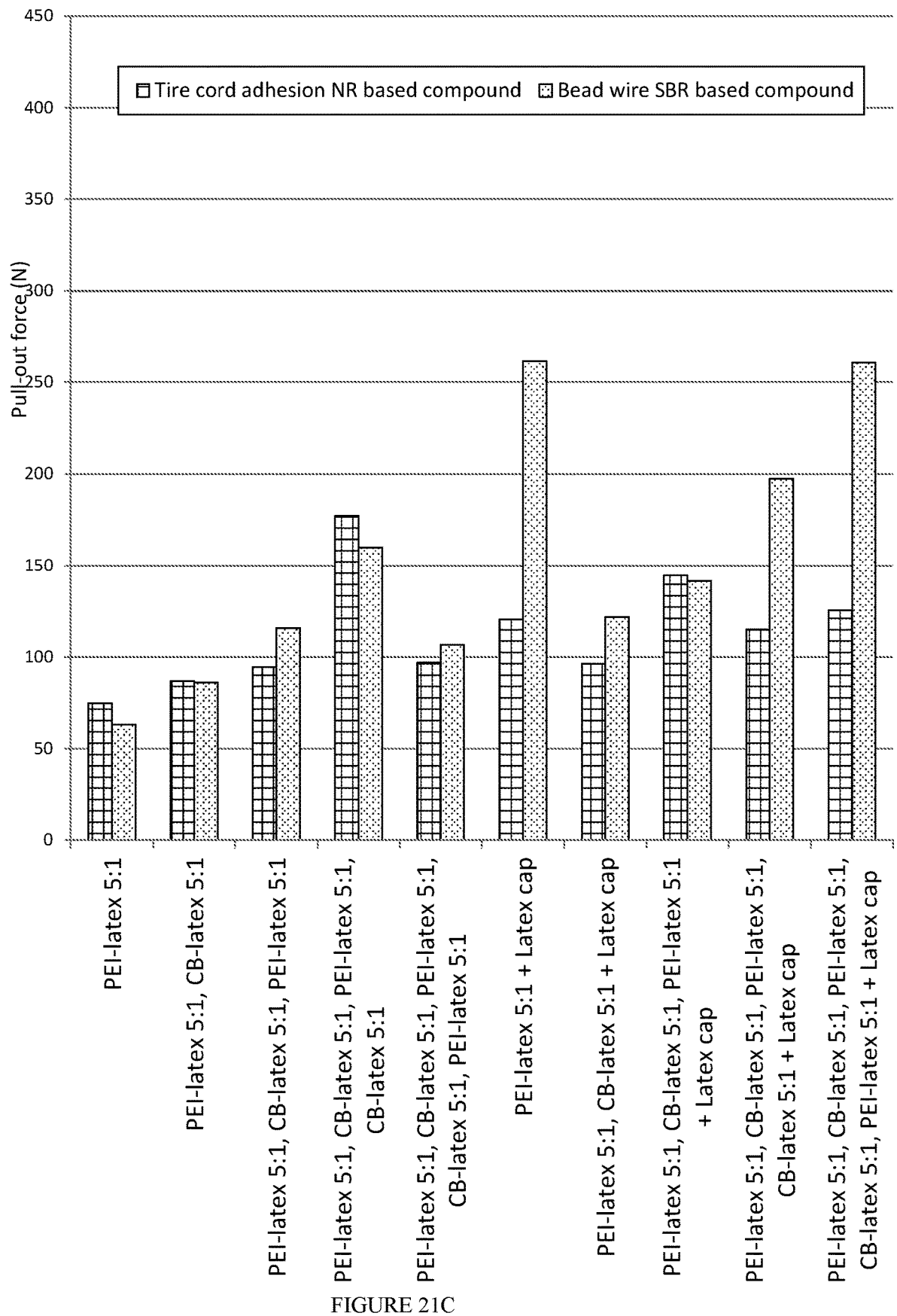
Figure 22:
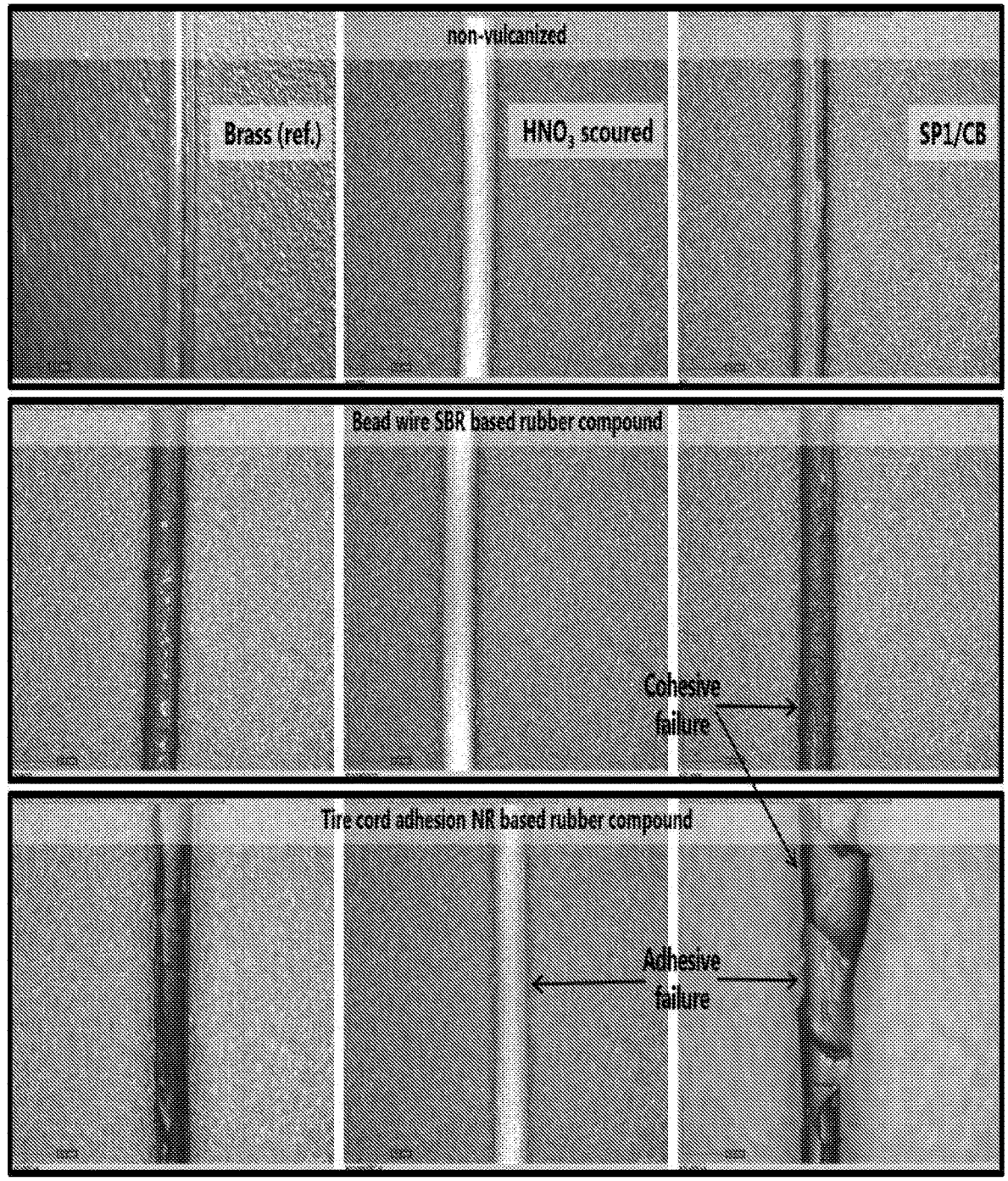
FIG. 22 depicts the appearance of the rubber coverage on the wire after pull-out test for brass coated, untreated and SP1/CB coated steel wire.
Figure 23:
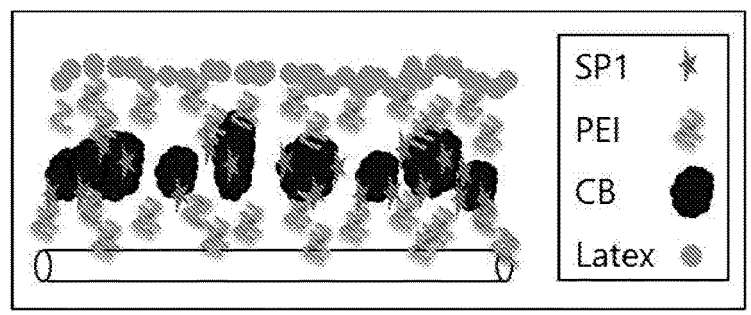
FIG. 23 depicts the simplest SP1/CB treatment of a steel cord that yielded 83%-84% adhesion of brass level to both rubbers.

Under the simplest treatment (FIG. 23) that yielded both strong adhesion to both rubbers (FIG. 21) and appearance rating of the wire (degree of rubber coverage on the wire after pull-out) (FIG. 22), 83%-84% of brass adhesion was achieved with one layer of SP1/CB with bead wire SBR based compound and tire cord adhesion NR based compound, respectively (FIG. 21).

Following the preliminary screen, more experiments were conducted to optimize the configuration of layers, layers content and addition of functional groups (e.g., silanes). The goal of the optimization process was to reach brass adhesion level and the degree of rubber coverage on the wire after pull-out.

The simplest treatment that yielded adhesion similar to brass contained another layer of latex on top of the first PEI layer.

Each step in the process of yarn coating in a batch dying machine takes 10-60 minutes. Since steel cords or wires should (but not limited to) be coated in a continuous manner, each step of the coating process should take no more than few seconds. Shortening the dwell time to 10-20 seconds was accomplished without affecting adhesion results, by enhancing the binding rate as a result of increase in the reactants concentrations: SP1/CB, PEI and latex concentrations were increased from 0.1% (SP1/CB), 0.05% (PEI) and 0.4% (latex) to 0.25% (SP1/CB), 1-5% (PEI) and 2-5% (latex), respectively.

Figure 25:
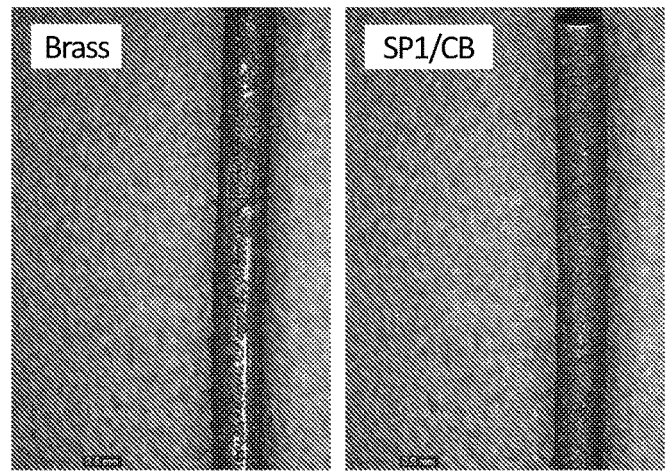
FIG. 25 depicts the appearance of the rubber coverage on the steel cord after pull-out test.
Figure 25:
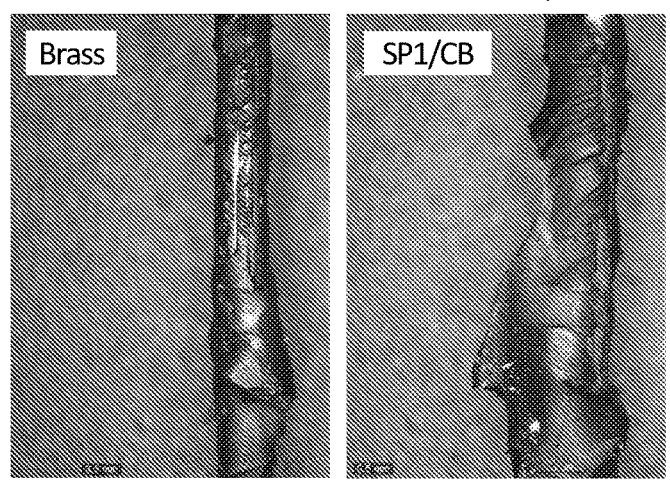

Finally, the following protocol (Table 16) was adopted to allow short dwell time (10-20 seconds) and adhesion (Table 16) and rubber coverage on the wire after pull-out (FIG. 25) similar to brass.

TABLE 16

Figure 24:
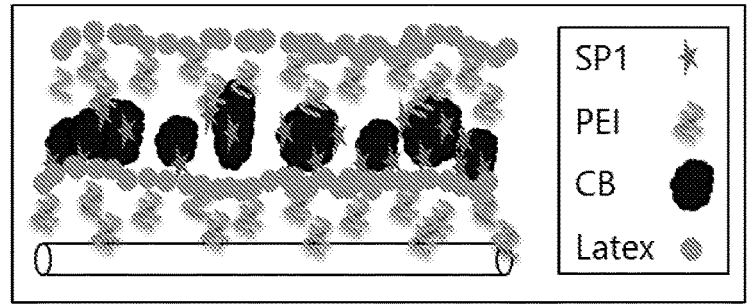
FIG. 24 depicts the simplest SP1/CB based coating treatment of a steel cord that yielded adhesion similar to brass level to both rubbers.

FIG. 24). Protocol allowing short dwell time (10-20 seconds) and adhesion similar to brass

| step | time | repetitions | description |
|---|---|---|---|
| 1 | 25 sec | 1 | 20 mM carbonate pH 8.8 |
| 2 | ‖ | 1 | 1-5% BASF PEI in 20 mM carbonate pH 8.8 |
| 3 | ‖ | 4 | DI—H₂O |
| 4 | ‖ | 1 | 20 mM carbonate pH 8.8 |

TABLE 16-continued

FIG. 24). Protocol allowing short dwell time
(10-20 seconds) and adhesion similar to brass

| step | time | repetitions | description |
|------|------|-------------|-------------|
| 5 | ‖ | 1 | 2-5% Encord 106 VP in 20 mM carbonate pH 8.8 |
| 6 | ‖ | 4 | DI—$H_2O$ |
| 7 | ‖ | 1 | 20 mM carbonate pH 8.8 |
| 8 | ‖ | 1 | 0.25% CB/SP1 (7:1) in 20 mM carbonate pH 8.8 |
| 9 | ‖ | 4 | DI—$H_2O$ |
| 10 | ‖ | 1 | 20 mM carbonate pH 8.8 |
| 11 | ‖ | 1 | 1-5% BASF PEI in 20 mM carbonate pH 8.8 |
| 12 | ‖ | 4 | DI—$H_2O$ |
| 13 | ‖ | 1 | 20 mM carbonate pH 8.8 |
| 14 | ‖ | 1 | 2-5% Encord 106 VP in 20 mM carbonate pH 8.8 |
| 15 | ‖ | 5 | DI—$H_2O$ |
| 16 | | | Drying at 40° C. |

TABLE 17

Pull out of steel wire from rubber
after co-vulcanization (ASTM D2229)

| Rubber | Brass (ref.) | SP1/CB treatment on scoured |
|--------|--------------|------------------------------|
| Bead wire SBR based compound | 272N | 297N |
| Tire cord adhesion NR based compound | 330N | 394N |

In summary, an SP1 based coating was developed to replace brass as the adhesion promoter to different relevant rubber compounds. In addition the dwell time was reduced from 30-60 minutes to 10-20 seconds to allow a continuous coating process. Wires coated at this manner demonstrated no statistical significant difference from brass coated wires on both, pull-out force (N) of steel wire from rubber after co-vulcanization and appearance rating of the wire (% degree of rubber coverage on the wire after pull-out) (ASTM D2229).

Example 26

Improved Adhesion of DVA Films to Rubber Using SP1/CB/Latex Based Composition

Treatment

A dispersion of SP1/CB/latex was prepared by sonication as described previously (with Encord 106 vp latex) A DVA Film (thin dynamically vulcanized alloy (DVA) resin. Non permeable, air tight polymer, based on nylon resin) was incubated in a shaking machine at 40° C. The DVA film treated with one or two layers of SP1/CB or SP1/CNT (dispersion with Latex. Ratio CB/SP1—7:1 (w/w). Ratio CB/Latex—5:1 (w/w)) and dried at 50° C. for 1 hour.

Rubber-Film System.

A DVA film was placed between two NR sheets reinforced with Charmeuse fabric. Charmeuse fabric is a fabric comprising satin weave, fibers of rayon, viscose, polyester and/or mixed fibers. Charmeuse fabric is used in rubber-film systems in order to prevent elongation of the rubber during the peel-test, enabling only the measurement of adhesion between the rubber and the film after vulcanization. The total thickness of the sample was 2 mm, and its dimensions were 5×6 inch (FIG. 26).

Adhesion Test Conditions

Vulcanization: performed at 150° C., 25 bar, for 20 minutes using tire carcass natural rubber (NR) in a pre-heated mold.

Peel test at −20° C.: vulcanized samples were incubated for 1 hour at −20° C. and then immediately the adhesion was measured.

Peel test at 120° C.: vulcanized samples were incubated for 10 mins at 120° C. and then immediately tested.

Peel test at high humidity: vulcanized samples were immersed in water for 12 hours and then tested.

The results from the peel tests are summarized in Table 18.

TABLE 18

Peel test results. For each condition average and maximal loads are shown.

| | Peel test condition | | | | | | | |
|---|---|---|---|---|---|---|---|---|
| | −20° C. | | RT | | 120° C. | | High humidity | |
| | Average N/inch | Maximum N/inch | Average N/inch | Maximum N/inch | Average N/inch | Maximum N/inch | Average N/inch | Maximum N/inch |
| SP1/CB (1:7) treated DVA film | 70 | 81 | 133 | 157 | 74 | 95 | 92 | 108 |
| Un-treated DVA film | 39 | 42 | 49 | 55 | 36 | 39 | 27 | 36 |

Following screening of several SP1/CB and SP1/CB/Latex treatments (Dispersions with and without Encord 106 VP Latex) of the DVA film, 130 N/inch were achieved in peel test (Table 18). Dimensions of pre-peeled sample are shown in FIG. 28. Peel strength was checked at various conditions and a significant benefit was demonstrated for SP1/CB/latex treated film compared to untreated film.

Variety of peel test conditions were examined. Low and high temperatures together with high humidity tests showed that SP1/CB/Latex treated DVA film was able to keep a good adhesion to the rubber compared to untreated DVA film. This adhesion was demonstrated with natural rubber (NR) received from international tires company which is used as an inner liner at tire technology (also suitable for DVA film application) following 25 minutes vulcanization at 150° C. according to the model showed at FIG. 26. Other rubber types were tested as well, including SBR, nitrile rubber and their combinations (results are not shown). In all cases of SP1/CB/Latex treated films, the failure was cohesive. Cohesive failure of the film was evident as parallel longitudinal footprints of the torn film on the opposite rubber (FIG. 27), most probably due to the film structure.

Adhesion of the SP1/CB/latex treated DVA film surface to NR was excellent, as the failure was converted to cohesive failure with complete cover of the film by the rubber as shown in FIG. 29.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition of matter comprising carbon black (CB) bound to a Stable Protein 1 (SP1) based polypeptide.

2. The composition of matter of claim 1, wherein said CB is non: covalently bound to said SP1 based polypeptide.

3. The composition of matter of claim 1, wherein said SP1 based polypeptide has the amino acid sequence as set forth in any one of SEQ ID NOs: 3, 4, 6, 8, 9, 14-18 and 86; wherein said CB:SP1 ratio is between 0.1:1 to 30:1 dry w/w; wherein said composition is in the form of an aqueous dispersion in a concentration of between 0.001% and 30% w/w; or any combination thereof.

4. The composition of matter of claim 3, wherein said CB:SP1 ratio is between 5:1 to 7:1 dry w/w; wherein said composition is in the form of an aqueous dispersion in a concentration between 0.05% and 0.15% w/w, a concentration of 15% w/w; or any combination thereof.

5. The composition of matter of claim 1, further comprising latex.

6. The composition of matter of claim 5, wherein said latex is natural latex or synthetic latex and is selected from: Carboxylated Styrene Butadiene polymers, Styrene-butadiene-2-vinylpyridine, vinyl pyridine latex, vinyl pyridine/butadiene/styrene blend, ammonia prevulcanized natural rubber, colloidal dispersion of a polymer of 2-chlorobutadiene (1,3), Anionic stabilized aqueous latex of a carboxylated butadiene based product, an aqueous dispersion of a terpolymer of butadiene, styrene and 2-vinylpyridine, a random ter-polymer of Vinyl Pyridine, Styrene and Butadiene monomer dispersed in an aqueous medium or any combination thereof.

7. The composition of matter of claim 5, wherein said CB:latex ratio is between 1:10 to 50:1.

8. A surface coated with the composition of matter of claim 1.

9. The surface of claim 8, wherein said surface is metal wire or cord, or a polymeric or non polymeric fiber, yarn, film, or fabric; wherein the applied load of said composition on said surface is between 0.1 gr/kg and 50 gr/kg; wherein the surface further comprises at least one layer of latex; at least one layer of polyethyleneimine (PEI); a plurality of layers of said composition of matter bound to said surface; or any combination thereof.

10. The surface of claim 9, wherein said fiber, yarn, film, or fabric comprises at least one of: carbon, basalt, cotton, rayon, wool, silk, nylon, DVA, polyester, aramid, polypropylene, glass fiber, and elastane; or wherein said wire or cord is a steel wire or cord.

11. The surface of claim 9, wherein the latex is Styrene-butadiene-2-vinylpyridine; wherein the surface comprises two layers of said composition of matter bound to said surface; wherein the applied load of said composition on said surface is between 1 gr/kg and 14 gr/kg; or any combination thereof.

12. The surface of claim 8, attached to a rubber compound.

13. A rubber compound composite comprising the surface of claim 8.

14. The rubber compound composite of claim 13, wherein said rubber is selected from: Natural rubber (NR), Polychloroprene (CR), Nitrile (NBR), Ethylene Propylene (EPDM), natural rubber, Aflas (AG Fluoropolymers), Butyl (IIR), Chlorsulfonated Polyethylene (CSM), Epichlorohydrin (ECO), Fluoroelastomer (FKM), Flurosilicone (FQ), Hydrogenated Nitrile (HNBR), Perfluoroelastomer (FFKM), Polyacrylic (ACM), Plyurethan (PU), Silicone (Q) and Styrene Butadiene (SBR).

15. A mechanical rubber good or a pneumatic or semi-pneumatic tire, comprising the surface of claim 8.

16. The mechanical rubber good of claim 15, selected from: a tire; Power Transmission belt; Conveyor, Elevator-Transmission Belting; a hydraulic hose, a timing belt and a rubber boat.

17. A method of producing a surface coated with the composition of matter of claim 1, comprising contacting a dispersion comprising the composition of claim 1 with a surface.

18. The method of claim 17, wherein said method is repeated at least once; wherein said method further comprises a step of desizing said surface prior to contacting it with said composition; a step of washing the unbound composition from said surface; a step of contacting the surface with latex prior to and/or after contacting the surface with said composition, and after said desizing; a step of contacting the surface with a solution comprising polyethyleneimine (PEI) prior to and/or after contacting the surface with said composition, and after said desizing; a step of contacting said surface with solution comprising PEI, latex, or a silane coupling agent as the last step; a step of contacting said surface with a rubber-to-substrate adhesive; or any combination thereof.

19. The method of claim 18, wherein the solution comprising PEI, further comprises latex.

20. The method of claim 19, wherein the PEI:latex ratio in said solution is between 1:20 to 20:1.

21. A method of producing a surface coated with the composition of matter of claim 1, comprising:
(a) Optionally desizing a surface;
(b) Optionally contacting said surface with a solution comprising polyethyleneimine (PEI);
(c) Optionally contacting said surface with latex;
(d) Contacting a dispersion comprising the composition of claim 1 with said surface;
(e) Optionally repeating steps (b) and/or (c) and/or (d) at least once; and
(f) Optionally contacting said surface, with at least one of: PEI, latex, a silane coupling agent, or a rubber-to-substrate adhesive.

22. The method of claim 21, wherein the optional desizing of method step (a) is scouring a steel wire or cord with an acid, wherein the surface of method step (b) is a steel wire or cord, and wherein the surface of step (f) is contacted with PEI followed by latex.

23. The method of claim 21, wherein the desizing of method step (a) is desizing a polymeric or non-polymeric fiber, yarn, film or fabric, wherein the contacting of method step (b) is
contacting said polymeric or non-polymeric fiber, yarn, film or fabric with solution comprising polyethyleneimine (PEI), and wherein the surface of step (f) is contacted with PEI followed by latex or a silane coupling agent.

24. The method of claim 23, wherein the silane coupling agent is Tetrasulfidosilane; the latex is Styrene-butadiene-2-vinylpyridine latex; wherein the method further comprises a step of washing said surface with a buffer or water after each step of the method; wherein said contacting is utilizing a textile dying machine; or any combination thereof.

25. A mechanical rubber good or a pneumatic or semi-pneumatic tire, comprising the composition of matter of claim 1.

* * * * *

SEQUENCE LISTING

```
<160> NUMBER OF SEQ ID NOS: 89

<210> SEQ ID NO 1
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      M43C mutated

<400> SEQUENCE: 1

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Cys Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 2
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted,
      L81C mutated 21

<400> SEQUENCE: 2

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Cys Asp Ser Ala Ala
65                  70                  75                  80
```

```
Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 3
<211> LENGTH: 114
<212> TYPE: PRT
<213> ORGANISM: Artificial sequence
<220> FEATURE:
<223> OTHER INFORMATION: mTB peptide fused to N' of Sp1 (2-6 deleted and
      M43C mutated)

<400> SEQUENCE: 3

Met Arg Lys Leu Pro Asp Ala Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30

Asp Asn Tyr Ile Asn Asp Tyr Thr Asn Leu Leu Asp Leu Ile Pro Ser
        35                  40                  45

Met Lys Ser Phe Asn Trp Gly Thr Asp Leu Gly Met Glu Ser Ala Glu
    50                  55                  60

Leu Asn Arg Gly Tyr Thr His Ala Phe Glu Ser Thr Phe Glu Ser Lys
65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 4
<211> LENGTH: 108
<212> TYPE: PRT
<213> ORGANISM: Populus tremula
<220> FEATURE:
<221> NAME/KEY: misc_feature
<223> OTHER INFORMATION: Wild type Sp1 polypeptide

<400> SEQUENCE: 4

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 5
<211> LENGTH: 6
<212> TYPE: PRT
<213> ORGANISM: Artificial sequence
<220> FEATURE:
```

<223> OTHER INFORMATION: mTBP peptide

<400> SEQUENCE: 5

Arg Lys Leu Pro Asp Ala
1               5

<210> SEQ ID NO 6
<211> LENGTH: 120
<212> TYPE: PRT
<213> ORGANISM: Artificial sequence
<220> FEATURE:
<223> OTHER INFORMATION: L1-Sp1 fusion polypeptide

<400> SEQUENCE: 6

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Arg Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 7
<211> LENGTH: 333
<212> TYPE: DNA
<213> ORGANISM: Artificial sequence
<220> FEATURE:
<223> OTHER INFORMATION: Delta N' SP1 coding sequence

<400> SEQUENCE: 7
ccacagagag aaagggaaga catgaagctt gtgaagcaca cattgttgac tcggttcaag      60
gatgagatca cacgagaaca gatcgacaac tacattaatg actataccaa tctgctcgat     120
ctcattccaa gcatgaagag tttcaattgg ggcacggatc tgggcatgga gtctgcggag     180
ctaaaccgag atacactca tgcctttgaa tctacatttg agagcaagtc tggttttgcaa     240 gagtacctcg attctgctgc tcttgctgca tttgcagaag gttttttgcc tactttgtca     300
cagcgtcttg tgatagacta ctttctctac taa                                  333

<210> SEQ ID NO 8
<211> LENGTH: 120
<212> TYPE: PRT
<213> ORGANISM: Artificial sequence
<220> FEATURE:
<223> OTHER INFORMATION: L3-Sp1 fusion polypeptide

<400> SEQUENCE: 8

Met Asp Tyr Phe Ser Ser Pro Tyr Tyr Glu Gln Leu Phe Ala Thr Arg
1               5                   10                  15

Thr Pro Lys Leu Val Lys His Thr Leu Leu Thr Arg Phe Lys Asp Glu
            20                  25                  30

```
Ile Thr Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
 50                      55                  60

Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
                 85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 9
<211> LENGTH: 120
<212> TYPE: PRT
<213> ORGANISM: Artificial sequence
<220> FEATURE:
<223> OTHER INFORMATION: L4-Sp1 fusion polypeptide

<400> SEQUENCE: 9

Met His Trp Ser Ala Trp Trp Ile Arg Ser Asn Gln Ser Ala Thr Arg
 1               5                  10                  15

Thr Pro Lys Leu Val Lys His Thr Leu Leu Thr Arg Phe Lys Asp Glu
            20                  25                  30

Ile Thr Lys Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
 50                      55                  60

Gly Met Glu Ser Ala Glu Leu Asn Arg Gly Tyr Thr His Ala Phe Glu
 65                  70                  75                  80

Ser Thr Phe Glu Ser Lys Ser Gly Leu Gln Glu Tyr Leu Asp Ser Ala
                 85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 10
<211> LENGTH: 12
<212> TYPE: PRT
<213> ORGANISM: Artificial sequence
<220> FEATURE:
<223> OTHER INFORMATION: L1 peptide

<400> SEQUENCE: 10

His Trp Ser Ala Trp Trp Ile Arg Ser Asn Gln Ser
 1               5                  10

<210> SEQ ID NO 11
<211> LENGTH: 12
<212> TYPE: PRT
<213> ORGANISM: Artificial sequence
<220> FEATURE:
<223> OTHER INFORMATION: L2 peptide

<400> SEQUENCE: 11

His Ser Ser Tyr Trp Tyr Ala Phe Asn Asn Lys Thr
 1               5                  10
```

```
<210> SEQ ID NO 12
<211> LENGTH: 12
<212> TYPE: PRT
<213> ORGANISM: Artificial sequence
<220> FEATURE:
<223> OTHER INFORMATION: L3 peptide

<400> SEQUENCE: 12

Asp Tyr Phe Ser Ser Pro Tyr Tyr Glu Gln Leu Phe
1               5                   10

<210> SEQ ID NO 13
<211> LENGTH: 4
<212> TYPE: PRT
<213> ORGANISM: Artificial sequence
<220> FEATURE:
<223> OTHER INFORMATION: L6 peptide

<400> SEQUENCE: 13

Ser Asn Gln Ser
1

<210> SEQ ID NO 14
<211> LENGTH: 120
<212> TYPE: PRT
<213> ORGANISM: Artificial sequence
<220> FEATURE:
<223> OTHER INFORMATION: L2-Sp1 fusion polypeptde

<400> SEQUENCE: 14

Met His Ser Ser Tyr Trp Tyr Ala Phe Asn Asn Lys Thr Ala Thr Arg
1               5                   10                  15

Thr Pro Lys Leu Val Lys His Thr Leu Leu Thr Arg Phe Lys Asp Glu
                20                  25                  30

Ile Thr Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
        50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120

<210> SEQ ID NO 15
<211> LENGTH: 112
<212> TYPE: PRT
<213> ORGANISM: Artificial sequence
<220> FEATURE:
<223> OTHER INFORMATION: L6-Sp1 fusion polypeptide

<400> SEQUENCE: 15

Met Ser Asn Gln Ser Ala Thr Arg Thr Pro Lys Leu Val Lys His Thr
1               5                   10                  15

Leu Leu Thr Arg Phe Lys Asp Glu Ile Thr Arg Glu Gln Ile Asp Asn
                20                  25                  30

Tyr Ile Asn Asp Tyr Thr Asn Leu Leu Asp Leu Ile Pro Ser Met Lys
            35                  40                  45

Ser Phe Asn Trp Gly Thr Asp Leu Gly Met Glu Ser Ala Glu Leu Asn
```

Arg Gly Tyr Thr His Ala Phe Glu Ser Thr Phe Glu Ser Lys Ser Gly
65                  70                  75                  80

Leu Gln Glu Tyr Leu Asp Ser Ala Ala Leu Ala Ala Phe Ala Glu Gly
                85                  90                  95

Phe Leu Pro Thr Leu Ser Gln Arg Leu Val Ile Asp Tyr Phe Leu Tyr
            100                 105                 110

<210> SEQ ID NO 16
<211> LENGTH: 120
<212> TYPE: PRT
<213> ORGANISM: Artificial sequence
<220> FEATURE:
<223> OTHER INFORMATION: L7-Sp1 fusion polypeptide

<400> SEQUENCE: 16

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
                20                  25                  30

Ile Thr Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 17
<211> LENGTH: 120
<212> TYPE: PRT
<213> ORGANISM: Artificial sequence
<220> FEATURE:
<223> OTHER INFORMATION: L5-Sp1 fusion polypeptide

<400> SEQUENCE: 17

Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
                20                  25                  30

Ile Cys Arg Glu Gln Ile Asp Asn Tyr Ile Asn Asp Tyr Thr Asn Leu
            35                  40                  45

Leu Asp Leu Ile Pro Ser Met Lys Ser Phe Asn Trp Gly Thr Asp Leu
50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
            115                 120

<210> SEQ ID NO 18
<211> LENGTH: 120
<212> TYPE: PRT
<213> ORGANISM: Artificial sequence
<220> FEATURE:
<223> OTHER INFORMATION: L8-Sp1 fusion polypeptide

<400> SEQUENCE: 18

```
Met His Trp Ser Ala Trp Trp Ile Arg Ser Asn Gln Ser Ala Thr Arg
1               5                   10                  15

Thr Pro Lys Leu Val Lys His Thr Leu Leu Thr Arg Phe Lys Asp Glu
            20                  25                  30

Ile Thr Lys Glu Gln Ile Asp Asn Tyr Ile Asn Asp Tyr Thr Asn Leu
        35                  40                  45

Leu Asp Leu Ile Pro Ser Met Lys Ser Phe Asn Trp Gly Thr Asp Leu
    50                  55                  60

Gly Met Glu Ser Ala Glu Leu Asn Arg Gly Tyr Thr His Ala Phe Glu
65                  70                  75                  80

Ser Thr Phe Glu Ser Lys Ser Gly Leu Gln Glu Tyr Leu Asp Ser Ala
                85                  90                  95

Ala Leu Ala Ala Phe Ala Glu Gly Phe Leu Pro Thr Leu Ser Gln Arg
            100                 105                 110

Leu Val Ile Asp Tyr Phe Leu Tyr
        115                 120
```

<210> SEQ ID NO 19
<211> LENGTH: 6
<212> TYPE: PRT
<213> ORGANISM: Artificial sequence
<220> FEATURE:
<223> OTHER INFORMATION: Exemplary heterologous titanium binding peptide

<400> SEQUENCE: 19

```
Arg Ala Leu Pro Asp Ala
1               5
```

<210> SEQ ID NO 20
<211> LENGTH: 10
<212> TYPE: PRT
<213> ORGANISM: Artificial sequence
<220> FEATURE:
<223> OTHER INFORMATION: Exemplary peptide that binds inorganic substances

<400> SEQUENCE: 20

```
Ala Lys Pro Ser Tyr Pro Pro Thr Tyr Lys
1               5                   10
```

<210> SEQ ID NO 21
<211> LENGTH: 6
<212> TYPE: PRT
<213> ORGANISM: Artificial sequence
<220> FEATURE:
<223> OTHER INFORMATION: Exemplary peptide that binds inorganic substances

<400> SEQUENCE: 21

```
Ala Lys Pro Thr Tyr Lys
1               5
```

<210> SEQ ID NO 22
<211> LENGTH: 10
<212> TYPE: PRT

```
<213> ORGANISM: Artificial sequence
<220> FEATURE:
<223> OTHER INFORMATION: Exemplary peptide that binds inorganic
      substances

<400> SEQUENCE: 22

Pro Lys Ile Ser Tyr Pro Pro Thr Tyr Lys
1               5                   10

<210> SEQ ID NO 23
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Ala Pro Pro Pro Ala Xaa Thr Ala Xaa Lys
1               5                   10

<210> SEQ ID NO 24
<211> LENGTH: 10
<212> TYPE: PRT
<213> ORGANISM: Artificial sequence
<220> FEATURE:
<223> OTHER INFORMATION: Exemplary peptide that binds inorganic
      substances
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 24

Ala Thr Pro Lys Pro Xaa Thr Ala Xaa Lys
1               5                   10

<210> SEQ ID NO 25
<211> LENGTH: 4
<212> TYPE: PRT
<213> ORGANISM: Artificial sequence
<220> FEATURE:
<223> OTHER INFORMATION: Exemplary peptide that binds inorganic
      substances

<400> SEQUENCE: 25

Pro Tyr Val Lys
1

<210> SEQ ID NO 26
<211> LENGTH: 12
<212> TYPE: PRT
<213> ORGANISM: Artificial sequence
<220> FEATURE:
<223> OTHER INFORMATION: Exemplary peptide that binds inorganic
      substances

<400> SEQUENCE: 26
```

```
Ala Lys Pro Ser Pro Tyr Val Pro Thr Gly Tyr Lys
1               5                   10
```

<210> SEQ ID NO 27
<211> LENGTH: 13
<212> TYPE: PRT
<213> ORGANISM: Artificial sequence
<220> FEATURE:
<223> OTHER INFORMATION: Exemplary peptide that binds inorganic
      substances

<400> SEQUENCE: 27

```
Gly Gln Gln Lys Gln Thr Ala Tyr Asp Pro Gly Tyr Lys
1               5                   10
```

<210> SEQ ID NO 28
<211> LENGTH: 567
<212> TYPE: DNA
<213> ORGANISM: Populus tremula

<400> SEQUENCE: 28

```
atccacagag agaaagggaa gacatggcaa ccagaactcc aaagcttgtg aagcacacat      60
tgttgactcg gttcaaggat gagatcacac gagaacagat cgacaactac attaatgact    120
ataccaatct gctcgatctc attccaagca tgaagagttt caattggggc acggatctgg    180
gcatggagtc tgcggagcta aaccgaggat acactcatgc ctttgaatct acatttgaga    240
gcaagtctgg tttgcaagag tacctcgatt ctgctgctct tgctgcattt gcagaagggt    300
ttttgcctac tttgtcacag cgtcttgtga tagactactt tctctactaa acgctcagga    360
gtaacgactt cggccgggct atttcatggt aataaagtaa tgtaatgttc aataaatgct    420
ggttttgaac cactgaatgt tcgtgtcttg atttcttgtc tgtgctaagt gaagggagtg    480
ctgctattcc tttaaaaata aagcccttgg ggttgagttg tagtttttca atcttttttcc   540 ccgatttatt tcggtcttgg tgttgtt                                         567
```

<210> SEQ ID NO 29
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 29

```
Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe
```

<210> SEQ ID NO 30

-continued

```
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 30

Val Val Lys His Leu Val Ile Val Gln Phe Lys Glu Asp Val Thr Pro
1               5                   10                  15

Glu Arg Leu Asp Gly Leu Ile Arg Gly Tyr Ala Gly Leu Val Asp Lys
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
        50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 31
<211> LENGTH: 98
<212> TYPE: PRT
<213> ORGANISM: Triticum aestivum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 31

Val Val Lys His Leu Val Ile Val Gln Phe Lys Glu Asp Val Thr Pro
1               5                   10                  15

Glu Arg Leu Glu Gly Leu Ile Arg Gly Tyr Ala Gly Leu Val Asp Lys
                20                  25                  30

Val Pro Ser Met Lys Ala Phe His Trp Gly Thr Asp Val Ser Ile Glu
            35                  40                  45

Asn Xaa Xaa Met His Gln Gly Phe Thr His Val Phe Glu Ser Thr Phe
        50                  55                  60

Glu Ser Thr Glu Gly Val Lys Glu Tyr Val Tyr His Pro Ala His Val
65                  70                  75                  80

Glu Phe Ala Thr Asp Phe Leu Gly Ser Thr Glu Lys Val Leu Ile Ile
                85                  90                  95

Asp Phe

<210> SEQ ID NO 32
<211> LENGTH: 84
<212> TYPE: PRT
<213> ORGANISM: Zea mays
<220> FEATURE:
<221> NAME/KEY: misc_feature
<222> LOCATION: (50)..(51)
<223> OTHER INFORMATION: Xaa can be any naturally occurring amino acid

<400> SEQUENCE: 32

Val Val Lys His Ile Leu Leu Ala Ser Phe Lys Glu Glu Val Thr Gln
1               5                   10                  15

Glu Arg Leu Asp Glu Leu Ile Arg Gly Tyr Ala Ala Leu Val Gly Val
                20                  25                  30
```

-continued

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Ile Lys Glu Tyr Ile Glu His Pro Ala His Val
65                  70                  75                  80

Glu Phe Ala Lys

<210> SEQ ID NO 33
<211> LENGTH: 98
<212> TYPE: PRT
<213> ORGANISM: Oryza sativa
<220> FEATURE:
<221> NAME/KEY: misc_feature
<222> LOCATION: (50)..(51)
<223> OTHER INFORMATION: Xaa can be any naturally occurring amino acid

<400> SEQUENCE: 33

Val Val Lys His Ile Leu Leu Ala Arg Phe Lys Glu Asp Val Ala Pro
1               5                   10                  15

Glu Arg Leu Asp Gln Leu Ile Arg Gly Tyr Ala Gly Leu Val Asp Leu
            20                  25                  30

Val Pro Ser Met Lys Ala Phe His Trp Gly Thr Asp Val Ser Ile Glu
        35                  40                  45

Asn Xaa Xaa Met His Gln Gly Phe Thr His Val Phe Glu Ser Thr Phe
    50                  55                  60

Glu Ser Thr Glu Gly Val Lys Glu Tyr Ile Glu His Pro Ala His Val
65                  70                  75                  80

Glu Phe Ala Asn Glu Phe Leu Pro Val Leu Glu Lys Thr Leu Ile Ile
                85                  90                  95

Asp Tyr

<210> SEQ ID NO 34
<211> LENGTH: 98
<212> TYPE: PRT
<213> ORGANISM: Triticum aestivum
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (48)..(49)
<223> OTHER INFORMATION: Xaa can be any naturally occurring amino acid

<400> SEQUENCE: 34

Val Val Lys His Leu Val Leu Ala Arg Phe Lys Glu Glu Ala Thr Pro
1               5                   10                  15

Glu Ala Leu Asp Xaa Leu Ile Arg Arg Tyr Ala Gly Leu Val Asp Ala
            20                  25                  30

Val Pro Ser Met Lys Ala Phe His Trp Gly Thr Asp Val Thr Val Xaa
        35                  40                  45

Xaa Leu Asp Thr His Glu Gly Phe Thr His Val Phe Glu Ser Thr Phe
    50                  55                  60

Glu Ser Ala Glu Gly Val Lys Glu Tyr Ile Ala His Pro Ser His Val
65                  70                  75                  80

Glu Phe Val Asp Glu Phe Leu Ala Leu Ala Glu Lys Met Leu Ile Val
                85                  90                  95

Asp Tyr

<210> SEQ ID NO 35
<211> LENGTH: 109
<212> TYPE: PRT
<213> ORGANISM: Arabidopsis thaliana

<400> SEQUENCE: 35

Met Glu Glu Ala Lys Gly Pro Val Lys His Val Leu Leu Ala Ser Phe
1               5                   10                  15

Lys Asp Gly Val Ser Pro Glu Lys Ile Glu Glu Leu Ile Lys Gly Tyr
            20                  25                  30

Ala Asn Leu Val Asn Leu Ile Glu Pro Met Lys Ala Phe His Trp Gly
        35                  40                  45

Lys Asp Val Ser Ile Glu Asn Leu His Gln Gly Tyr Thr His Ile Phe
    50                  55                  60

Glu Ser Thr Phe Glu Ser Lys Glu Ala Val Ala Glu Tyr Ile Ala His
65                  70                  75                  80

Pro Ala His Val Glu Phe Ala Thr Ile Phe Leu Gly Ser Leu Asp Lys
                85                  90                  95

Val Leu Val Ile Asp Tyr Lys Pro Thr Ser Val Ser Leu
            100                 105

<210> SEQ ID NO 36
<211> LENGTH: 47
<212> TYPE: PRT
<213> ORGANISM: Arabidopsis thaliana

<400> SEQUENCE: 36

Leu His Gln Gly Tyr Thr His Ile Leu Glu Ser Thr Phe Glu Ser Lys
1               5                   10                  15

Glu Ala Val Ala Glu Tyr Ile Ala His Pro Ala His Val Glu Phe Ala
            20                  25                  30

Thr Ile Phe Leu Gly Ser Leu Asp Lys Val Leu Val Ile Asp Tyr
        35                  40                  45

<210> SEQ ID NO 37
<211> LENGTH: 98
<212> TYPE: PRT
<213> ORGANISM: Glycine max
<220> FEATURE:
<221> NAME/KEY: misc_feature
<222> LOCATION: (50)..(51)
<223> OTHER INFORMATION: Xaa can be any naturally occurring amino acid

<400> SEQUENCE: 37

Val Val Lys His Val Leu Leu Ala Lys Phe Lys Asp Asp Val Thr Pro
1               5                   10                  15

Glu Arg Ile Glu Glu Leu Ile Lys Asp Tyr Ala Asn Leu Val Asn Leu
            20                  25                  30

Ile Pro Pro Met Lys Ser Phe His Trp Gly Lys Asp Val Ser Ala Glu
        35                  40                  45

Asn Xaa Xaa Leu His Gln Gly Phe Thr His Val Phe Glu Ser Thr Phe
    50                  55                  60

Glu Ser Pro Glu Gly Val Ala Glu Tyr Val Ala His Pro Ala His Val
65                  70                  75                  80

Glu Tyr Ala Asn Leu Phe Leu Ser Cys Leu Glu Lys Val Ile Val Ile
                85                  90                  95

Asp Tyr

```
<210> SEQ ID NO 38
<211> LENGTH: 98
<212> TYPE: PRT
<213> ORGANISM: Lycopersicon esculentum
<220> FEATURE:
<221> NAME/KEY: misc_feature
<222> LOCATION: (50)..(51)
<223> OTHER INFORMATION: Xaa can be any naturally occurring amino acid

<400> SEQUENCE: 38

Val Val Lys His Ile Leu Leu Ala Lys Phe Lys Asp Gly Ile Pro Pro
1               5                   10                  15

Glu Gln Ile Asp Gln Leu Ile Lys Gln Tyr Ala Asn Leu Val Asn Leu
            20                  25                  30

Val Glu Pro Met Lys Ala Phe Gln Trp Gly Lys Asp Val Ser Ile Glu
        35                  40                  45

Asn Xaa Xaa Leu His Gln Gly Phe Thr His Val Phe Glu Ser Thr Phe
    50                  55                  60

Asp Ser Leu Glu Gly Val Ala Glu Tyr Ile Ala His Pro Val His Val
65                  70                  75                  80

Glu Tyr Ala Asn Thr Leu Leu Pro Gln Leu Glu Lys Phe Leu Ile Val
                85                  90                  95

Asp Tyr

<210> SEQ ID NO 39
<211> LENGTH: 93
<212> TYPE: PRT
<213> ORGANISM: Glycine max
<220> FEATURE:
<221> NAME/KEY: misc_feature
<222> LOCATION: (49)..(50)
<223> OTHER INFORMATION: Xaa can be any naturally occurring amino acid

<400> SEQUENCE: 39

His Val Leu Leu Pro Lys Leu Lys Asp Tyr Phe Thr Pro Glu Arg Ile
1               5                   10                  15

Glu Leu Met Val Asp Tyr Ala Asn Leu Val Asn Leu Met Pro Arg Met
            20                  25                  30

Lys Ser Phe His Ser Gly Arg Asp Val Ser Ala Glu Tyr Leu His Leu
        35                  40                  45

Xaa Xaa Gly Cys Thr His Val Tyr Glu Ser Thr Phe Asp Ser Pro Gly
    50                  55                  60

Val Ala Glu Tyr Val Ala His Ala His Val Glu Tyr Ala Asn Gln
65                  70                  75                  80

Asp Leu Ser Cys Leu Glu Lys Val Ile Ala Ile Asp Tyr
                85                  90

<210> SEQ ID NO 40
<211> LENGTH: 108
<212> TYPE: PRT
<213> ORGANISM: Populus tremula x Populus tremuloides

<400> SEQUENCE: 40

Met Ala Thr Arg Thr Pro Lys Leu Val Lys His Thr Leu Ala Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45
```

```
Gly Thr Asp Leu Gly Met Glu Ser Ala Glu Leu Asn Arg Gly Tyr Thr
    50                  55                  60

His Ala Phe Glu Ser Thr Phe Glu Ser Lys Gly Leu Gln Glu Tyr
 65                  70                  75                  80

Leu Asp Ser Ala Ala Leu Ala Ala Phe Ala Glu Gly Phe Leu Pro Thr
                 85                  90                  95

Leu Ser Gln Arg Leu Val Ile Asp Tyr Phe Leu Tyr
            100                 105
```

<210> SEQ ID NO 41
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 41

```
Lys His Leu Cys Leu Val Arg Phe Lys Glu Gly Val Val Val Glu Asp
 1               5                  10                  15

Ile Xaa Xaa Xaa Ile Glu Glu Leu Thr Lys Leu Ala Ala Glu Leu Asp
             20                  25                  30

Thr Val Lys Phe Phe Gly Trp Gly Lys Asp Val Leu Asn Gln Glu Ala
         35                  40                  45

Xaa Leu Thr Gln Gly Phe Thr His Val Phe Ser Met Ser Phe Ala Ser
     50                  55                  60

Ala Glu Asp Leu Ala Ala Tyr Met Gly His Glu Lys His Ser Ala Phe
 65                  70                  75                  80

Ala Ala Thr Phe Met Ala Val Leu Asp Lys Val Val Val Leu Asp Phe
                 85                  90                  95
```

<210> SEQ ID NO 42
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 42

```
Lys His Leu Cys Leu Val Arg Phe Lys Glu Gly Val Val Val Glu Asp
 1               5                  10                  15

Ile Xaa Xaa Xaa Ile Glu Glu Leu Thr Lys Leu Ala Ala Glu Leu Asp
             20                  25                  30

Thr Val Lys Phe Phe Gly Trp Gly Lys Asp Val Leu Asn Gln Glu Ala
         35                  40                  45

Xaa Leu Thr Gln Gly Phe Thr His Val Phe Ser Met Ser Phe Ala Ser
     50                  55                  60

Ala Glu Asp Leu Ala Ala Cys Met Gly His Glu Lys His Ser Ala Phe
 65                  70                  75                  80

Ala Ala Thr Phe Met Ala Val Leu Asp Lys Val Val Val Leu Asp Phe
                 85                  90                  95
```

<210> SEQ ID NO 43
<211> LENGTH: 96
<212> TYPE: PRT
<213> ORGANISM: Triticum aestivum
<220> FEATURE:
<221> NAME/KEY: misc_feature
<222> LOCATION: (18)..(20)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 43

Lys His Leu Cys Met Ala Lys Phe Lys Glu Gly Val Val Val Glu Asp
1               5                   10                  15

Ile Xaa Xaa Xaa Ile Gln Glu Leu Thr Lys Leu Ala Ala Glu Leu Asp
                20                  25                  30

Thr Val Lys Tyr Phe Gly Trp Gly Lys Asp Val Leu Asn Gln Glu Ala
            35                  40                  45

Xaa Leu Thr Gln Gly Phe Thr His Val Phe Val Met Thr Phe Ala Ser
        50                  55                  60

Ala Glu Asp Leu Ala Ala Cys Met Gly His Glu Lys His Thr Ala Phe
65                  70                  75                  80

Ala Ala Thr Phe Met Ala Ala Leu Asp Lys Val Val Val Met Asp Phe
                85                  90                  95

<210> SEQ ID NO 44
<211> LENGTH: 97
<212> TYPE: PRT
<213> ORGANISM: Oryza sativa
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 44

Val Lys His Leu Cys Leu Val Lys Phe Lys Glu Glu Val Leu Xaa Xaa
1               5                   10                  15

Xaa Val Asp Asp Ile Leu Gln Gly Met Thr Lys Leu Val Ser Glu Met
                20                  25                  30

Asp Met Val Lys Ser Phe Glu Trp Gly Lys Asp Val Xaa Leu Asn Gln
            35                  40                  45

Glu Met Leu Thr Gln Gly Phe Thr His Val Phe Ser Leu Thr Phe Ala
        50                  55                  60

Ser Ser Glu Asp Leu Thr Thr Tyr Met Ser His Glu Arg His Gln Glu
65                  70                  75                  80

Phe Ala Gly Thr Phe Met Ala Ala Ile Asp Lys Val Val Val Val Asp
                85                  90                  95

Phe

<210> SEQ ID NO 45
<211> LENGTH: 104
<212> TYPE: PRT
<213> ORGANISM: Sorghum bicolor
<220> FEATURE:
<221> NAME/KEY: misc_feature
<222> LOCATION: (40)..(42)

```
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 45

Arg Arg Pro Thr Met Gly Glu Val Lys His Leu Cys Leu Val Lys Phe
1               5                   10                  15

Lys Glu Gly Val Val Val Glu Asp Val Leu Lys Gly Met Thr Asp Leu
            20                  25                  30

Val Ala Gly Met Asp Met Val Xaa Xaa Xaa Lys Ser Phe Glu Trp Gly
        35                  40                  45

Gln Asp Val Xaa Leu Asn Gln Glu Met Leu Thr Gln Gly Phe Thr His
    50                  55                  60

Val Phe Ser Leu Thr Phe Ala Phe Ala Asp Leu Ala Thr Tyr Met
65                  70                  75                  80

Gly His Asp Arg His Ala Ala Phe Ala Ala Thr Phe Met Ala Ala Leu
                85                  90                  95

Asp Lys Val Val Val Ile Asp Phe
            100

<210> SEQ ID NO 46
<211> LENGTH: 77
<212> TYPE: PRT
<213> ORGANISM: Zea mays
<220> FEATURE:
<221> NAME/KEY: misc_feature
<222> LOCATION: (25)..(25)
<223> OTHER INFORMATION: Xaa can be any naturally occurring amino acid

<400> SEQUENCE: 46

Glu Ser Thr Phe Glu Ser Thr Glu Gly Ile Lys Glu Tyr Ile Glu His
1               5                   10                  15

Pro Ala His Val Glu Phe Ala Lys Xaa Leu Asn Gln Glu Met Leu Thr
            20                  25                  30

Gln Gly Phe Thr His Val Phe Ser Leu Thr Phe Ala Thr Ala Ala Asp
        35                  40                  45

Leu Ala Ala Tyr Met Ala His Asp Ser His Thr Ala Phe Ala Ala Thr
    50                  55                  60

Phe Met Ala Ala Ile Asp Lys Val Leu Val Asp Phe
65                  70                  75

<210> SEQ ID NO 47
<211> LENGTH: 97
<212> TYPE: PRT
<213> ORGANISM: Lycopersicon esculentum
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 47

Lys His Leu Val Leu Val Lys Phe Lys Glu Asp Val Val Val Glu Asp
1               5                   10                  15

Ile Leu Lys Glu Leu Glu Lys Leu Val Gln Glu Met Asp Ile Val Xaa
            20                  25                  30

Xaa Xaa Lys Ser Phe Val Trp Gly Lys Asp Val Xaa Xaa Glu Ser His
```

```
                    35                  40                  45

Glu Met Leu Arg Gln Gly Phe Thr His Ala Ile Ile Met Thr Phe Asn
        50                  55                  60

Ser Lys Glu Asp Tyr Gln Thr Phe Ala Asn His Pro Asn His Val Gly
65                  70                  75                  80

Phe Ser Ala Thr Phe Ala Thr Val Ile Asp Lys Ala Val Leu Leu Asp
                85                  90                  95

Phe

<210> SEQ ID NO 48
<211> LENGTH: 94
<212> TYPE: PRT
<213> ORGANISM: Solanum tuberosum
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid

<400> SEQUENCE: 48

Leu Leu Val Lys Phe Lys Gln Asp Val Val Glu Glu Asp Val Leu Lys
1               5                   10                  15

Gln Ile Glu Gln Leu Val Asn Glu Ile Asp Leu Ile Xaa Xaa Xaa Lys
            20                  25                  30

Ser Phe Val Trp Gly Lys Asp Thr Xaa Xaa Glu Ser Asn Glu Met Val
        35                  40                  45

Thr Gln Gly Tyr Thr His Ala Met Ile Met Thr Phe Asn Ser Lys Glu
    50                  55                  60

Asp Tyr Glu Ala Cys Val Val Lys Glu Val Xaa Xaa Glu Phe Ser Ala
65                  70                  75                  80

Ile Phe Val Thr Val Val Glu Lys Ile Leu Val Leu Asn Phe
                85                  90

<210> SEQ ID NO 49
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 49

His Tyr Val Ile Val Lys Phe Lys Asp Gly Val Ala Xaa Xaa Xaa Val
1               5                   10                  15

Asp Asp Leu Ile Gln Gly Leu Glu Lys Met Val Phe Gly Ile Asp His
            20                  25                  30

Val Lys Ser Phe Glu Trp Gly Lys Asp Ile Xaa Xaa Glu Ser His Asp
        35                  40                  45

Met Leu Arg Gln Gly Phe Thr His Ala Phe Leu Met Thr Phe Asn Gly
    50                  55                  60
```

```
Lys Glu Glu Phe Asn Ala Phe Gln Thr His Pro Asn His Leu Glu Phe
 65                  70                  75                  80

Ser Gly Val Phe Ser Pro Ala Ile Glu Lys Ile Val Val Leu Asp Phe
                 85                  90                  95

<210> SEQ ID NO 50
<211> LENGTH: 96
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 50

His Tyr Val Ile Val Lys Phe Lys Asp Gly Val Ala Xaa Xaa Xaa Val
 1               5                  10                  15

Asp Glu Leu Ile Gln Gly Leu Glu Lys Met Val Ser Gly Ile Asp His
                 20                  25                  30

Val Lys Ser Phe Glu Trp Gly Lys Asp Ile Xaa Xaa Glu Ser His Asp
             35                  40                  45

Met Leu Arg Gln Gly Phe Thr His Val Phe Leu Met Ala Phe Asn Gly
 50                  55                  60

Lys Glu Glu Phe Asn Ala Phe Gln Thr His Pro Asn His Leu Glu Phe
 65                  70                  75                  80

Thr Gly Val Phe Ser Pro Ala Ile Glu Lys Ile Val Val Leu Asp Phe
                 85                  90                  95

<210> SEQ ID NO 51
<211> LENGTH: 97
<212> TYPE: PRT
<213> ORGANISM: Glycine max
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 51

Lys His Phe Val Ile Val Lys Phe Lys Glu Gly Val Ala Xaa Xaa Xaa
 1               5                  10                  15

Val Asp Glu Leu Thr Lys Gly Met Glu Lys Leu Val Thr Glu Ile Gly
                 20                  25                  30

Ala Val Lys Ser Phe Glu Trp Gly Gln Asp Ile Xaa Xaa Glu Ser Leu
             35                  40                  45

Asp Val Leu Arg Gln Gly Phe Thr His Ala Phe Leu Met Thr Phe Asn
 50                  55                  60

Lys Lys Glu Asp Phe Val Ala Phe Gln Ser His Pro Asn His Val Glu
 65                  70                  75                  80

Phe Ser Thr Lys Phe Ser Ala Ala Ile Glu Asn Ile Val Leu Leu Asp
                 85                  90                  95

Phe

<210> SEQ ID NO 52
<211> LENGTH: 43
```

```
<212> TYPE: PRT
<213> ORGANISM: Glycine max
<220> FEATURE:
<221> NAME/KEY: misc_feature
<222> LOCATION: (18)..(19)
<223> OTHER INFORMATION: Xaa can be any naturally occurring amino acid

<400> SEQUENCE: 52

Leu Val Ser Glu Ile His Ala Val Lys Ser Phe Glu Trp Gly Gln Asp
1               5                   10                  15

Ile Xaa Xaa Glu Ser Leu Asp Val Leu Arg Gln Gly Phe Thr His Ala
            20                  25                  30

Phe Leu Met Thr Phe Asn Lys Lys Arg Arg Leu
        35                  40

<210> SEQ ID NO 53
<211> LENGTH: 111
<212> TYPE: PRT
<213> ORGANISM: Arabidopsis thaliana

<400> SEQUENCE: 53

Met Ala Thr Ser Gly Phe Lys His Leu Val Val Lys Phe Lys Glu
1               5                   10                  15

Asp Thr Lys Val Asp Glu Ile Leu Lys Gly Leu Glu Asn Leu Val Ser
            20                  25                  30

Gln Ile Asp Thr Val Lys Ser Phe Glu Trp Gly Glu Asp Lys Glu Ser
        35                  40                  45

His Asp Met Leu Arg Gln Gly Phe Thr His Ala Phe Ser Met Thr Phe
    50                  55                  60

Glu Asn Lys Asp Gly Tyr Val Ala Phe Thr Ser His Pro Leu His Val
65                  70                  75                  80

Glu Phe Ser Ala Ala Phe Thr Ala Val Ile Asp Lys Ile Val Leu Leu
                85                  90                  95

Asp Phe Pro Val Ala Ala Val Lys Ser Ser Val Val Ala Thr Pro
            100                 105                 110

<210> SEQ ID NO 54
<211> LENGTH: 100
<212> TYPE: PRT
<213> ORGANISM: Glycine max
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid

<400> SEQUENCE: 54

Lys Thr Val Glu His Ile Val Leu Phe Lys Val Lys Glu Glu Thr Glu
1               5                   10                  15

Pro Ser Lys Val Ser Asp Met Val Asn Gly Leu Gly Ser Leu Val Ser
            20                  25                  30

Leu Asp Pro Val Leu His Xaa Leu Ser Val Gly Pro Leu Leu Arg Asn
        35                  40                  45

Arg Ser Ser Ala Leu Thr Xaa Xaa Phe Thr His Met Leu His Ser Arg
    50                  55                  60

Tyr Lys Ser Lys Glu Asp Leu Glu Ala Tyr Ser Ala His Pro Ser His
65                  70                  75                  80

Val Ser Val Val Lys Gly Tyr Val Leu Pro Ile Ile Asp Asp Ile Met
```

Ser Val Asp Trp
         100

<210> SEQ ID NO 55
<211> LENGTH: 352
<212> TYPE: DNA
<213> ORGANISM: Artificial sequence
<220> FEATURE:
<223> OTHER INFORMATION: mtbSP coding sequence

<400> SEQUENCE: 55

```
aaaacatatg cgcaaacttc cggatgcggc aaccagaact ccaaagcttg tgaagcacac     60
attgttgact cggttcaagg atgagatcac acgagaacag atcgacaact acattaatga    120
ctataccaat ctgctcgatc tcattccaag catgaagagt ttcaattggg gcacggatct    180
gggcatggag tctgcggagc taaaccgagg atacactcat gcctttgaat ctacatttga    240
gagcaagtct ggtttgcaag agtacctcga ttctgctgct cttgctgcat ttgcagaagg    300
gttttttgcct actttgtcac agcgtcttgt gatagactac tttctctact aa           352
```

<210> SEQ ID NO 56
<211> LENGTH: 383
<212> TYPE: DNA
<213> ORGANISM: Artificial sequence
<220> FEATURE:
<223> OTHER INFORMATION: L1-SP1 coding sequence

<400> SEQUENCE: 56

```
aaggagatat acaaaaacat atgcactggt cagcatggtg gatacgatca aatcaatcag     60
caaccagaac tccaaagctt gtgaagcaca cattgttgac tcggttcaag gatgagatca    120
cacgagaaca gatcgacaac tacattaatg actataccaa tctgctcgat ctcattccaa    180
gcatgaagag tttcaattgg ggcacggatc tgggcatgga gtctgcggag ctaaaccgag    240
gatacactca tgcctttgaa tctacatttg agagcaagtc tggtttgcaa gagtacctcg    300
attctgctgc tcttgctgca tttgcagaag gttttttgcc tactttgtca gcgtcttg     360
tgatagacta ctttctctac taa                                          383
```

<210> SEQ ID NO 57
<211> LENGTH: 384
<212> TYPE: DNA
<213> ORGANISM: Artificial sequence
<220> FEATURE:
<223> OTHER INFORMATION: L2-Sp1 coding sequence

<400> SEQUENCE: 57

```
gaaggagata tacaaaaaca tatgcactca tcatactggt acgcattcaa caacaaaaca     60
gcaaccagaa ctccaaagct tgtgaagcac acattgttga ctcggttcaa ggatgagatc    120
acacgagaac agatcgacaa ctacattaat gactatacca atctgctcga tctcattcca    180
agcatgaaga gtttcaattg gggcacggat ctgggcatgg agtctgcgga gctaaaccga    240
ggatacactc atgcctttga atctacattt gagagcaagt ctggtttgca agagtacctc    300
gattctgctg ctcttgctgc atttgcagaa gggttttttgc ctactttgtc acagcgtctt    360
gtgatagact actttctcta ctaa                                          384
```

<210> SEQ ID NO 58
<211> LENGTH: 375
<212> TYPE: DNA

<213> ORGANISM: Artificial sequence
<220> FEATURE:
<223> OTHER INFORMATION: L3-SP1 coding sequence

<400> SEQUENCE: 58

```
atacaaaaac atatggatta ttttcatca ccatattatg aacaattatt tgcaaccaga      60
actccaaagc ttgtgaagca cacattgttg actcggttca aggatgagat cacacgagaa    120
cagatcgaca actacattaa tgactatacc aatctgctcg atctcattcc aagcatgaag    180
agtttcaatt ggggcacgga tctgggcatg gagtctgcgg agctaaaccg aggatacact    240
catgcctttg aatctacatt tgagagcaag tctggtttgc aagagtacct cgattctgct    300
gctcttgctg catttgcaga agggttttg cctactttgt cacagcgtct tgtgatagac    360
tactttctct actaa                                                     375
```

<210> SEQ ID NO 59
<211> LENGTH: 361
<212> TYPE: DNA
<213> ORGANISM: Artificial sequence
<220> FEATURE:
<223> OTHER INFORMATION: L6-SP1 coding sequence

<400> SEQUENCE: 59

```
agaaggagat atacaaaaac atatgtcaaa tcaatcagca accagaactc caaagcttgt     60
gaagcacaca ttgttgactc ggttcaagga tgagatcaca cgagaacaga tcgacaacta   120
cattaatgac ataccaatc tgctcgatct cattccaagc atgaagagtt tcaattgggg    180
cacggatctg ggcatggagt ctgcggagct aaaccgagga tacactcatg cctttgaatc    240
tacatttgag agcaagtctg gtttgcaaga gtacctcgat tctgctgctc ttgctgcatt    300
tgcagaaggg tttttgccta ctttgtcaca gcgtcttgtg atagactact ttctctacta    360
a                                                                    361
```

<210> SEQ ID NO 60
<211> LENGTH: 383
<212> TYPE: DNA
<213> ORGANISM: Artificial sequence
<220> FEATURE:
<223> OTHER INFORMATION: L4-Sp1 coding sequence

<400> SEQUENCE: 60

```
aaggagatat acaaaaacat atgcactggt cagcatggtg gatacgatca atcaatcag      60
caaccagaac tccaaagctt gtgaagcaca cattgttgac tcggttcaag gatgagatca   120
caaagaaca gatcgacaac tacattaatg actataccaa tctgctcgat ctcattccaa    180
gcatgaagag tttcaattgg ggcacggatc tgggcatgga gtctgcggag ctaaaccgag    240
gatacactca tgcctttgaa tctacatttg agcaagtc tggtttgcaa gagtacctcg    300
attctgctgc tcttgctgca tttgcagaag ggttttttgcc tactttgtca cagcgtcttg    360
tgatagacta ctttctctac taa                                            383
```

<210> SEQ ID NO 61
<211> LENGTH: 383
<212> TYPE: DNA
<213> ORGANISM: Artificial sequence
<220> FEATURE:
<223> OTHER INFORMATION: L5-Sp1 coding sequence

<400> SEQUENCE: 61

```
aaggagatat acaaaaacat atgcactggt cagcatggtg gatacgatca atcaatcag      60
```

```
caaccagaac tccaaagctt gtgaagcaca cattgttgac tcggttcaag gatgagatct    120
gccgagaaca gatcgacaac tacattaatg actataccaa tctgctcgat ctcattccaa    180
gcatgaagag tttcaattgg ggcacggatc tgggcatgga gtctgcggag ctaaaccgag    240
gatacactca tgcctttgaa tctacatttg agagcaagtc tggtttgcaa gagtacctcg    300
attctgctgc tcttgctgca tttgcagaag ggttttttgcc tactttgtca cagcgtcttg    360
tgatagacta ctttctctac taa                                              383
```

<210> SEQ ID NO 62
<211> LENGTH: 383
<212> TYPE: DNA
<213> ORGANISM: Artificial sequence
<220> FEATURE:
<223> OTHER INFORMATION: L7-SP1 coding sequence

<400> SEQUENCE: 62

```
aaggagatat acaaaaacat atgcactggt cagcatggtg gattcgttca atcaatcag     60 caaccagaac tccaaagctt gtgaagcaca cattgttgac tcggttcaag gatgagatca    120
cacgagaaca gatcgacaac tacattaatg actataccaa tctgctcgat ctcattccaa    180
gcatgaagag tttcaattgg ggcacggatc tgggcatgga gtctgcggag ctaaaccgag    240
gatacactca tgcctttgaa tctacatttg agagcaagtc tggtttgcaa gagtacctcg    300
attctgctgc tcttgctgca tttgcagaag ggttttttgcc tactttgtca cagcgtcttg    360
tgatagacta ctttctctac taa                                              383
```

<210> SEQ ID NO 63
<211> LENGTH: 383
<212> TYPE: DNA
<213> ORGANISM: Artificial sequence
<220> FEATURE:
<223> OTHER INFORMATION: L8_Sp1 coding sequence

<400> SEQUENCE: 63

```
aaggagatat acaaaaacat atgcactggt cagcatggtg gattcgttca atcaatcag     60 caaccagaac tccaaagctt gtgaagcaca cattgttgac tcggttcaag gatgagatca    120
caaaagaaca gatcgacaac tacattaatg actataccaa tctgctcgat ctcattccaa    180
gcatgaagag tttcaattgg ggcacggatc tgggcatgga gtctgcggag ctaaaccgag    240
gatacactca tgcctttgaa tctacatttg agagcaagtc tggtttgcaa gagtacctcg    300
attctgctgc tcttgctgca tttgcagaag ggttttttgcc tactttgtca cagcgtcttg    360
tgatagacta ctttctctac taa                                              383
```

<210> SEQ ID NO 64
<211> LENGTH: 103
<212> TYPE: PRT
<213> ORGANISM: Artificial sequence
<220> FEATURE:
<223> OTHER INFORMATION: Sp1 mutant variant: amino acid 2-6 deleted

<400> SEQUENCE: 64

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

```
Met Glu Ser Ala Glu Leu Asn Arg Gly Tyr Thr His Ala Phe Glu Ser
 50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
            100
```

<210> SEQ ID NO 65
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 65
ctgctcgatc tcattccaag ctgtaagagt tcaattggg gcacg        45

<210> SEQ ID NO 66
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 66
gcaagtctgg tttgcaagag tactgcgatt ctgctgctct tgctg        45

<210> SEQ ID NO 67
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 67
aaaacatatg cgcaaacttc cggatgcggc aaccagaact ccaaagcttg        50

<210> SEQ ID NO 68
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 68
aaaagagctc ttagtaaaga agtaatcaa taac        34

<210> SEQ ID NO 69
<211> LENGTH: 312
<212> TYPE: DNA
<213> ORGANISM: Artificial sequence
<220> FEATURE:
<223> OTHER INFORMATION: M43C delta N' SP1 coding sequence

<400> SEQUENCE: 69
atgaagcttg tgaagcacac attgttgact cggttcaagg atgagatcac acgagaacag        60
atcgacaact acattaatga ctataccaat ctgctcgatc tcattccaag ctgtaagagt       120
ttcaattggg gcacggatct gggcatggag tctgcggagc taaaccgagg atacactcat       180
gcctttgaat ctcacatttga gagcaagtct ggtttgcaag agtacctcga ttctgctgct       240

```
cttgctgcat tgcagaagg gttttgcct actttgtcac agcgtcttgt gatagactac    300
tttctctact aa                                                     312

<210> SEQ ID NO 70
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 70
aaggagatat acaaaaacat atgcactggt cagcatggtg gatacgatca aatcaatcag  60
caaccagaac tccaaag                                                 77

<210> SEQ ID NO 71
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 71
ctttggagtt ctggttgctg attgatttga tcgtatccac catgctgacc agtgcatatg  60
tttttgtata tctcctt                                                 77

<210> SEQ ID NO 72
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 72
agaaggagat atacaaaaac atatgcactc atcatactgg tacgcattca acaacaaaac  60
agcaaccaga actccaaagc                                              80

<210> SEQ ID NO 73
<211> LENGTH: 80
<212> TYPE: DNA
<213> ORGANISM: Artificial sequence
<220> FEATURE:
<223> OTHER INFORMATION: Single strand DNA oligonucleotide

<400> SEQUENCE: 73
gctttggagt tctggttgct gttttgttgt tgaatgcgta ccagtatgat gagtgcatat  60
gtttttgtat atctccttct                                              80

<210> SEQ ID NO 74
<211> LENGTH: 65
<212> TYPE: DNA
<213> ORGANISM: Artificial sequence
<220> FEATURE:
<223> OTHER INFORMATION: Single strand DNA oligonucleotide

<400> SEQUENCE: 74
atacaaaaac atatggatta tttttcatca ccatattatg aacaattatt tgcaaccaga  60
actcc                                                              65

<210> SEQ ID NO 75
<211> LENGTH: 65
<212> TYPE: DNA
<213> ORGANISM: Artificial sequence
```

<220> FEATURE:
<223> OTHER INFORMATION: Single strand DNA oligonucleotide

<400> SEQUENCE: 75
ggagttctgg ttgcaaataa ttgttcataa tatggtgatg aaaaataatc catatgtttt    60
tgtat                                                                65

<210> SEQ ID NO 76
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 76
agaaggagat atacaaaaac atatgtcaaa tcaatcagca accagaactc caaagc        56

<210> SEQ ID NO 77
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 77
gctttggagt tctggttgct gattgatttg acatatgttt ttgtatatct ccttct        56

<210> SEQ ID NO 78
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 78
actggtcagc atggtggatt cgatcaaatc aatcag                              36

<210> SEQ ID NO 79
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 79
ctgattgatt tgatcgaatc caccatgctg accagt                              36

<210> SEQ ID NO 80
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 80
gtcagcatgg tggattcgtt caaatcaatc agcaacc                             37

<210> SEQ ID NO 81
<211> LENGTH: 37
<212> TYPE: DNA
<213> ORGANISM: Artificial sequence
<220> FEATURE:
<223> OTHER INFORMATION: Single strand DNA oligonucleotide

<400> SEQUENCE: 81
ggttgctgat tgatttgaac gaatccacca tgctgac					37

<210> SEQ ID NO 82
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 82
tgactcggtt caaggatgag atcacaaaag aacagatcga ca					42

<210> SEQ ID NO 83
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 83
tgtcgatctg ttctttttgtg atctcatcct tgaaccgagt ca					42

<210> SEQ ID NO 84
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 84
actcggttca aggatgagat ctgccgagaa cagatcgaca actac					45

<210> SEQ ID NO 85
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 85
gtagttgtcg atctgttctc ggcagatctc atccttgaac cgagt					45

<210> SEQ ID NO 86
<211> LENGTH: 301
<212> TYPE: PRT
<213> ORGANISM: Artificial sequence
<220> FEATURE:
<223> OTHER INFORMATION: SP1-CBD chimeric polypeptide

<400> SEQUENCE: 86

Met Ala Ala Thr Ser Ser Met Ser Val Glu Phe Tyr Asn Ser Asn Lys
1               5                   10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Arg Ala Thr Leu Lys Lys Gly Gln

```
                100                 105                 110
Phe Ile Thr Ile Gln Gly Arg Ile Thr Lys Ser Asp Trp Ser Asn Tyr
            115                 120                 125

Thr Gln Thr Asn Asp Tyr Ser Phe Asp Ala Ser Ser Ser Thr Pro Val
        130                 135                 140

Val Asn Pro Lys Val Thr Gly Tyr Ile Gly Gly Ala Lys Val Leu Gly
145                 150                 155                 160

Thr Ala Pro Ala Val Pro Ser Gly Ser Val Thr Ser Thr Ser Lys Thr
                165                 170                 175

Thr Thr Thr Ala Ser Lys Thr Ser Thr Ser Thr Ser Thr Ser Glu
            180                 185                 190

Phe Met Ala Thr Ser Thr Pro Lys Leu Val Lys His Thr Leu Leu Thr
        195                 200                 205

Arg Phe Lys Asp Glu Ile Thr Arg Glu Gln Ile Asp Asn Tyr Ile Asn
    210                 215                 220

Asp Tyr Thr Asn Leu Leu Asp Leu Ile Pro Ser Met Lys Ser Phe Asn
225                 230                 235                 240

Trp Gly Thr Asp Leu Gly Met Glu Ser Ala Glu Leu Asn Arg Gly Tyr
                245                 250                 255

Thr His Ala Phe Glu Ser Thr Phe Glu Ser Lys Ser Gly Leu Gln Glu
            260                 265                 270

Tyr Leu Asp Ser Ala Ala Leu Ala Ala Phe Ala Glu Gly Phe Leu Pro
        275                 280                 285

Thr Leu Ser Gln Arg Leu Val Ile Asp Tyr Phe Leu Tyr
    290                 295                 300

<210> SEQ ID NO 87
<211> LENGTH: 163
<212> TYPE: PRT
<213> ORGANISM: Artificial sequence
<220> FEATURE:
<223> OTHER INFORMATION: CBD domain

<400> SEQUENCE: 87

Met Ala Ala Thr Ser Ser Met Ser Val Glu Phe Tyr Asn Ser Asn Lys
1               5                   10                  15

Ser Ala Gln Thr Asn Ser Ile Thr Pro Ile Ile Lys Ile Thr Asn Thr
            20                  25                  30

Ser Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Arg Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Thr Gln Thr Asn Asp Tyr Ser Phe Asp Ala Ser Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro
```

```
<210> SEQ ID NO 88
<211> LENGTH: 108
<212> TYPE: PRT
<213> ORGANISM: Artificial sequence
<220> FEATURE:
<223> OTHER INFORMATION: Sp1 polypeptide

<400> SEQUENCE: 88

Met Ala Thr Ser Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 89
<211> LENGTH: 30
<212> TYPE: PRT
<213> ORGANISM: Artificial sequence
<220> FEATURE:
<223> OTHER INFORMATION: SP1-CBD fusion protein peptide linker.

<400> SEQUENCE: 89

Ala Val Pro Ser Gly Ser Val Thr Ser Thr Ser Lys Thr Thr Thr Thr
1               5                   10                  15

Ala Ser Lys Thr Ser Thr Ser Thr Ser Ser Thr Ser Glu Phe
            20                  25                  30
```